US012709619B2

(12) United States Patent
Nencka et al.

(10) Patent No.: US 12,709,619 B2
(45) Date of Patent: Aug. 18, 2026

(54) SELECTIVE LIGANDS OF HUMAN CONSTITUTIVE ANDROSTANE RECEPTOR

(71) Applicants: USTAV ORGANICKE CHEMIE A BIOCHEMIE AV CR, V. V. I., Prague (CZ); UNIVERZITA KARLOVA, Prague (CZ)

(72) Inventors: Radim Nencka, Roztoky (CZ); Ivana Mejdrova, Prague (CZ); Petr Pavek, Hradec Kralove (CZ); Jan Dusek, Prelouc (CZ)

(73) Assignees: USTAV ORGANICKE CHEMIE A BIOCHEMIE AV CR, V.V.I., Prague (CZ); UNIVERZITA KARLOVA, Prague (CZ)

( * ) Notice: Subject to any disclaimer, the term of this patent is extended or adjusted under 35 U.S.C. 154(b) by 1106 days.

(21) Appl. No.: 17/605,186

(22) PCT Filed: Apr. 25, 2020

(86) PCT No.: PCT/CZ2020/050025
§ 371 (c)(1),
(2) Date: Oct. 20, 2021

(87) PCT Pub. No.: WO2020/221380
PCT Pub. Date: Nov. 5, 2020

(65) Prior Publication Data
US 2022/0185822 A1 Jun. 16, 2022

(30) Foreign Application Priority Data
Apr. 30, 2019 (EP) .................................... 19171938
Aug. 16, 2019 (EP) .................................... 19192020

(51) Int. Cl.
*C07D 513/04* (2006.01)
*A61P 3/00* (2006.01)
*C07D 471/04* (2006.01)
*C07D 487/04* (2006.01)

(52) U.S. Cl.
CPC .............. *C07D 513/04* (2013.01); *A61P 3/00* (2018.01); *C07D 471/04* (2013.01); *C07D 487/04* (2013.01)

(58) Field of Classification Search
CPC ............................ C07D 513/04; C07D 471/04
See application file for complete search history.

(56) References Cited

U.S. PATENT DOCUMENTS

2013/0059845 A1* 3/2013 Song ........................ A61P 1/16 514/249

FOREIGN PATENT DOCUMENTS

JP WO 2002/034748 * 5/2002 ........... C07D 471/04
WO 2009086123 A1 7/2009

OTHER PUBLICATIONS

Milu T Cherian et al: “Small-molecule modulators of the constitutive androstane receptor”, Expert Opinion on Drug Metabolism & Toxicology, Jul. 3, 2015, Ashley Productions London, GB—ISSN 1742-5255, vol. 11, Nr:7, pp. 1099-1114, http://dx.doi.org/10.1517/17425255.2015.1043887, retrieved Oct. 18, 2021.
Singhaus RR et al: “3-(3-Aryloxyaryl)imidazo[I,2-a]pyridine sulfones as liver X receptor agonists”, Bioorganic & Medicinal Chemistry Letters, Pergamon, Amsterdam, NL, vol. 20, No. 2, Jan. 15, 2010 (Jan. 15, 2010), pp. 521-525, XP026812523, retrieved Oct. 18, 2021.
International Search Report and Written Opinion for corresponding PCT application No. PCT/CZ2020/050025m mailed May 20, 2020.

* cited by examiner

*Primary Examiner* — Adam C Milligan
*Assistant Examiner* — Karen Cheng
(74) *Attorney, Agent, or Firm* — Notaro, Michalos & Zaccaria P.C.

(57) ABSTRACT

A structurally novel class of heterocyclic compounds of general formula I wherein L1 is heteroaryl and L2 is heteroaryl or aryl is disclosed. The novel compounds are useful in a method of prevention or treatment of a condition that is mediated by the action, or by loss of action of Constitutive androstane receptor (CAR) receptor or its endogenous ligands. The present invention provides the novel compounds for medicinal use as well as pharmaceutical composition containing the compounds.

3 Claims, 6 Drawing Sheets

SELECTIVE LIGANDS OF HUMAN CONSTITUTIVE ANDROSTANE RECEPTOR

FIELD OF THE INVENTION

The present invention relates to novel heterocyclic compounds of formula (I) which are capable of highly selective modulation of human constitutive androstane receptor (CAR, NR1I3), and to use thereof in the treatment of metabolic or liver disorders, as well as to pharmaceutical compositions thereof.

BACKGROUND ART

Constitutive androstane receptor (CAR, NR1I3) is a ligand-activated transcription factor belonging to the nuclear receptor subfamily NR1I.

Nuclear receptors (NRs) are currently known as key transcriptional regulators of several key metabolic processes including hepatic glucose and lipid metabolism, bile acid and cholesterol homeostasis, and energy expenditure as well as inflammation, fibrosis, and cellular proliferation in the liver. Dysregulation of these processes contributes to the pathogenesis and progression of metabolic diseases, metabolic syndrome or nonalcoholic fatty liver disease (NAFLD).

Some NRs provide strategies for research and treatment of metabolic disease and are already pharmacologically targeted in metabolic disorders such as hyperlipidemia (fibrates as ligands for peroxisomal proliferator-activated receptor α-PPARα), and diabetes (glitazones as ligands for PPARγ). But these groups of drugs suffer from numerous side effects and drawbacks.

Nonalcoholic fatty liver disease (NAFLD) often progress to less common subtype, nonalcoholic steatohepatitis (NASH), which has the potential to progress to advanced liver damage or cancer. However, current treatment strategies focus only on lifestyle management of some risk factors, namely weight, and on the management of individual components of metabolic syndrome. No other therapeutic interventions are available at present (Dibba et al., 2018).

Human CAR displays unique properties in comparison with other nuclear receptors including high constitutive activity, both direct (ligand-binding domain (LBD)-dependent) and LBD-independent activation, and spontaneous nuclear localization in tumor cell lines.

CAR is dominantly expressed in parenchymal (hepatocyte) cells of the liver where CAR wild-type variant (WT) (348 aa; NM_005122) and the low constitutive activity/highly inducible variant hCAR3 (a variant with 5 extra amino acids) are almost equally expressed (Chai et al., 2016a).

Recent studies suggest that mouse CAR plays important roles in the metabolism of glucose, lipids, and fatty acids; in the endobiotic metabolism of bile acids, cholesterol and bilirubin. It has been proposed in several independent animal studies that CAR activation may ameliorate glucose homeostasis and insulin sensibility in the treatment of type 2 diabetes by inhibition of gluconeogenetic genes expression (such as G6pc and Pck1) (Dong et al., 2009; Gao and Xie, 2012; Gao et al., 2015).

CAR activation reduces levels of lipoproteins and inhibits the expression of lipogenic genes in mice what might be a promising therapeutic intervention in the treatment of steatohepatitis, obesity, dyslipidemia, and metabolic syndrome or prevention of atherosclerosis (Baskin-Bey et al., 2007; Dong et al., 2009; Mackowiak et al., 2018; Sberna et al., 2011b; Xu et al., 2018).

CAR is also involved in cholesterol and bile acids homeostasis and its activation is supposed to have benefitial therapeutic activities in hypercholesterolemia, in cholesterol or bilirubin gallstone disease and cholestasis diseases (Cheng et al., 2017; Rezen et al., 2009; Sberna et al., 2011a).

These activities of CAR ligands are of great interest since there is currently no medication to treat metabolic syndrome connected with diabetes mellitus type 2, steatosis, and nonalcoholic steatohepatitis or to reduce obesity at the level of anabolic metabolism inhibition (Fuchs et al., 2016; Pu et al., 2019).

CAR up-regulates major xenobiotic- and endobiotic-metabolizing enzymes of cytochrome P450 such as CYP2B6, CYP3A4, and CYP2C9 in the hepatocytes or in enterocytes. In this way CAR activation may protect the liver and the whole body from toxic injury. However, the role of CAR in inducible regulation of CYP3A4 and CYP2C9 is quantitatively marginal in comparison with another nuclear receptor pregnane X receptor (PXR) and only CYP2B6 appears as a CAR target gene significantly regulated in human hepatocytes. Stimulation of endobiotic compounds (such as bilirubin) clearance by CAR activation is bennefitial in hyperbilirubinemia and jaundice, hyperthyreosis and in cytostatic prodrugs activation (Wagner et al., 2005; Wang et al., 2013).

CAR activation has been recently shown as potential regenerative treatment after partial hepatectomy due to pro-proliferative effects on hepatocytes in mice (Tschuor et al., 2016). However, the putative pro-proliferative effect of human CAR activators is unlikely connected with liver tumors (Lake, 2018).

No potent, specific (without cross reactivity to PXR receptor), high-affinity and drug-like (with suitable physicochemical and ADME properties) agonist of human CAR receptor has been discovered that can be used therapeutically or that can serve as a tool to address various diagnostic, biological or therapeutic functions of human CAR ligands to consider CAR as a therapeutic target (Chai et al., 2016b).

The unique properties of human CAR, such as small hydrophobic cavity, high constitutive activity of CAR in hepatocytes but little expression in tumour-derived cell lines and crosstalk activation of similar nuclear receptor such as Pregnane X receptor (PXR) by known CAR ligands, make discovery of specific ligands difficult. This is highly important, since PXR activation has been reported to cause opposite effects in comparison with CAR activation on promotion of hepatic lipogenesis and steatosis or on plasma glucose levels (glycemia) (Hakkola et al., 2018; Mackowiak et al., 2018).

Known to date is 6-(4-chlorophenyl)imidazo[2,1-b]thiazole-5-carbaldehyde dichlorobenzyl)oxime (CITCO) (Maglich et al., 2003), which is a potent human—but not mouse—CAR agonist. However, this highly lipophilic compound also significantly activates PXR. The potent mouse CAR ligand 1,4-bis[(3,5-dichloropyridine-2-yl)oxy]benzene (TCPOBOP) does not activate human or rat CAR. Phenobarbital, a nonspecific activator of CAR translocation widely used in experimental research of CAR is not a ligand of CAR and activates also PXR receptor (Chai et al., 2016b).

DISCLOSURE OF THE INVENTION

This invention discloses novel compounds of formula I, and compositions comprising these compounds, as human constitutive androstane receptor (CAR, NR1I3) agonists or partial agonists.

The present invention relates to a compound of general formula I

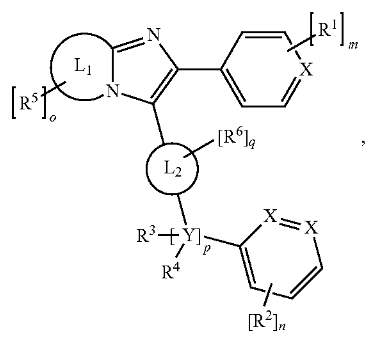

(I)

wherein $L_1$ is a 5- or 6-membered N-heteroaryl, which optionally further includes 1 to 3 heteroatoms selected from N, O and S;

$L_2$ is selected from the group consisting of bivalent 5- or 6-membered heteroaryls containing 1-4 heteroatoms selected from N, O and S; 5- or 6-membered heterocycles including 1-3 heteroatoms selected from N, O and S; C6-C12 aryls; C3-C6 cycloalkyl; and C3-C6 cycloalkenyl;

each of $R^1$ and $R^2$ is independently selected from the group consisting of halogen, pseudohalogen, amino, hydrocarbylamino, dihydrocarbylamino, nitro, C1-C6 alkyl, C1-C6 haloalkyl, C3-C6 cycloalkyl, C1-C6 alkoxy, C1-C6 alkylthio, acyl, alkylcarbamoyl, carbamoyl, alkylthiocarbamoyl, thiocarbamoyl, alkylsulfonyl, sulfonamido, N-alkylsulfonamido, N,N-dialkylsulfonamido, carboxyl, alkyloxycarbonyl, amide, N-alkylamide, N,N-dialkylamide, thioamide, N-alkylthioamide, N,N-dialkylthioamide, oxime, wherein each of these substituents may optionally be further substituted by one or more substitutents selected from the group consisting of halogen, pseudohalogen, C1-C6 alkyl, C1-C6 alkoxy, C1-C6 alkylthio, hydroxy, amino, hydrocarbylamino, dihydrocarbylamino;

each of $R^3$ and $R^4$ is independently selected from the group consisting of H, OH, C1-C6 alkyl, C2-C6 alkenyl, wherein each of these substituents may optionally be further substituted by one or more substitutents selected from the group consisting of halogen, pseudohalogen, OH; or $R^3$ and $R^4$ together form a C1-C4 alkylidene or =O;

each $R^5$ is independently selected from the group consisting of halogen, pseudohalogen;

each $R^6$ is independently selected from the group consisting of $^3H$, halogen, pseudohalogen, OH;

each X is independently selected from C or N;

each Y is independently selected from C, O, S, N; wherein when Y is O or S, $R^3$ and $R^4$ are not present, and when Y is N, $R^4$ is not present;

m, n, o, q are independently selected from 0, 1 and 2;

p is selected from 0, 1 and 2.

In one aspect, the substituents in formula I are as follows:

$L_1$ is a 5- or 6-membered N-heteroaryl, which optionally further includes 1 to 3 heteroatoms selected from N, O and S;

$L_2$ is selected from the group consisting of bivalent 5- or 6-membered heteroaryls containing 1-4 heteroatoms selected from N, O and S; 5- or 6-membered heterocycles including 1-3 heteroatoms selected from N, O and S; and C6-C12 aryls;

each of $R^1$ and $R^2$ is independently selected from the group consisting of halogen, pseudohalogen, amino, hydrocarbylamino, dihydrocarbylamino, nitro, C1-C6 alkyl, C1-C6 haloalkyl, C3-C6 cycloalkyl, C1-C6 alkoxy, C1-C6 alkylthio, acyl, alkylcarbamoyl, carbamoyl, alkylthiocarbamoyl, thiocarbamoyl, alkylsulfonyl, sulfonamido, N-alkylsulfonamido, N,N-dialkylsulfonamido, carboxyl, alkyloxycarbonyl, amide, N-alkylamide, N,N-dialkylamide, thioamide, N-alkylthioamide, N,N-dialkylthioamide, oxime, wherein each of these substituents may optionally be further substituted by one or more substitutents selected from the group consisting of halogen, pseudohalogen, C1-C6 alkyl, C1-C6 alkoxy, C1-C6 alkylthio, hydroxy, amino, hydrocarbylamino, dihydrocarbylamino;

each of $R^3$ and $R^4$ is independently selected from the group consisting of H, C1-C6 alkyl, C2-C6 alkenyl, wherein each of these substituents may optionally be further substituted by one or more substitutents selected from the group consisting of halogen, pseudohalogen; or $R^3$ and $R^4$ together form a C1-C4 alkylidene;

each $R^5$ is independently selected from the group consisting of halogen, pseudohalogen;

each $R^6$ is independently selected from the group consisting of $^3H$, halogen, pseudohalogen;

each X is independently selected from C or N;

each Y is independently selected from C, O, S, N; wherein when Y is O or S, $R^3$ and $R^4$ are not present, and when Y is N, $R^4$ is not present;

m, n, o, q are independently selected from 0, 1 and 2;

p is selected from 0, 1 and 2.

Compounds of general formula I are intended to include all isomers, including geometric, tautomeric and optical forms, as well as mixtures of isomers, including racemic mixtures, and pharmaceutically acceptable derivatives, salts and solvates.

Definitions the term "aryl" refers to a group having 6 to 12 atoms and containing at least one aromatic ring. Aryl may contain one aromatic ring or two aromatic rings, preferably fused. Aryl is preferably selected from phenyl, naphthyl;

the term "heteroaryl" refers to an aromatic cyclic group having 5 or 6 atoms and containing 1 to 4 heteroatoms (preferably 1 to 3 heteroatoms) selected from O, S, N, the remaining atoms being carbon atoms. The term "N-heteroaryl" refers to a heteroaryl containing at least one N as a heteroatom, and optionally containing further 1 to 3 (or preferably 1 to 2) heteratoms. Examples of heteroaryl include preferably selected are pyrrolyl, furanyl, thiophenyl, imidazolyl, thiazolyl, oxazolyl, indolyl, pyridinyl, pyrimidynyl, pyridazinyl, pyrazinyl, isothiazolyl, isoxazolyl, oxadiazolyl, thiadiazolyl, triazolyl;

the term "heterocycle" refers to an aliphatic cyclic group having 5 or 6 atoms and containing 1 to 4 heteroatoms (preferably 1 to 3 heteroatoms) selected from O, S, N, the remaining atoms being carbon atoms;

the term "alkyl" refers to a linear or branched saturated radical, typically containing one to six carbons. Alkyl is preferably selected from methyl, ethyl, n-propyl, iso-propyl, n-butyl, sec-butyl, tert-butyl, amyl, t-amyl, n-pentyl, n-hexyl;

the term "alkylidene" refers to a residue formed from an alkane by removal of two hydrogens from the same carbon atom. An example is a methylene;

the term "haloalkyl" refers to alkyl as defined herein above, substituted by at least one halogen. Haloalkyl is preferably selected from perfluoro(C1-C6)alkyl, fluoromethyl, difluoromethyl, trifluoromethyl, fluoroethyl, difluoroethyl, trifluoroethyl, mono- or polyhalo substituted propyl, butyl, pentyl, hexyl;

the term "alkenyl" refers to a linear radical containing at least one double bond, typically containing from two to six carbons. Alkyl is preferably selected from vinyl, allyl, 2-butenyl, 3-butenyl, 2-pentenyl, 3-pentanyl, 4-pentenyl, 2-hexenyl, 3-hexenyl, 4-hexenyl and the like; the "alkenyl" group includes dienes and trienes of straight and branched chains;

the term "cycloalkyl" refers to a saturated cyclic radical, typically containing three to six carbons. Cycloalkyl is preferably selected from cyclopropyl, cyclobutyl, cyclopentyl, cyclohexyl;

the term "cycloalkenyl" refers to a saturated cyclic radical, typically containing three to six carbons and at least one double bond. Cycloalkenyl is preferably selected from cyclopropenyl, cyclobutenyl, cyclopentenyl, cyclohexenyl;

the term "alkoxy" refers to a group alkyl-O—, wherein alkyl is as defined above. Alkoxy group is preferably selected from methoxy, ethoxy, n-propoxy, iso-propoxy, n-butoxy, iso-butoxy, pentyloxy, hexyloxy;

the term "alkylthio" denotes a group alkyl-S—, wherein alkyl is as defined above. Alkylthio is preferably selected from methylthio, ethylthio;

the term "amino" represents an $—NH_2$ group;

the term "hydrocarbylamino" represents an amino group substituted with one group selected from (C1-C6) alkyl, C6-C12 aryl. Examples include methylamine, ethylamine, n-propylamine, n-butylamine, n-pentylamine;

the term "dihydrocarbylamino" used either alone or in combination with other radicals, represents an amino group substituted with two radicals that may be the same or different selected from (C1-C6) alkyl, C6-C12 aryl. Examples include dimethylamino, methylethylamino, diethylamino;

the term "acyl" refers to a group of formula $R^aC(=O)—$, wherein $R^a$ represents hydrogen or C1-C6 alkyl as defined above. Acyl is preferably selected from formyl, acetyl, propanoyl, butanoyl, iso-butanoyl, pentanoyl, hexanoyl, heptanoyl, benzoyl;

the term "alkylcarbamoyl" represents a radical —NH—C(═O)—$R^b$ wherein $R^b$ is C1-C6 alkyl as defined above;

the term "carbamoyl" denotes —NH—CHO;

the term "alkylhiocarbamoyl" represents a radical —NH—C(═S)—$R^c$ wherein $R^c$ is C1-C6 alkyl as defined above;

the term "thiocarbamoyl" represents —NH—CHS;

the term "alkylsulfonyl" represents a radical $R^dSO_2—$, wherein $R^d$ is C1-C6 alkyl as defined above. Alkylsulfonyl is preferably selected from methylsulfonyl, ethylsulfonyl, propylsulfonyl;

the term "sulfonamido" represents a radical $—SO_2—NH_2$;

the term "N-alkylsulfonamido" represents a radical $—SO_2—NHR^e$, wherein W is C1-C6 alkyl as defined above;

the term "N,N-dialkylsulfonamido" represents a radical $—SO_2—N(R^{f1})(R^{f2})$, wherein each of $R^{f1}$ and $R^{f2}$ is independently C1-C6 alkyl as defined above, or $R^{f1}$ and $R^{f2}$ together form a C2-C5 alkylene or a 2- to 5-membered heteroalkylene containing one or more heteroatoms selected from O, S, N;

the term "carboxyl" denotes —COOH group;

the term "alkyloxycarbonyl" denotes —C(═O)O—$R^g$ group, wherein $R^g$ is C1-C6 alkyl as defined above. Examples of alkyloxycarbonyl include methoxycarbonyl, ethoxycarbonyl;

the term "amide" represents an aminocarbonyl radical $H_2N—(C═O)—$;

the term "N-alkylamide" represents an —C(═O)NH—$R^h$ group wherein $R^h$ is C1-C6 alkyl or C1-C6 alkoxy. Examples of alkylamide include methyl amide, methoxy amide, ethyl amide;

the term "N,N-dialkylamide" represents an —C(═O)N($R^{i1}$)($R^{i2}$) group wherein $R^{i1}$ and $R^{i2}$ are independently selected from C1-C6 alkyl, C1-C6 alkoxy; or $R^{i1}$ and $R^{i2}$ together form a C2-C5 alkylene or a 2- to 5-membered heteroalkylene containing one or more heteroatoms selected from O, S, N. Examples of dialkylamide include dimethyl amide, methylmethoxy amide, diethyl amide;

the term "thioamide" represents an aminothiocarbonyl radical $H_2N—(C═S)—$;

the term "N-alkylthioamide" represents an —C(═S)NH—$R^j$ group wherein $R^j$ is C1-C6 alkyl or C1-C6 alkoxy. Examples of alkylamide include methyl amide, methoxy amide, ethyl amide;

the term "N,N-dialkylthioamide" represents an —C(═S)N($R^{k1}$)($R^{k2}$) group wherein $R^{k1}$ and $R^{k2}$ are independently selected from C1-C6 alkyl, C1-C6 alkoxy; or $R^{k1}$ and $R^{k2}$ together form a C2-C5 alkylene or a 2- to 5-membered heteroalkylene containing one or more heteroatoms selected from O, S, N. Examples of dialkylamide include dimethyl amide, methylmethoxy amide, diethyl amide;

the term "nitro" refers to $—NO_2$;

the term "oxime" denotes a —C($R^x$)═N—OH group wherein $R^x$ is hydrogen or C1-C6 alkyl;

the term "hydroxy" refers to —OH;

the term "halogen" or "halide" includes —F, —Cl, —Br, and —I;

the term "pseudohalogen" includes cyanide, cyanate, thiocyanate, selenocyanate, trifluoromethyl, and azide.

In preferred embodiments of the present invention, $L_1$ is selected from pyridine, thiazole, pyrimidine, pyridazine, pyrazine.

$L_2$ is preferably selected from bivalent residues of pyridine, thiene, furane, oxazole, thiazole, isothiazole, isoxazole, oxadiazole, thiadiazole, triazole, tetrazole, imidazole, pyrrole, dihydropyrane, dihydrofurane, pyrimidine, triazine, tetrazine, benzene, cyclohexane, cyclohexene.

Preferably, at least one R1 and/or R2 is present, wherein the said at least one R1 and/or R2 is independently selected from halogen, pseudohalogen and alkoxy. Further R1 and R2 substituents can be present, selected from the group defined above.

Preferred embodiments of the invention are the compounds of general formula (I), selected from the group comprising:

2-(4-Chlorophenyl)-3-(1-(3,4-dichlorobenzyl)-1H-1,2,3-triazol-4-yl)imidazo[1,2-a]pyridine,
6-(4-Chlorophenyl)-5-(1-(3,4-dichlorobenzyl)-1H-1,2,3-triazol-4-yl)imidazo[2,1-b]thiazole,
5-(1-(3,4-Dimethoxybenzyl)-1H-1,2,3-triazol-4-yl)-6-phenylimidazo[2,1-b]thiazole,
6-(4-Chlorophenyl)-5-(1-(4-methoxybenzyl)-1H-1,2,3-triazol-4-yl)imidazo[2,1-b]thiazole,
2-(4-Chlorophenyl)-3-(1-(3,4-dimethoxybenzyl)-1H-1,2,3-triazol-4-yl)imidazo[1,2-a]pyridine,
2-(4-Chlorophenyl)-3-(1-(4-methoxybenzyl)-1H-1,2,3-triazol-4-yl)imidazo[1,2-a]pyridine,
3-(1-Benzyl-1H-1,2,3-triazol-4-yl)-2-(4-chlorophenyl)imidazo[1,2-a]pyridine,
2-(4-Chlorophenyl)-3-(1-(pyridin-2-ylmethyl)-1H-1,2,3-triazol-4-yl)imidazo[1,2-a]pyridine,
5-(1-Benzyl-1H-1,2,3-triazol-4-yl)-6-(4-chlorophenyl)imidazo[2,1-b]thiazole,
6-(4-Chlorophenyl)-5-(1-(pyridin-2-ylmethyl)-1H-1,2,3-triazol-4-yl)imidazo[2,1-b]thiazole,
3-(1-(4-Chlorobenzyl)-1H-1,2,3-triazol-4-yl)-2-(4-chlorophenyl)imidazo[1,2-a]pyridine,
5-(1-(4-Chlorobenzyl)-1H-1,2,3-triazol-4-yl)-6-(4-chlorophenyl)imidazo[2,1-b]thiazole,
6-Chloro-2-(4-chlorophenyl)-3-(1-(3,4-dichlorobenzyl)-1H-1,2,3-triazol-4-yl)imidazo[1,2-b]pyridazine,
3-Benzyl-5-(2-(4-chlorophenyl)imidazo[1,2-a]pyridin-3-yl)isoxazole,
4-((4-(2-(4-Chlorophenyl)imidazo[1,2-a]pyridin-3-yl)-1H-1,2,3-triazol-1-yl)methyl)benzonitrile,
4-((4-(6-(4-Chlorophenyl)imidazo[2,1-b]thiazol-5-yl)-1H-1,2,3-triazol-1-yl)methyl)benzonitrile,
2-(4-Chlorophenyl)-3-(1-(3,4-dichlorobenzyl)-1H-1,2,3-triazol-4-yl)imidazo[1,2-b]pyridazine,
3-(1-(3,4-Dichlorobenzyl)-1H-1,2,3-triazol-4-yl)-2-(3,4-dichlorophenyl)imidazo[1,2-a]pyridine,
5-(1-(3,4-Dichlorobenzyl)-1H-1,2,3-triazol-4-yl)-6-(3,4-dichlorophenyl)imidazo[2,1-b]thiazole,
6-Chloro-3-(1-(4-chlorobenzyl)-1H-1,2,3-triazol-4-yl)-2-(4-chlorophenyl)imidazo[1,2-b]pyridazine,
3-(1-Benzyl-1H-1,2,3-triazol-4-yl)-6-chloro-2-(4-chlorophenyl)imidazo[1,2-b]pyridazine,
5-(2-(4-Chlorophenyl)imidazo[1,2-a]pyridin-3-yl)-3-(3,4-dichlorobenzyl)-1,2,4-oxadiazole,
2-(2-(4-Chlorophenyl)imidazo[1,2-a]pyridin-3-yl)-5-(3,4-dichlorobenzyl)-1,3,4-oxadiazole,
5-(6-(4-Chlorophenyl)imidazo[2,1-b]thiazol-5-yl)-3-(3,4-dichlorobenzyl)-1,2,4-oxadiazole,
2-(4-Chlorophenyl)-3-(5-(3,4-dichlorobenzyl)-1H-1,2,4-triazol-3-yl)imidazo[1,2-a]pyridine,
6-(4-Chlorophenyl)-5-(2-(3,4-dichlorobenzyl)thiazol-4-yl)imidazo[2,1-b]thiazole,
4-(2-(4-Chlorophenyl)imidazo[1,2-a]pyridin-3-yl)-2-(3,4-dichlorobenzyl)thiazole,
2-(2-(4-Chlorophenyl)imidazo[1,2-a]pyridin-3-yl)-5-(3,4-dichlorobenzyl)-1,3,4-thiadiazole,
3-(1-(3,4-Dichlorobenzyl)-1H-1,2,3-triazol-4-yl)-2-(p-tolyl)imidazo[1,2-a]pyridine,
3-(1-(3,4-Dichlorobenzyl)-1H-1,2,3-triazol-4-yl)-2-(2,4-dichlorophenyl)imidazo[1,2-a]pyridine,
4-(3-(1-(3,4-Dichlorobenzyl)-1H-1,2,3-triazol-4-yl)imidazo[1,2-a]pyridin-2-yl)benzonitrile,
3-(1-(3,4-Dichlorobenzyl)-1H-1,2,3-triazol-4-yl)-2-(4-methoxyphenyl)imidazo[1,2-a]pyridine,
3-(1-(3,4-Dichlorobenzyl)-1H-1,2,3-triazol-4-yl)-2-(4-(trifluoromethyl)phenyl)imidazo[1,2-a]pyridine, 3-(1-(3,4-Dichlorobenzyl)-1H-1,2,3-triazol-4-yl)-2-(4-fluorophenyl)imidazo[1,2-a]pyridine,
3-(1-(3,4-Dichlorobenzyl)-1H-1,2,3-triazol-4-yl)-2-(4-ethylphenyl)imidazo[1,2-a]pyridine,
Methyl 2-chloro-5-((4-(2-(4-chlorophenyl)imidazo[1,2-a]pyridin-3-yl)-1H-1,2,3-triazol-1-yl)methyl)benzoate,
(2-Chloro-5-((4-(2-(4-chlorophenyl)imidazo[1,2-a]pyridin-3-yl)-1H-1,2,3-triazol-1-yl)methyl)phenyl)methanol
2-(4-Chlorophenyl)-3-(1-(3,4-dichlorophenyl)-1H-1,2,3-triazol-4-yl)imidazo[1,2-a]pyridine,
2-(4-Chlorophenyl)-3-(1-(3,4-dichlorobenzyl)-1H-pyrazol-4-yl)imidazo[1,2-a]pyridine,
2-(4-Chlorophenyl)-3-(1-(3,4-dichlorobenzyl)-1H-pyrrol-2-yl)imidazo[1,2-a]pyridine,
2-(4-Chlorophenyl)-3-(1-(3,4-dichlorophenethyl)-1H-1,2,3-triazol-4-yl)imidazo[1,2-a]pyridine,
2-Chloro-5-((4-(2-(4-chlorophenyl)imidazo[1,2-a]pyridin-3-yl)-1H-1,2,3-triazol-1-yl)methyl)benzamide,
2-Chloro-5-((4-(2-(4-chlorophenyl)imidazo[1,2-a]pyridin-3-yl)-1H-1,2,3-triazol-1-yl)methyl)-N,N-dimethylbenzamide,
2-Chloro-5-((4-(2-(4-chlorophenyl)imidazo[1,2-a]pyridin-3-yl)-1H-1,2,3-triazol-1-yl)methyl)benzoic acid,
2-Chloro-5-((4-(2-(4-chlorophenyl)imidazo[1,2-a]pyridin-3-yl)-1H-1,2,3-triazol-1-yl)methyl)-N-methoxy-N-methylbenzamide,
1-(2-Chloro-5-((4-(2-(4-chlorophenyl)imidazo[1,2-a]pyridin-3-yl)-1H-1,2,3-triazol-1-yl)methyl)phenyl)ethan-1-one,
2-Chloro-5-((4-(2-(4-chlorophenyl)imidazo[1,2-a]pyridin-3-yl)-1H-1,2,3-triazol-1-yl)methyl)-N-methylbenzamide,
1-(2-Chloro-5-((4-(2-(4-chlorophenyl)imidazo[1,2-a]pyridin-3-yl)-1H-1,2,3-triazol-1-yl)methyl)phenyl)propan-1-one,
2-Chloro-5-((5-(2-(4-chlorophenyl)imidazo[1,2-a]pyridin-3-yl)-1,3,4-thiadiazol-2-yl)methyl)-N,N-dimethylbenzamide,
2-Chloro-5-((5-(2-(4-chlorophenyl)imidazo[1,2-a]pyridin-3-yl)-1,3,4-thiadiazol-2-yl)methyl)-N,N-dimethylbenzothioamide,
2-Chloro-5-((5-(2-(4-chlorophenyl)imidazo[1,2-a]pyridin-3-yl)-1,3,4-oxadiazol-2-yl)methyl)-N-methylbenzothioamide,
2-Chloro-5-((5-(2-(4-chlorophenyl)imidazo[1,2-a]pyridin-3-yl)-1,3,4-oxadiazol-2-yl)methyl)-N-methylbenzamide,
2-(4-Chlorophenyl)-3-(1-(4-(pyrrolidin-1-ylsulfonyl)benzyl)-1H-1,2,3-triazol-4-yl)imidazo[1,2-a]pyridine,
2-(4-Chlorophenyl)-3-(1-(4-(methylsulfonyl)benzyl)-1H-1,2,3-triazol-4-yl)imidazo[1,2-a]pyridine,
2-(4-Chlorophenyl)-3-(1-(1-phenylethyl)-1H-1,2,3-triazol-4-yl)imidazo[1,2-a]pyridine,
2-(4-Chlorophenyl)-3-(1-(4-nitrobenzyl)-1H-1,2,3-triazol-4-yl)imidazo[1,2-a]pyridine,
4-((4-(2-(4-Chlorophenyl)imidazo[1,2-a]pyridin-3-yl)-1H-1,2,3-triazol-1-yl)methyl)aniline,
2-Chloro-5-(1-(4-(2-(4-chlorophenyl)imidazo[1,2-a]pyridin-3-yl)-1H-1,2,3-triazol-1-yl)ethyl)benzamide,
2-Chloro-5-((5-(2-(4-chlorophenyl)imidazo[1,2-a]pyridin-3-yl)pyridin-2-yl)amino)benzamide,
2-Chloro-5-((5-(2-(4-chlorophenyl)imidazo[1,2-a]pyridin-3-yl)pyridin-2-yl)oxy)benzamide,
2-(4-Chlorophenyl)-3-(1-(4-(methylthio)benzyl)-1H-1,2,3-triazol-4-yl)imidazo[1,2-a]pyridine,
2-Chloro-5-((4-(2-(4-chlorophenyl)-8-fluoroimidazo[1,2-a]pyridin-3-yl)-1H-1,2,3-triazol-1-yl)methyl)benzamide,
2-Chloro-5-((4-(2-(4-chlorophenyl)-7-fluoroimidazo[1,2-a]pyridin-3-yl)-1H-1,2,3-triazol-1-yl)methyl)benzamide, 2-Chloro-5-((4-(2-(4-chlorophenyl)-6-fluoroimidazo[1,2-a]pyridin-3-yl)-1H-1,2,3-triazol-1-yl)methyl)benzamide, 2-Chloro-5-((4-(2-(4-chlorophenyl)-6,8-difluoroimidazo[1,2-a]pyridin-3-yl)-1H-1,2,3-triazol-1-yl)methyl)benzamide, 2-Chloro-5-((4-(2-(4-cyclopropylphenyl)imidazo[1,2-a]pyridin-3-yl)-1H-1,2,3-triazol-1-yl)methyl)benzamide, 2-Chloro-5-((4-(2-(4-chlorophenyl)imidazo[1,2-a]pyridin-3-yl)-1H-1,2,3-triazol-1-yl)methyl)benzaldehyde, (E)-2-chloro-5-((4-(2-(4-chlorophenyl)imidazo[1,2-a]pyridin-3-yl)-1H-1,2,3-triazol-1-yl)methyl)benzaldehyde oxime, N-(4-((4-(2-(4-chlorophenyl)imidazo[1,2-a]pyridin-3-yl)-1H-1,2,3-triazol-1-yl)methyl)phenyl)acetamide, 3-(1-(4-Chloro-3-nitrobenzyl)-1H-1,2,3-triazol-4-yl)-2-(4-chlorophenyl)imidazo[1,2-a]pyridine, 2-Chloro-5-((4-(2-(4-chlorophenyl)imidazo[1,2-a]pyridin-3-yl)-1H-1,2,3-triazol-1-yl)methyl)aniline, N-(2-chloro-5-((4-(2-(4-chlorophenyl)imidazo[1,2-a]pyridin-3-yl)-1H-1,2,3-triazol-1-yl)methyl)phenyl)acetamide, 3-(4-Benzylphenyl)-2-(4-chlorophenyl)imidazo[1,2-a]pyridine, 3-(6-Benzylpyridin-3-yl)-2-(4-chlorophenyl)imidazo[1,2-a]pyridine, 2-(4-Chlorophenyl)-3-(6-(1-phenylvinyl)pyridin-3-yl)imidazo[1,2-a]pyridine, 2-Chloro-5-((4-(2-(4-chlorophenyl)imidazo[1,2-a]pyridin-3-yl)-5-iodo-1H-1,2,3-triazol-1-yl)methyl)benzamide, 2-(4-Chlorophenyl)-3-(1H-1,2,3-triazol-4-yl)imidazo[1,2-a]pyridine, 3-(4-Benzylcyclohex-1-en-1-yl)-2-(4-chlorophenyl)imidazo[1,2-a]pyridine, 4-Benzyl-1-(2-(4-chlorophenyl)imidazo[1,2-a]pyridin-3-yl)cyclohexan-1-ol, 1-(5-(2-(4-Chlorophenyl)imidazo[1,2-a]pyridin-3-yl)pyridin-2-yl)-1-phenylethane-1,2-diol, (5-(2-(4-Chlorophenyl)imidazo[1,2-a]pyridin-3-yl)pyridin-2-yl)(phenyl)methanone, 2-Chloro-5-((4-(2-(pyridine-4-yl)imidazo[1,2-a]pyridine-3-yl)-1H-1,2,3-triazol-1-yl)methyl)benzamide.

One embodiment of the present invention is a compound of general formula I for use as a medicament.

Another aspect of the present invention is a compound of general formula I for use in prevention or treatment of a condition which is mediated by the action, or by loss of action, of constitutive androstane receptor (CAR) receptor or its endogenous ligands, preferably in the liver or in other organs with CAR expression such as in the kidney, intestine, brain, thyroid, heart, ovary or prostate.

One aspect of the present invention is a compound of the general formula I for use in prevention or treatment of metabolic disorders such as defects in glucose, cholesterol and lipid metabolism, including impaired glucose tolerance and insulin sensitivity, metabolic syndrome, type II diabetes, gestational diabetes as a risk factor for preeclampsia, obesity, obesity related atherosclerosis, cholesterol gallstone disease, dyslipidemia, cholelithiasis, cholangitis, lipid metabolic disorders, cholesterol or bilirubin gallstone disease, high cholesterol diseases, acute liver failure, cholelithiasis and choledocholithiasis, hyperbilirubinemia and jaundice, hyperthyreosis, inflammation of the gallbladder and pancreas, cholestasis diseases, liver steatosis, inflammatory liver diseases connected with metabolic diseases such as non-alcoholic steatohepatitits (NASH) or non-alcoholic fatty liver disease (NAFLD), in protection against liver stress, intoxication or liver infection such as viral infection or intracellular parasite infection, in the treatment of cancers or leukemia and as a cytostatic prodrugs activator.

An aspect of the present invention is a compound of general formula I for use in a method of stimulation of liver regeneration after partial hepatectomy or in liver injuries connected with the need of fast liver regeneration and parenchymal cells proliferation.

Another aspect of the present invention is a compound of general formula I, for use in human adjuvant treatment of a condition or disease connected with malignancy and in the metabolic activation of antineoplastic drugs.

The medical uses of compounds of general formula I are relevant in particular for human subjects.

This invention relates to compounds for treating or preventing the aforementioned disease or medical condition, wherein said compounds have high selectivity or affinity for human CAR receptor and/or its transcript variants (including variant 3), but does not significantly activate Pregnane X receptor (PXR) in comparison with CAR or other nuclear receptors involved in regulation of endogenous intermediary metabolism or hormonal regulation. More specifically, said compounds have direct agonistic, inverse agonistic or partial agonistic activity for human CAR and interact with the human CAR.

Another embodiment of the present invention is a pharmaceutical composition comprising as an active ingredient a compound of general formula (I) and/or its pharmaceutically acceptable salt or solvates, and one or more pharmaceutically acceptable carriers, polymers, or excipients.

Pharmaceutically acceptable salts may be salts derived from inorganic or organic acids. A person skilled in the art will be able to determine which are pharmaceutically acceptable salts; particularly they are salts having one or more desirable physical properties, such as enhanced pharmaceutical stability at different temperatures, the required higher solubility in water or oil, or they are non-toxic.

Suitable pharmaceutically acceptable salts of substances according to the invention preferably comprise anions derived from inorganic acids such as hydrochloric, hydrobromic, hydrofluoric, boric, fluoboric, phosphoric, metaphosphoric, nitric, carbonic, sulphurous and sulfuric acids, and organic acids such as acetic acid, benzenesulfonic, benzoic, citric, ethanesulfonic, fumaric, gluconic, glycolic, isethionic, lactic, lactobionic, maleic, malonic, methanesulfonic, trifluoromethanesulfonic, succinic, toluenesulfonic, tartaric, and trifluoroacetic acids. Suitable organic acids generally include, for example, the following classes of organic acids: aliphatic, cycloaliphatic, aromatic, araliphatic, heterocyclic, carboxylic and sulfonic acids.

Specific examples of suitable organic acids include acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, pamoate, methanesulfonate, ethanesulfonate, benzenesulfonate, pantothenate, toluenesulfonate, 2-hydroxyethanesulfonate, sulfanilate, cyclohexylaminosulfonate, 13-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalenesulfonate, oxalate, palmoate, pectinate, 3-phenylpropionate, picrate, pivalate, thiocyanate, and undecanoate.

The compounds of formula I may be prepared in a crystalline or an amorphous form, and may be optionally hydrated or solvated.

The compounds of general formula I according to this invention can also be used in the form of a precursor (prodrug) or in another suitable form which releases the active substance in vivo.

In the framework of the present invention, it was found that compounds of the invention activate human CAR receptor or its variant CAR3 in luciferase gene reporter assays (Table 1, FIG. 1) or in the TR-FRET CAR Coactivator in vitro assay with recombinant human CAR LBD (see FIG. 1). The compounds of formula I are agonists for human CAR with higher activity or affinity to activate human CAR in comparison with human Pregnane X receptor (PXR) (see Table 1 and FIG. 2) In comparison with CITCO, the only known high-affinity human CAR ligand, the compounds of EXAMPLES 89, 93, 109, 110, 111 and 112 of the invention are highly selective and specific for human CAR (FIG. 2).

The compounds of formula I may be administered by any convenient method, for example by oral, parenteral (e.g. intravenous), buccal, sublingual, nasal, rectal, subcutaneous or transdermal administration and the pharmaceutical compositions adapted accordingly.

For use in human medicine, the compounds of the present invention are usually administered as a standard pharmaceutical composition. The present invention therefore provides a pharmaceutical composition comprising a compound of formula (I) or a pharmaceutically (i.e physiologically) acceptable salt thereof and a pharmaceutically acceptable carrier or excipient to form appropriate formulation, microformulation or nanoformulation. The pharmaceutical composition can be for use in the treatment of any of the conditions described herein.

A composition in the form of a tablet can be prepared using any suitable pharmaceutical carrier(s) routinely used for preparing solid pharmaceutical formulations. Examples of such carriers include lactose, sucrose, cellulose magnesium stearate or starch.

A composition in the form of a capsule can be prepared using routine encapsulation procedures. For example, pellets containing the active ingredient can be prepared using standard carriers and filled into a hard gelatin capsule. Alternatively, a dispersion or suspension can be prepared using any suitable pharmaceutical carrier(s) and then filled into a soft gelatin capsule.

BRIEF DESCRIPTION OF THE DRAWINGS

To further clarify the invention and its features, a more particular description of the invention will be rendered by reference to specific embodiments thereof which are illustrated in the appended drawings in which:

FIG. 7 also shows that compound of EXAMPLE 93 reduces the body weight in the experiments, decreases plasma cholesterol and LDL levels, but does not display hepatotoxicity as indicated by no effects on ALT, AST, ALP or LDH biochemical markers.

EXAMPLES

Abbreviations

Ac Acetyl

Boc tert-Butoxycarbonyl

BPPO $N^1$,$N^2$-di([1,1'-biphenyl]-2-yl)oxalamide

CAR Constitutive androstane receptor

Figure 1:
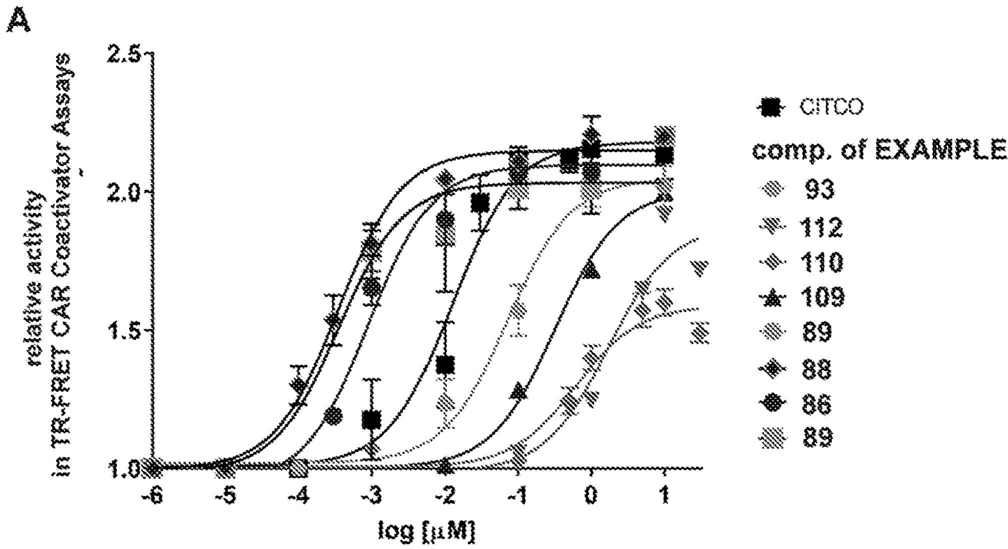
FIG. 1 shows the dose-response curves for selected compounds of the invention in TR-FRET CAR Coactivation assay. Data show relative activities of compounds of the invention to activate human CAR LBD with respect to increasing concentration tested. Data have been fitted using GraphPad software and $EC_{50}$ (Half-maximum activating concentration) values are presented in Table 1. In addition, activation of human CAR receptor by selected compounds of the invention in CAR LBD assembly assay and in luciferase reporter gene assay with CAR variant 3 is presented in FIG. 1 and Table 1.
Figure 1:
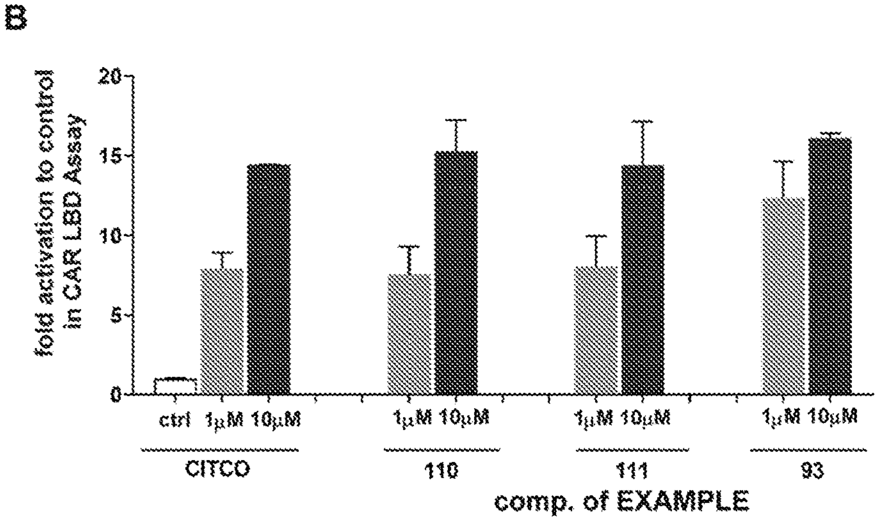
Figure 1:
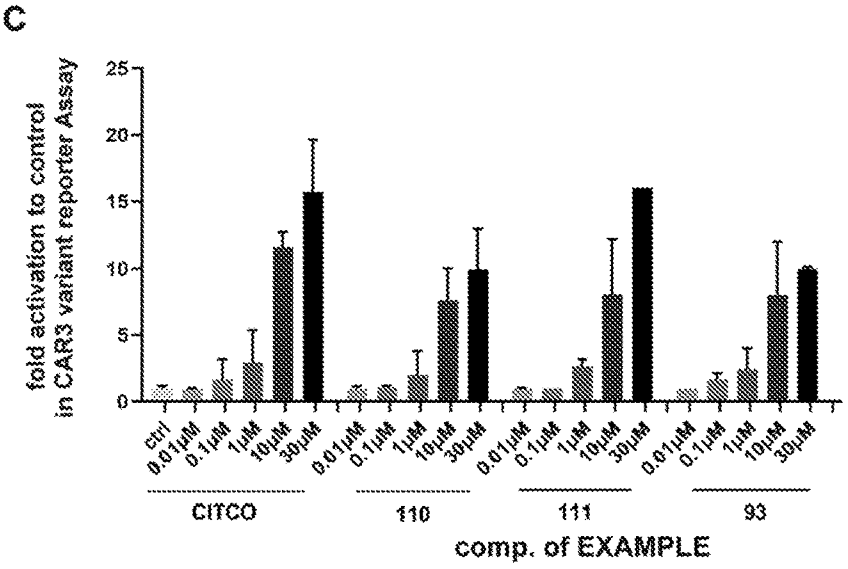

CAR+A-EGFP Fusion protein of CAR with extra alanine and EGFP

CYP3A4, CYP3A7, CYP2B6 Cytochrome P450 enzyme 3A4, 3A7 or 2B6

DCM Dichloromethane

DEE Diethyl ether

DIPEA N,N-Diisopropylethylamine
DMF N,N-Dimenthylformamide
DMSO Dimethylsulfoxide
$EC_{50}$ Half maximal effective concentration
EDC N-(3-Dimethylaminopropyl)-N'-ethylcarbodiimide hydrochloride
EI Electron ionization
EMA European Medicines Agency
ESI Electrospray ionization
Et Ethyl
EtOAc Ethyl acetate
eq. Eqvivalent
Fasn Fatty acid synthase
GAPDH Glyceraldehyde 3-phosphate dehydrogenase gene
HATU 1-[Bis(dimethylamino)methylene]-1H-1,2,3-triazolo[4,5-b]pyridinium 3-oxide hexafluorophosphate
HepG2 Human hepatocyte derived cell line
HepaRG KO CAR cells Differentiated human hepatocyte cell line without CAR expression
HOBt 1-Hydroxybenzotriazole hydrate
HRMS High resolution mass spectrometry
ICH International Conference on Harmonisation of Technical Requirements for Registration of Pharmaceuticals for Human Use
IPGTT Glucose tolerance test after intraperitoneal application of glucose solution
IR Infrared spectroscopy
ITT Insulin tolerance test
Ki67 Marker of proliferation Ki-67, NKI67 gene
LAH Lithium aluminum hydride
LBD Ligand binding domain
LXRα Liver X receptor alpha
Me Methyl
MEME Minimal essential medium
MS Mass spectrometry
MTD Maximum Tolerated Dose
NBS N-Bromosuccinimide
NIS N-Iodosuccinimide
NMR Nuclear magnetic resonance
OECD Organisation for Economic Co-operation and Development
PPAR Peroxisome proliferator-activated receptor
PXR Pregnane X receptor
RP Reverse-phase
r.t. Room temperature
RT-qPCR Reverse transcription quantitative Polymerase Chain Reaction
Scd1 Stearoyl-Coenzyme A desaturase 1
t-Bu Tertial butyl
TEA Triethylamine
THF Tetrahydrofuran
TLC Thin-layer chromatography
TMS Trimethylsilyl
TR-FRET Time-resolved fluorescence energy transfer
UPLC Ultra-high-pressure liquid chromatography
XantPhos 4,5-Bis(diphenylphosphino)-9,9-dimethylxanthene
XREM Xenobiotic response element Scheme 1.

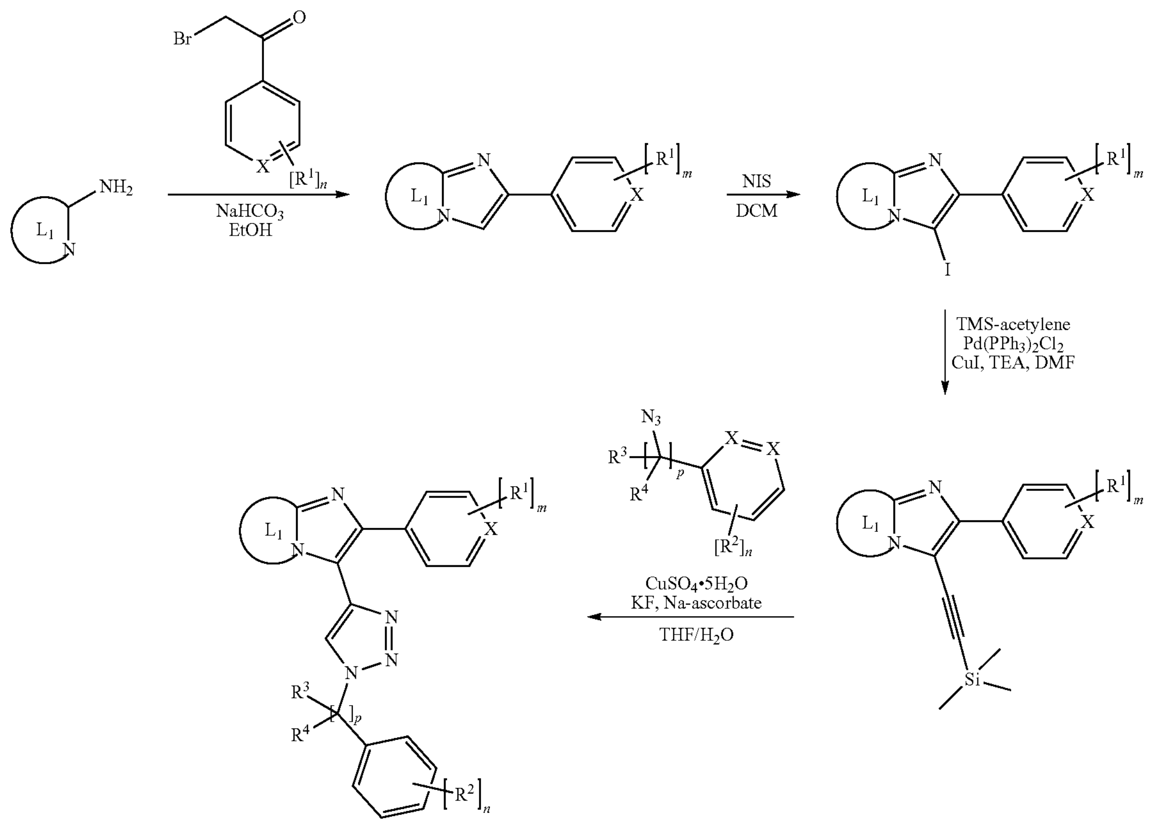

General Procedure I. Cyclization of Heterocycle

2-Aminopyridine (or 2-aminothiazole) was dissolved in EtOH and substituted or unsubstituted bromoacetophenone derivative (1 eq) was added followed by an addition of $NaHCO_3$ (1 eq). The reaction mixture was heated at 70° C. overnight. After the completion of the reaction (monitored by TLC or UPLC), the solvent was evaporated to a minimal volume, a residue was diluted with EtOAc and washed with water. Water phase was extracted twice more with EtOAc, combined organic phases were dried over sodium sulfate and evaporated. The residue was purified by flash column chromatography (eluent petrolether/EtOAc or EtOAc/MeOH).

Example 1

6-(4-Chlorophenyl)imidazo[2,1-b]thiazole (Intermediate Compound)

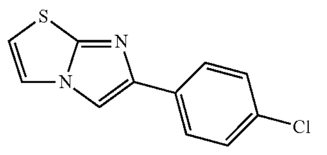 [SMILES: Clc1ccc(-c2cn3ccsc3n2)cc1]

Title compound was prepared according to the General Procedure I (Scheme 1). Mobile phase petrolether/EtOAc (20-60%). Yield: 981 mg (82%). 1H NMR (401 MHz, DMSO-d6) δ 8.26 (s, 1H), 7.94 (d, J=4.4 Hz, 1H), 7.90-7.80 (m, 2H), 7.48-7.39 (m, 2H), 7.28 (d, J=4.4 Hz, 1H). 13C NMR (101 MHz, DMSO) δ 149.88, 145.54, 133.64, 131.78, 129.09, 126.85, 120.52, 113.85, 110.30. EI MS: calcd for [M+H], 234.0018; found, 234.0020.

Example 2

2-(4-Chlorophenyl)imidazo[1,2-a]pyridine (Intermediate Compound)

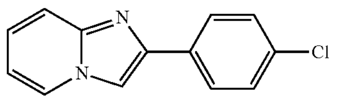 [SMILES: Clc1ccc(-c2cn3ccccc3n2)cc1]

Title compound was prepared according to the General Procedure I (Scheme 1). Mobile phase petrolether/EtOAc (20-60%). Yield: 1.49 g (88%). $^{1}H$ NMR (401 MHz, Chloroform-d) δ 8.12 (dt, J=1.2 Hz, J=6.8 Hz, 1H), 7.93-7.87 (m, 2H), 7.84 (d, J=0.7 Hz, 1H), 7.64 (dq, J=1.0 Hz, J=9.2 Hz, 1H), 7.44-7.40 (m, 2H), 7.20 (ddd, J=1.3 Hz, J=6.8 Hz, J=9.2 Hz, 1H), 6.80 (td, J=1.2 Hz, J=6.8 Hz, 1H). $^{13}C$ NMR (101 MHz, $CDCl_3$) δ 145.86, 144.82, 133.79, 132.45, 129.02, 127.38, 125.73, 125.03, 117.69, 112.72, 108.31. EI MS: calcd for [M+H], 228.0454; found, 228.0456.

Example 3

6-Chloro-2-(4-chlorophenyl)imidazo[1,2-b]pyridazine (Intermediate Compound)

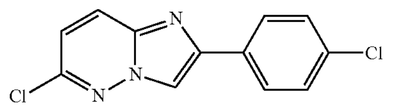 [SMILES: Clc1ccc(-c2cn3nc(Cl)ccc3n2)cc1]

Title compound was prepared according to the General Procedure I (Scheme 1). Mobile phase petrolether/EtOAc (10-30%). Yield 152 mg (63%). $^{1}H$ NMR (401 MHz, DMSO-$d_6$) δ 8.94 (d, J=0.7 Hz, 1H), 8.22 (dd, J=9.5, 0.7 Hz, 1H), 8.09-8.01 (m, 2H), 7.60-7.48 (m, 2H), 7.38 (d, J=9.5 Hz, 1H). $^{13}C$ NMR (101 MHz, DMSO) δ 146.48, 144.39, 138.00, 133.18, 132.01, 129.08, 127.55, 127.44, 119.70, 114.40. HRMS: calcd for [M+Na], 264.00898; found, 264.00901.

Example 4

2-(3,4-Dichlorophenyl)imidazo[1,2-a]pyridine (Intermediate Compound)

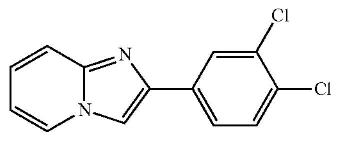 [SMILES: Clc1ccc(-c2cn3ccccc3n2)cc1Cl]

Title compound was prepared according to the General Procedure I (Scheme 1). Mobile phase petrolether/EtOAc (20-50%). Yield 533 mg (87%). $^{1}H$ NMR (401 MHz, DMSO-$d_6$) δ 8.54-8.49 (m, 2H), 8.18 (d, J=2.0 Hz, 1H), 7.93 (dd, J=8.4, 2.0 Hz, 1H), 7.68 (d, J=8.4 Hz, 1H), 7.58 (dq, J=9.1, 1.0 Hz, 1H), 7.27 (ddd, J=9.1, 6.7, 1.3 Hz, 1H), 6.91 (td, J=6.8, 1.2 Hz, 1H). $^{13}C$ NMR (101 MHz, DMSO) δ 145.10, 141.99, 134.88, 131.74, 131.13, 130.02, 127.25, 127.23, 125.73, 125.70, 116.94, 112.84, 110.47. HRMS: calcd for [M+H], 263.01373; found, 263.01393.

Example 5

4-(Imidazo[1,2-a]pyridin-2-yl)benzonitrile (Intermediate Compound)

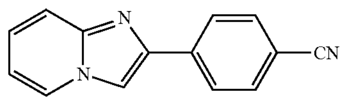

Title compound was prepared according to the General Procedure I (Scheme 1). Mobile phase petrolether/EtOAc (20-50%). Yield 952 mg (82%). $^{1}H$ NMR (401 MHz, DMSO-$d_6$) δ 8.56 (s, 1H), 8.54 (dt, J=6.8, 1.2 Hz, 1H), 8.18-8.12 (m, 2H), 7.91-7.85 (m, 2H), 7.60 (dq, J=9.1, 1.0 Hz, 1H), 7.28 (ddd, J=9.1, 6.7, 1.3 Hz, 1H), 6.92 (td, J=6.7, 1.2 Hz, 1H). $^{13}C$ NMR (101 MHz, DMSO) δ 145.40, 142.63, 138.68, 133.03, 127.44, 126.39, 126.10, 119.33, 117.14, 113.13, 111.41, 110.06. HRMS: calcd for [M+H], 220.08692; found, 220.08686.

Example 6

6-(3,4-Dichlorophenyl)imidazo[2,1-b]thiazole (Intermediate Compound)

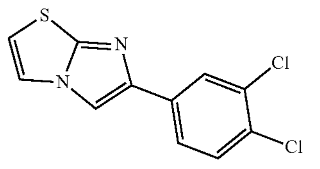 [SMILES: Clc1ccc(-c2cn3ccsc3n2)cc1Cl]

Title compound was prepared according to the General Procedure I (Scheme 1). Mobile phase petrolether/EtOAc (20-50%). Yield 878 mg (65%). $^1$H NMR (401 MHz, DMSO-$d_6$) δ 8.37 (s, 1H), 8.06 (d, J=2.0 Hz, 1H), 7.97 (d, J=4.5 Hz, 1H), 7.82 (dd, J=8.4, 2.1 Hz, 1H), 7.64 (d, J=8.4 Hz, 1H), 7.30 (d, J=4.5 Hz, 1H). $^{13}$C NMR (101 MHz, DMSO) δ 149.83, 143.93, 135.18, 131.65, 131.04, 129.21, 126.38, 124.93, 120.26, 113.98, 110.90. HRMS: calcd for [M+Na], 268.97015; found, 268.97029.

Example 7

6-Phenylimidazo[2,1-b]thiazole (Intermediate Compound)

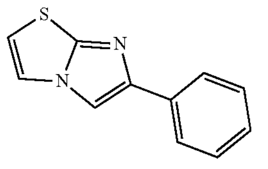 [SMILES: c1ccc(-c2cn3ccsc3n2)cc1]

Title compound was prepared according to the General Procedure I (Scheme 1). Mobile phase petrolether/EtOAc (20-50%). Yield 564 mg (55%). $^1$H NMR (401 MHz, DMSO-$d_6$) δ 8.22 (s, 1H), 7.93 (d, J=4.4 Hz, 1H), 7.86-7.80 (m, 2H), 7.39 (dd, J=8.4, 7.0 Hz, 2H), 7.29-7.22 (m, 2H). $^{13}$C NMR (101 MHz, DMSO) δ 149.66, 146.74, 134.71, 129.08, 127.47, 125.18, 120.49, 113.55, 109.85. HRMS: calcd for [M+H], 201.04810; found, 201.04796.

Example 8

2-Phenylimidazo[1,2-a]pyridine (Intermediate Compound)

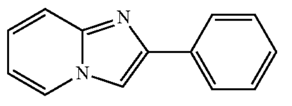 [SMILES: c1ccc(-c2cn3ccccc3n2)cc1]

Title compound was prepared according to the General Procedure I (Scheme 1). Mobile phase petrolether/EtOAc (20-50%). Yield 739 mg (77%). $^1$H NMR (401 MHz, DMSO-$d_6$) δ 8.51 (dt, J=6.8, 1.2 Hz, 1H), 8.39 (d, J=0.7 Hz, 1H), 8.02-7.93 (m, 2H), 7.59 (dq, J=9.1, 1.0 Hz, 1H), 7.48-7.40 (m, 2H), 7.31 (ddt, J=8.0, 6.8, 1.3 Hz, 1H), 7.24 (ddd, J=9.1, 6.7, 1.3 Hz, 1H), 6.88 (td, J=6.8, 1.2 Hz, 1H). $^{13}$C NMR (101 MHz, DMSO) δ 145.30, 144.83, 134.38, 129.17, 128.16, 127.32, 126.03, 125.40, 117.10, 112.73, 109.56. HRMS: calcd for [M+H], 195.09167; found, 195.09161.

Example 9

2-(Pyridin-4-yl)imidazo[1,2-a]pyridine (Intermediate Compound)

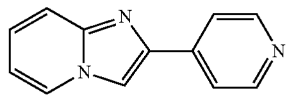 [SMILES: c1ccn2cc(-c3ccncc3)nc2c1]

Title compound was prepared according to the General Procedure I (Scheme 1). Mobile phase petrolether/EtOAc (40-100%). Yield 98 mg (48%). $^1$H NMR (401 MHz, DMSO-$d_6$) δ 8.64-8.59 (m, 3H), 8.56 (dt, J=6.8, 1.2 Hz, 1H), 7.94-7.86 (m, 2H), 7.62 (dq, J=9.1, 1.0 Hz, 1H), 7.30 (ddd, J=9.1, 6.7, 1.3 Hz, 1H), 6.94 (td, J=6.8, 1.2 Hz, 1H). $^{13}$C NMR (101 MHz, DMSO) δ 150.33, 145.29, 141.82, 141.26, 127.41, 125.95, 120.08, 117.18, 113.03, 111.62. HRMS: calcd for [M+H], 196.08692; found, 196.08678.

Example 10

2-(4-Nitrophenyl)imidazo[1,2-a]pyridine (Intermediate Compound)

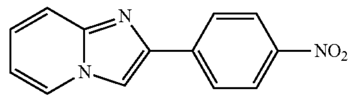 [SMILES: O=[N+]([O-])c1ccc(-c2cn3ccccc3n2)cc1]

Title compound was prepared according to the General Procedure I (Scheme 1). Mobile phase petrolether/EtOAc (20-70%). Yield 214 mg (77%). $^1$H NMR (401 MHz, DMSO-$d_6$) δ 8.64 (d, J=0.7 Hz, 1H), 8.57 (dt, J=6.8, 1.2 Hz, 1H), 8.33-8.27 (m, 2H), 8.24-8.19 (m, 2H), 7.62 (dq, J=9.1, 1.1 Hz, 1H), 7.31 (ddd, J=9.1, 6.7, 1.3 Hz, 1H), 6.95 (td, J=6.7, 1.2 Hz, 1H). $^{13}$C NMR (101 MHz, DMSO) δ 146.93, 145.71, 142.45, 140.97, 127.73, 126.76, 126.39, 124.65, 117.46, 113.39, 112.16. HRMS: calcd for [M+H], 240.07675; found, 240.07674.

Example 11

2-(4-Methoxyphenyl)imidazo[1,2-a]pyridine (Intermediate Compound)

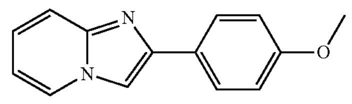 [SMILES: COc1ccc(-c2cn3ccccc3n2)cc1]

Title compound was prepared according to the General Procedure I (Scheme 1). Mobile phase petrolether/EtOAc (20-70%). Yield 200 mg (84%). $^{1}$H NMR (401 MHz, DMSO-$d_6$) δ 8.49 (dt, J=6.8, 1.2 Hz, 1H), 7.92-7.87 (m, 2H), 7.54 (dq, J=9.1, 1.0 Hz, 1H), 7.21 (ddd, J=9.1, 6.7, 1.3 Hz, 1H), 7.03-6.98 (m, 2H), 6.86 (td, J=6.7, 1.2 Hz, 1H). $^{13}$C NMR (101 MHz, DMSO) δ 159.48, 145.19, 144.90, 127.33, 127.16, 127.00, 125.09, 116.86, 114.59, 112.51, 108.48, 55.60. HRMS: calcd for [M+H], 240.07675; found, 240.07674

Example 12

2-(2,4-Dichlorophenyl)imidazo[1,2-a]pyridine (Intermediate Compound)

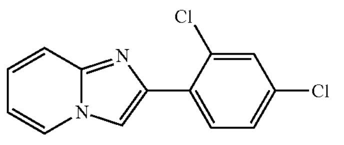 [SMILES: Clc1ccc(-c2cn3ccccc3n2)c(Cl)c1]

Title compound was prepared according to the General Procedure I (Scheme 1). Mobile phase petrolether/EtOAc (20-70%). Yield 634 mg (76%). $^{1}$H NMR (401 MHz, DMSO-$d_6$) δ 8.64 (d, J=0.7 Hz, 1H), 8.61 (dt, J=6.8, 1.2 Hz, 1H), 8.29 (d, J=8.5 Hz, 1H), 7.71 (d, J=2.2 Hz, 1H), 7.60 (dq, J=9.1, 1.0 Hz, 1H), 7.54 (dd, J=8.6, 2.2 Hz, 1H), 7.30 (ddd, J=9.1, 6.7, 1.3 Hz, 1H), 6.94 (td, J=6.8, 1.2 Hz, 1H). $^{13}$C NMR (101 MHz, DMSO) δ 144.26, 139.80, 132.92, 132.22, 131.75, 131.67, 130.15, 128.08, 127.69, 126.21, 117.15, 113.42, 113.01. HRMS: calcd for [M+H], 263.01373; found, 263.01390

Example 13

2-(4-(Trifluoromethyl)phenyl)imidazo[1,2-a]pyridine (Intermediate Compound)

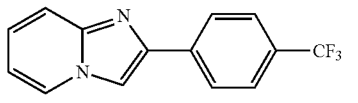 [SMILES: FC(F)(F)c1ccc(-c2cn3ccccc3n2)cc1]

Title compound was prepared according to the General Procedure I (Scheme 1). Mobile phase petrolether/EtOAc (20-70%). Yield 1.07 g (77%). $^{1}$H NMR (401 MHz, DMSO-$d_6$) δ 8.57-8.53 (m, 1H), 8.21-8.15 (m, 1H), 7.82-7.77 (m, 1H), 7.61 (dq, J=9.1, 1.0 Hz, 0H), 7.29 (ddd, J=9.1, 6.7, 1.3 Hz, 1H), 6.93 (td, J=6.8, 1.2 Hz, 1H). $^{13}$C NMR (101 MHz, DMSO) δ 145.20, 142.84, 138.12, 128.06, 127.75, 127.30, 126.21, 125.89, 125.86, 125.82, 125.78, 125.71, 117.04, 112.84, 110.73. HRMS: calcd for [M+H], 263.07906; found, 263.07907

Example 14

2-(4-Fluorophenyl)imidazo[1,2-a]pyridine (Intermediate Compound)

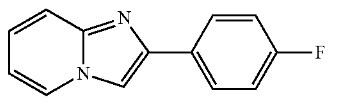 [SMILES: Fc1ccc(-c2cn3ccccc3n2)cc1]

Title compound was prepared according to the General Procedure I (Scheme 1). Mobile phase petrolether/EtOAc (20-70%). Yield 988 mg (88%). $^{1}$H NMR (401 MHz, DMSO-$d_6$) δ 8.52 (dt, J=1.2, 7.0 Hz, 1H), 8.38 (s, 1H), 8.04-7.96 (m, 2H), 7.57 (d, J=9.1 Hz, 1H), 7.31-7.21 (m, 3H), 6.89 (td, J=1.3, 6.8 Hz, 1H). $^{13}$C NMR (101 MHz, DMSO) δ 145.30, 143.91, 130.93, 127.37, 125.51, 117.06, 112.80, 109.41. $^{13}$C NMR (101 MHz, DMSO-$d_6$) δ 162.29 (d, J=244.2 Hz), 130.93, 127.97 (d, J=8.2 Hz), 116.05 (d, J=21.5 Hz). HRMS: calcd for [M+H], 213.08225; found, 213.08226.

Example 15

2-(4-Ethylphenyl)imidazo[1,2-a]pyridine (Intermediate Compound)

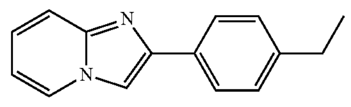 [SMILES: CCc1ccc(-c2cn3ccccc3n2)cc1]

Title compound was prepared according to the General Procedure I (Scheme 1). Mobile phase petrolether/EtOAc (20-70%). Yield 1.02 g (74%). $^{1}$H NMR (401 MHz, DMSO-$d_6$) δ 8.51 (dt, J=6.8, 1.2 Hz, 1H), 8.34 (d, J=0.7 Hz, 1H), 7.90-7.85 (m, 2H), 7.56 (dq, J=9.1, 1.0 Hz, 1H), 7.29-7.26 (m, 2H), 7.23 (ddd, J=9.1, 6.7, 1.3 Hz, 1H), 6.88 (td, J=6.7, 1.2 Hz, 1H), 2.63 (q, J=7.6 Hz, 2H), 1.21 (t, J=7.6 Hz, 3H). $^{13}$C NMR (101 MHz, DMSO) δ 145.21, 144.97, 143.79, 131.88, 128.56, 127.25, 126.04, 125.24, 117.00, 112.63, 109.14, 28.44, 16.01. HRMS: calcd for [M+H], 223.12298; found, 223.12301.

Example 16

2-(4-Chlorophenyl)-8-fluoroimidazo[1,2-a]pyridine (Intermediate Compound)

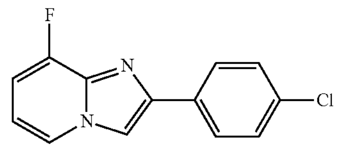 [SMILES: Fc1cccn2cc(-c3ccc(Cl)cc3)nc12]

Title compound was prepared according to the General Procedure I (Scheme 1). Mobile phase petrolether/EtOAc (20-70%). Yield 1.01 g (93%). $^{1}$H NMR (401 MHz, DMSO-$d_6$) δ 8.55 (d, J=3.1 Hz, 1H), 8.39 (dd, J=6.7, 0.9 Hz, 1H), 8.02-7.94 (m, 2H), 7.54-7.45 (m, 2H), 7.15 (ddd, J=11.4, 7.7, 0.9 Hz, 1H), 6.87 (ddd, J=7.7, 6.8, 4.7 Hz, 1H). $^{13}$C NMR (101 MHz, DMSO-$d_6$) δ 150.88 (d, J=249.1 Hz), 143.85, 137.77 (d, J=28.4 Hz), 132.93, 132.69, 129.27, 127.84, 124.17 (d, J=4.8 Hz), 112.02 (d, J=6.8 Hz), 111.77-111.62 (m), 108.35 (d, J=16.1 Hz). HRMS: calcd for [M+H], 247.0438; found, 247.0439.

Example 17

2-(4-Chlorophenyl)-7-fluoroimidazo[1,2-a]pyridine (Intermediate Compound)

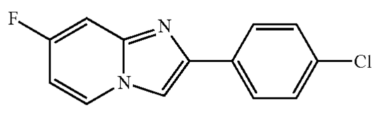 [SMILES: Fc1ccn2cc(-c3ccc(Cl)cc3)nc2c1]

Title compound was prepared according to the General Procedure I (Scheme 1). Mobile phase petrolether/EtOAc (20-70%). Yield 510 mg (83%). $^1$H NMR (401 MHz, DMSO-$d_6$) δ 8.59 (ddd, J=7.5, 5.9, 0.8 Hz, 1H), 8.40 (d, J=0.7 Hz, 1H), 8.01-7.89 (m, 2H), 7.51-7.46 (m, 2H), 7.43 (ddt, J=10.1, 2.7, 0.8 Hz, 1H), 6.97 (td, J=7.6, 2.6 Hz, 1H). $^{13}$C NMR (101 MHz, DMSO-$d_6$) δ 160.04 (d, J=248.4 Hz), 145.15 (d, J=14.3 Hz), 144.32 (d, J=1.5 Hz), 132.72, 132.41, 129.14 (d, J=11.1 Hz), 128.94, 104.74 (d, J=29.4 Hz), 100.36 (d, J=23.7 Hz). HRMS: calcd for [M+H], 247.0438; found, 247.0439.

Example 18

2-(4-Chlorophenyl)-6-fluoroimidazo[1,2-a]pyridine (Intermediate Compound)

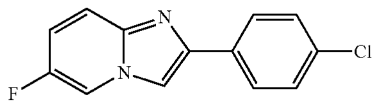 [SMILES: Fc1ccc2nc(-c3ccc(Cl)cc3)cn2c1]

Title compound was prepared according to the General Procedure I (Scheme 1). Mobile phase petrolether/EtOAc (20-70%). Yield 1.2 g (91%). $^1$H NMR (401 MHz, DMSO-$d_6$) δ 8.75 (ddd, J=4.6, 2.5, 0.8 Hz, 1H), 8.41 (d, J=0.7 Hz, 1H), 8.00-7.94 (m, 2H), 7.64 (ddt, J=9.9, 5.4, 0.8 Hz, 1H), 7.52-7.45 (m, 2H), 7.34 (ddd, J=9.9, 8.4, 2.5 Hz, 1H). $^{13}$C NMR (101 MHz, DMSO-$d_6$) δ 152.79 (d, J=232.7 Hz), 144.61 (d, J=2.0 Hz), 143.00, 132.73, 132.49, 128.97, 127.43, 117.57 (d, J=9.4 Hz), 117.16 (d, J=25.9 Hz), 113.84 (d, J=41.4 Hz), 111.16 (d, J=2.3 Hz). HRMS: calcd for [M+H], 247.0438; found, 247.0439.

Example 19

2-(4-Chlorophenyl)-5-fluoroimidazo[1,2-a]pyridine (Intermediate Compound)

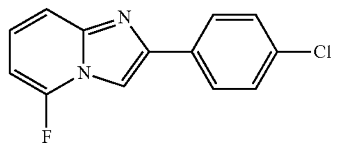 [SMILES: Fc1cccc2nc(-c3ccc(Cl)cc3)cn12]

Title compound was prepared according to the General Procedure I (Scheme 1) with modification. 2-Amino-6-fluoropyridine was combined with 1-(2-bromo-1,1-dimethoxyethyl)-4-chlorobenzene (1 eq) and $CH_3CN$ was added followed by a catalytic amount of $Sc(OTf)_3$. The reaction mixture was stirred in the sealed tube at 120° C. overnight. Mobile phase petrolether/EtOAc (20-100%). Yield 70 mg (18%). $^1$H NMR (401 MHz, DMSO-$d_6$) δ 8.58 (s, 1H), 8.10-8.04 (m, 2H), 7.54-7.47 (m, 3H), 7.37 (dt, J=9.0, 6.9 Hz, 1H), 6.83 (dd, J=7.4, 5.2 Hz, 1H). $^{13}$C NMR (101 MHz, DMSO-$d_6$) δ 148.78 (d, J=265.0 Hz), 146.93 (d, J=5.0 Hz), 144.16, 132.78, 132.35, 128.94, 127.72, 126.53 (d, J=6.6 Hz), 112.83 (d, J=4.7 Hz), 104.54, 93.06 (d, J=15.7 Hz). HRMS: calcd for [M+H], 247.0439; found, 247.0439.

Example 20

2-(4-Bromophenyl)imidazo[1,2-a]pyridine (Intermediate Compound)

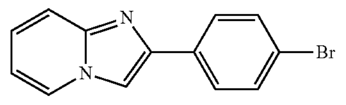 [SMILES: Brc1ccc(-c2cn3ccccc3n2)cc1]

Title compound was prepared according to the General Procedure I (Scheme 1). Mobile phase petrolether/EtOAc (20-70%). Yield 1.87 g (94%). $^1$H NMR (401 MHz, DMSO-$d_6$) δ 8.52 (dt, J=6.8, 1.2 Hz, 1H), 8.43 (d, J=0.7 Hz, 1H), 7.98-7.86 (m, 2H), 7.65-7.60 (m, 2H), 7.58 (dq, J=9.1, 1.0 Hz, 1H), 7.25 (ddd, J=9.1, 6.7, 1.3 Hz, 1H), 6.90 (td, J=6.7, 1.2 Hz, 1H). $^{13}$C NMR (101 MHz, DMSO) δ 145.04, 143.33, 133.38, 131.81, 127.71, 127.13, 125.38, 120.85, 116.85, 112.61, 109.68. HRMS: calcd for [M+H], 273.0027; found, 273.0028.

Example 21

2-(4-Chlorophenyl)-6,8-difluoroimidazo[1,2-a]pyridine (Intermediate Compound)

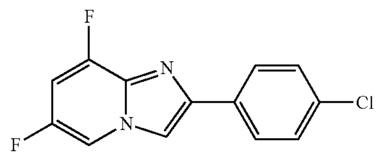 [SMILES: Fc1cc(F)c2nc(-c3ccc(Cl)cc3)cn2c1]

Title compound was prepared according to the General Procedure I (Scheme 1). Mobile phase petrolether/EtOAc (20-70%). Yield 0.45 g (87%). $^1$H NMR (401 MHz, DMSO-$d_6$) δ 8.70 (ddd, J=4.3, 2.1, 0.9 Hz, 1H), 8.55 (d, J=3.1 Hz, 1H), 8.01-7.96 (m, 2H), 7.57-7.48 (m, 3H). $^{13}$C NMR (101 MHz, DMSO-$d_6$) δ 151.59 (dd, J=233.31, 11.12 Hz), 150.03 (dd, J=252.4, 14.9 Hz), 144.75 (d, J=1.7 Hz), 135.76 (d, J=27.8 Hz), 133.11, 132.41, 129.31, 127.86, 113.25 (d, J=2.6 Hz), 111.38 (dd, J=41.5, 5.9 Hz), 102.38 (dd, J=30.3, 20.3 Hz). HRMS: calcd for [M+H], 265.0344; found, 265.0343.

Example 22

2-(4-Cyclopropylphenyl)imidazo[1,2-a]pyridine (Intermediate Compound)

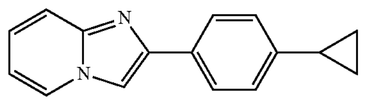 [SMILES: c1ccn2cc(-c3ccc(C4CC4)cc3)nc2c1]

Title compound was prepared from Example 20 (0.1 g, 0.36 mmol), which was dissolved in $H_2O/CH_3CN$ (1:1) mixture and cyclopropylboronic acid (1.5 eq) was added. The reaction mixture was degassed and refilled with argon. Subsequently $K_3PO_4$ (3.5 eq), $Pd(OAc)_2$ (5 mol %) and $Pcy_3$ (10 mol %) were added and the reaction mixture was stirred at 110° C. under argon. After completion of the reaction, the mixture was filtrated over celite, extracted with EtOAc, the organic phase was dried over sodium sulfate and evaporated. The residue was purified by flash column chromatography. Mobile phase petrolether/EtOAc (20-70%). Yield 86 mg (73%). $^{1}H$ NMR (401 MHz, DMSO-$d_6$) δ 8.50 (dt, J=6.8, 1.3 Hz, 1H), 8.33 (s, 1H), 7.85-7.80 (m, 2H), 7.55 (dq, J=9.1, 1.0 Hz, 1H), 7.22 (ddd, J=9.1, 6.7, 1.3 Hz, 1H), 7.16-7.10 (m, 2H), 6.87 (td, J=6.7, 1.2 Hz, 1H), 1.94 (tt, J=8.4, 5.1 Hz, 1H), 1.00-0.92 (m, 2H), 0.74-0.66 (m, 2H). $^{13}C$ NMR (101 MHz, DMSO) δ 144.88, 144.61, 143.51, 131.17, 126.93, 125.78, 125.71, 125.66, 124.93, 116.66, 112.31, 108.75, 15.17, 9.67. HRMS: calcd for [M+H], 235.1235; found, 235.1234.

General Procedure II. Iodination

2-Substituted imidazo[1,2-a]pyridines or imidazo[2,1-b]thiazoles were dissolved in $CH_3CN$ (5 ml/mmol) and NIS (1.05 eq) was added in one portion. The suspension was stirred at r.t. and the conversion was monitored by TLC. After the completion of the reaction (1-4 h), the reaction mixture was diluted with EtOAc and washed with saturated $Na_2S_2O_3$ solution. Inorganic phase was extracted twice more with EtOAc, combined organic phases were dried over sodium sulfate and evaporated. The residue was purified by flash column chromatography, mobile phase petrolether/EtOAc (10-50%).

Example 23

2-(4-Chlorophenyl)-3-iodoimidazo[1,2-a]pyridine (Intermediate Compound)

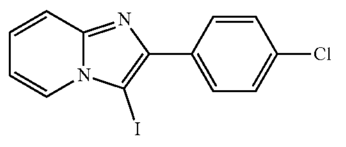 [SMILES: Clc1ccc(-c2nc3ccccn3c2I)cc1]

Title compound was prepared according to the General Procedure II (Scheme 1). Mobile phase petrolether/EtOAc (10-50%). Yield: 352 mg (98%). $^{1}H$ NMR (401 MHz, DMSO-$d_6$) δ 8.42 (dt, J=6.9, 1.2 Hz, 1H), 8.11-8.06 (m, 2H), 7.63 (dt, J=9.0, 1.2 Hz, 1H), 7.60-7.55 (m, 2H), 7.38 (ddd, J=9.0, 6.8, 1.3 Hz, 1H), 7.09 (td, J=6.8, 1.2 Hz, 1H). $^{13}C$ NMR (101 MHz, $CDCl_3$) δ 147.52, 145.52, 132.99, 132.85, 129.73, 128.67, 127.35, 126.47, 117.16, 113.93, 63.82. HRMS: calcd for [M+H], 354.94935; found, 354.94944.

Example 24

6-(4-Chlorophenyl)-5-iodoimidazo[2,1-b]thiazole (Intermediate Compound)

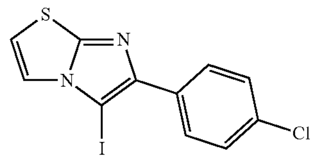 [SMILES: Clc1ccc(-c2nc3sccn3c2I)cc1]

Title compound was prepared according to the General Procedure II (Scheme 1). Mobile phase petrolether/EtOAc (10-50%). Yield: 421 mg (89%). $^{1}H$ NMR (401 MHz, DMSO-$d_6$) δ 7.98 (m, 2H), 7.87 (d, J=4.5 Hz, 1H), 7.52 (m, 2H), 7.42 (d, J=4.5 Hz, 1H). $^{13}C$ NMR (101 MHz, DMSO) δ 149.88, 145.54, 133.64, 131.78, 129.09, 126.85, 120.52, 113.85, 110.30. HRMS: calcd for [M+H], 360.90577; found, 360.90586.

Example 25

6-Chloro-2-(4-chlorophenyl)-3-iodoimidazo[1,2-b]pyridazine (Intermediate Compound)

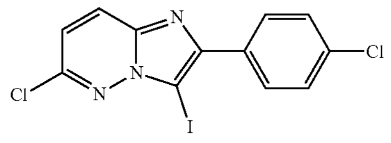 [SMILES: Clc1ccc(-c2nc3ccc(Cl)nn3c2I)cc1]

Title compound was prepared according to the General Procedure II (Scheme 1). Mobile phase petrolether/EtOAc (10-50%). Yield: 150 mg (82%). $^{1}H$ NMR (401 MHz, DMSO-$d_6$) δ 8.21 (d, J=9.4 Hz, 1H), 8.15-8.10 (m, 2H), 7.62-7.58 (m, 2H), 7.46 (d, J=9.4 Hz, 1H). $^{13}C$ NMR (101 MHz, DMSO) δ 147.51, 146.14, 140.77, 133.85, 132.40, 129.88, 129.11, 127.84, 121.02, 72.31. HRMS: calcd for [M+Na], 389.90562; found, 389.90582.

Example 26

2-(3,4-Dichlorophenyl)-3-iodoimidazo[1,2-a]pyridine (Intermediate Compound)

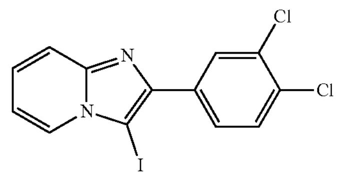 [SMILES: Clc1ccc(-c2nc3ccccn3c2I)cc1Cl]

Title compound was prepared according to the General Procedure II (Scheme 1). Mobile phase petrolether/EtOAc (10-50%). Yield: 638 mg (98%). $^{1}H$ NMR (401 MHz, Chloroform-d) δ 8.24 (dt, J=6.9, 1.1 Hz, 1H), 8.22 (d, J=2.1

Hz, 1H), 7.96 (dd, J=8.4, 2.1 Hz, 1H), 7.66 (dt, J=9.0, 1.2 Hz, 1H), 7.55 (d, J=8.4 Hz, 1H), 7.33 (ddd, J=9.1, 6.8, 1.3 Hz, 1H), 6.99 (td, J=6.9, 1.2 Hz, 1H). $^{13}$C NMR (101 MHz, DMSO) δ 179.90, 147.82, 144.25, 134.93, 131.66, 131.24, 131.09, 129.70, 128.14, 127.74, 127.08, 117.55, 114.43, 64.93. HRMS: calcd for [M+H], 388.91037; found, 388.91052.

Example 27

6-(3,4-Dichlorophenyl)-5-iodoimidazo[2,1-b]thiazole (Intermediate Compound)

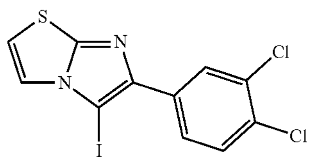 [SMILES: Clc1ccc(-c2nc3sccn3c2I)cc1Cl]

Title compound was prepared according to the General Procedure II (Scheme 1). Mobile phase petrolether/EtOAc (10-50%). Yield: 514 mg (96%). $^{1}$H NMR (401 MHz, DMSO-$d_6$) δ 8.17 (d, J=2.1 Hz, 1H), 7.99 (dd, J=8.5, 2.1 Hz, 1H), 7.90 (d, J=4.5 Hz, 1H), 7.75 (d, J=8.5 Hz, 1H), 7.46 (d, J=4.5 Hz, 1H). $^{13}$C NMR (101 MHz, DMSO) δ 150.98, 145.37, 134.98, 131.61, 131.21, 130.34, 128.53, 126.97, 120.67, 114.97, 60.96. HRMS: calcd for [M+H], 394.86679; found, 394.86699.

Example 28

3-Iodo-2-phenylimidazo[1,2-a]pyridine (Intermediate Compound)

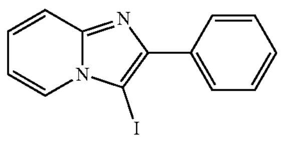 [SMILES: Ic1c(-c2ccccc2)nc2ccccn12]

Title compound was prepared according to the General Procedure II (Scheme 1). Mobile phase petrolether/EtOAc (10-50%). Yield: 468 mg (95%). $^{1}$H NMR (401 MHz, DMSO-$d_6$) δ 8.43 (dt, J=6.9, 1.1 Hz, 1H), 8.11-8.01 (m, 2H), 7.63 (dt, J=9.0, 1.2 Hz, 1H), 7.54-7.47 (m, 2H), 7.44-7.35 (m, 2H), 7.08 (td, J=6.8, 1.2 Hz, 1H). $^{13}$C NMR (101 MHz, DMSO) δ 147.43, 146.70, 133.92, 128.54, 128.30, 128.27, 128.13, 127.25, 126.21, 117.08, 113.76, 63.44. HRMS: calcd for [M+H], 320.98832; found, 320.98819.

Example 29

5-Iodo-6-phenylimidazo[2,1-b]thiazole (Intermediate Compound)

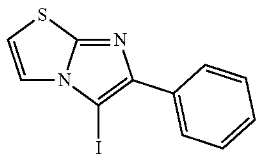 [SMILES: Ic1c(-c2ccccc2)nc2sccn12]

Title compound was prepared according to the General Procedure II (Scheme 1). Mobile phase petrolether/EtOAc (10-50%). Yield: 425 mg (87%). $^{1}$H NMR (401 MHz, DMSO-$d_6$) δ 7.99-7.93 (m, 2H), 7.85 (d, J=4.5 Hz, 1H), 7.45 (m, 2H), 7.40 (d, J=4.5 Hz, 1H), 7.37-7.29 (m, 1H). $^{13}$C NMR (101 MHz, DMSO) δ 150.27, 147.85, 134.02, 128.51, 127.71, 127.03, 120.30, 113.93, 59.05. HRMS: calcd for [M+H], 326.94474; found, 326.94476.

Example 30

3-Iodo-2-(p-tolyl)imidazo[1,2-a]pyridine (Intermediate Compound)

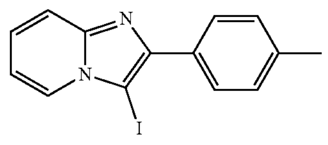 [SMILES: Cc1ccc(-c2nc3ccccn3c2I)cc1]

Title compound was prepared according to the General Procedure II (Scheme 1). Mobile phase petrolether/EtOAc (10-50%). Yield: 501 mg (94%). $^{1}$H NMR (401 MHz, DMSO-$d_6$) δ 8.41 (dt, J=6.9, 1.2 Hz, 1H), 7.98-7.92 (m, 2H), 7.61 (dt, J=9.0, 1.1 Hz, 1H), 7.36 (ddd, J=9.0, 6.7, 1.3 Hz, 1H), 7.31 (d, J=8.0 Hz, 2H), 7.06 (td, J=6.8, 1.2 Hz, 1H), 2.36 (s, 3H). $^{13}$C NMR (101 MHz, DMSO) δ 147.70, 147.12, 137.95, 131.41, 129.41, 128.32, 127.44, 126.35, 117.29, 113.92, 63.23, 21.36. HRMS: calcd for [M+H], 335.00397; found, 335.00397.

Example 31

3-Iodo-2-(pyridin-4-yl)imidazo[1,2-a]pyridine (Intermediate Compound)

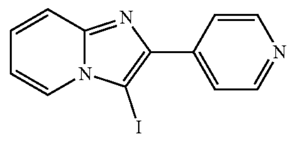 [SMILES: Ic1c(-c2ccncc2)nc2ccccn12]

Title compound was prepared according to the General Procedure II (Scheme 1). Mobile phase petrolether/EtOAc (10-50%). Yield: 253 mg (87%). $^{1}$H NMR (401 MHz, DMSO-$d_6$) δ 8.71-8.66 (m, 2H), 8.43 (dt, J=6.9, 1.2 Hz, 1H), 8.10-8.05 (m, 2H), 7.65 (dt, J=9.1, 1.1 Hz, 1H), 7.39 (ddd, J=9.0, 6.7, 1.2 Hz, 1H), 7.09 (td, J=6.8, 1.2 Hz, 1H). $^{13}$C NMR (101 MHz, DMSO) δ 150.37, 147.91, 143.89, 141.53, 127.75, 127.17, 122.29, 117.73, 114.54, 65.91. HRMS: calcd for [M+H], 321.98357; found, 321.98367.

Example 32

3-Iodo-2-(4-methoxyphenyl)imidazo[1,2-a]pyridine (Intermediate Compound)

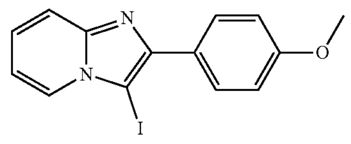 [SMILES: COc1ccc(-c2nc3ccccn3c2I)cc1]

Title compound was prepared according to the General Procedure II (Scheme 1). Mobile phase petrolether/EtOAc (10-50%). Yield: 238 mg (89%). $^1$H NMR (401 MHz, DMSO-$d_6$) δ 8.39 (dt, J=6.9, 1.1 Hz, 1H), 8.05-7.96 (m, 2H), 7.60 (dt, J=9.0, 1.1 Hz, 1H), 7.35 (ddd, J=9.0, 6.7, 1.2 Hz, 1H), 7.09-7.05 (m, 3H), 3.82 (s, 3H). $^{13}$C NMR (101 MHz, DMSO) δ 159.68, 147.67, 146.99, 129.70, 127.38, 126.59, 126.27, 117.16, 114.27, 113.83, 62.62, 55.66. HRMS: calcd for [M+H], 350.99888; found, 350.99893.

Example 33

2-(2,4-Dichlorophenyl)-3-iodoimidazo[1,2-a]pyridine (Intermediate Compound)

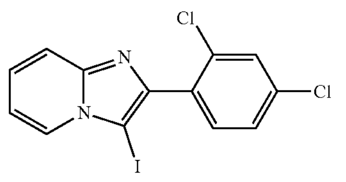 [SMILES: Clc1ccc(-c2nc3ccccn3c2I)c(Cl)c1]

Title compound was prepared according to the General Procedure II (Scheme 1). Mobile phase petrolether/EtOAc (10-50%). Yield: 238 mg (89%). $^1$H NMR (401 MHz, DMSO-$d_6$) δ 8.40 (dt, J=6.9, 1.2 Hz, 1H), 7.79 (d, J=2.0 Hz, 1H), 7.64 (dt, J=9.0, 1.1 Hz, 1H), 7.59-7.51 (m, 2H), 7.40 (ddd, J=9.0, 6.8, 1.3 Hz, 1H), 7.12 (td, J=6.8, 1.2 Hz, 1H). $^{13}$C NMR (101 MHz, DMSO) δ 147.39, 146.72, 134.57, 134.42, 134.34, 132.87, 129.62, 127.72, 127.46, 126.52, 117.62, 114.32, 67.98. HRMS: calcd for [M+H], 388.91037; found, 388.91071.

Example 34

4-(3-Iodoimidazo[1,2-a]pyridin-2-yl)benzonitrile (Intermediate Compound)

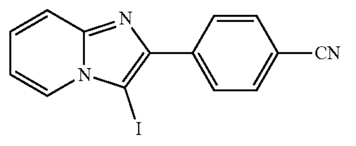 [SMILES: N#Cc1ccc(-c2nc3ccccn3c2I)cc1]

Title compound was prepared according to the General Procedure II. Mobile phase petrolether/EtOAc (10-50%). Yield: 245 mg (90%). $^1$H NMR (401 MHz, DMSO-$d_6$) δ 8.46 (dt, J=7.0, 1.1 Hz, 1H), 8.31-8.26 (m, 2H), 8.00-7.95 (m, 2H), 7.66 (dt, J=9.1, 1.1 Hz, 1H), 7.41 (ddd, J=9.1, 6.8, 1.2 Hz, 1H), 7.11 (td, J=6.8, 1.2 Hz, 1H). $^{13}$C NMR (101 MHz, DMSO) δ 147.64, 144.64, 138.54, 132.60, 128.49, 127.49, 126.85, 119.02, 117.37, 114.20, 110.54, 65.39. HRMS: calcd for [M+H], 345.98357; found, 345.98370.

Example 35

3-Iodo-2-(4-(trifluoromethyl)phenyl)imidazo[1,2-a]pyridine (Intermediate Compound)

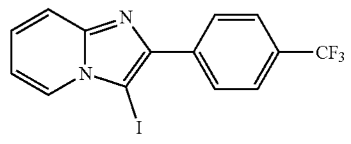 [SMILES: FC(F)(F)c1ccc(-c2nc3ccccn3c2I)cc1]

Title compound was prepared according to the General Procedure II (Scheme 1). Mobile phase petrolether/EtOAc (10-50%). Yield: 1.25 g (92%). $^1$H NMR (401 MHz, DMSO-$d_6$) δ 8.46 (d, J=6.9 Hz, 1H), 8.31 (d, J=8.0 Hz, 2H), 7.88 (d, J=8.1 Hz, 2H), 7.67 (d, J=9.0 Hz, 1H), 7.42 (dd, J=8.9, 6.9 Hz, 1H), 7.12 (t, J=6.8 Hz, 1H). $^{13}$C NMR (101 MHz, DMSO) δ 147.90, 145.35, 138.31, 128.87, 128.65 127.74, 126.96, 125.81 (J=3.78 Hz), 124.77, 117.61, 114.38, 65.13. HRMS: calcd for [M+H], 388.97570; found, 388.97582.

Example 36

2-(4-Fluorophenyl)-3-iodoimidazo[1,2-a]pyridine (Intermediate Compound)

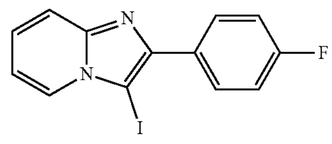 [SMILES: Fc1ccc(-c2nc3ccccn3c2I)cc1]

Title compound was prepared according to the General Procedure II (Scheme 1). Mobile phase petrolether/EtOAc (10-50%). Yield: 1.42 g (97%). $^1$H NMR (401 MHz, DMSO-$d_6$) δ 8.40 (dt, J=6.9, 1.1 Hz, 1H), 8.12-8.06 (m, 2H), 7.62 (dt, J=9.0, 1.1 Hz, 1H), 7.40-7.30 (m, 3H), 7.07 (td, J=6.8, 1.2 Hz, 1H). $^{13}$C NMR (101 MHz, DMSO) δ 162.15 (d, J=245.5 Hz), 147.44, 145.88, 130.42 (d, J=3.0 Hz), 130.15 (d, J=8.3 Hz), 127.25, 126.28, 117.05, 115.48 (d, J=21.5 Hz), 113.78, 63.34. HRMS: calcd for [M+H], 338.97890; found, 338.97902.

Example 37

2-(4-Ethylphenyl)-3-iodoimidazo[1,2-a]pyridine (Intermediate Compound)

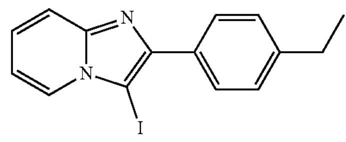

Title compound was prepared according to the General Procedure II (Scheme 1). Mobile phase petrolether/EtOAc (10-50%). Yield: 1.23 g (86%). $^1$H NMR (401 MHz, DMSO-$d_6$) δ 8.41 (dt, J=6.9, 1.1 Hz, 1H), 8.00-7.95 (m, 2H), 7.62 (dt, J=9.0, 1.1 Hz, 1H), 7.39-7.36 (m, 3H), 7.35-7.31

(m, 2H), 7.07 (td, J=6.8, 1.2 Hz, 1H), 2.66 (q, J=7.6 Hz, 2H), 1.22 (t, J=7.6 Hz, 3H). $^{13}C$ NMR (101 MHz, DMSO) δ 147.41, 146.83, 143.95, 131.35, 128.10, 127.93, 127.16, 126.08, 117.00, 113.65, 62.95, 28.15, 15.67. HRMS: calcd for [M+H], 349.01962; found, 349.01982.

Example 38

2-(4-Chlorophenyl)-8-fluoro-3-iodoimidazo[1,2-a] pyridine (Intermediate Compound)

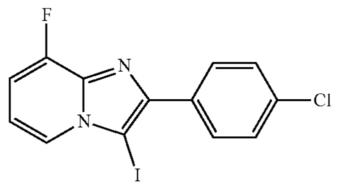 [SMILES: Fc1cccn2c(I)c(-c3ccc(Cl)cc3)nc12]

Title compound was prepared according to the General Procedure II (Scheme 1). Mobile phase petrolether/EtOAc (10-50%). Yield: 0.35 g (92%). $^{1}H$ NMR (401 MHz, DMSO-$d_6$) δ 8.30 (dd, J=6.9, 0.9 Hz, 1H), 8.11-8.04 (m, 2H), 7.63-7.55 (m, 2H), 7.32 (ddd, J=11.0, 7.7, 0.9 Hz, 1H), 7.06 (ddd, J=7.6, 6.9, 4.8 Hz, 1H). $^{13}C$ NMR (101 MHz, DMSO-$d_6$) δ 150.29 (d, J=250.5 Hz), 145.73, 139.66 (d, J=28.7 Hz), 133.22, 132.30, 129.80, 128.69, 124.18 (d, J=4.8 Hz), 112.71 (d, J=7.1 Hz), 109.01 (d, J=16.0 Hz), 66.13. HRMS: calcd for [M+H], 372.9405; found, 372.9407.

Example 39

2-(4-Chlorophenyl)-7-fluoro-3-iodoimidazo[1,2-a] pyridine (Intermediate Compound)

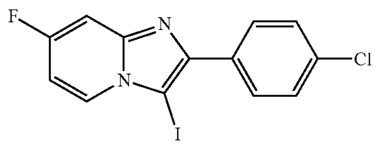 [SMILES: Fc1ccn2c(I)c(-c3ccc(Cl)cc3)nc2c1]

Title compound was prepared according to the General Procedure II (Scheme 1). Mobile phase petrolether/EtOAc (10-50%). Yield: 0.32 g (93%). $^{1}H$ NMR (401 MHz, DMSO-$d_6$) δ 8.49 (t, J=6.6 Hz, 1H), 8.07 (d, J=8.2 Hz, 2H), 7.57 (dd, J=9.0, 6.0 Hz, 3H), 7.12 (td, J=7.6, 2.6 Hz, 1H). $^{13}C$ NMR (101 MHz, DMSO-$d_6$) δ 160.72 (d, J=249.8 Hz), 147.16 (d, J=14.2 Hz), 146.55, 133.05, 132.58, 129.57, 128.94, 128.68, 127.37, 105.83 (d, J=29.7 Hz), 100.73 (d, J=23.8 Hz), 63.43. HRMS: calcd for [M+H], 372.9405; found, 372.9407.

Example 40

2-(4-Chlorophenyl)-6-fluoro-3-iodoimidazo[1,2-a] pyridine (Intermediate Compound)

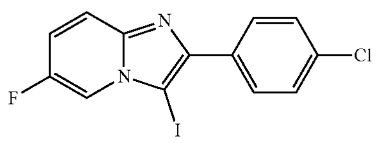 [SMILES: Fc1ccc2nc(-c3ccc(Cl)cc3)c(I)n2c1]

Title compound was prepared according to the General Procedure II (Scheme 1). Mobile phase petrolether/EtOAc (10-50%). Yield: 0.29 g (92%). $^{1}H$ NMR (401 MHz, DMSO-$d_6$) δ 8.57 (ddd, J=4.6, 2.4, 0.8 Hz, 1H), 8.09-8.03 (m, 2H), 7.73 (ddd, J=9.8, 5.3, 0.8 Hz, 1H), 7.60-7.55 (m, 2H), 7.47 (ddd, J=9.8, 8.3, 2.4 Hz, 1H). $^{13}C$ NMR (101 MHz, DMSO-$d_6$) δ 153.66 (d, J=235.2 Hz), 146.82 (d, J=2.3 Hz), 145.33, 133.08, 132.63, 129.65, 128.68, 118.23 (d, J=13.6 Hz), 118.05 (d, J=3.0 Hz), 114.46 (d, J=42.7 Hz), 65.73. HRMS: calcd for [M+H], 372.9405; found, 372.9406.

Example 41

2-(4-Chlorophenyl)-5-fluoro-3-iodoimidazo[1,2-a] pyridine (Intermediate Compound)

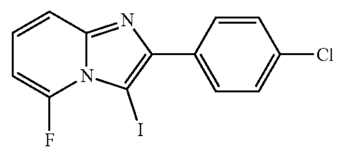 [SMILES: Fc1cccc2nc(-c3ccc(Cl)cc3)c(I)n12]

Title compound was prepared according to the General Procedure II (Scheme 1). Mobile phase petrolether/EtOAc (10-50%). Yield: 14 mg (75%). $^{1}H$ NMR (401 MHz, DMSO-$d_6$) δ 7.98-7.92 (m, 2H), 7.60-7.55 (m, 2H), 7.55-7.50 (m, 1H), 7.38 (ddd, J=9.0, 7.5, 6.0 Hz, 1H), 6.83 (td, J=7.5, 1.0 Hz, 1H). $^{13}C$ NMR (101 MHz, DMSO-$d_6$) δ 149.83 (d, J=268.7 Hz), 149.66 (d, J=4.6 Hz), 148.00, 126.85 (d, J=6.9 Hz), 113.62 (d, J=4.9 Hz), 94.58 (d, J=17.4 Hz), 54.45 (d, J=2.2 Hz). HRMS: calcd for [M+H], 372.9405; found, 372.9407.

Example 42

2-(4-Chlorophenyl)-6,8-difluoro-3-iodoimidazo[1,2-a]pyridine (Intermediate Compound)

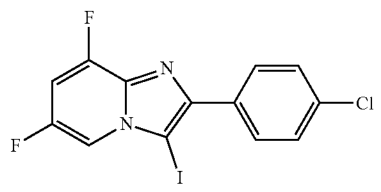 [SMILES: Fc1cc(F)c2nc(-c3ccc(Cl)cc3)c(I)n2c1]

Title compound was prepared according to the General Procedure II (Scheme 1). Mobile phase petrolether/EtOAc (10-50%). Yield: 0.345 g (94%). $^{1}H$ NMR (401 MHz, DMSO-$d_6$) δ 8.49 (ddd, J=4.4, 2.1, 0.9 Hz, 1H), 8.07-8.01 (m, 2H), 7.67 (ddd, J=11.1, 9.2, 2.1 Hz, 1H), 7.59-7.52 (m, 2H). $^{13}C$ NMR (101 MHz, DMSO-$d_6$) δ 151.95 (dd, J=235.62 Hz, J=11.32 Hz), 149.72 (dd, J=253.9, 14.6 Hz), 146.63 (d, J=1.9 Hz), 137.70 (d, J=28.1 Hz), 133.34, 132.10, 129.72, 128.71, 111.71 (dd, J=42.6, 5.8 Hz), 103.00 (dd, J=30.2, 20.3 Hz), 68.18 (d, J=2.5 Hz). HRMS: calcd for [M+H], 390.9311; found, 390.9312.

Example 43

2-(4-Cyclopropylphenyl)-3-iodoimidazo[1,2-a]pyridine (Intermediate Compound)

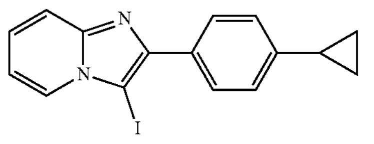 [SMILES: Ic1c(-c2ccc(C3CC3)cc2)nc2ccccn12]

Title compound was prepared according to the General Procedure II (Scheme 1). Mobile phase petrolether/EtOAc (10-50%). Yield: 0.287 g (99%). $^1$H NMR (401 MHz, DMSO-$d_6$) δ 8.40 (d, J=6.9 Hz, 1H), 7.95 (d, J=8.0 Hz, 2H), 7.61 (d, J=9.0 Hz, 1H), 7.35 (t, J=7.9 Hz, 1H), 7.19 (d, J=7.9 Hz, 2H), 7.06 (t, J=6.9 Hz, 1H), 1.97 (td, J=8.5, 4.3 Hz, 1H), 0.98 (d, J=7.7 Hz, 2H), 0.73 (d, J=5.4 Hz, 2H). $^{13}$C NMR (101 MHz, DMSO) δ 147.37, 146.72, 144.04, 130.89, 127.98, 127.13, 126.06, 125.43, 116.95, 113.62, 62.86, 15.18, 9.83. HRMS: calcd for [M+H], 361.0202; found, 361.0206.

General Procedure III. Sonogashira Coupling

3-Iodoimidazo[1,2-a]pyridines or 5-iodoimidazo[2,1-b] thiazoles were placed in dried round bottom flask, diluted with dry DMF and degassed at 0° C. and flushed with argon. CuI (10 mol %), $Pd(PPh_3)_2Cl_2$ (5 mol %) were added and the mixture was properly degassed and dry TEA (3 eq) was added and the mixture degassed again. Finally TMS-acetylene (5 eq) was added in one portion. The reaction mixture was stirred at r.t. under the argon atmosphere. After the completion of the reaction (monitored by TLC), the mixture was if necessary diluted with $CHCl_3$ and filtered over celite. Filtrate was washed with water, water phase was extracted twice more with $CHCl_3$, combined organic phases were dried over sodium sulfate and evaporated. A residue was purified by flash column chromatography (mobile phase petrolether/EtOAc).

Example 44

2-(4-Chlorophenyl)-3-((trimethylsilyl)ethynyl)imidazo[1,2-a]pyridine (Intermediate Compound)

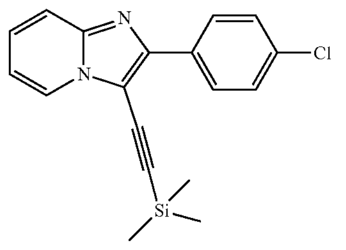 [SMILES: C[Si](C)(C)C#Cc1c(-c2ccc(Cl)cc2)nc2ccccn12]

Title compound was prepared according to the General Procedure III (Scheme 1). Mobile phase petrolether/EtOAc (10-50%). Yield: 625 mg (56%). $^1$H NMR (401 MHz, DMSO-$d_6$) δ 8.41 (dt, J=6.8, 1.2 Hz, 1H), 8.28-8.21 (m, 2H), 7.70 (dt, J=9.0, 1.1 Hz, 1H), 7.59-7.53 (m, 2H), 7.46 (ddd, J=9.0, 6.8, 1.3 Hz, 1H), 7.14 (td, J=6.8, 1.2 Hz, 1H), 0.34 (s, 9H). $^{13}$C NMR (101 MHz, DMSO) δ 146.17, 144.70, 133.43, 132.04, 128.88, 128.28, 127.82, 125.82, 117.30, 114.28, 108.95, 104.06, 93.27, −0.10. HRMS: calcd for [M+H], 325.09223; found, 325.09232.

Example 45

6-(4-Chlorophenyl)-5-((trimethylsilyl)ethynyl)imidazo[2,1-b]thiazole (Intermediate Compound)

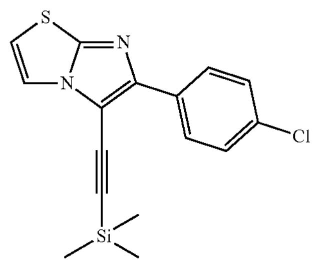 [SMILES: C[Si](C)(C)C#Cc1c(-c2ccc(Cl)cc2)nc2sccn12]

Title compound was prepared according to the General Procedure III (Scheme 1). Mobile phase petrolether/EtOAc (10-50%). Yield: 458 mg (61%). $^1$H NMR (500 MHz, DMSO-$d_6$) δ 8.10 (m, 2H), 7.92 (d, J=4.4 Hz, 1H), 7.51-7.54 (m, 2H), 7.44 (d, J=4.4 Hz, 1H), 0.31. $^{13}$C NMR (101 MHz, DMSO) δ 149.86, 145.03, 133.72, 132.31, 128.81, 127.46, 119.32, 115.60, 106.93, 105.19, 93.51, −0.17. EI MS: calcd for [M+H], 330.0414; found, 330.0416.

Example 46

6-Chloro-2-(4-chlorophenyl)-3-((trimethylsilyl)ethynyl)imidazo[1,2-b]pyridazine (Intermediate Compound)

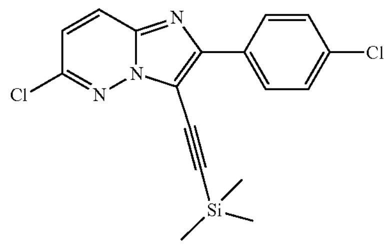 [SMILES: C[Si](C)(C)C#Cc1c(-c2ccc(Cl)cc2)nc2ccc(Cl)nn12]

Title compound was prepared according to the General Procedure III (Scheme 1). Mobile phase petrolether/EtOAc (10-50%). Yield: 165 mg (46%). $^1$H NMR (401 MHz, Chloroform-d) δ 7.53-7.47 (m, 2H), 7.09 (d, J=9.4 Hz, 1H), 6.68-6.61 (m, 2H), 6.33 (d, J=9.4 Hz, 1H), −0.43 (s, 9H). $^{13}$C NMR (101 MHz, $CDCl_3$) δ 147.66, 147.41, 137.38, 135.17, 131.02, 128.95, 128.78, 128.58, 128.47, 127.47, 126.23, 120.62, 109.89, 91.62, −0.26. HRMS: calcd for [M+H], 360.04851; found, 360.04867.

Example 47

2-Phenyl-3-((trimethylsilyl)ethynyl)imidazo[1,2-a]pyridine (Intermediate Compound)

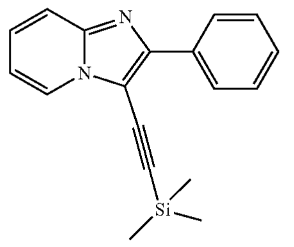 [SMILES: C[Si](C)(C)C#Cc1c(-c2ccccc2)nc2ccccn12]

Title compound was prepared according to the General Procedure III (Scheme 1). Mobile phase petrolether/EtOAc (10-50%). Yield: 78 mg (62%). $^1$H NMR (401 MHz, DMSO-$d_6$) δ 8.41 (dt, J=6.7, 1.2 Hz, 1H), 8.32-8.24 (m, 2H), 7.71 (dt, J=9.0, 1.2 Hz, 1H), 7.53-7.38 (m, 4H), 7.13 (td, J=6.8, 1.2 Hz, 1H), 0.34 (s, 9H). $^{13}$C NMR (101 MHz, DMSO) δ 147.48, 144.68, 133.17, 128.91, 128.81, 128.76, 127.57, 126.71, 125.73, 117.26, 114.11, 108.44, 103.86, 93.66, −0.08. HRMS: calcd for [M+H], 291.13120; found, 291.13125.

Example 48

6-Phenyl-5-((trimethylsilyl)ethynyl)imidazo[2,1-b]thiazole (Intermediate Compound)

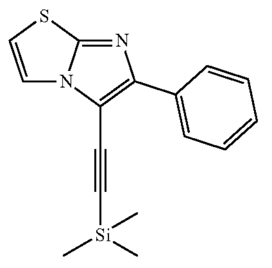 [SMILES: C[Si](C)(C)C#Cc1c(-c2ccccc2)nc2sccn12]

Title compound was prepared according to the General Procedure III (Scheme 1). Mobile phase petrolether/EtOAc (10-50%). Yield: 82 mg (71%). $^1$H NMR (401 MHz, DMSO-$d_6$) δ 8.16-8.10 (m, 2H), 7.88 (d, J=4.4 Hz, 1H), 7.46-7.39 (m, 3H), 7.35-7.30 (m, 1H), 0.30 (s, 9H). $^{13}$C NMR (101 MHz, DMSO) δ 149.93, 149.66, 133.78, 128.93, 128.53, 126.20, 119.51, 115.53, 106.59, 105.28, 94.25, 0.14. HRMS: calcd for [M+H], 297.08762; found, 297.08771.

Example 49

2-(p-Tolyl)-3-((trimethylsilyl)ethynyl)imidazo[1,2-a]pyridine (Intermediate Compound)

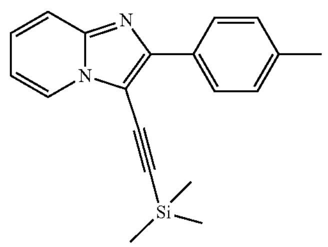 [SMILES: Cc1ccc(-c2nc3ccccn3c2C#C[Si](C)(C)C)cc1]

Title compound was prepared according to the General Procedure III (Scheme 1). Mobile phase petrolether/EtOAc (10-50%). Yield: 117 mg (64%). $^1$H NMR (401 MHz, DMSO-$d_6$) δ 8.39 (d, J=6.8 Hz, 1H), 8.16 (d, J=7.8 Hz, 2H), 7.69 (d, J=9.0 Hz, 1H), 7.43 (dd, J=8.9, 6.9 Hz, 1H), 7.30 (d, J=7.9 Hz, 2H), 7.12 (t, J=6.8 Hz, 1H), 2.36 (s, 3H), 0.34 (s, 9H). $^{13}$C NMR (101 MHz, DMSO) δ 147.99, 144.94, 138.80, 130.71, 129.64, 127.79, 126.95, 125.98, 117.43, 114.32, 108.68, 103.79, 94.13, 21.38, 0.24. HRMS: calcd for [M+H], 305.14685; found, 305.14690.

Example 50

2-(4-Nitrophenyl)-3-((trimethylsilyl)ethynyl)imidazo[1,2-a]pyridine (Intermediate Compound)

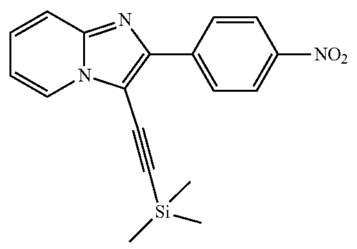 [SMILES: C[Si](C)(C)C#Cc1c(-c2ccc([N+](=O)[O-])cc2)nc2ccccn12]

Title compound was prepared according to the General Procedure III (Scheme 1). Mobile phase petrolether/EtOAc (10-50%). Yield: 25 mg (11%). $^1$H NMR (401 MHz, Chloroform-d) δ 8.59-8.52 (m, 2H), 8.38-8.31 (m, 3H), 7.70 (dt, J=9.1, 1.1 Hz, 1H), 7.40-7.34 (m, 1H), 7.02 (td, J=6.8, 1.2 Hz, 1H), 0.41 (s, 9H). $^{13}$C NMR (101 MHz, $CDCl_3$) δ 127.60, 127.21, 125.51, 123.82, 117.85, 113.65, 92.75, −0.12. HRMS: calcd for [M+H], 336.11628; found, 336.11584.

Example 51

2-(2,4-Dichlorophenyl)-3-((trimethylsilyl)ethynyl) imidazo[1,2-a]pyridine (Intermediate Compound)

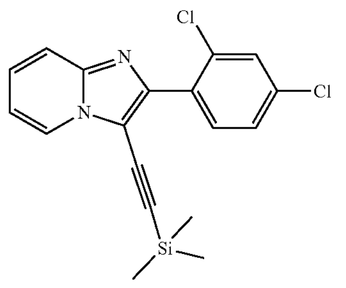 [SMILES: C[Si](C)(C)C#Cc1c(-c2ccc(Cl)cc2Cl)nc2ccccn12]

Title compound was prepared according to the General Procedure III (Scheme 1). Mobile phase petrolether/EtOAc (10-50%). Yield: 98 mg (64%). $^{1}$H NMR (401 MHz, Chloroform-d) δ 8.30 (dt, J=6.8, 1.2 Hz, 1H), 7.64 (m, 2H), 7.54 (d, J=2.1 Hz, 1H), 7.38-7.27 (m, 2H), 6.97 (td, J=6.8, 1.2 Hz, 1H), 0.27 (s, 9H). $^{13}$C NMR (101 MHz, $CDCl_3$) δ 146.79, 144.80, 135.05, 134.32, 133.22, 131.39, 130.12, 126.95, 126.52, 125.55, 117.98, 113.42, 108.14, 92.17, 0.04. HRMS: calcd for [M+H], 321.14177; found, 321.14179.

Example 52

2-(4-Methoxyphenyl-3-((trimethylsilyl)ethynyl)imidazo[1,2-a]pyridine (Intermediate Compound)

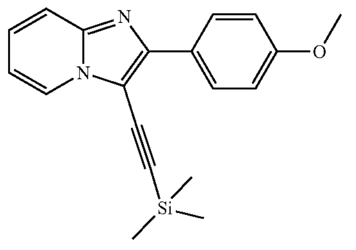 [SMILES: COc1ccc(-c2nc3ccccn3c2C#C[Si](C)(C)C)cc1]

Title compound was prepared according to the General Procedure III (Scheme 1). Mobile phase petrolether/EtOAc (10-50%). Yield: 98 mg (64%). $^{1}$H NMR (401 MHz, DMSO-$d_6$) δ 8.38 (dt, J=6.8, 1.2 Hz, 1H), 8.26-8.18 (m, 2H), 7.67 (dt, J=9.0, 1.1 Hz, 1H), 7.42 (ddd, J=9.0, 6.8, 1.3 Hz, 1H), 7.11 (td, J=6.8, 1.2 Hz, 1H), 7.08-7.03 (m, 2H), 3.82 (s, 3H), 0.34 (s, 9H). $^{13}$C NMR (101 MHz, DMSO) δ 159.83, 147.63, 144.60, 128.13, 127.19, 125.75, 125.49, 116.93, 114.07, 113.72, 108.09, 102.92, 94.03, 55.32, −0.04, −0.06, −0.08. HRMS: calcd for [M+H], 321.14177; found, 321.14179

Example 53

4-(3-((Trimethylsilyl)ethynyl)imidazo[1,2-a]pyridin-2-yl)benzonitrile (Intermediate Compound)

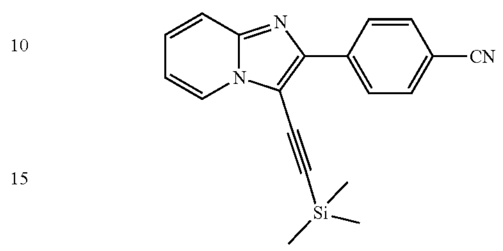

Title compound was prepared according to the General Procedure III (Scheme 1). Mobile phase petrolether/EtOAc (10-50%). Yield: 170 mg (65%). $^{1}$H NMR (401 MHz, DMSO-$d_6$) δ 8.44 (dt, J=6.8, 1.2 Hz, 1H), 8.42-8.38 (m, 2H), 7.99-7.94 (m, 2H), 7.74 (dt, J=9.0, 1.1 Hz, 1H), 7.49 (ddd, J=9.1, 6.8, 1.3 Hz, 1H), 7.17 (td, J=6.8, 1.1 Hz, 1H). $^{13}$C NMR (101 MHz, DMSO) δ 145.16, 144.88, 137.51, 132.85, 128.24, 127.06, 125.97, 118.91, 117.56, 114.62, 110.97, 109.67, 105.24, 92.83, −0.14. HRMS: calcd for [M+H], 316.12645; found, 316.12656.

Example 54

2-(4-(Trifluoromethyl)phenyl)-3-((trimethylsilyl) ethynyl)imidazo[1,2-a]pyridine (Intermediate Compound)

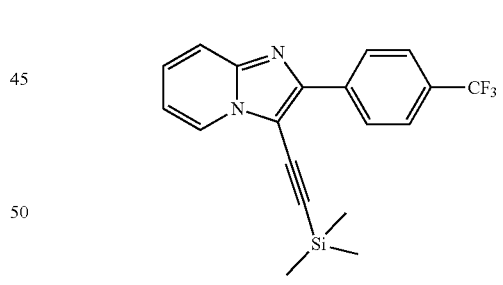

Title compound was prepared according to the General Procedure III (Scheme 1). Mobile phase petrolether/EtOAc (10-50%). Yield: 123 mg (54%). $^{1}$H NMR (401 MHz, DMSO-$d_6$) δ 8.45 (tt, J=6.8, 1.0 Hz, 3H), 7.91-7.82 (m, 2H), 7.74 (dt, J=9.1, 1.1 Hz, 1H), 7.49 (ddd, J=9.1, 6.8, 1.3 Hz, 1H), 7.17 (td, J=6.8, 1.2 Hz, 1H), 0.37 (s, 9H). $^{13}$C NMR (101 MHz, DMSO) δ 145.80, 145.12, 137.36, 137.35, 129.25, 128.93, 128.38, 127.42, 126.23, 126.08 (q, J=3.9 Hz), 117.80, 114.82, 109.61, 105.20, 93.24, 0.18. HRMS: calcd for [M+H], 359.11859; found, 359.11862.

Example 55

2-(4-Fluorophenyl)-3-((trimethylsilyl)ethynyl)imidazo[1,2-a]pyridine (Intermediate Compound)

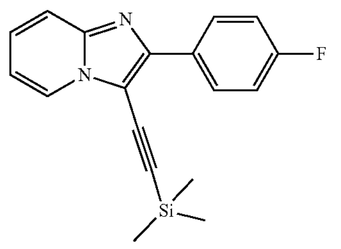 [SMILES: C[Si](C)(C)C#Cc1c(-c2ccc(F)cc2)nc2ccccn12]

Title compound was prepared according to the General Procedure III (Scheme 1). Mobile phase petrolether/EtOAc (10-50%). Yield: 250 mg (69%). $^1$H NMR (401 MHz, DMSO-$d_6$) δ 8.41 (dd, J=6.9, 1.4 Hz, 1H), 8.32-8.25 (m, 2H), 7.70 (dd, J=9.1, 1.4 Hz, 1H), 7.45 (ddt, J=9.0, 6.8, 1.3 Hz, 1H), 7.38-7.31 (m, 2H), 7.13 (tt, J=6.9, 1.3 Hz, 1H), 0.36-0.31 (m, 9H). $^{13}$C NMR (101 MHz, DMSO) δ 162.46 (d, J=246.2 Hz), 146.53, 144.70, 129.74 (d, J=3.0 Hz), 128.79 (d, J=8.4 Hz), 127.74, 125.81, 117.24, 117.24, 115.81 (d, J=21.6 Hz), 114.21, 114.21, 108.58, 103.68, 93.46, −0.05. HRMS: calcd for [M+H], 309.12178; found, 309.12195.

Example 56

2-(4-Ethylphenyl)-3-((trimethylsilyl)ethynyl)imidazo[1,2-a]pyridine (Intermediate Compound)

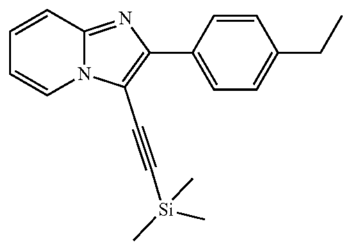 [SMILES: CCc1ccc(-c2nc3ccccn3c2C#C[Si](C)(C)C)cc1]

Title compound was prepared according to the General Procedure III (Scheme 1). Mobile phase petrolether/EtOAc (10-50%). Yield: 126 mg (63%). $^1$H NMR (401 MHz, DMSO-$d_6$) δ 8.39 (dt, J=6.8, 1.2 Hz, 1H), 8.22-8.16 (m, 2H), 7.69 (dt, J=9.0, 1.1 Hz, 1H), 7.42 (ddd, J=9.0, 6.8, 1.3 Hz, 1H), 7.35-7.29 (m, 2H), 7.11 (td, J=6.8, 1.2 Hz, 1H), 2.65 (q, J=7.6 Hz, 2H), 1.20 (t, J=7.6 Hz, 3H), 0.34 (s, 9H). $^{13}$C NMR (101 MHz, DMSO) δ 147.66, 144.72, 144.65, 130.69, 128.12, 127.44, 126.73, 125.64, 117.14, 113.98, 108.33, 103.51, 93.84, 28.18, 15.57, −0.06. HRMS: calcd for [M+H], 319.16250; found, 319.16255.

Example 57

2-(4-Chlorophenyl)-8-fluoro-3-((trimethylsilyl)ethynyl)imidazo[1,2-a]pyridine (Intermediate Compound)

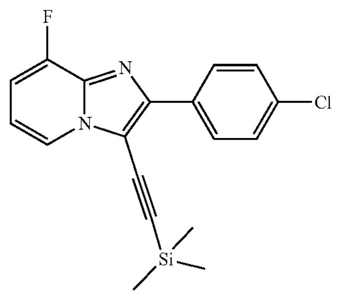 [SMILES: C[Si](C)(C)C#Cc1c(-c2ccc(Cl)cc2)nc2c(F)cccn12]

Title compound was prepared according to the General Procedure III (Scheme 1). Mobile phase petrolether/EtOAc (10-50%). Yield: 125 mg (76%). $^1$H NMR (401 MHz, DMSO-$d_6$) δ 8.28-8.21 (m, 3H), 7.59-7.54 (m, 2H), 7.36 (ddd, J=11.0, 7.8, 0.9 Hz, 1H), 7.09 (ddd, J=7.7, 6.7, 4.6 Hz, 1H), 0.35 (s, 9H). $^{13}$C NMR (101 MHz, DMSO-$d_6$) δ 150.88 (d, J=250.2 Hz), 146.41, 137.25 (d, J=28.8 Hz), 134.04, 131.82, 129.27, 128.67, 122.87 (d, J=4.7 Hz), 113.82 (d, J=7.0 Hz), 110.96 (d, J=16.0 Hz), 109.84, 106.00, 92.94. HRMS: calcd for [M+H], 343.0834; found, 343.0836.

Example 58

2-(4-Chlorophenyl)-7-fluoro-3-((trimethylsilyl)ethynyl)imidazo[1,2-a]pyridine (Intermediate Compound)

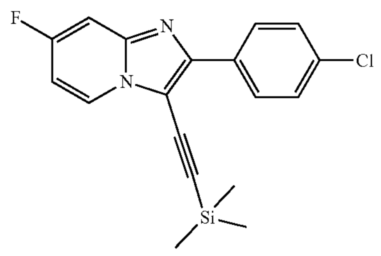 [SMILES: C[Si](C)(C)C#Cc1c(-c2ccc(Cl)cc2)nc2cc(F)ccn12]

Title compound was prepared according to the General Procedure III (Scheme 1). Mobile phase petrolether/EtOAc (10-50%). Yield: 171 mg (58%). $^1$H NMR (401 MHz, DMSO-$d_6$) δ 8.44 (dd, J=7.5, 5.6 Hz, 1H), 8.25-8.19 (m, 2H), 7.64-7.58 (m, 1H), 7.57-7.53 (m, 2H), 7.16 (td, J=7.6, 2.6 Hz, 1H), 0.34 (s, 9H). $^{13}$C NMR (101 MHz, DMSO-$d_6$) δ 161.38 (d, J=251.3 Hz), 147.05, 145.42, 133.58, 131.78, 128.97, 128.23, 109.11, 106.21 (d, J=29.3 Hz), 101.39 (d, J=24.0 Hz), 92.91, −0.12. HRMS: calcd for [M+H], 343.0834; found, 343.0833.

Example 59

2-(4-Chlorophenyl)-6-fluoro-3-((trimethylsilyl)ethynyl)imidazo[1,2-a]pyridine (Intermediate Compound)

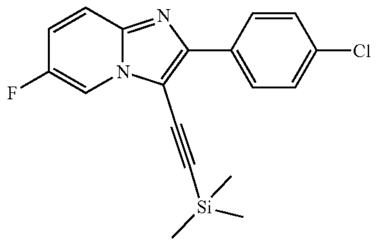 [SMILES: C[Si](C)(C)C#Cc1c(-c2ccc(Cl)cc2)nc2ccc(F)cn12]

Title compound was prepared according to the General Procedure III (Scheme 1). Mobile phase petrolether/EtOAc (10-50%). Yield: 74 mg (40%). $^{1}H$ NMR (401 MHz, DMSO-$d_6$) δ 8.54 (ddd, J=4.0, 2.5, 0.8 Hz, 1H), 8.28-8.18 (m, 2H), 7.77 (ddd, J=9.8, 5.1, 0.8 Hz, 1H), 7.61-7.50 (m, 3H), 0.35 (s, 9H). $^{13}C$ NMR (101 MHz, DMSO-$d_6$) δ 153.80 (d, J=236.5 Hz), 147.10, 142.48, 133.58, 131.85, 128.96, 128.24, 119.52 (d, J=25.6 Hz), 118.26 (d, J=9.0 Hz), 112.95 (d, J=41.3 Hz), 109.91, 92.54, −0.15. HRMS: calcd for [M+H], 343.0834; found, 343.0835.

Example 60

2-(4-Chlorophenyl)-5-fluoro-3-((trimethylsilyl)ethynyl)imidazo[1,2-a]pyridine (Intermediate Compound)

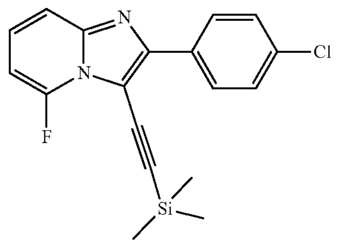 [SMILES: C[Si](C)(C)C#Cc1c(-c2ccc(Cl)cc2)nc2cccc(F)n12]

Title compound was prepared according to the General Procedure III (Scheme 1) and used as crude for the next step without further purification.

Example 61

2-(4-Chlorophenyl)-6,8-difluoro-3-((trimethylsilyl)ethynyl)imidazo[1,2-a]pyridine (Intermediate Compound)

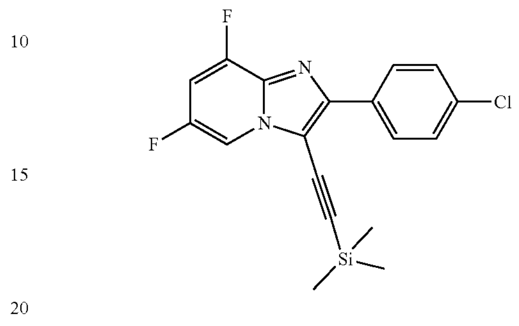

Title compound was prepared according to the General Procedure III (Scheme 1) and used as crude for the next step without further purification.

Example 62

2-(4-Cyclopropylphenyl)-3-((trimethylsilyl)ethynyl)imidazo[1,2-a]pyridine (Intermediate Compound)

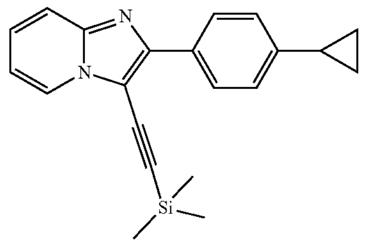 [SMILES: C[Si](C)(C)C#Cc1c(-c2ccc(C3CC3)cc2)nc2ccccn12]

Title compound was prepared according to the General Procedure III (Scheme 1). Mobile phase petrolether/EtOAc (10-50%). Yield: 211 mg (93%). $^{1}H$ NMR (401 MHz, DMSO-$d_6$) δ 8.38 (dt, J=6.8, 1.2 Hz, 1H), 8.19-8.11 (m, 2H), 7.68 (dt, J=9.0, 1.1 Hz, 1H), 7.42 (ddd, J=9.0, 6.8, 1.3 Hz, 1H), 7.22-7.14 (m, 2H), 7.11 (td, J=6.8, 1.2 Hz, 1H), 1.99-1.89 (m, 1H), 1.02-0.90 (m, 2H), 0.77-0.68 (m, 2H), 0.34 (s, 9H). $^{13}C$ NMR (101 MHz, DMSO) δ 147.62, 144.87, 144.64, 130.25, 127.43, 126.63, 125.61, 117.10, 113.95, 108.37, 103.39, 93.85, 15.25, 9.90, −0.04. HRMS: calcd for [M+H], 331.1631; found, 331.1630.

Generale Procedure IV. Click Reaction

Trimethylsilyl(ethynyl)imidazo[2,1-b]thiazole or trimethylsilyl(ethynyl)imidazo[1,2-a]pyridine derivatives were dissolved in THF/$H_2O$ mixture (1:1) and an appropriate azido intermediate (1 eq) was added. The reaction mixture was degassed at 0° C., refilled with argon and $CuSO_4 \cdot 5H_2O$ (10 mol %), KF (1 eq), Na-ascorbate (1 eq) were added in one portion. The reaction mixture was stirred at r.t. and monitored by TLC. After the completion of the reaction, the mixture was diluted with EtOAc and washed with water. The water phase was extracted twice more with EtOAc, combined organic phases were dried over sodium sulfate and evaporated. The residue was purified by flash column chromatography (eluent petrolether/EtOAc or EtOAc/MeOH).

Example 63

2-(4-Chlorophenyl)-3-(1-(3,4-dichlorobenzyl)-1H-1,2,3-triazol-4-yl)imidazo[1,2-a]pyridine

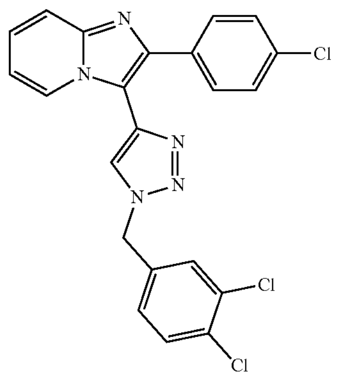 [SMILES: Clc1ccc(-c2nc3ccccn3c2-c2cn(Cc3ccc(Cl)c(Cl)c3)nn2)cc1]

Title compound was prepared according to the General procedure IV (Scheme 1). Mobile phase petrolether/EtOAc (20-70%). Yield 130 mg (57%). $^1$H NMR (500 MHz, DMSO-d6) δ 8.53 (s, 1H), 8.48 (dt, J=1.1 Hz, J=6.9 Hz, 1H), 7.67-7.71 (m, 5H), 7.41-7.44 (m, 2H), 7.39 (ddd, J=1.2 Hz, J=6.8 Hz, J=9.1 Hz, 1H), 7.35 (dd, J=2.1 Hz, J=8.4 Hz, 1H), 7.00 (td, J=1.2 Hz, J=6.8 Hz, 1H), 5.75 (s, 2H). $^{13}$C NMR (101 MHz, $CDCl_3$) δ 144.95, 142.52, 137.05, 136.40, 133.04, 132.86, 131.53, 131.28, 131.21, 130.34, 129.67, 128.71, 128.59, 126.30, 125.95, 125.45, 117.13, 113.38, 111.57, 51.94. HRMS: calcd for [M+H], 454.03876; found, 454.03886.

Example 64

6-(4-Chlorophenyl)-5-(1-(3,4-dichlorobenzyl)-1H-1,2,3-triazol-4-yl)imidazo[2,1-b]thiazole

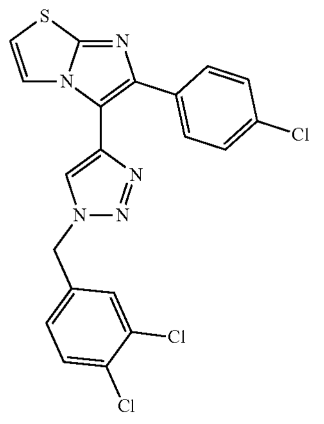 [SMILES: Clc1ccc(-c2nc3sccn3c2-c2cn(Cc3ccc(Cl)c(Cl)c3)nn2)cc1]

Title compound was prepared according to the General procedure IV (Scheme 1). Mobile phase petrolether/EtOAc (20-50%). Yield 268 mg (90%). $^1$H NMR (500 MHz, DMSO-$d_6$) δ 8.49 (s, 1H), 8.04 (d, J=4.5 Hz, 1H), 7.67-7.70 (m, 4H), 7.42-7.45 (m, 2H), 7.39 (d, J=4.5 Hz, 1H), 7.34 (ddm, J=2.1 Hz, J=8.3 Hz, 1H), 5.69 (bs, 2H). $^{13}$C NMR (101 MHz, DMSO) δ 149.63, 142.82, 137.13, 136.99, 133.30, 132.39, 131.49, 131.24, 131.19, 130.42, 129.30, 128.73, 128.66, 123.62, 120.02, 114.52, 113.92, 51.85. HRMS: calcd for [M+H], 459.99518; found, 459.99522.

Example 65

5-(1-(3,4-Dimethoxybenzyl)-1H-1,2,3-triazol-4-yl)-6-phenylimidazo[2,1-b]thiazole

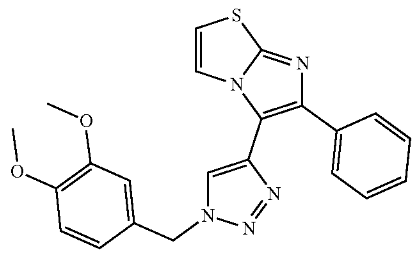 [SMILES: COc1ccc(Cn2cc(-c3c(-c4ccccc4)nc4sccn34)nn2)cc1OC]

Title compound was prepared according to the General procedure IV (Scheme 1). Mobile phase petrolether/EtOAc (20-50%). Yield 120 mg (86%). $^1$H NMR (401 MHz, DMSO-$d_6$) δ 8.40 (s, 1H), 8.01 (d, J=4.5 Hz, 1H), 7.71-7.64 (m, 2H), 7.45-7.40 (m, 2H), 7.38 (d, J=4.5 Hz, 1H), 7.05 (d, J=2.0 Hz, 1H), 6.95 (d, J=8.2 Hz, 1H), 6.90 (dd, J=2.0, 8.2 Hz, 1H), 5.56 (s, 2H), 3.74 (s, 6H). $^{13}$C NMR (101 MHz, DMSO) δ 149.80, 149.24, 142.95, 137.18, 133.60, 132.60, 129.53, 128.95, 128.45, 123.44, 121.13, 120.20, 114.75, 114.35, 112.48, 112.30, 56.00, 55.97, 53.45. HRMS: calcd for [M+H], 452.09425; found, 452.09438.

Example 66

6-(4-Chlorophenyl)-5-(1-(4-methoxybenzyl)-1H-1,2,3-triazol-4-yl)imidazo[2,1-b]thiazole

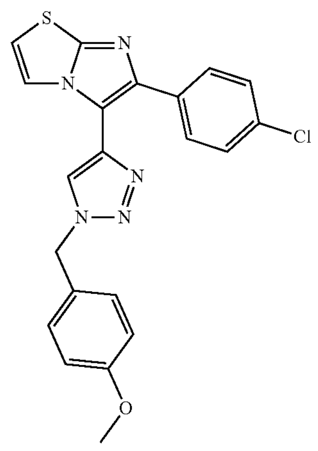 [SMILES: COc1ccc(Cn2cc(-c3c(-c4ccc(Cl)cc4)nc4sccn34)nn2)cc1]

Title compound was prepared according to the General procedure IV (Scheme 1). Mobile phase petrolether/EtOAc (20-50%). Yield 121 mg (86%). $^1$H NMR (401 MHz, DMSO-$d_6$) δ 8.40 (s, 1H), 8.02 (d, J=4.5 Hz, 1H), 7.76-7.61 (m, 3H), 7.45-7.41 (m, 3H), 7.38 (d, J=4.5 Hz, 1H), 7.33 (d, J=8.7 Hz, 2H), 7.01-6.88 (m, 3H), 5.59 (s, 2H), 3.75 (s, 3H). $^{13}$C NMR (101 MHz, DMSO) δ 159.63, 149.81, 142.96, 137.20, 133.60, 132.60, 130.06, 129.52, 128.97, 128.22, 123.42, 120.23, 114.60, 114.34, 55.62, 53.06. HRMS: calcd for [M+H], 422.08369; found, 422.08372.

Example 67

2-(4-Chlorophenyl)-3-(1-(3,4-dimethoxybenzyl)-1H-1,2,3-triazol-4-yl)imidazo[1,2-a]pyridine

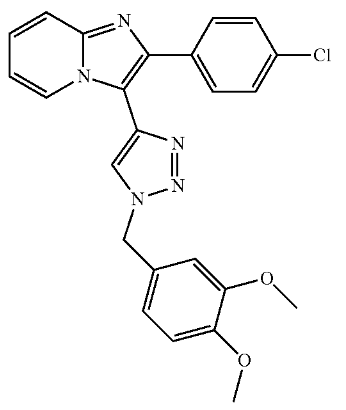 [SMILES: COc1ccc(Cn2cc(-c3c(-c4ccc(Cl)cc4)nc4ccccn34)nn2)cc1OC]

Title compound was prepared according to the General procedure IV (Scheme 1). Mobile phase petrolether/EtOAc (30-60%). Yield 111 mg (81%). $^{1}$H NMR (401 MHz, DMSO-$d_6$) δ 8.47-8.42 (m, 2H), 7.71-7.66 (m, 3H), 7.43-7.36 (m, 3H), 7.05 (d, J=1.9 Hz, 1H), 7.03-6.95 (m, 2H), 6.91 (dd, J=2.0, 8.2 Hz, 1H), 5.62 (s, 2H), 3.75 (d, J=3.8 Hz, 6H). $^{13}$C NMR (101 MHz, DMSO) δ 149.27, 149.24, 145.12, 142.55, 136.41, 133.26, 133.11, 129.92, 128.94, 128.51, 126.60, 125.78, 125.63, 121.03, 117.34, 113.67, 112.40, 112.33, 112.05, 56.00, 55.97, 53.53. HRMS: calcd for [M+Na], 446.13783; found, 446.13786.

Example 68

2-(4-Chlorophenyl)-3-(1-(4-methoxybenzyl)-1H-1,2,3-triazol-4-yl)imidazo[1,2-a]pyridine

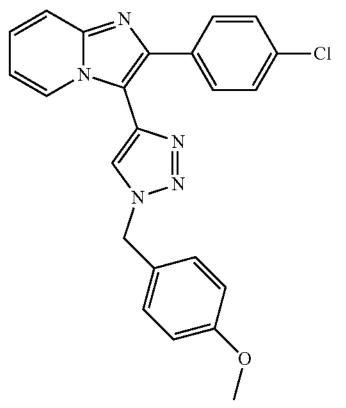 [SMILES: COc1ccc(Cn2cc(-c3c(-c4ccc(Cl)cc4)nc4ccccn34)nn2)cc1]

Title compound was prepared according to the General procedure IV (Scheme 1). Mobile phase petrolether/EtOAc (20-50%). Yield 96 mg (75%). $^{1}$H NMR (401 MHz, DMSO-$d_6$) δ 8.50-8.35 (m, 2H), 7.71-7.66 (m, 3H), 7.44-7.31 (m, 5H), 7.02-6.93 (m, 1H), 5.63 (s, 2H), 3.76 (s, 3H). $^{13}$C NMR (101 MHz, DMSO) δ 159.64, 145.18, 142.68, 136.46, 133.33, 133.07, 129.96, 129.90, 128.95, 128.27, 126.51, 125.76, 125.62, 117.40, 114.64, 113.63, 112.01, 55.63, 53.16. HRMS: calcd for [M+H], 416.12726; found, 416.12730.

Example 69

3-(1-Benzyl-1H-1,2,3-triazol-4-yl)-2-(4-chlorophenyl)imidazo[1,2-a]pyridine

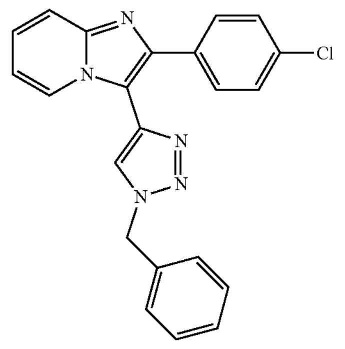 [SMILES: Clc1ccc(-c2nc3ccccn3c2-c2cn(Cc3ccccc3)nn2)cc1]

Title compound was prepared according to the General procedure IV (Scheme 1). Mobile phase petrolether/EtOAc (20-50%). Yield 139 mg (78%). $^{1}$H NMR (401 MHz, DMSO-$d_6$) δ 8.50 (s, 1H), 8.45 (dt, J=1.1, 6.9 Hz, 1H), 7.69 (m, 3H), 7.44-7.37 (m, 8H), 7.00 (td, J=1.2, 6.8 Hz, 2H), 5.73 (s, 2H). $^{13}$C NMR (101 MHz, DMSO) δ 145.20, 142.73, 136.53, 136.40, 133.32, 133.09, 129.92, 129.29, 128.95, 128.65, 128.24, 126.54, 126.12, 125.63, 117.40, 113.65, 111.95, 53.57. HRMS: calcd for [M+H], 386.11670; found, 386.11681.

Example 70

2-(4-Chlorophenyl)-3-(1-(pyridin-2-ylmethyl)-1H-1,2,3-triazol-4-yl)imidazo[1,2-a]pyridine

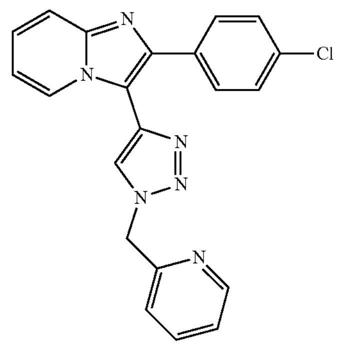 [SMILES: Clc1ccc(-c2nc3ccccn3c2-c2cn(Cc3ccccn3)nn2)cc1]

Title compound was prepared according to the General procedure IV (Scheme 1). Mobile phase petrolether/EtOAc (20-50%). Yield 147 mg (83%). $^{1}$H NMR (401 MHz, DMSO-$d_6$) δ 8.58 (dt, J=4.7, 1.4 Hz, 1H), 8.52 (s, 1H), 8.47 (dt, J=6.9, 1.2 Hz, 1H), 7.85 (td, J=7.7, 1.8 Hz, 1H), 7.77-7.71 (m, 2H), 7.68 (dt, J=9.1, 1.2 Hz, 1H), 7.44-7.39 (m, 2H), 7.39-7.33 (m, 3H), 6.99 (td, J=6.8, 1.2 Hz, 1H), 5.87 (s, 2H). $^{13}$C NMR (101 MHz, DMSO) δ 155.00, 149.65, 144.91, 142.41, 137.55, 136.14, 133.05, 132.80, 129.64, 128.63, 126.55, 126.16, 125.31, 123.45, 122.21, 117.10, 113.29, 111.70, 54.75. HRMS: calcd for [M+H], 387.11195; found, 387.11198.

Example 71

5-(1-Benzyl-1H-1,2,3-triazol-4-yl)-6-(4-chlorophenyl)imidazo[2,1-b]thiazole

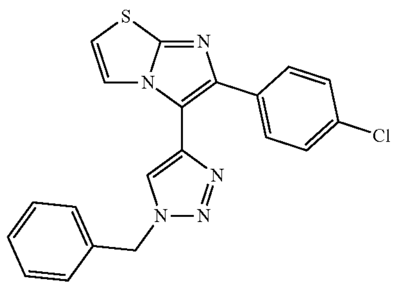 [SMILES: Clc1ccc(-c2nc3sccn3c2-c2cn(Cc3ccccc3)nn2)cc1]

Title compound was prepared according to the General procedure IV (Scheme 1). Mobile phase petrolether/EtOAc (20-50%). Yield 154 mg (87%). $^1$H NMR (401 MHz, DMSO-$d_6$) δ 8.45 (s, 1H), 8.03 (d, J=4.5 Hz, 1H), 7.75-7.65 (m, 2H), 7.45-7.41 (m, 1H), 7.40-7.32 (m, 8H), 5.68 (s, 2H). $^{13}$C NMR (101 MHz, DMSO) δ 149.84, 143.02, 137.27, 136.33, 133.59, 132.62, 129.54, 129.25, 128.97, 128.64, 128.34, 123.75, 120.24, 114.75, 114.29, 53.49. HRMS: calcd for [M+Na], 392.07312; found, 392.07318.

Example 72

6-(4-Chlorophenyl)-5-(1-(pyridin-2-ylmethyl)-1H-1,2,3-triazol-4-yl)imidazo[2,1-b]thiazole

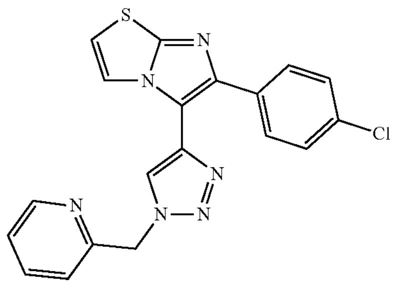 [SMILES: Clc1ccc(-c2nc3sccn3c2-c2cn(Cc3ccccn3)nn2)cc1]

Title compound was prepared according to the General procedure IV (Scheme 1). Mobile phase petrolether/EtOAc (20-50%). Yield 143 mg (80%). $^1$H NMR (401 MHz, DMSO-$d_6$) δ 8.57 (ddd, J=4.8, 1.9, 1.0 Hz, 1H), 8.46 (s, 1H), 8.05 (d, J=4.5 Hz, 1H), 7.85 (td, J=7.7, 1.8 Hz, 1H), 7.77-7.69 (m, 2H), 7.47-7.42 (m, 2H), 7.41-7.35 (m, 2H), 7.33 (dd, J=7.8, 1.1 Hz, 1H), 5.81 (s, 2H). $^{13}$C NMR (101 MHz, DMSO) δ 154.95, 149.61, 149.53, 142.69, 137.55, 136.85, 133.31, 132.31, 129.26, 128.67, 124.16, 123.44, 122.24, 119.94, 114.47, 114.02, 54.64. HRMS: calcd for [M+H], 393.06837; found, 393.06845.

Example 73

3-(1-(4-Chlorobenzyl)-1H-1,2,3-triazol-4-yl)-2-(4-chlorophenyl)imidazo[1,2-a]pyridine

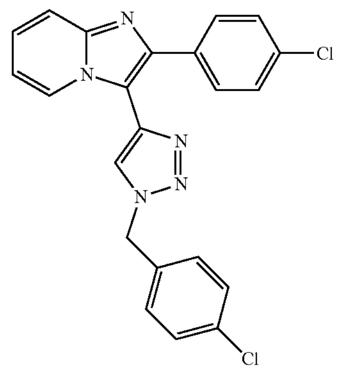 [SMILES: Clc1ccc(Cn2cc(-c3c(-c4ccc(Cl)cc4)nc4ccccn34)nn2)cc1]

Title compound was prepared according to the General procedure IV (Scheme 1). Mobile phase petrolether/EtOAc (20-50%). Yield 145 mg (92%). $^1$H NMR (401 MHz, DMSO-$d_6$) δ 8.49 (s, 1H), 8.45 (dt, J=7.0, 1.2 Hz, 1H), 7.71-7.66 (m, 3H), 7.51-7.47 (m, 2H), 7.45-7.36 (m, 5H), 7.00 (td, J=6.8, 1.2 Hz, 1H), 5.73 (s, 2H). $^{13}$C NMR (101 MHz, DMSO) δ 149.57, 142.75, 137.05, 135.01, 133.28, 133.07, 132.35, 130.04, 129.25, 128.95, 128.69, 123.45, 119.96, 114.46, 113.94, 52.40. HRMS: calcd for [M+H], 420.07773; found, 420.07765.

Example 74

5-(1-(4-Chlorobenzyl)-1H-1,2,3-triazol-4-yl)-6-(4-chlorophenyl)imidazo[2,1-b]thiazole

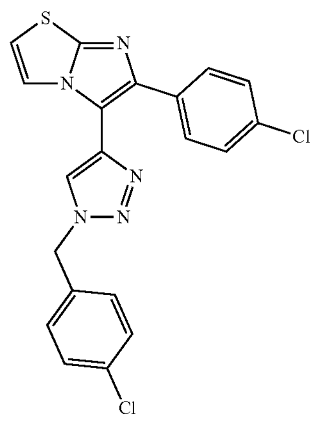 [SMILES: Clc1ccc(Cn2cc(-c3c(-c4ccc(Cl)cc4)nc4sccn34)nn2)cc1]

Title compound was prepared according to the General procedure IV (Scheme 1). Mobile phase petrolether/EtOAc (20-60%). Yield 136 mg (88%). $^1$H NMR (401 MHz, DMSO-$d_6$) δ 8.45 (s, 1H), 8.03 (d, J=4.5 Hz, 1H), 7.75-7.64 (m, 2H), 7.49-7.41 (m, 4H), 7.40-7.36 (m, 3H), 5.68 (s, 2H). $^{13}$C NMR (101 MHz, DMSO) δ 149.57, 142.75, 137.05, 135.01, 133.28, 133.07, 132.35, 130.04, 129.25, 128.95, 128.69, 123.45, 119.96, 114.46, 113.94, 52.40. HRMS: calcd for [M+H], 426.03415; found, 426.03423.

Example 75

6-Chloro-2-(4-chlorophenyl)-3-(1-(3,4-dichlorobenzyl)-1H-1,2,3-triazol-4-yl)imidazo[1,2-b]pyridazine

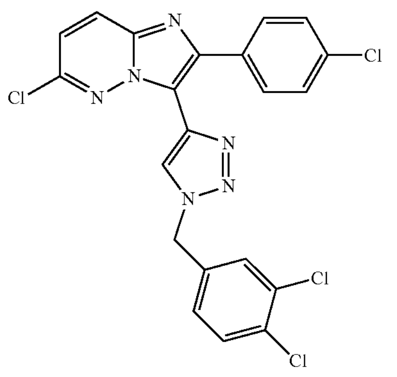 [SMILES: Clc1ccc(-c2nc3ccc(Cl)nn3c2-c2cn(Cc3ccc(Cl)c(Cl)c3)nn2)cc1]

Title compound was prepared according to the General procedure IV (Scheme 1). Mobile phase EtOAc/MeOH (0-10%). Yield 190 mg (89%). $^1$H NMR (401 MHz, DMSO-$d_6$) δ 8.78 (s, 1H), 8.33 (d, J=9.5 Hz, 1H), 7.94-7.82 (m, 2H), 7.73-7.66 (m, 2H), 7.53-7.44 (m, 3H), 7.38 (dd, J=8.4, 2.1 Hz, 1H), 5.82 (s, 2H). $^{13}$C NMR (101 MHz, DMSO) δ 147.12, 143.30, 138.19, 137.36, 135.24, 133.71, 132.67, 131.84, 131.57, 131.52, 130.60, 130.31, 128.90, 128.84, 128.14, 126.57, 120.71, 117.02, 52.16. HRMS: calcd for [M+H], 488.99503; found, 488.99520.

Example 76

6-Chloro-3-(1-(4-chlorobenzyl)-1H-1,2,3-triazol-4-yl)-2-(4-chlorophenyl)imidazo[1,2-b]pyridazine

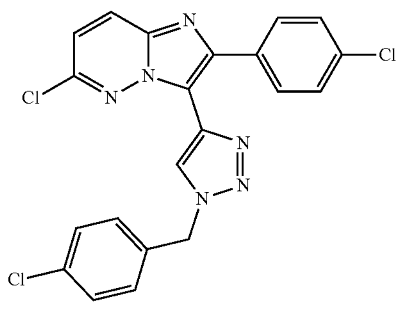 [SMILES: Clc1ccc(Cn2cc(-c3c(-c4ccc(Cl)cc4)nc4ccc(Cl)nn34)nn2)cc1]

Title compound was prepared according to the General procedure IV (Scheme 1). Mobile phase petrolether/EtOAc (30-60%). Yield 63 mg (87%). $^1$H NMR (401 MHz, DMSO-$d_6$) δ 8.74 (s, 1H), 8.33 (d, J=9.4 Hz, 1H), 7.93-7.82 (m, 2H), 7.52-7.46 (m, 6H), 7.44-7.40 (m, 2H), 5.80 (s, 2H). $^{13}$C NMR (101 MHz, DMSO) δ 146.81, 142.97, 137.87, 135.09, 134.87, 133.40, 133.15, 132.40, 130.08, 130.02, 129.02, 128.55, 127.84, 126.10, 120.38, 116.80, 52.44. HRMS: calcd for [M+H], 455.03400; found, 455.03402.

Example 77

3-(1-Benzyl-1H-1,2,3-triazol-4-yl)-6-chloro-2-(4-chlorophenyl)imidazo[1,2-b]pyridazine

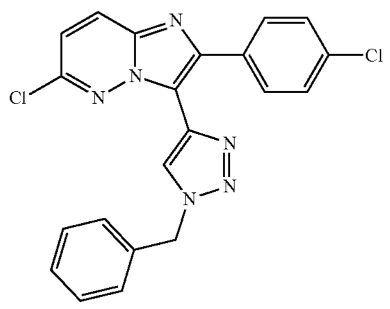 [SMILES: Clc1ccc(-c2nc3ccc(Cl)nn3c2-c2cn(Cc3ccccc3)nn2)cc1]

Title compound was prepared according to the General procedure IV (Scheme 1). Mobile phase petrolether/EtOAc (30-80%). Yield 36 mg (62%). $^1$H NMR (401 MHz, DMSO-$d_6$) δ 8.73 (s, 1H), 8.33 (d, J=9.5 Hz, 1H), 7.89 (d, J=6.6 Hz, 2H), 7.51-7.33 (m, 8H), 5.79 (s, 2H). $^{13}$C NMR (101 MHz, DMSO) δ 146.79, 142.95, 137.85, 136.10, 134.81, 133.39, 132.41, 130.00, 129.01, 128.53, 128.42, 128.07, 127.83, 126.10, 120.36, 116.86, 53.23. HRMS: calcd for [M+H], 421.07298; found, 421.07299.

Example 78

2-(4-Chlorophenyl)-3-(1-(3,4-dichlorobenzyl)-1H-1,2,3-triazol-4-yl)imidazo[1,2-b]pyridazine

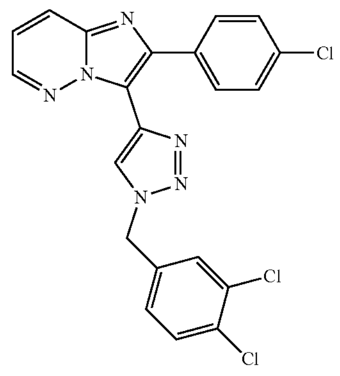 [SMILES: Clc1ccc(-c2nc3cccnn3c2-c2cn(Cc3ccc(Cl)c(Cl)c3)nn2)cc1]

Example 56 (36 mg, 0.07 mmol) was dissolved in MeOH/THF mixture (2 ml, 1:1) and TEA (0.02 ml, 2 eq) was added. The mixture was cooled in an ice bath, degassed and $Pd(OH)_2$ (5 mg, 10 mol %) was added. The reaction mixture was stirred under the hydrogen atmosphere (balloon) overnight at r.t. After the completion the mixture was filtrated over celite, evaporated and the residue purified by flash column chromatography. Mobile phase petrolether/EtOAc (50-100%). Yield 29 mg (90%). $^1$H NMR (401 MHz, DMSO-$d_6$) δ 8.73 (s, 1H), 8.57 (dd, J=4.4, 1.6 Hz, 1H), 8.25 (dd, J=9.2, 1.6 Hz, 1H), 7.89-7.84 (m, 2H), 7.44-7.32 (m, 8H), 5.77 (s, 2H). $^{13}$C NMR (101 MHz, DMSO) δ 144.17, 143.52, 138.93, 136.19, 135.61, 133.91, 131.17, 129.01, 128.39, 128.36, 128.28, 128.06, 125.98, 125.58, 118.51, 115.93, 53.18. HRMS: calcd for [M+H], 353.15092; found, 353.15104.

Example 79

4-((4-(2-(4-Chlorophenyl)imidazo[1,2-a]pyridin-3-yl)-1H-1,2,3-triazol-1-yl)methyl)benzonitrile

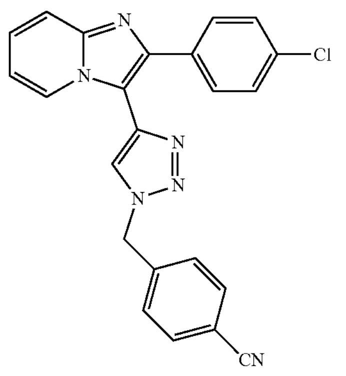 [SMILES: N#Cc1ccc(Cn2cc(-c3c(-c4ccc(Cl)cc4)nc4ccccn34)nn2)cc1]

Title compound was prepared according to the General procedure IV (Scheme 1). Mobile phase petrolether/EtOAc (40-80%). Yield 148 mg (82%). $^{1}H$ NMR (401 MHz, DMSO-$d_6$) δ 8.53 (s, 1H), 8.48 (dt, J=6.9, 1.2 Hz, 1H), 7.94-7.88 (m, 2H), 7.72-7.67 (m, 3H), 7.53-7.48 (m, 2H), 7.47-7.42 (m, 2H), 7.39 (ddd, J=9.1, 6.7, 1.3 Hz, 1H), 7.01 (td, J=6.8, 1.2 Hz, 1H), 5.85 (s, 2H). $^{13}C$ NMR (101 MHz, DMSO) δ 145.23, 142.82, 141.84, 136.69, 133.31, 133.27, 133.14, 129.94, 129.06, 129.00, 126.57, 126.42, 125.70, 119.02, 117.41, 113.65, 111.82, 111.44, 52.96. HRMS: calcd for [M+H], 411.11195; found, 411.11215.

Example 80

3-(1-(3,4-Dichlorobenzyl)-1H-1,2,3-triazol-4-yl)-2-(2,4-dichlorophenyl)imidazo[1,2-a]pyridine

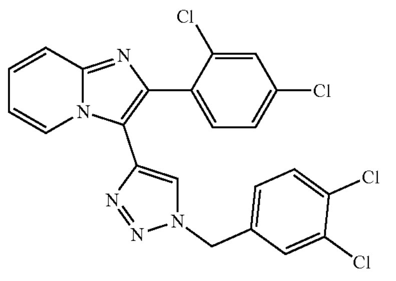 [SMILES: Clc1ccc(-c2nc3ccccn3c2-c2cn(Cc3ccc(Cl)c(Cl)c3)nn2)c(Cl)c1]

Title compound was prepared according to the General procedure IV (Scheme 1). Mobile phase petrolether/EtOAc (40-80%). Yield 120 mg (74%). $^{1}H$ NMR (401 MHz, DMSO-$d_6$) δ 9.11 (dt, J=7.0, 1.1 Hz, 1H), 8.02 (s, 1H), 7.71 (dt, J=9.1, 1.2 Hz, 1H), 7.68 (d, J=2.1 Hz, 1H), 7.64 (d, J=8.3 Hz, 1H), 7.58 (d, J=8.3 Hz, 1H), 7.54 (d, J=2.1 Hz, 1H), 7.52 (dd, J=8.3, 2.1 Hz, 1H), 7.42 (ddd, J=9.1, 6.7, 1.3 Hz, 1H), 7.25 (dd, J=8.3, 2.1 Hz, 1H), 7.11 (td, J=6.8, 1.2 Hz, 1H), 5.67 (s, 2H). $^{13}C$ NMR (101 MHz, DMSO) δ 144.69, 140.47, 137.27, 137.05, 134.19, 133.95, 133.64, 132.58, 131.46, 131.09, 130.00, 129.45, 128.30, 127.75, 126.19, 126.02, 123.26, 117.31, 113.72, 113.61, 51.61. HRMS: calcd for [M+H], 417.06837; found, 417.06839.

Example 81

5-(1-(3,4-Dichlorobenzyl)-1H-1,2,3-triazol-4-yl)-6-(3,4-dichlorophenyl)imidazo[2,1-b]thiazole

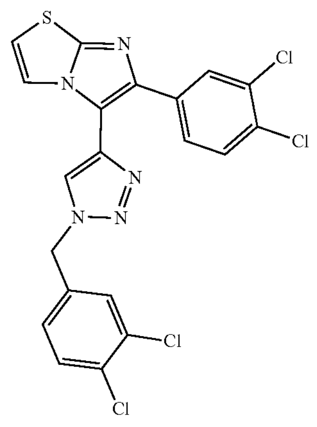 [SMILES: Clc1ccc(Cn2cc(-c3c(-c4ccc(Cl)c(Cl)c4)nc4sccn34)nn2)cc1Cl]

Title compound was prepared according to the General procedure IV (Scheme 1). Mobile phase petrolether/EtOAc (30-60%). Yield 51 mg (92%). $^{1}H$ NMR (401 MHz, DMSO-$d_6$) δ 8.57 (s, 1H), 8.01 (d, J=4.5 Hz, 1H), 7.87 (d, J=2.0 Hz, 1H), 7.71 (d, J=2.1 Hz, 1H), 7.69-7.64 (m, 2H), 7.61 (d, J=8.4 Hz, 1H), 7.40 (d, J=4.5 Hz, 1H), 7.36 (dd, J=8.3, 2.1 Hz, 1H), 5.70 (s, 2H). $^{13}C$ NMR (101 MHz, DMSO) δ 149.77, 141.34, 136.86, 136.81, 135.00, 131.52, 131.39, 131.24, 131.21, 130.87, 130.44, 130.14, 128.90, 128.65, 127.44, 123.91, 119.85, 114.89, 114.40, 51.92. HRMS: calcd for [M+H], 493.95620; found, 493.95625.

Example 82

3-(1-(3,4-Dichlorobenzyl)-1H-1,2,3-triazol-4-yl)-2-(p-tolyl)imidazo[1,2-a]pyridine

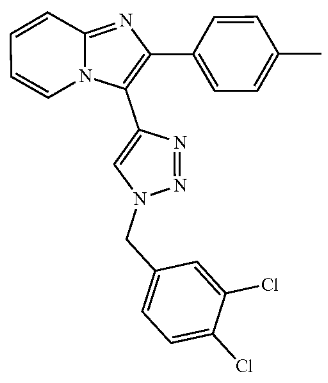 [SMILES: Cc1ccc(-c2nc3ccccn3c2-c2cn(Cc3ccc(Cl)c(Cl)c3)nn2)cc1]

Title compound was prepared according to the General procedure IV (Scheme 1). Mobile phase petrolether/EtOAc (20-70%). Yield 140 mg (84%). $^{1}H$ NMR (401 MHz, DMSO-$d_6$) δ 8.47 (dd, J=7.1, 1.5 Hz, 1H), 8.45 (d, J=1.5 Hz, 0H), 7.72-7.65 (m, 1H), 7.56-7.51 (m, 1H), 7.39-7.33 (m, 1H), 7.16 (d, J=7.8 Hz, 1H), 6.97 (td, J=6.9, 1.7 Hz, 0H), 5.74 (s, 1H), 2.32 (s, 2H). $^{13}C$ NMR (101 MHz, DMSO) δ 144.82, 143.87, 137.48, 137.11, 136.79, 131.51, 131.27, 131.23, 131.16, 130.25, 129.17, 128.54, 125.88, 125.74, 125.30, 116.96, 113.06, 110.91, 51.86, 21.01. HRMS: calcd for [M+H], 434.09338; found, 434.09355.

Example 83

4-((4-(6-(4-Chlorophenyl)imidazo[2,1-b]thiazol-5-yl)-1H-1,2,3-triazol-1-yl)methyl)-benzonitrile

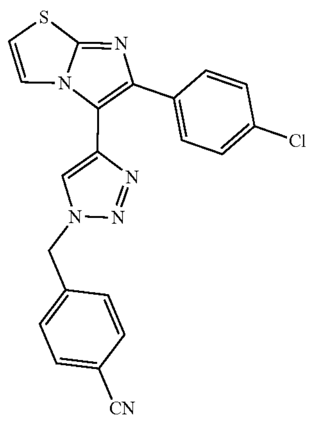 [SMILES: N#Cc1ccc(Cn2cc(-c3c(-c4ccc(Cl)cc4)nc4sccn34)nn2)cc1]

Title compound was prepared according to the General procedure IV (Scheme 1). Mobile phase petrolether/EtOAc (20-70%). Yield 87 mg (87%). $^{1}H$ NMR (401 MHz, DMSO-$d_6$) δ 8.49 (s, 1H), 8.05 (d, J=4.5 Hz, 1H), 7.92-7.79 (m, 2H), 7.73-7.66 (m, 2H), 7.52-7.47 (m, 2H), 7.47-7.42 (m, 2H), 7.39 (d, J=4.5 Hz, 1H), 5.80 (s, 2H). $^{13}C$ NMR (101 MHz, DMSO) δ 149.61, 142.82, 141.48, 137.13, 133.27, 132.93, 132.37, 129.28, 128.83, 128.72, 123.76, 120.00, 118.72, 114.49, 113.87, 111.11, 52.56. HRMS: calcd for [M+H], 487.99978; found, 487.99993.

Example 84

4-(3-(1-(3,4-Dichlorobenzyl)-1H-1,2,3-triazol-4-yl) imidazo[1,2-a]pyridin-2-yl)benzonitrile

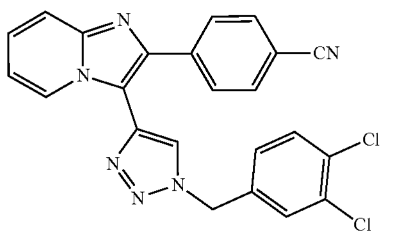 [SMILES: N#Cc1ccc(-c2nc3ccccn3c2-c2cn(Cc3ccc(Cl)c(Cl)c3)nn2)cc1]

Title compound was prepared according to the General procedure IV (Scheme 1). Mobile phase petrolether/EtOAc (30-80%). Yield 189 mg (89%). $^{1}H$ NMR (401 MHz, DMSO-$d_6$) δ 8.59 (s, 1H), 8.44 (dt, J=7.0, 1.1 Hz, 1H), 7.89-7.81 (m, 4H), 7.75-7.69 (m, 3H), 7.42 (ddd, J=9.1, 6.7, 1.3 Hz, 1H), 7.36 (dd, J=8.3, 2.1 Hz, 1H), 7.03 (td, J=6.8, 1.2 Hz, 1H), 5.75 (s, 2H). $^{13}C$ NMR (101 MHz, DMSO) δ 178.80, 132.59, 131.51, 131.28, 131.21, 130.39, 128.58, 128.51, 126.70, 126.27, 125.49, 117.31, 113.66, 52.00. HRMS: calcd for [M+H], 445.07298; found, 445.07299.

Example 85

3-(1-(3,4-Dichlorobenzyl)-1H-1,2,3-triazol-4-yl)-2-(4-methoxyphenyl)imidazo[1,2-a]pyridine

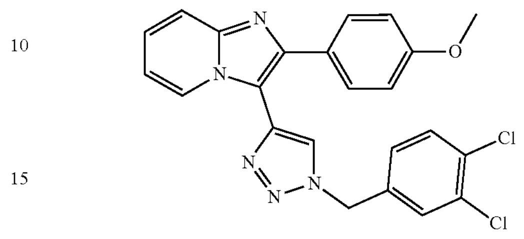

Title compound was prepared according to the General procedure IV (Scheme 1). Mobile phase petrolether/EtOAc (30-80%). Yield 385 mg (92%). $^{1}H$ NMR (401 MHz, DMSO-$d_6$) δ 8.46 (d, J=6.5 Hz, 1H), 7.72-7.64 (m, 1H), 7.63-7.57 (m, 1H), 7.38-7.32 (m, 1H), 6.96 (td, J=6.8, 1.2 Hz, 0H), 6.95-6.90 (m, 1H), 5.74 (s, 1H), 3.78 (s, 2H). $^{13}C$ NMR (101 MHz, DMSO) δ 159.28, 144.78, 143.76, 137.11, 136.88, 131.49, 131.23, 131.14, 130.23, 129.21, 128.52, 126.50, 125.77, 125.70, 125.23, 116.84, 114.00, 112.96, 110.44, 55.28, 51.88. HRMS: calcd for [M+H], 450.08829; found, 450.08826.

Example 86

3-(1-(3,4-Dichlorobenzyl)-1H-1,2,3-triazol-4-yl)-2-(4-(trifluoromethyl)phenyl)imidazo[1,2-a]pyridine

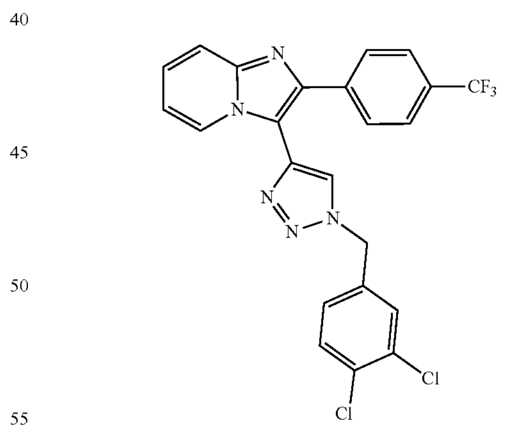

Title compound was prepared according to the General procedure IV (Scheme 1). Mobile phase petrolether/EtOAc (30-80%). Yield 143 mg (86%). $^{1}H$ NMR (401 MHz, DMSO-$d_6$) δ 8.52 (dt, J=7.0, 1.2 Hz, 1H), 8.38 (s, 1H), 8.04-7.96 (m, 2H), 7.57 (d, J=9.1 Hz, 1H), 7.31-7.21 (m, 3H), 6.89 (td, J=6.8, 1.3 Hz, 1H). $^{13}C$ NMR (101 MHz, DMSO) δ 162.01 (d, J=244.2 Hz), 145.01, 143.63, 130.65, 127.68 (d, J=8.2 Hz), 127.09, 125.23, 116.78, 115.77 (d, J=21.5 Hz), 112.51, 109.12. HRMS: calcd for [M+H], 488.06511; found, 488.06511.

Example 87

3-(1-(3,4-Dichlorobenzyl)-1H-1,2,3-triazol-4-yl)-2-(4-fluorophenyl)imidazo[1,2-a]pyridine

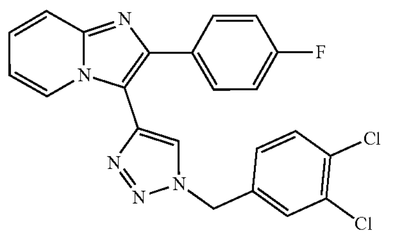 [SMILES: Fc1ccc(-c2nc3ccccn3c2-c2cn(Cc3ccc(Cl)c(Cl)c3)nn2)cc1]

Title compound was prepared according to the General procedure IV (Scheme 1). Mobile phase petrolether/EtOAc (30-80%). Yield 211 mg (74%). $^{1}$H NMR (401 MHz, DMSO-$d_6$) δ 8.50 (s, 1H), 8.48 (dt, J=7.0, 1.2 Hz, 1H), 7.75-7.65 (m, 6H), 7.41-7.32 (m, 2H), 7.24-7.15 (m, 2H), 6.99 (td, J=6.8, 1.2 Hz, 1H), 5.74 (s, 2H). $^{13}$C NMR (101 MHz, DMSO) δ 162.40 (d, J=245.1 Hz), 145.14, 143.14, 137.30, 136.80, 131.80, 131.53, 131.47, 130.91 (d, J=3.1 Hz), 130.62, 130.31 (d, J=8.3 Hz), 128.81, 126.41, 126.10, 125.68, 117.33, 115.82 (d, J=21.5 Hz), 113.53, 111.49, 52.21. HRMS: calcd for [M+H], 438.06831; found, 438.06851.

Example 88

3-(1-(3,4-Dichlorobenzyl)-1H-1,2,3-triazol-4-yl)-2-(4-ethylphenyl)imidazo[1,2-a]pyridine

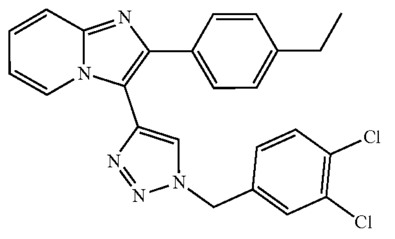 [SMILES: CCc1ccc(-c2nc3ccccn3c2-c2cn(Cc3ccc(Cl)c(Cl)c3)nn2)cc1]

Title compound was prepared according to the General procedure IV (Scheme 1). Mobile phase petrolether/EtOAc (20-70%). Yield 350 mg (70%). $^{1}$H NMR (401 MHz, DMSO-$d_6$) δ 8.48-8.43 (m, 2H), 7.72-7.65 (m, 3H), 7.59-7.54 (m, 2H), 7.38-7.33 (m, 2H), 7.20-7.15 (m, 2H), 6.97 (td, J=6.9, 1.2 Hz, 1H), 5.74 (s, 2H), 2.61 (q, J=7.6 Hz, 2H), 1.19 (t, J=7.6 Hz, 3H). $^{13}$C NMR (101 MHz, DMSO) δ 144.85, 143.88, 143.75, 137.12, 136.79, 131.52, 131.24, 131.19, 130.26, 128.56, 127.95, 127.90, 125.90, 125.86, 125.28, 116.98, 113.09, 110.92, 51.91, 28.10, 15.55. HRMS: calcd for [M+H], 448.10903; found, 448.10914.

Example 89

Methyl 2-chloro-5-((4-(2-(4-chlorophenyl)imidazo[1,2-a]pyridin-3-yl)-1H-1,2,3-triazol-1-yl)-methyl)benzoate

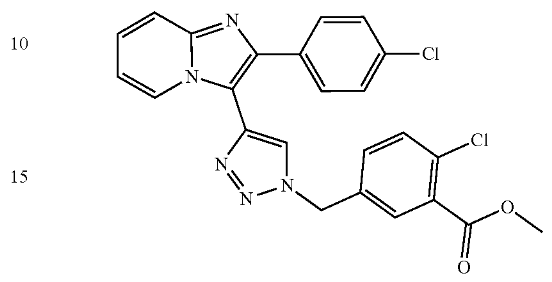

Title compound was prepared according to the General procedure IV (Scheme 1). Mobile phase petrolether/EtOAc (60-90%). Yield 456 mg (84%). $^{1}$H NMR (401 MHz, DMSO-$d_6$) δ 8.54 (s, 1H), 8.46 (dt, J=7.0, 1.1 Hz, 1H), 7.84-7.81 (m, 1H), 7.72-7.67 (m, 3H), 7.65 (d, J=8.3 Hz, 1H), 7.56 (dd, J=8.3, 2.3 Hz, 1H), 7.44-7.40 (m, 2H), 7.40-7.36 (m, 1H), 7.00 (td, J=6.8, 1.2 Hz, 1H), 5.79 (s, 2H), 3.87 (s, 3H). $^{13}$C NMR (101 MHz, DMSO) δ 165.39, 144.95, 142.46, 136.39, 135.56, 133.01, 132.84, 132.82, 131.82, 131.52, 130.65, 130.46, 129.62, 128.68, 126.29, 125.94, 125.39, 117.12, 113.37, 111.55, 52.89, 52.07. HRMS: calcd for [M+H], 478.08328; found, 478.08321.

Example 90

2-(4-Chlorophenyl)-3-(1-(3,4-dichlorophenyl)-1H-1,2,3-triazol-4-yl)imidazo[1,2-a]pyridine

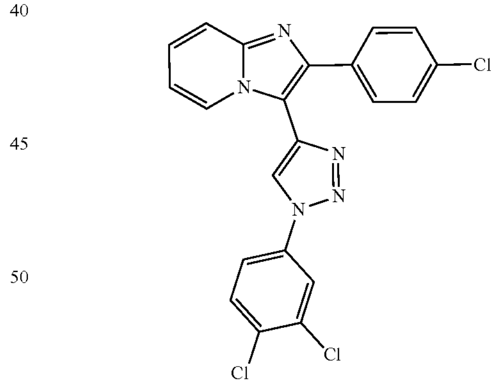

Title compound was prepared according to the General procedure IV (Scheme 1). Mobile phase petrolether/EtOAc (30-100%). Yield 225 mg (73%). $^{1}$H NMR (401 MHz, DMSO-$d_6$) δ 9.31 (s, 1H), 8.49 (dt, J=6.9, 1.1 Hz, 2H), 8.37 (d, J=2.5 Hz, 1H), 8.07 (dd, J=8.8, 2.5 Hz, 1H), 7.95 (d, J=8.8 Hz, 1H), 7.85-7.78 (m, 3H), 7.73 (dt, J=9.1, 1.0 Hz, 2H), 7.48-7.44 (m, 3H), 7.44-7.39 (m, 1H), 7.02 (td, J=6.8, 1.2 Hz, 1H). $^{13}$C NMR (101 MHz, DMSO) δ 145.10, 142.84, 136.98, 136.19, 132.88, 132.84, 132.55, 132.06, 131.49, 129.65, 128.73, 126.53, 125.45, 124.34, 122.30, 120.57, 117.14, 113.39, 110.89. HRMS: calcd for [M+H], 440.02311; found, 440.02321.

Example 91

2-(4-Chlorophenyl)-3-(1-(3,4-dichlorophenethyl)-1H-1,2,3-triazol-4-yl)imidazo[1,2-a]pyridine

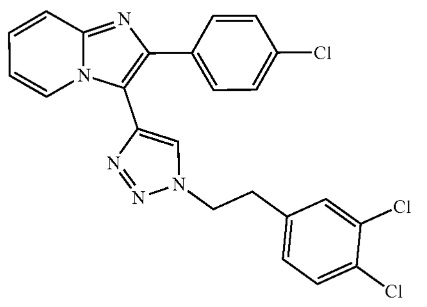 [SMILES: Clc1ccc(-c2nc3ccccn3c2-c2cn(CCc3ccc(Cl)c(Cl)c3)nn2)cc1]

Title compound was prepared according to the General procedure IV (Scheme 1). Mobile phase petrolether/EtOAc (30-100%). Yield 138 mg (95%). $^{1}$H NMR (401 MHz, DMSO-$d_6$) δ 8.33 (s, 0H), 8.25 (d, J=6.9 Hz, 1H), 7.69 (d, J=9.0 Hz, 1H), 7.64 (d, J=8.5 Hz, 1H), 7.58-7.49 (m, 1H), 7.39 (d, J=8.5 Hz, 2H), 7.21-7.13 (m, 1H), 6.99 (t, J=6.6 Hz, 1H), 4.78 (t, J=6.7 Hz, 1H), 3.26 (t, J=6.7 Hz, 1H). $^{13}$C NMR (101 MHz, DMSO) δ 144.84, 142.21, 139.06, 135.60, 132.98, 132.77, 131.08, 131.05, 130.64, 129.49, 129.46, 129.40, 128.61, 126.20, 125.77, 125.00, 117.13, 113.27, 111.64, 50.51, 34.70. HRMS: calcd for [M+H], 468.05441; found, 468.05450.

Example 92

2-Chloro-5-((4-(2-(4-chlorophenyl)-8-fluoroimidazo[1,2-a]pyridin-3-yl)-1H-1,2,3-triazol-1-yl)methyl)benzamide

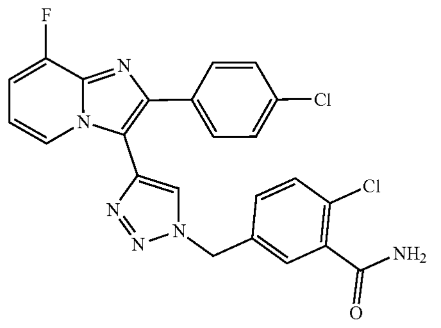 [SMILES: NC(=O)c1cc(Cn2cc(-c3c(-c4ccc(Cl)cc4)nc4c(F)cccn34)nn2)ccc1Cl]

Title compound was prepared according to the General procedure IV (Scheme 1). Mobile phase petrolether/EtOAc (30-100%). Yield 105 mg (89%). $^{1}$H NMR (401 MHz, DMSO-$d_6$) δ 8.59 (s, 1H), 8.35 (dd, J=6.9, 0.9 Hz, 1H), 7.93 (s, 1H), 7.74-7.69 (m, 2H), 7.69-7.67 (m, 1H), 7.54 (d, J=8.2 Hz, 1H), 7.49-7.45 (m, 3H), 7.43 (dd, J=8.2, 2.3 Hz, 1H), 7.31 (ddd, J=11.0, 7.7, 0.9 Hz, 1H), 6.98 (ddd, J=7.7, 6.9, 4.8 Hz, 1H), 5.76 (s, 2H). $^{13}$C NMR (101 MHz, DMSO-$d_6$) δ 168.25, 150.90 (d, J=249.7 Hz), 142.85, 137.98, 137.64 (d, J=28.8 Hz), 136.22 (d, J=1.3 Hz), 135.31, 133.50, 132.72, 131.94 (d, J=9.8 Hz), 130.53, 129.99, 129.94, 129.12, 128.62, 126.38, 122.50 (d, J=4.9 Hz), 113.70, 112.83 (d, J=6.9 Hz), 109.32 (d, J=15.9 Hz), 52.54. HRMS: calcd for [M+H], 481.07412; found, 481.07324.

Example 93

2-Chloro-5-((4-(2-(4-chlorophenyl)-7-fluoroimidazo[1,2-a]pyridin-3-yl)-1H-1,2,3-triazol-1-yl)methyl)benzamide

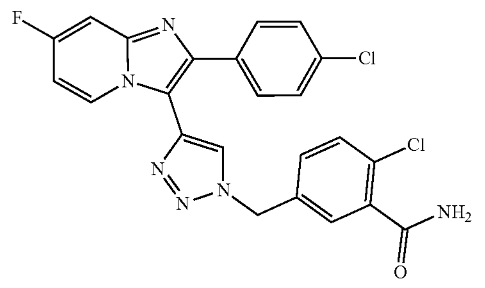 [SMILES: NC(=O)c1cc(Cn2cc(-c3c(-c4ccc(Cl)cc4)nc4cc(F)ccn34)nn2)ccc1Cl]

Title compound was prepared according to the General procedure IV (Scheme 1). Mobile phase petrolether/EtOAc (30-100%). Yield 75 mg (83%). $^{1}$H NMR (401 MHz, DMSO-$d_6$) δ 8.58-8.51 (m, 2H), 7.92 (s, 1H), 7.72-7.65 (m, 3H), 7.58 (ddd, J=9.9, 2.7, 0.8 Hz, 1H), 7.53 (s, 1H), 7.49-7.38 (m, 4H), 7.05 (td, J=7.6, 2.7 Hz, 1H), 5.75 (s, 2H). $^{13}$C NMR (101 MHz, DMSO-$d_6$) δ 167.96, 160.47 (d, J=249.8 Hz), 145.15 (d, J=14.2 Hz), 143.16, 137.68, 136.07, 135.04, 133.02, 132.72, 131.66 (d, J=9.6 Hz), 130.24, 129.63, 129.53, 128.80, 128.32, 127.69 (d, J=11.2 Hz), 125.88, 111.61 (d, J=1.5 Hz), 105.38 (d, J=29.4 Hz), 100.73 (d, J=23.7 Hz), 52.23. HRMS: calcd for [M+H], 481.07412; found, 481.07370.

Example 94

2-Chloro-5-((4-(2-(4-chlorophenyl)-6-fluoroimidazo[1,2-a]pyridin-3-yl)-1H-1,2,3-triazol-1-yl)methyl)benzamide

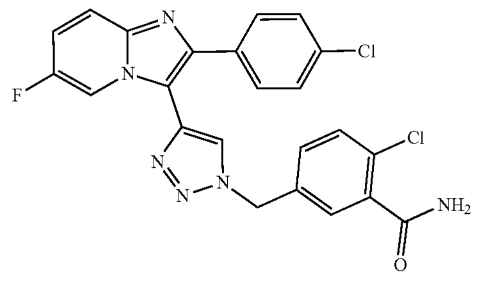 [SMILES: NC(=O)c1cc(Cn2cc(-c3c(-c4ccc(Cl)cc4)nc4ccc(F)cn34)nn2)ccc1Cl]

Title compound was prepared according to the General procedure IV (Scheme 1). Mobile phase petrolether/EtOAc (30-100%). Yield 63 mg (84%). $^{1}$H NMR (401 MHz, DMSO-$d_6$) δ 8.65 (dd, J=4.8, 2.4 Hz, 1H), 8.57 (s, 1H), 7.92 (s, 1H), 7.78 (dd, J=9.8, 5.2 Hz, 1H), 7.69 (dd, J=7.9, 5.8 Hz, 3H), 7.54 (d, J=8.2 Hz, 1H), 7.49-7.43 (m, 4H), 5.75 (s, 2H). $^{13}$C NMR (101 MHz, DMSO-$d_6$) δ 167.98, 153.23 (d, J=234.3 Hz), 143.62 (d, J=2.2 Hz), 142.77, 137.67, 135.98, 135.01, 133.06, 132.77, 131.66 (d, J=9.8 Hz), 130.27 (d, J=8.0 Hz), 129.63, 128.80, 128.38, 125.79, 118.09 (d, J=3.6

Hz), 117.92 (d, J=12.9 Hz), 113.25 (d, J=2.0 Hz), 112.30 (d, J=42.5 Hz), 52.25. HRMS: calcd for [M+H], 481.07412; found, 481.07346.

Example 95

2-Chloro-5-((4-(2-(4-chlorophenyl)-6,8-difluoroimidazo[1,2-a]pyridin-3-yl)-1H-1,2,3-triazol-1-yl) methyl)-benzamide

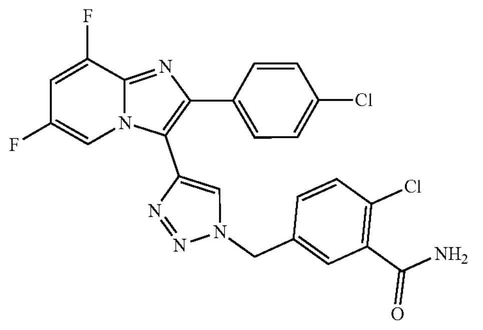 [SMILES: NC(=O)c1cc(Cn2cc(-c3c(-c4ccc(Cl)cc4)nc4c(F)cc(F)cn34)nn2)ccc1Cl]

Title compound was prepared according to the General procedure IV (Scheme 1). Mobile phase petrolether/EtOAc (40-100%). Yield 79 mg (88%). $^{1}$H NMR (401 MHz, DMSO-$d_6$) δ 8.60 (s, 1H), 8.59 (s, 1H), 7.91 (s, 1H), 7.74-7.65 (m, 4H), 7.54 (d, J=8.2 Hz, 1H), 7.51-7.40 (m, 4H), 5.75 (s, 2H). $^{13}$C NMR (101 MHz, DMSO-$d_6$) δ 167.95, 151.91 (dd, J=234.7 Hz, J=11.2 Hz), 149.90 (dd, J=253.3 Hz, J=14.6 Hz), 143.36 (d, J=2.0 Hz), 137.67, 135.47, 135.16, 134.93, 133.35, 132.22, 130.32, 130.21, 129.68, 128.87, 128.39, 126.11, 115.20-114.94 (m), 109.62 (dd, J=43.0, 6.1 Hz), 103.01 (dd, J=30.1, 20.3 Hz), 52.27. HRMS: calcd for [M+H], 499.06470; found, 499.06396.

Example 96

2-Chloro-5-((4-(2-(4-cyclopropylphenyl)imidazo[1,2-a]pyridin-3-yl)-1H-1,2,3-triazol-1-yl)methyl)benzamide

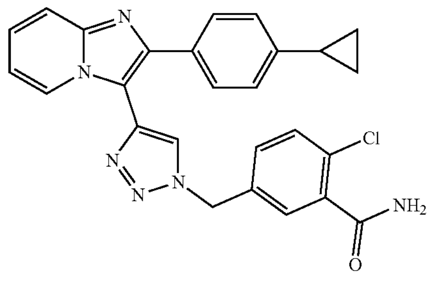 [SMILES: NC(=O)c1cc(Cn2cc(-c3c(-c4ccc(C5CC5)cc4)nc4ccccn34)nn2)ccc1Cl]

Title compound was prepared according to the General procedure IV (Scheme 1). Mobile phase petrolether/EtOAc (40-100%). Yield 200 mg (92%). $^{1}$H NMR (401 MHz, DMSO-$d_6$) δ 8.50 (s, 1H), 8.47 (dt, J=7.0, 1.2 Hz, 1H), 8.01-7.92 (m, 1H), 7.71 (s, 1H), 7.67 (dt, J=9.1, 1.2 Hz, 1H), 7.60-7.52 (m, 3H), 7.48 (d, J=2.2 Hz, 1H), 7.43 (dd, J=8.3, 2.3 Hz, 1H), 7.35 (ddd, J=9.1, 6.7, 1.3 Hz, 1H), 7.10-7.05 (m, 2H), 6.97 (td, J=6.8, 1.3 Hz, 1H), 5.76 (s, 2H), 1.93 (tt, J=8.4, 5.1 Hz, 1H), 1.01-0.87 (m, 2H), 0.74-0.66 (m, 2H).

$^{13}$C NMR (101 MHz, DMSO) δ 168.00, 144.86, 143.97, 143.81, 137.72, 136.79, 135.17, 131.08, 130.24, 130.19, 129.66, 128.27, 127.82, 125.84, 125.75, 125.53, 125.24, 116.96, 113.04, 110.88, 52.20, 15.18, 9.84. HRMS: calcd for [M+H], 469.15381; found, 469.15344.

Example 97

2-(4-Chlorophenyl)-3-(1-(4-(methylthio)benzyl)-1H-1,2,3-triazol-4-yl)imidazo[1,2-a]pyridine

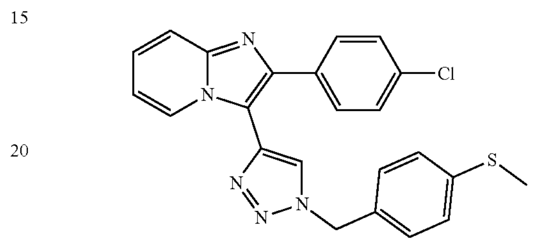

Title compound was prepared according to the General procedure IV (Scheme 1). Mobile phase petrolether/EtOAc (40-100%). Yield 72 mg (80%). $^{1}$H NMR (401 MHz, DMSO-$d_6$) δ 8.46 (s, 1H), 8.44 (dt, J=6.9, 1.2 Hz, 1H), 7.72-7.65 (m, 3H), 7.44-7.35 (m, 3H), 7.33-7.27 (m, 3H), 6.99 (td, J=6.8, 1.2 Hz, 1H), 5.67 (s, 2H), 2.47 (s, 3H). $^{13}$C NMR (101 MHz, DMSO) δ 144.91, 142.43, 138.60, 136.24, 133.02, 132.81, 132.52, 129.62, 128.76, 128.67, 126.28, 126.24, 125.67, 125.34, 117.10, 113.35, 111.67, 52.88. HRMS: calcd for [M+H], 431.09715; found, 431.09723.

Example 98

2-(4-Chlorophenyl)-3-(1-(4-(methylsulfonyl)benzyl)-1H-1,2,3-triazol-4-yl)imidazo[1,2-a]pyridine

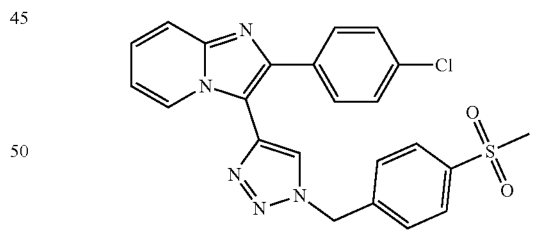

Title compound was prepared according to the General procedure IV (Scheme 1). Mobile phase petrolether/EtOAc (40-100%). Yield 613 mg (92%). $^{1}$H NMR (401 MHz, DMSO-$d_6$) δ 8.52 (dt, J=6.8, 1.1 Hz, 1H), 8.07 (s, 1H), 7.98 (m, 2H), 7.72 (dt, J=9.1, 1.1 Hz, 1H), 7.69 (m, 2H), 7.60 (m, 2H), 7.45 (m, 2H), 7.42 (ddd, J=9.1, 6.8, 1.1 Hz, 1H), 7.04 (td, J=6.8, 1.1 Hz, 1H), 5.97 (s, 2H), 3.23 (s, 3H). $^{13}$C NMR (101 MHz, DMSO-$d_6$) δ 145.13, 143.06, 141.54, 140.72, 137.61, 135.29, 133.03, 132.90, 129.83, 128.91, 128.72, 127.68, 126.50, 125.39, 117.20, 113.61, 111.13, 57.56, 43.65. HRMS: calcd for [M−H], 462.07970; found, 462.07935.

Example 99

2-(4-Chlorophenyl)-3-(1-(4-(pyrrolidin-1-ylsulfonyl) benzyl)-1H-1,2,3-triazol-4-yl)imidazo[1,2-a]pyridine

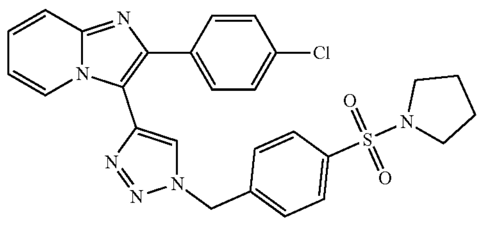 [SMILES: O=S(=O)(c1ccc(Cn2cc(-c3c(-c4ccc(Cl)cc4)nc4ccccn34)nn2)cc1)N1CCCC1]

Title compound was prepared according to the General procedure IV (Scheme 1). Mobile phase petrolether/EtOAc (40-100%). Yield 144 mg (93%). $^{1}$H NMR (401 MHz, DMSO-$d_6$) δ 8.49 (d, J=6.6 Hz, 1H), 8.03 (s, 1H), 7.85 (m, 2H), 7.67-7.73 (m, 3H), 7.57 (m, 2H), 7.43 (m, 2H), 7.40 (m, 1H), 7.02 (t, J=6.6 Hz, 1H), 5.94 (s, 2H), 3.17 (m, 4H), 1.66 (m, 4H). $^{13}$C NMR (101 MHz, DMSO-$d_6$) δ 144.97, 142.99, 140.4, 137.50, 136.50, 134.97, 132-132.89 (m), 129.62, 128.55, 127.63, 126.13, 125.07, 116.98, 113.26, 110.97, 57.43, 47.71, 24.65. HRMS: calcd for [M−H], 517.12190; found, 517.12134.

Example 100

2-(4-Chlorophenyl)-3-(1-(1-phenylethyl)-1H-1,2,3-triazol-4-yl)imidazo[1,2-a]pyridine

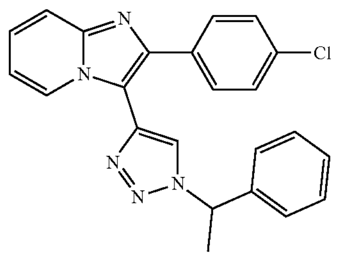 [SMILES: CC(c1ccccc1)n1cc(-c2c(-c3ccc(Cl)cc3)nc3ccccn23)nn1]

Title compound was prepared according to the General procedure IV (Scheme 1). Mobile phase petrolether/EtOAc (40-100%). Yield 72 mg (80%). $^{1}$H NMR (401 MHz, DMSO-$d_6$) δ 8.58 (s, 1H), 8.41 (dt, J=6.9, 1.2 Hz, 1H), 7.69 (dd, J=8.4, 1.7 Hz, 3H), 7.44-7.32 (m, 9H), 6.99 (td, J=6.8, 1.2 Hz, 1H), 6.08 (q, J=7.1 Hz, 1H), 1.96 (d, J=7.1 Hz, 3H). $^{13}$C NMR (101 MHz, DMSO) δ 144.88, 142.41, 141.14, 136.02, 133.00, 132.75, 129.52, 128.95, 128.58, 128.24, 126.43, 126.20, 125.28, 124.60, 117.08, 113.30, 111.70, 59.89, 21.25. HRMS: calcd for [M+H], 400.13235; found, 400.13214.

Example 101

2-(4-Chlorophenyl)-3-(1-(4-nitrobenzyl)-1H-1,2,3-triazol-4-yl)imidazo[1,2-a]pyridine

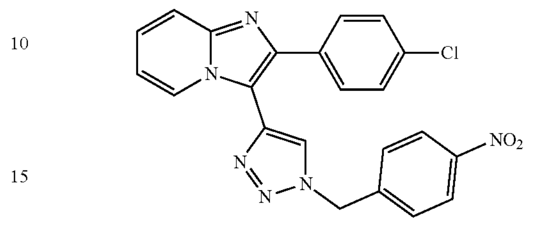

Title compound was prepared according to the General procedure IV (Scheme 1). Mobile phase petrolether/EtOAc (40-100%). Yield 253 mg (88%). $^{1}$H NMR (401 MHz, DMSO-$d_6$) δ 8.56 (s, 1H), 8.49 (dt, J=6.9, 1.2 Hz, 1H), 8.31-8.21 (m, 2H), 7.73-7.67 (m, 3H), 7.62-7.54 (m, 2H), 7.47-7.41 (m, 2H), 7.39 (ddd, J=9.0, 6.7, 1.3 Hz, 1H), 7.00 (td, J=6.8, 1.3 Hz, 1H), 5.92 (s, 2H). $^{13}$C NMR (101 MHz, DMSO) δ 147.73, 145.24, 143.78, 142.85, 136.75, 133.30, 133.14, 129.95, 129.39, 129.00, 126.55, 126.44, 125.70, 124.43, 117.40, 113.64, 111.80, 52.70. HRMS: calcd for [M−H], 430.09; found, 429.555.

Example 102

3-(1-(4-Chloro-3-nitrobenzyl)-1H-1,2,3-triazol-4-yl)-2-(4-chlorophenyl)imidazo[1,2-a]pyridine

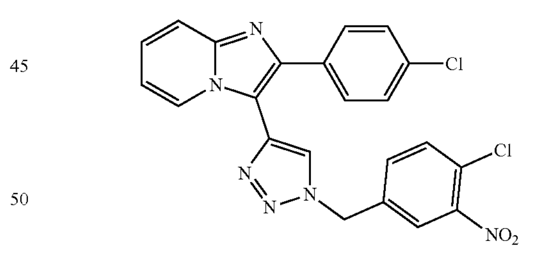

Title compound was prepared according to the General procedure IV (Scheme 1). Mobile phase petrolether/EtOAc (40-100%). Yield 835 mg (83%). $^{1}$H NMR (401 MHz, DMSO-$d_6$) δ 8.58 (s, 1H), 8.50 (dt, J=6.9, 1.2 Hz, 1H), 8.15 (d, J=2.1 Hz, 1H), 7.82 (d, J=8.4 Hz, 1H), 7.73-7.65 (m, 4H), 7.43-7.38 (m, 2H), 7.36 (ddd, J=9.1, 6.7, 1.3 Hz, 1H), 6.98 (td, J=6.8, 1.2 Hz, 1H). $^{13}$C NMR (101 MHz, DMSO) δ 147.65, 144.93, 142.50, 136.94, 136.53, 133.62, 132.99, 132.85, 132.31, 129.63, 128.62, 126.15, 125.94, 125.41, 125.39, 125.10, 117.06, 113.23, 111.50, 51.70. HRMS: calcd for [M−H], 465.06281; found, 465.06250.

Example 103

2-Chloro-5-(1-(4-(2-(4-chlorophenyl)imidazo[1,2-a]pyridin-3-yl)-1H-1,2,3-triazol-1-yl)ethyl)benzamide

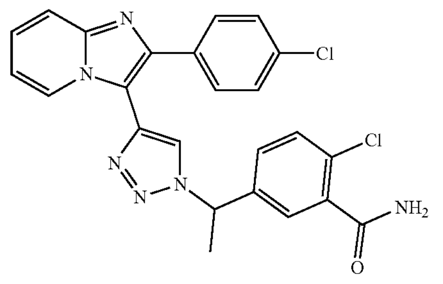

Title compound was prepared according to the General procedure IV (Scheme 1). Mobile phase petrolether/EtOAc (40-100%). Yield 56 mg (81%). $^{1}H$ NMR (401 MHz, DMSO-$d_6$) δ 8.67 (s, 1H), 8.42 (dt, J=7.0, 1.2 Hz, 1H), 7.96 (s, 1H), 7.74-7.67 (m, 4H), 7.54 (d, J=8.3 Hz, 1H), 7.45 (ddt, J=9.2, 7.5, 2.4 Hz, 4H), 7.38 (ddd, J=9.1, 6.7, 1.3 Hz, 1H), 6.99 (td, J=6.8, 1.2 Hz, 1H), 6.15 (q, J=7.1 Hz, 1H), 1.97 (d, J=7.1 Hz, 3H). $^{13}C$ NMR (101 MHz, DMSO) δ 168.06, 144.94, 142.43, 140.11, 137.69, 136.14, 132.97, 132.88, 130.24, 129.51, 128.71, 126.87, 126.27, 125.32, 124.66, 117.10, 113.32, 111.63, 59.04, 21.07. HRMS: calcd for [M+H], 477.09919; found, 477.09891.

Scheme 2.

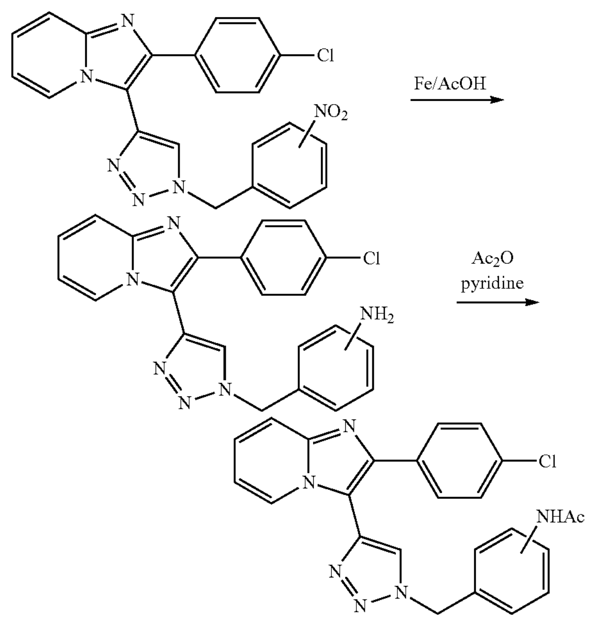

General Procedure V. Nitro Group Reduction

Nitro derivative was dissolved in MeOH and AcOH (7 eq) and Fe (3.5 eq) was added (Scheme 2). The reaction mixture was stirred at reflux until the completion of the reaction. After cooling to r.t., the mixture was extracted with EtOAc, washed with $NaHCO_3$ solution and the organic phase was dried over sodium sulfate and evaporated. The residue was purified by flash column chromatography.

Example 104

4-((4-(2-(4-Chlorophenyl)imidazo[1,2-a]pyridin-3-yl)-1H-1,2,3-triazol-1-yl)methyl)aniline

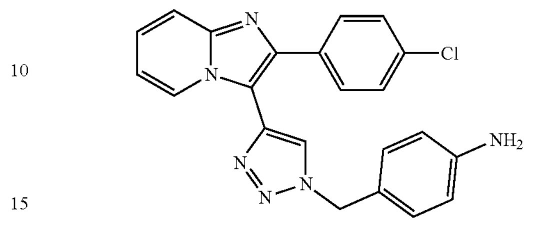

Title compound was prepared according to the General procedure V (Scheme 2). Mobile phase cyclohexan/EtOAc (40-100%). Yield 123 mg (78%). $^{1}H$ NMR (401 MHz, DMSO-$d_6$) δ 8.41 (dt, J=7.0, 1.3 Hz, 1H), 8.39 (s, 1H), 7.72-7.65 (m, 3H), 7.43-7.32 (m, 3H), 7.10-7.04 (m, 2H), 6.98 (td, J=6.8, 1.3 Hz, 1H), 6.59-6.53 (m, 2H), 5.48 (s, 2H), 5.20 (s, 2H). $^{13}C$ NMR (101 MHz, DMSO) δ 149.31, 145.14, 142.57, 136.35, 133.35, 133.06, 129.86, 129.63, 128.90, 126.44, 125.58, 125.47, 122.83, 117.37, 114.23, 113.57, 112.10, 53.72. HRMS: calcd for [M+H], 401.12760; found, 401.12735.

Example 105

2-Chloro-5-((4-(2-(4-chlorophenyl)imidazo[1,2-a]pyridin-3-yl)-1H-1,2,3-triazol-1-yl)methyl)-aniline

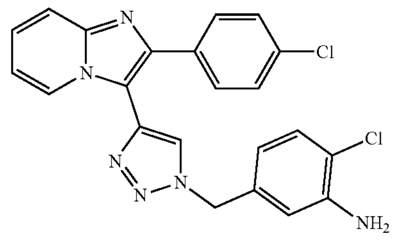 [SMILES: O=[N+]([O-])c1cc(Cn2cc(-c3c(-c4ccc(Cl)cc4)nc4ccccn34)nn2)ccc1Cl]

Title compound was prepared according to the General procedure V (Scheme 2). Mobile phase cyclohexan/EtOAc (40-100%). Yield 490 mg (79%). $^{1}H$ NMR (401 MHz, DMSO-$d_6$) δ 8.46 (dt, J=7.0, 1.2 Hz, 1H), 8.44 (s, 1H), 7.73-7.66 (m, 3H), 7.44-7.39 (m, 2H), 7.37 (ddd, J=9.1, 6.7, 1.2 Hz, 1H), 7.21 (d, J=8.2 Hz, 1H), 6.99 (td, J=6.8, 1.2 Hz, 1H), 6.71 (d, J=2.1 Hz, 1H), 6.52-6.47 (m, 1H), 5.59 (s, 2H), 5.50 (s, 2H). $^{13}C$ NMR (101 MHz, DMSO) δ 145.11, 144.88, 142.37, 136.29, 135.75, 132.96, 132.81, 132.80, 129.65, 129.60, 129.49, 128.65, 128.61, 126.19, 126.14, 125.74, 125.33, 117.07, 116.94, 116.02, 114.31, 113.30, 111.65, 52.95. HRMS: calcd for [M+H], 435.08863; found, 435.08815.

General Procedure VI. Acetylation of Aniline Moieties

Compounds with aniline moiety was dissolved in dioxane and $Ac_2O$ (1.5 eq) was added followed by pyridine (1.5 eq). The reaction mixture was stirred at r.t. overnight. After the completion of the reaction the mixture was evaporated, diluted with EtOAc and washed with water. Organic phase was dried over sodium sulfate and evaporated. The residue was purified by flash column chromatography.

Example 106

N-(4-((4-(2-(4-chlorophenyl)imidazo[1,2-a]pyridin-3-yl)-1H-1,2,3-triazol-1-yl)methyl)phenyl)-acetamide

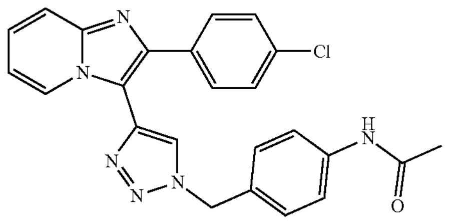 [SMILES: CC(=O)Nc1ccc(Cn2cc(-c3c(-c4ccc(Cl)cc4)nc4ccccn34)nn2)cc1]

Title compound was prepared according to the General procedure VI (Scheme 2). Mobile phase cyclohexan/EtOAc (40-100%). Yield 63 mg (92%). $^{1}H$ NMR (401 MHz, DMSO-$d_6$) δ 10.02 (s, 1H), 8.45 (s, 1H), 8.45-8.42 (m, 1H), 7.72-7.66 (m, 3H), 7.63-7.58 (m, 2H), 7.39 (s, 2H), 7.39-7.34 (m, 1H), 7.33-7.28 (m, 2H), 6.99 (td, J=6.8, 1.2 Hz, 1H), 5.65 (s, 2H), 2.04 (s, 3H). $^{13}C$ NMR (101 MHz, DMSO) δ 168.54, 144.88, 142.37, 139.48, 136.20, 133.04, 132.78, 130.37, 129.59, 128.65, 128.62, 126.18, 125.58, 125.34, 119.31, 117.08, 113.30, 111.69, 66.52, 53.00, 24.17. HRMS: calcd for [M+H], 443.13816; found, 443.13773.

Example 107

N-(2-chloro-5-((4-(2-(4-chlorophenyl)imidazo[1,2-a]pyridin-3-yl)-1H-1,2,3-triazol-1-yl)methyl)-phenyl)acetamide

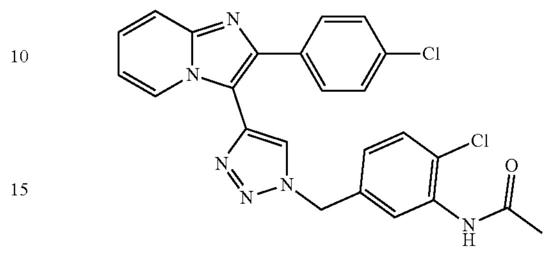

Title compound was prepared according to the General procedure VI (Scheme 2). Mobile phase cyclohexan/EtOAc (30-100%). Yield 75 mg (90%). $^{1}H$ NMR (401 MHz, DMSO-$d_6$) δ 9.58 (s, 1H), 8.54 (s, 1H), 8.46 (dt, J=6.9, 1.2 Hz, 1H), 7.73-7.67 (m, 4H), 7.54 (d, J=8.3 Hz, 1H), 7.46-7.41 (m, 2H), 7.38 (ddd, J=9.0, 6.7, 1.3 Hz, 1H), 7.17 (dd, J=8.3, 2.2 Hz, 1H), 6.99 (td, J=6.8, 1.2 Hz, 1H), 5.74 (s, 2H), 2.11 (s, 3H). $^{13}C$ NMR (101 MHz, DMSO) δ 169.27, 145.22, 142.68, 136.54, 135.83, 135.80, 133.25, 133.11, 130.25, 129.85, 129.00, 127.90, 126.58, 126.28, 125.78, 125.66, 125.41, 117.35, 114.34, 113.64, 111.84, 52.79, 23.86. HRMS: calcd for [M+H], 477.09919; found, 477.09866.

Scheme 3.

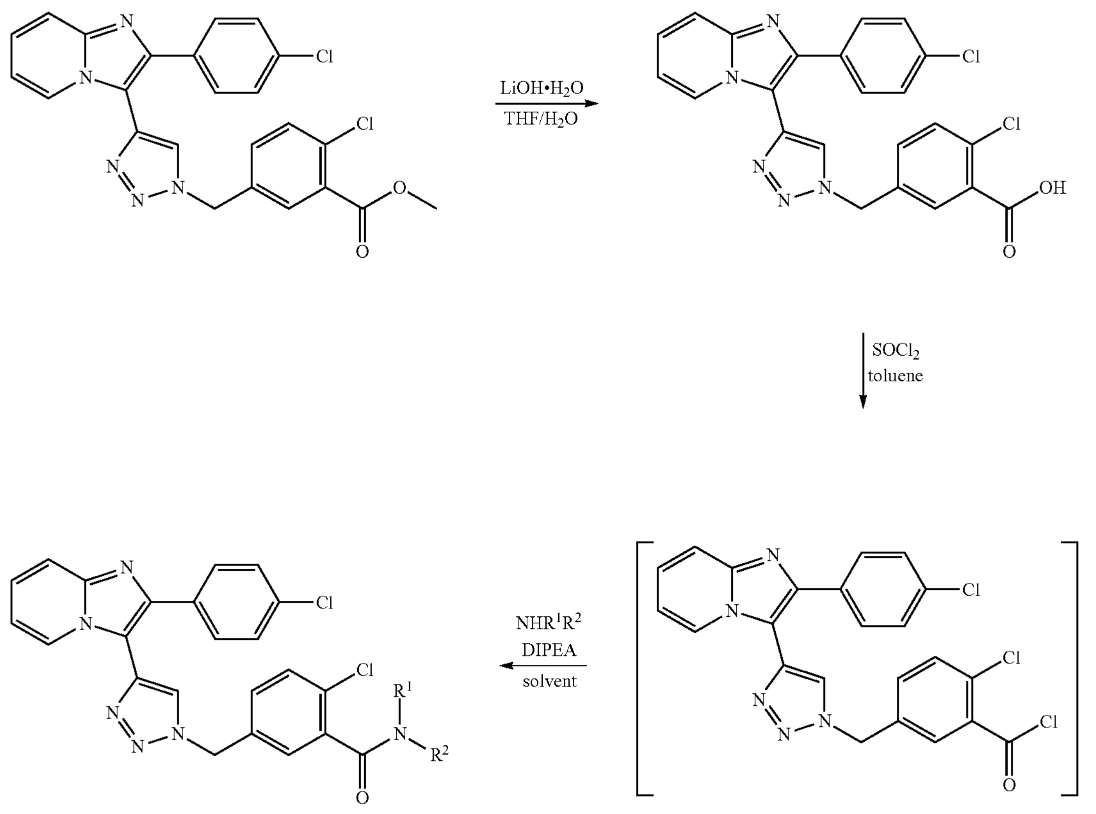

General Procedure VII. Ester Hydrolysis

Methyl or ethyl ester derivative was dissolved in THF/$H_2O$ 2:1 and $LiOH{\cdot}H_2O$ (4 eq) was added in one portion. A Reaction was stirred at r.t. and monitored by TLC. After the completion of the reaction, the mixture was extracted with EtOAc, water phase was acidified to pH 2 and extracted again with EtOAc. Organic phase was dried over sodium sulfate and purified by reverse-phase flash column chromatography.

Example 108

2-Chloro-5-((4-(2-(4-chlorophenyl)imidazo[1,2-a]pyridin-3-yl)-1H-1,2,3-triazol-1-yl)methyl)-benzoic acid

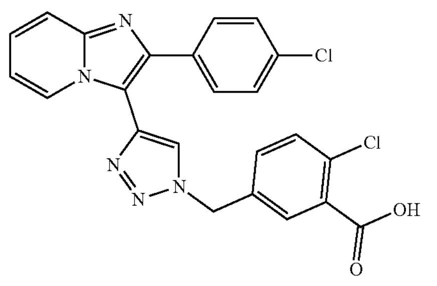 [SMILES: O=C(O)c1cc(Cn2cc(-c3c(-c4ccc(Cl)cc4)nc4ccccn34)nn2)ccc1Cl]

Title compound was prepared according to the General Procedure VII (Scheme 3). Mobile phase: $H_2O$/MeOH (10-80%). Yield 528 mg (92%). $^1$H NMR (401 MHz, DMSO-$d_6$) δ 8.56 (s, 1H), 8.46 (d, J=6.9 Hz, 1H), 7.78 (d, J=2.3 Hz, 1H), 7.73-7.67 (m, 3H), 7.62 (d, J=8.3 Hz, 1H), 7.52 (dd, J=8.3, 2.3 Hz, 1H), 7.41 (dd, J=18.9, 8.6 Hz, 3H), 7.01 (t, J=6.8 Hz, 1H), 5.79 (s, 2H). $^{13}$C NMR (101 MHz, DMSO) δ 166.58, 144.94, 142.42, 136.36, 135.43, 133.00, 132.85, 132.14, 131.83, 131.66, 131.37, 130.37, 129.57, 128.70, 126.28, 125.98, 125.36, 117.11, 113.35, 111.54, 52.11. HRMS: calcd for [M+H], 430.10653; found, 430.10615.

General Procedure VIII. Amide Preparation

Carboxylic acid derivative was placed in a round bottom flask and toluene was added (5 ml) followed by an addition of thionyl chloride (0.5 ml, in excess). The reaction mixture was stirred at 90° C. overnight. The reaction mixture was evaporated to dryness, co-evaporated with toluene and used directly for the next step without any purification. Acyl chloride derivative was dissolved in dry DCM and cooled in an ice bath. An appropriate amine (1.2 eq) was added followed by an addition of DIPEA (1.5 eq or 2 eq in case of amine salts). Reaction mixture was stirred at r.t. and monitored by TLC or LCMS. After completion of the reaction, the mixture was diluted with DCM, washed with water and purified by reverse phase flash CC or flash column chromatography.

Example 109

2-Chloro-5-((4-(2-(4-chlorophenyl)imidazo[1,2-a]pyridin-3-yl)-1H-1,2,3-triazol-1-yl)methyl)-N-methoxy-N-methylbenzamide

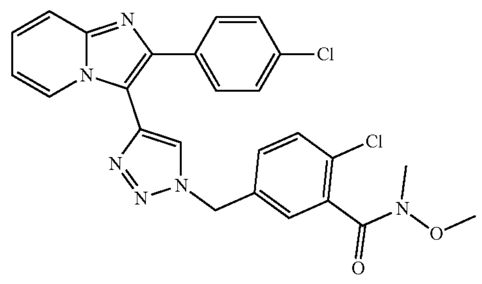 [SMILES: CON(C)C(=O)c1cc(Cn2cc(-c3c(-c4ccc(Cl)cc4)nc4ccccn34)nn2)ccc1Cl]

Title compound was prepared according to the General procedure VIII (Scheme 3) with a minor modification. 2-Chloro-5-((4-(2-(4-chlorophenyl)imidazo[1,2-a]pyridin-3-yl)-1H-1,2,3-triazol-1-yl)methyl)-benzoic acid (528 mg, 1.13 mmol) was dissolved in dry DCM (8 ml) and cooled in a ice bath. Oxalyl chloride (0.2 mL, 2 eq) was added followed by catalytic amount of DMF. The reaction mixture was stirred at r.t. overnight. The solvent was evaporated and crude acyl chloride was used in the next step without further purification. Crude acyl chloride was dissolved in dry DCM (10 mL) and N,O-dimethylhydroxylamine hydrochloride (112 mg, 1 eq) was added followed by TEA (0.32 mL, 2 eq). Reaction mixture was stirred at r.t. for 3 h. Then the mixture was diluted with DCM, washed with water and purified by flash column chromatography, mobile phase petrolether/EtOAc (60-100%). Yield 521 (91%). $^1$H NMR (401 MHz, DMSO-$d_6$) δ 8.55 (s, 1H), 8.50-8.39 (m, 1H), 7.69 (dd, J=8.7, 2.0 Hz, 3H), 7.58 (d, J=8.1 Hz, 2H), 7.48-7.40 (m, 4H), 7.38 (ddd, J=9.0, 6.7, 1.3 Hz, 1H), 6.99 (td, J=6.8, 1.2 Hz, 1H), 5.78 (s, 2H), 3.39 (s, 3H), 3.29 (s, 3H). $^{13}$C NMR (101 MHz, DMSO) δ 166.91, 144.93, 142.44, 136.35, 135.93, 135.22, 133.01, 132.85, 130.22, 129.83, 129.57, 129.40, 128.69, 127.15, 126.24, 125.90, 125.34, 117.11, 113.32, 111.55, 61.20, 52.22, 31.99. HRMS: calcd for [M+H], 507.10976; found, 507.10983.

Example 110

2-Chloro-5-((4-(2-(4-chlorophenyl)imidazo[1,2-a]pyridin-3-yl)-1H-1,2,3-triazol-1-yl)methyl)benzamide

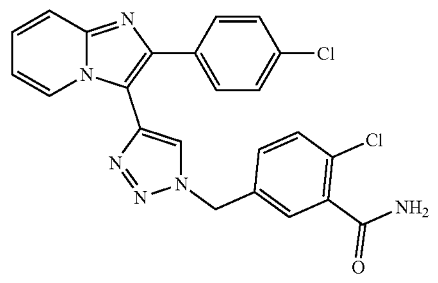 [SMILES: NC(=O)c1cc(Cn2cc(-c3c(-c4ccc(Cl)cc4)nc4ccccn34)nn2)ccc1Cl]

Title compound was prepared according to the General Procedure VIII (Scheme 3). Mobile phase: $H_2O$/MeOH (30-100%). Yield 251 mg (88%). $^1H$ NMR (401 MHz, DMSO-$d_6$) δ 8.56 (s, 1H), 8.51-8.43 (m, 1H), 8.00-7.84 (m, 1H), 7.70 (td, J=6.8, 2.1 Hz, 4H), 7.53 (t, J=7.3 Hz, 1H), 7.49-7.34 (m, 4H), 7.00 (qd, J=6.8, 6.1, 1.1 Hz, 1H), 5.76 (s, 2H). $^{13}C$ NMR (101 MHz, DMSO) δ 167.85, 140.71, 137.56, 135.11, 134.72, 134.37, 133.41, 133.00, 130.31, 130.17, 129.63, 129.36, 128.39, 127.21, 127.06, 126.55, 117.19, 113.25, 113.19, 52.31. HRMS: calcd for [M+H], 463.08354; found, 463.08359.

Example 111

2-Chloro-5-((4-(2-(4-chlorophenyl)imidazo[1,2-a]pyridin-3-yl)-1H-1,2,3-triazol-1-yl)methyl)-N,N-dimethylbenzamide

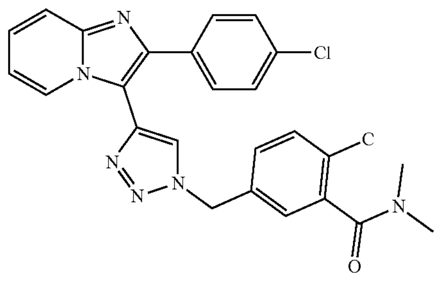 [SMILES: Cc1ccc(Cn2cc(-c3c(-c4ccc(Cl)cc4)nc4ccccn34)nn2)cc1C(=O)N(C)C]

Title compound was prepared according to the General Procedure VIII (Scheme 3). Mobile phase: $H_2O$/MeOH (30-100%). Yield 228 mg (95%). $^1H$ NMR (401 MHz, DMSO-$d_6$) δ 8.54 (s, 1H), 8.46 (dt, J=6.9, 1.2 Hz, 1H), 8.31 (s, 1H), 7.71-7.66 (m, 3H), 7.58 (d, J=8.3 Hz, 1H), 7.43 (dd, J=8.6, 2.2 Hz, 3H), 7.38 (ddd, J=9.1, 6.7, 1.3 Hz, 1H), 7.35 (d, J=2.2 Hz, 1H), 6.99 (td, J=6.8, 1.2 Hz, 1H), 5.76 (s, 2H), 3.02 (s, 3H), 2.75 (s, 3H). $^{13}C$ NMR (101 MHz, DMSO) δ 166.79, 144.94, 142.44, 136.80, 136.38, 135.78, 133.01, 132.85, 130.03, 130.02, 129.57, 129.06, 128.70, 127.44, 126.26, 125.92, 125.37, 117.11, 113.34, 111.55, 52.23, 37.65, 34.22. HRMS: calcd for [M+H], 491.11484; found, 491.11493.

Example 112

2-Chloro-5-((4-(2-(4-chlorophenyl)imidazo[1,2-a]pyridin-3-yl)-1H-1,2,3-triazol-1-yl)methyl)-N-methylbenzamide

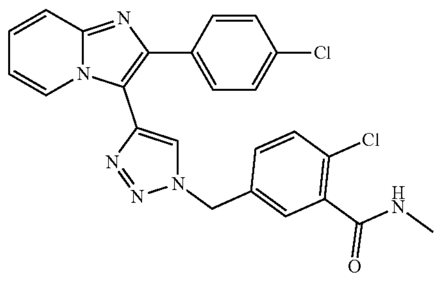 [SMILES: CNC(=O)c1cc(Cn2cc(-c3c(-c4ccc(Cl)cc4)nc4ccccn34)nn2)ccc1Cl]

Title compound was prepared according to the General Procedure VIII (Scheme 3). Mobile phase: $H_2O$/MeOH (30-100%). Yield 87 mg (89%). $^1H$ NMR (401 MHz, DMSO-$d_6$) δ 8.57 (s, 1H), 8.47 (dt, J=7.0, 1.1 Hz, 1H), 8.41 (q, J=4.4 Hz, 1H), 7.72-7.67 (m, 3H), 7.55 (d, J=8.2 Hz, 1H), 7.47-7.41 (m, 4H), 7.39 (ddd, J=9.1, 6.7, 1.2 Hz, 1H), 7.00 (td, J=6.8, 1.2 Hz, 1H), 5.75 (s, 2H), 2.77 (d, J=4.6 Hz, 3H). $^{13}C$ NMR (101 MHz, DMSO) δ 166.58, 144.96, 142.43, 137.62, 136.35, 135.20, 133.01, 132.89, 130.40, 130.24, 129.86, 129.60, 128.75, 128.44, 126.31, 125.94, 125.40, 117.13, 113.38, 111.57, 52.22, 26.17. HRMS: calcd for [M+H], 477.09919; found, 477.09927.

Scheme 4.

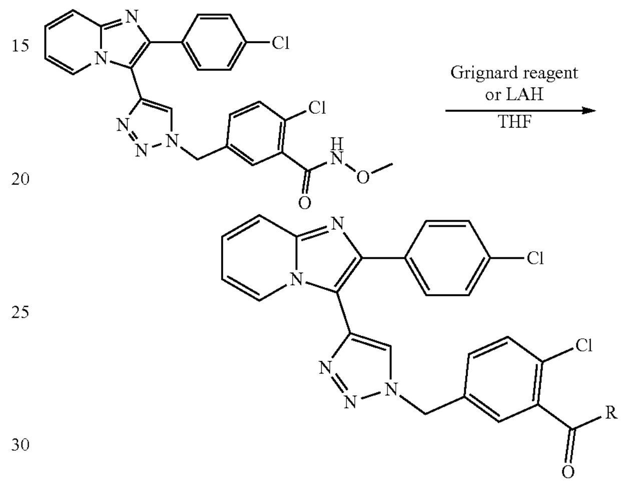

General Procedure IX. Ketones Preparation via Grignard Reagent

2-Chloro-5-((4-(2-(4-chlorophenyl)imidazo[1,2-a]pyridin-3-yl)-1H-1,2,3-triazol-1-yl)methyl)-N-methoxy-N-methylbenzamide was dissolved in dry THF (6 ml), cooled in an ice bath, degassed and refilled with argon. Grignard reagent (3M in DEE, 2 eq) was added in one portion and the mixture was allowed to warm to r.t. and stirred overnight. For the LAH reduction, the mixture was stirred at 5° C. for 2 h. The mixture was quenched with saturated $NH_4Cl$ solution and extracted with EtOAc. Combined organic phases were dried over sodium sulfate, evaporated and purified if necessary by flash column chromatography (petrolether:EtOAc 70-100%) (Scheme 3).

Example 113

1-(2-Chloro-5-((4-(2-(4-chlorophenyl)imidazo[1,2-a]pyridin-3-yl)-1H-1,2,3-triazol-1-yl)methyl)-phenyl)ethan-1-one

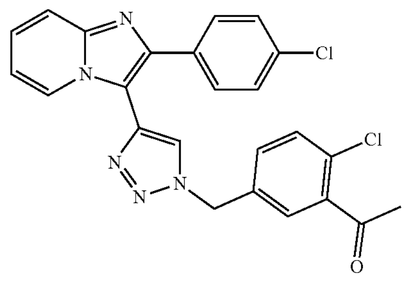 [SMILES: CC(=O)c1cc(Cn2cc(-c3c(-c4ccc(Cl)cc4)nc4ccccn34)nn2)ccc1Cl]

Title compound was prepared according to the General Procedure IX (Scheme 4). Mobile phase: $H_2O$/MeOH (30-100%). Yield 68 mg (72%). $^1$H NMR (401 MHz, DMSO-$d_6$) δ 8.54 (s, 1H), 8.47 (dt, J=6.9, 1.1 Hz, 1H), 7.73-7.67 (m, 4H), 7.61 (d, J=8.3 Hz, 1H), 7.50 (dd, J=8.3, 2.2 Hz, 1H), 7.45-7.41 (m, 2H), 7.38 (ddd, J=9.0, 6.8, 1.3 Hz, 1H), 7.00 (td, J=6.8, 1.1 Hz, 1H), 5.78 (s, 2H), 2.59 (s, 3H). $^{13}$C NMR (101 MHz, DMSO) δ 199.81, 144.92, 142.46, 139.01, 136.36, 135.53, 133.01, 132.82, 131.95, 131.18, 129.76, 129.62, 129.14, 128.68, 126.25, 125.89, 125.38, 117.11, 113.32, 111.56, 52.20, 30.64. HRMS: calcd for [M+H], 462.08829; found, 462.08840.

Example 114

1-(2-Chloro-5-((4-(2-(4-chlorophenyl)imidazo[1,2-a]pyridin-3-yl)-1H-1,2,3-triazol-1-yl)methyl)phenyl)propan-1-one

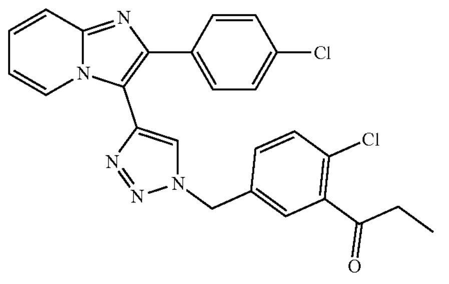 [SMILES: CCC(=O)c1cc(Cn2cc(-c3c(-c4ccc(Cl)cc4)nc4ccccn34)nn2)ccc1Cl]

Title compound was prepared according to the General Procedure IX (Scheme 4). Mobile phase: $H_2O$/MeOH (30-100%). Yield 51 mg (69%). $^1$H NMR (401 MHz, DMSO-$d_6$) δ 8.54 (s, 1H), 8.49-8.42 (m, 1H), 7.72-7.67 (m, 3H), 7.65 (d, J=2.1 Hz, 1H), 7.60 (d, J=8.3 Hz, 1H), 7.50-7.46 (m, 1H), 7.44-7.36 (m, 3H), 7.00 (td, J=6.8, 1.1 Hz, 1H), 5.77 (s, 2H), 2.93 (q, J=7.2 Hz, 2H), 1.12-1.02 (m, 3H). $^{13}$C NMR (101 MHz, DMSO) δ 203.21, 144.92, 142.44, 139.56, 136.35, 135.51, 133.01, 132.82, 131.52, 130.94, 129.60, 129.30, 128.67, 128.46, 126.26, 125.91, 125.38, 117.11, 113.32, 111.56, 52.23, 35.75, 8.03. HRMS: calcd for [M+H], 476.10394; found, 476.10407.

Example 115

2-Chloro-5-((4-(2-(4-chlorophenyl)imidazo[1,2-a]pyridin-3-yl)-1H-1,2,3-triazol-1-yl)methyl)benzaldehyde

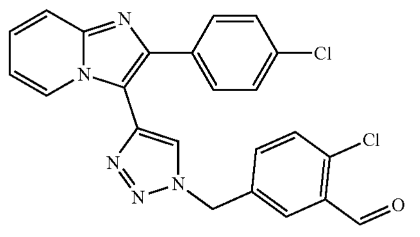 [SMILES: O=Cc1cc(Cn2cc(-c3c(-c4ccc(Cl)cc4)nc4ccccn34)nn2)ccc1Cl]

Title compound was prepared according to the General Procedure IX (Scheme 4). $^1$H NMR (401 MHz, DMSO-$d_6$) δ 10.34 (s, 1H), 8.56 (s, 1H), 8.47 (dt, J=6.9, 1.2 Hz, 1H), 7.83 (t, J=1.4 Hz, 1H), 7.72-7.67 (m, 5H), 7.45-7.41 (m, 2H), 7.38 (ddd, J=9.1, 6.7, 1.3 Hz, 1H), 6.99 (td, J=6.8, 1.3 Hz, 1H), 5.83 (s, 2H). $^{13}$C NMR (101 MHz, DMSO) δ 189.72, 144.93, 142.46, 136.39, 136.33, 136.13, 135.17, 133.00, 132.83, 132.36, 131.43, 129.59, 128.79, 128.70, 126.24, 125.95, 125.35, 117.11, 113.33, 111.52, 52.06. HRMS: calcd for [M+H], 448.07264; found, 448.07224.

Scheme 5.

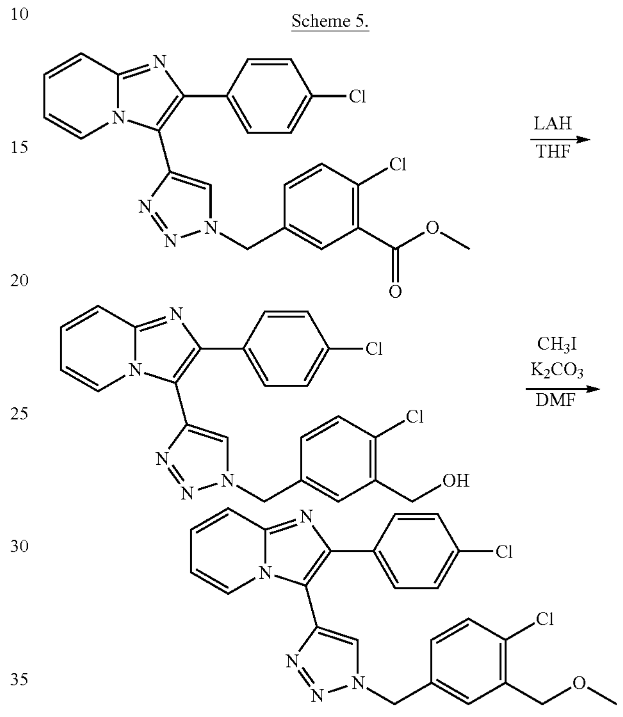

Example 116

(2-Chloro-5-((4-(2-(4-chlorophenyl)imidazo[1,2-a]pyridin-3-yl)-1H-1,2,3-triazol-1-yl)methyl)-phenyl)methanol

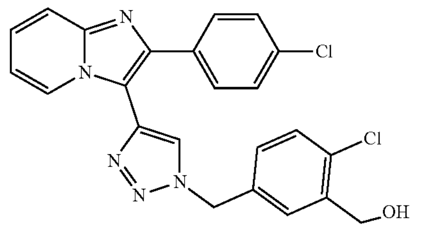 [SMILES: OCc1cc(Cn2cc(-c3c(-c4ccc(Cl)cc4)nc4ccccn34)nn2)ccc1Cl]

Methyl 2-chloro-5-((4-(2-(4-chlorophenyl)imidazo[1,2-a]pyridin-3-yl)-1H-1,2,3-triazol-1-yl)-methyl)benzoate (160 mg, 0.334 mmol) was dissolved in dry THF (6 mL), cooled in an ice bath and degassed. A flask was refilled with argon and LAH (0.35 mL, 1 eq) was added. A reaction mixture was allowed to warm to r.t. and stirred overnight (Scheme 5). After the completion of the reaction, the mixture was carefully quenched with ice and extracted with EtOAc. Combined organic phases were dried over sodium sulfate and evaporated. A residue was purified by flash column chromatography (cyclohexane/EtOAc 40-70%). Yield 85 mg (57%). $^{1}$H NMR (401 MHz, DMSO-$d_6$) δ 8.52 (s, 1H), 8.46 (dt, J=6.9, 1.2 Hz, 1H), 7.73-7.67 (m, 4H), 7.51 (d, J=2.3 Hz, 1H), 7.47-7.41 (m, 3H), 7.38 (ddd, J=9.1, 6.7, 1.3 Hz, 1H), 7.30-7.26 (m, 1H), 7.00 (td, J=6.8, 1.2 Hz, 1H), 5.76 (s, 2H), 5.51 (t, J=5.4 Hz, 1H), 4.57 (dt, J=5.4, 0.9 Hz, 2H). $^{13}$C NMR (101 MHz, DMSO) δ 144.93, 142.41, 140.22, 136.29, 135.16, 133.00, 132.82, 130.72, 129.59, 129.31, 128.71, 127.79, 127.22, 126.24, 125.87, 125.33, 117.11, 113.34, 111.60, 60.22, 52.73. HRMS: calcd for [M+H], 450.08829; found, 450.08835.

Example 117

3-(1-(4-Chloro-3-(methoxymethyl)benzyl)-1H-1,2,3-triazol-4-yl)-2-(4-chlorophenyl)imidazo[1,2-a]pyridine

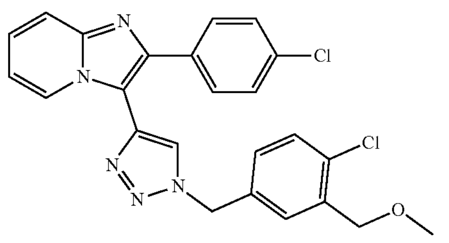 [SMILES: COCc1cc(Cn2cc(-c3c(-c4ccc(Cl)cc4)nc4ccccn34)nn2)ccc1Cl]

(2-Chloro-5-((4-(2-(4-chlorophenyl)imidazo[1,2-a]pyridin-3-yl)-1H-1,2,3-triazol-1-yl)methyl)phenyl)methanol (85 mg, 0.188 mml) was dissolved in dry THF (4 mL) and NaH (8 mg, 1.1 eq) was added. After 10 min, $CH_3I$ (0.013 mL, 1 eq) was added and the mixture was stirred at r.t. overnight (Scheme 5). The mixture was purified by flash column chromatography (cyclohexane/EtOAc 30-80%). Yield: 35 mg (40%). $^{1}$H NMR (401 MHz, DMSO-$d_6$) δ 8.51 (s, 1H), 8.46 (dt, J=7.0, 1.3 Hz, 1H), 7.71-7.65 (m, 3H), 7.51-7.45 (m, 2H), 7.40 (dd, J=8.6, 2.0 Hz, 2H), 7.35 (d, J=1.3 Hz, 0H), 7.32 (dd, J=8.2, 2.3 Hz, 1H), 6.99 (td, J=6.8, 1.3 Hz, 1H), 5.75 (s, 2H), 4.48 (s, 2H), 3.36 (d, J=1.8 Hz, 3H, water overlapping). $^{13}$C NMR (101 MHz, DMSO) δ 144.92, 142.42, 136.41, 136.33, 135.26, 133.01, 132.81, 131.72, 129.69, 129.59, 128.71, 128.64, 128.46, 126.20, 125.79, 125.30, 117.10, 113.31, 111.60, 70.77, 58.30, 52.58. HRMS: calcd for [M+H], 464.10394; found, 464.10396.

Scheme 6.

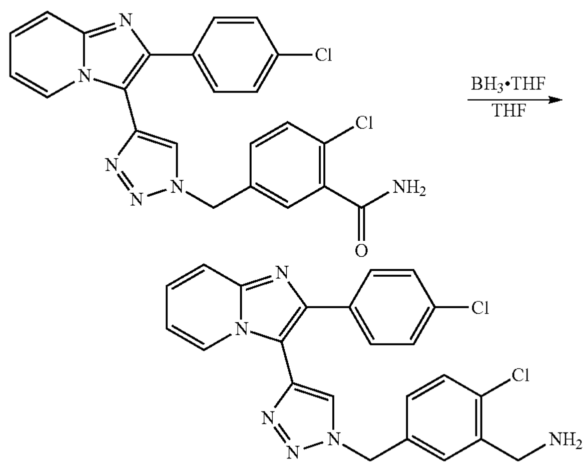

Example 118

(2-Chloro-5-((4-(2-(4-chlorophenyl)imidazo[1,2-a]pyridin-3-yl)-1H-1,2,3-triazol-1-yl)methyl)phenyl)methanamine 2-Chloro-5-((4-(2-(4-chlorophenyl)imidazo[1,2-a]pyridin-3-yl)-1H-1,2,3-triazol-1-yl)methyl)benzamide (160 mg, 0.35 mmol) was dissolved in dry THF (5 ml), degassed and refilled with argon and $BH_3 \cdot THF$ (1 ml, 3 eq) was added (Scheme 6). The reaction mixture was stirred at 70° C. overnight. After cooling to r.t. the mixture was carefully quenched with ice and extracted with EtOAc. Combined organic phases were dried over sodium sulfate and evaporated. Residue was purified by flash column chromatography EtOAc/MeOH (0-40%+1% TEA). Yield: 100 mg (65%). $^{1}$H NMR (401 MHz, DMSO-$d_6$) δ 8.54 (s, 1H), 8.50-8.41 (m, 2H), 7.75-7.61 (m, 5H), 7.51 (d, J=8.3 Hz, 1H), 7.45-7.23 (m, 4H), 7.00 (td, J=6.8, 1.4 Hz, 1H), 5.75 (s, 2H), 3.93 (s, 2H). $^{13}$C NMR (101 MHz, DMSO) δ 144.92, 142.45, 137.98, 136.29, 136.27, 135.15, 133.03, 133.02, 132.82, 132.42, 129.65, 128.68, 128.59, 126.22, 125.80, 125.39, 117.10, 113.32, 111.63, 60.92, 52.71. HRMS: calcd for [M+H], 449.10428; found, 449.10414.

Scheme 7.

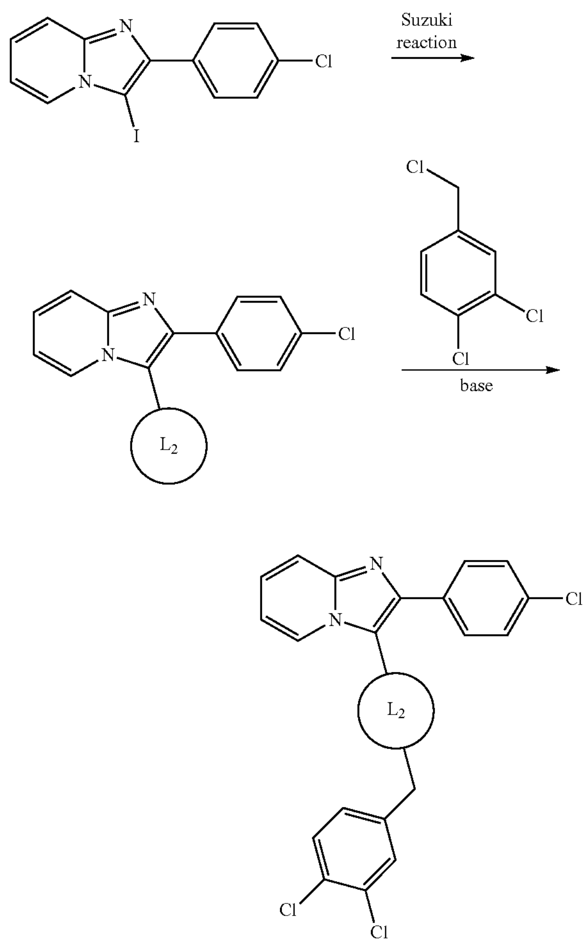

Example 119

2-(4-Chlorophenyl)-3-(1H-pyrazol-4-yl)imidazo[1,2-a]pyridine (Intermediate Compound)

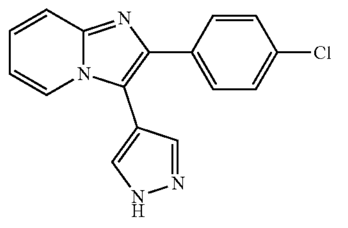 [SMILES: Clc1ccc(-c2nc3ccccn3c2-c2cn[nH]c2)cc1]

2-(4-Chlorophenyl)-3-iodoimidazo[1,2-a]pyridine (334 mg, 0.94 mmol) was dissolved in dioxane (8 ml) and 4-(4,4,5,5-tetramethyl-1,3,2-dioxaborolan-2-yl)-1H-pyrazole (183 mg, 1 eq) was added followed by a solution of $Na_2CO_3$ (3 eq) in 2 ml of $H_2O$. A reaction mixture was degassed and refilled with argon. Pd(dppf)$Cl_2$ (40 mg, 5% mol) was added and the mixture was degassed again and refilled with argon. The reaction mixture was stirred at 90° C. overnight (Scheme 7). After cooling to r.t. the mixture was diluted with water and extracted with EtOAc. Combined organic phases were dried over sodium sulfate and evaporated. The residue was purified by flash column chromatography, mobile phase petrolether/EtOAc (20-70%). Yield: 112 mg (40%). $^1H$ NMR (401 MHz, DMSO-$d_6$) δ 8.54 (d, J=6.7 Hz, 1H), 8.45 (s, 1H), 8.00 (d, J=8.3 Hz, 2H), 7.59 (d, J=9.1 Hz, 1H), 7.51 (d, J=8.3 Hz, 2H), 7.29-7.22 (m, 1H), 6.92 (t, J=6.7 Hz, 1H). HRMS: calcd for [M+H], 295.07450; found, 295.07467.

Example 120

2-(4-Chlorophenyl)-3-(1H-pyrrol-2-yl)imidazo[1,2-a]pyridine (Intermediate Compound)

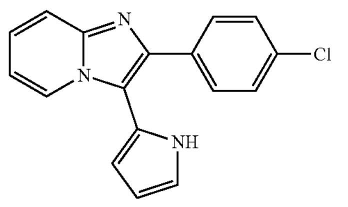 [SMILES: Clc1ccc(-c2nc3ccccn3c2-c2ccc[nH]2)cc1]

2-(4-Chlorophenyl)-3-iodoimidazo[1,2-a]pyridine (430 mg, 1.21 mmol) was dissolved in dioxane (12 ml) and (1-(tert-butoxycarbonyl)-1H-pyrrol-3-yl)boronic acid (260 mg, 1 eq) was added followed by solution of $Na_2CO_3$ (392 mg, 3 eq) in 3 ml of $H_2O$. A reaction mixture was degassed and refilled with argon. Pd($PPh_3$)$_4$ (72 mg, 5% mol) was added and the mixture was degassed again and refilled with argon. The reaction mixture was stirred at 90° C. overnight (Scheme 7). After cooling to r.t. the mixture was diluted with water and extracted with EtOAc. Combined organic phases were dried over sodium sulfate and evaporated. The residue was purified by flash column chromatography, mobile phase petrolether/EtOAc (20-70%). Yield: 103 mg (35%). $^1H$ NMR (401 MHz, DMSO-$d_6$) δ 11.28 (s, 1H), 7.99 (dt, J=6.9, 1.2 Hz, 1H), 7.69-7.62 (m, 3H), 7.42-7.37 (m, 2H), 7.32 (ddd, J=9.1, 6.7, 1.3 Hz, 1H), 7.07 (td, J=2.7, 1.5 Hz, 1H), 6.93 (td, J=6.8, 1.2 Hz, 1H), 6.40-6.37 (m, 1H), 6.34 (dt, J=3.3, 2.5 Hz, 1H). $^{13}C$ NMR (101 MHz, DMSO) δ 144.27, 141.30, 133.34, 132.24, 128.58, 128.51, 125.77, 124.66, 120.79, 117.38, 116.91, 114.57, 112.91, 111.12, 109.48. HRMS: calcd for [M+H], 294.07925; found, 294.07926.

Example 121

2-(4-Chlorophenyl)-3-(pyridin-3-yl)imidazo[1,2-a]pyridine (Intermediate Compound)

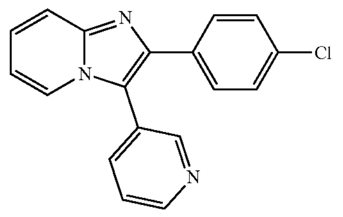 [SMILES: Clc1ccc(-c2nc3ccccn3c2-c2cccnc2)cc1]

2-(4-Chlorophenyl)-3-iodoimidazo[1,2-a]pyridine (605 mg, 1.71 mmol) was dissolved in dioxane (16 ml) and pyridin-3-ylboronic acid (210 mg, 1 eq) was added followed by solution of $Na_2CO_3$ (540 mg, 3 eq) in 4 ml of $H_2O$. A reaction mixture was degassed and refilled with argon. Pd($PPh_3$)$_4$ (72 mg, 5% mol) was added and the mixture was degassed again and refilled with argon. The reaction mixture was stirred at 90° C. overnight (Scheme 7). After cooling to r.t. the mixture was diluted with water and extracted with EtOAc. Combined organic phases were dried over sodium sulfate and evaporated. The residue was purified by flash column chromatography, mobile phase petrolether/EtOAc (30-60%). Yield: 292 mg (56%). $^1H$ NMR (401 MHz, DMSO-$d_6$) δ 8.74 (dd, J=4.7, 1.6 Hz, 1H), 8.66 (d, J=2.3 Hz, 1H), 8.10 (d, J=6.9 Hz, 1H), 8.01 (dt, J=8.0, 1.8 Hz, 1H), 7.70 (d, J=9.1 Hz, 1H), 7.63 (dd, J=7.9, 4.9 Hz, 1H), 7.58-7.52 (m, 2H), 7.38 (dd, J=14.8, 8.7 Hz, 3H), 6.93 (td, J=6.8, 1.3 Hz, 1H). $^{13}C$ NMR (101 MHz, DMSO) δ 151.25, 150.19, 144.72, 141.36, 138.65, 132.97, 132.53, 129.36, 128.72, 126.11, 125.59, 124.71, 124.21, 118.01, 117.14, 113.29. HRMS: calcd for [M+H], 306.07925; found, 306.07933.

Example 122

2-(4-Chlorophenyl)-3-(1-(3,4-dichlorobenzyl)-1H-pyrazol-4-yl)imidazo[1,2-a]pyridine

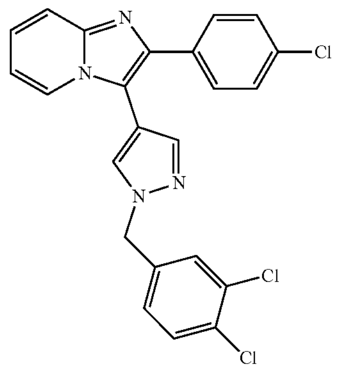 [SMILES: Clc1ccc(-c2nc3ccccn3c2-c2cnn(Cc3ccc(Cl)c(Cl)c3)c2)cc1]

2-(4-Chlorophenyl)-3-(1H-pyrazol-4-yl)imidazo[1,2-a]pyridine (30 mg, 0.1 mmol) was dissolved in $CH_3CN$ (2 ml) and the solution was degassed and refilled with argon. $K_2CO_3$ (15 mg, 1.1 eq) was added followed by an addition of 1,2-dichloro-4-(chloromethyl)benzene (0.02 mL, 1 eq). The reaction mixture was refluxed overnight under the argon atmosphere (Scheme 7). The product was isolated from preparative TLC, mobile phase petrolether/EtOAc 3:2. Yield: 15 mg (32%). $^1$H NMR (401 MHz, DMSO-$d_6$) δ 8.26 (s, 0H), 8.09 (dd, J=6.9, 1.5 Hz, 0H), 7.80 (s, 0H), 7.73-7.68 (m, 1H), 7.68-7.60 (m, 1H), 7.58 (d, J=2.1 Hz, 1H), 7.41 (dd, J=8.5, 1.7 Hz, 1H), 7.36-7.24 (m, 1H), 6.97-6.90 (m, 1H), 5.49 (s, 1H). $^{13}$C NMR (101 MHz, DMSO) δ 144.74, 141.23, 140.90, 139.00, 133.78, 132.57, 132.37, 131.36, 130.87, 130.02, 129.79, 129.36, 128.82, 128.38, 125.81, 124.78, 117.28, 113.42, 113.20, 109.08, 54.16. HRMS: calcd for [M+H], 453.04351; found, 453.04356.

Example 123

2-(4-chlorophenyl)-3-(1-(3,4-dichlorobenzyl)-1H-pyrrol-2-yl)imidazo[1,2-a]pyridine

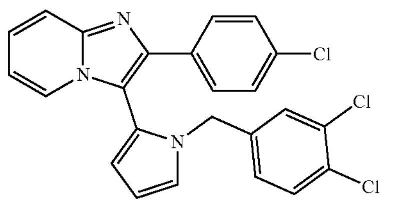 [SMILES: Clc1ccc(-c2nc3ccccn3c2-c2cccn2Cc2ccc(Cl)c(Cl)c2)cc1]

2-(4-Chlorophenyl)-3-(1H-pyrrol-2-yl)imidazo[1,2-a]pyridine (76 mg, 0.26 mmol) was dissolved in dry DMF (2 ml), degassed and refilled with argon. NaH (10 mg, 1.3 eq, 60% in mineral oil) was added and the mixture was stirred at r.t. for 30 min. 1,2-Dichloro-4-(chloromethyl)benzene (0.05 mL, 1.3 eq) was added and the reaction mixture was stirred at r.t. overnight (Scheme 7). Then the mixture was diluted with water and extracted with EtOAc. Combined organic phases were dried over sodium sulfate and evaporated. The residue was purified by flash column chromatography, mobile phase petrolether/EtOAc (15-50%). Yield: 25 mg (21%). $^1$H NMR (401 MHz, DMSO-$d_6$) δ 7.57 (m, 3H), 7.47 (d, J=6.8 Hz, 1H), 7.39 (dd, J=2.7, 1.7 Hz, 1H), 7.38-7.33 (m, 2H), 7.27 (ddd, J=9.0, 6.7, 1.2 Hz, 1H), 7.17 (d, J=8.2 Hz, 1H), 6.74 (td, J=6.8, 1.1 Hz, 1H), 6.64 (d, J=2.0 Hz, 1H), 6.58 (dd, J=8.3, 2.0 Hz, 1H), 6.51 (dd, J=3.6, 1.7 Hz, 1H), 6.43-6.38 (m, 1H), 4.80 (d, J=15.4 Hz, H), 4.53 (d, J=15.4 Hz, 1H). $^{13}$C NMR (101 MHz, DMSO) δ 144.60, 142.39, 138.69, 132.84, 132.59, 130.86, 130.34, 129.80, 128.70, 128.62, 127.99, 127.04, 126.00, 125.48, 123.94, 118.69, 116.79, 113.98, 112.70, 112.19, 109.16, 49.78. HRMS: calcd for [M+H], 452.04826; found, 452.04842.

Scheme 8.

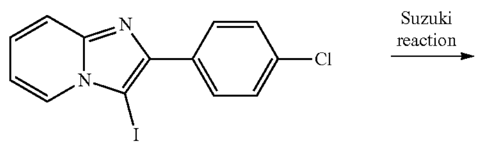

-continued

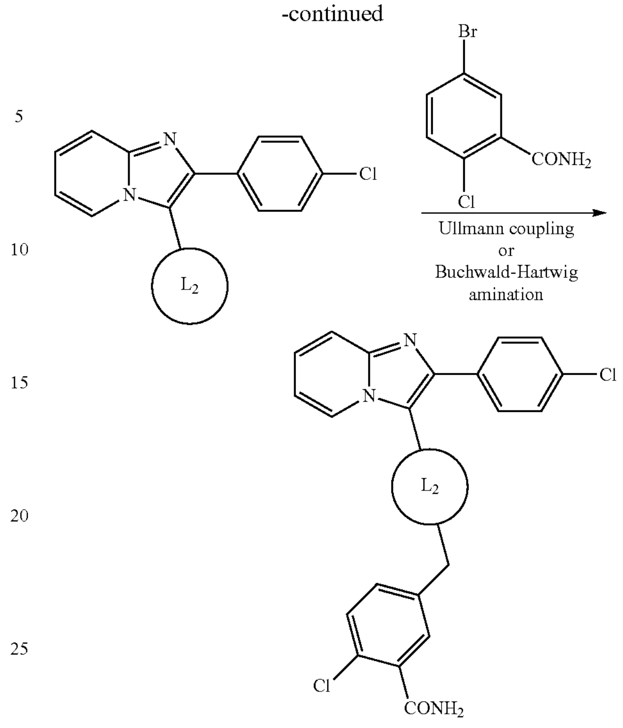

Example 124

2-(4-Chlorophenyl)-3-(6-methoxypyridin-3-yl)imidazo[1,2-a]pyridine (Intermediate Compound)

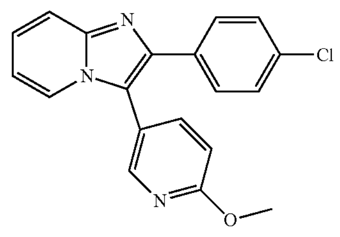 [SMILES: COc1ccc(-c2c(-c3ccc(Cl)cc3)nc3ccccn23)cn1]

Title compound was prepared according to the Scheme 8. 2-(4-Chlorophenyl)-3-iodoimidazo[1,2-a]pyridine (0.2 g, 0.56 mmol) was combined with (6-methoxypyridin-3-yl) boronic acid (1.1 eq) and dissolved in dioxane (8 ml), followed by solution of $Na_2CO_3$ in 2 ml of $H_2O$. A reaction mixture was degassed and refilled with argon. Pd(dppf)$Cl_2$ (5 mol %) was added and the mixture was degassed again and refilled with argon. The reaction mixture was stirred at 90° C. overnight (Scheme 8). After cooling to r.t. the mixture was diluted with water and extracted with EtOAc. Combined organic phases were dried over sodium sulfate and evaporated. The residue was purified by flash column chromatography, mobile phase petrolether/EtOAc (20-70%). Yield: 100 mg (53%). $^1$H NMR (401 MHz, DMSO-$d_6$) δ 8.29 (dd, J=2.5, 0.8 Hz, 1H), 8.03 (dt, J=6.9, 1.2 Hz, 1H), 7.85 (dd, J=8.5, 2.4 Hz, 1H), 7.66 (dt, J=9.0, 1.2 Hz, 1H), 7.63-7.57 (m, 2H), 7.42-7.36 (m, 2H), 7.33 (ddd, J=9.0, 6.7, 1.3 Hz, 1H), 7.05 (dd, J=8.6, 0.8 Hz, 1H), 6.90 (td, J=6.8, 1.3 Hz, 1H), 3.95 (s, 3H), $^{13}$C NMR (101 MHz, DMSO) δ 164.28, 149.39, 144.77, 142.09, 141.25, 133.43, 132.65, 129.46, 128.97, 126.10, 124.57, 118.88, 118.25, 117.33, 113.36, 112.12, 53.94. HRMS: calcd for [M+H], 336.0904; found, 336.0902.

Example 125

5-(2-(4-chlorophenyl)imidazo[1,2-a]pyridin-3-yl) pyridin-2-ol (Intermediate Compound)

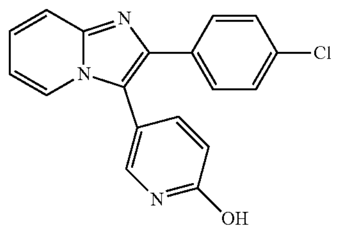 [SMILES: Oc1ccc(-c2c(-c3ccc(Cl)cc3)nc3ccccn23)cn1]

Title compound was prepared from Ex. 124. 2-(4-Chlorophenyl)-3-(6-methoxypyridin-3-yl)imidazo[1,2-a]pyridine was treated with 4M HCl/dioxane at 95° C. overnight. After completion of the reaction, the solvent was evaporated and the residue neutralized with saturated $NaHCO_3$ solution and extracted with EtOAc. Organic phase was dried over sodium sulfate, evaporated a purified by RP-flash column chromatography. Mobile phase $H_2O$/MeOH 15-90%. Yield 72 mg (73%). $^1$H NMR (401 MHz, DMSO-$d_6$) δ 12.04 (s, 1H), 8.12 (dt, J=6.9, 1.2 Hz, 1H), 7.74-7.69 (m, 2H), 7.67-7.59 (m, 2H), 7.48-7.41 (m, 3H), 7.32 (ddd, J=9.0, 6.7, 1.2 Hz, 1H), 6.92 (td, J=6.8, 1.2 Hz, 1H), 6.52 (dd, J=9.4, 0.7 Hz, 1H). $^{13}$C NMR (101 MHz, DMSO) δ 162.36, 144.57, 143.64, 140.96, 138.82, 133.48, 132.60, 129.35, 129.01, 126.01, 124.89, 121.73, 117.63, 117.22, 113.19, 106.40. HRMS: calcd for [M+H], 322.07417; found, 322.07397.

Example 126

5-(2-(4-Chlorophenyl)imidazo[1,2-a]pyridin-3-yl) pyridin-2-amine (Intermediate Compound)

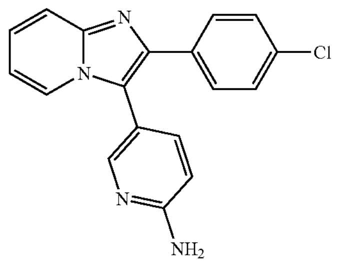 [SMILES: Nc1ccc(-c2c(-c3ccc(Cl)cc3)nc3ccccn23)cn1]

Title compound was prepared according to the Scheme 8. 2-(4-Chlorophenyl)-3-iodoimidazo[1,2-a]pyridine (0.2 g, 0.56 mmol) was combined with 2-aminopyridine-5-boronic acid pinacol ester (1.1 eq) and dissolved in dioxane (8 ml) followed by solution of $Na_2CO_3$ in 2 ml of $H_2O$. A reaction mixture was degassed and refilled with argon. Pd(dppf)$Cl_2$ (5 mol %) was added and the mixture was degassed again and refilled with argon. The reaction mixture was stirred at 90° C. overnight (Scheme 8). After cooling to r.t. the mixture was diluted with water and extracted with EtOAc. Combined organic phases were dried over sodium sulfate and evaporated. The residue was purified by flash column chromatography, mobile phase petrolether/EtOAc (20-70%). Yield: 100 mg (53%). $^1$H NMR (401 MHz, DMSO-$d_6$) δ 8.00 (dt, J=6.9, 1.2 Hz, 1H), 7.96 (d, J=2.3 Hz, 1H), 7.71-7.65 (m, 2H), 7.62 (dt, J=9.1, 1.2 Hz, 1H), 7.47 (dd, J=8.5, 2.4 Hz, 1H), 7.44-7.37 (m, 2H), 7.30 (ddd, J=9.0, 6.7, 1.3 Hz, 1H), 6.88 (td, J=6.8, 1.2 Hz, 1H), 6.64 (d, J=8.5 Hz, 1H), 6.38 (s, 2H). $^{13}$C NMR (101 MHz, DMSO) δ 160.23, 149.97, 144.19, 140.26, 139.39, 133.53, 132.09, 128.97, 128.58, 125.43, 124.19, 119.37, 117.01, 112.82, 112.32, 108.79. HRMS: calcd for [M+H], 321.0907; found, 321.0909.

Example 127

2-Chloro-5-((5-(2-(4-chlorophenyl)imidazo[1,2-a] pyridin-3-yl)pyridin-2-yl)amino)benzamide

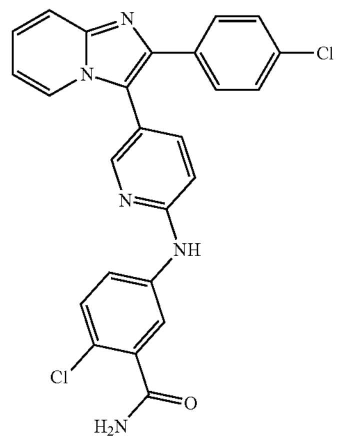 [SMILES: NC(=O)c1cc(Nc2ccc(-c3c(-c4ccc(Cl)cc4)nc4ccccn34)cn2)ccc1Cl]

Title compound was prepared according to the Scheme 8. 5-(2-(4-Chlorophenyl)imidazo[1,2-a]pyridin-3-yl)pyridin-2-amine was combined with 5-bromo-2-chlorobenzamide (1 eq) and diluted with dioxane and the mixture was degassed and refilled with argon. To the solution NatBuO (1.5 eq), XantPhos (10 mol %) and $Pd_2dba_3$ (5 mol %) were added and the mixture was stirred at 100° C. overnight (Scheme 8). The mixture was filtered through celite and the solvent was evaporated to a minimal volume and purified by the flash chromatography followed by RP-flash column chromatography. Mobile phase EtOAc, then $H_2O$/MeOH (20-100%). Yield 45 mg (51%). $^1$H NMR (401 MHz, DMSO-$d_6$) δ 9.67 (s, 1H), 8.30 (dd, J=2.3, 0.8 Hz, 1H), 8.10 (dt, J=6.9, 1.2 Hz, 1H), 7.90-7.82 (m, 3H), 7.71 (dd, J=8.6, 2.4 Hz, 1H), 7.68-7.63 (m, 3H), 7.58-7.55 (m, 1H), 7.43-7.39 (m, 2H), 7.38 (d, J=8.8 Hz, 1H), 7.33 (ddd, J=9.1, 6.7, 1.3 Hz, 1H), 7.04 (dd, J=8.7, 0.8 Hz, 1H), 6.91 (td, J=6.8, 1.2 Hz, 1H). $^{13}$C NMR (101 MHz, DMSO) δ 168.53, 155.68, 149.29, 144.40, 140.74, 140.26, 139.88, 137.53, 133.32, 132.27, 129.89, 129.16, 128.68, 125.71, 124.33, 120.63, 119.95, 118.64, 117.93, 117.06, 115.77, 113.00, 112.08. HRMS: calcd for [M+H], 474.08829; found, 474.08786.

Example 128

2-Chloro-5-((5-(2-(4-chlorophenyl)imidazo[1,2-a]pyridin-3-yl)pyridin-2-yl)oxy)benzamide

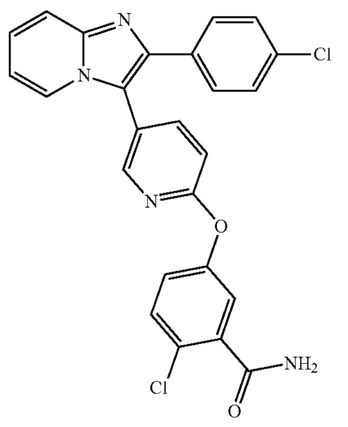 [SMILES: NC(=O)c1cc(Oc2ccc(-c3c(-c4ccc(Cl)cc4)nc4ccccn34)cn2)ccc1Cl]

5-(2-(4-Chlorophenyl)imidazo[1,2-a]pyridin-3-yl)pyridin-2-ol (1.5 eq) was combined with 5-bromo-2-chlorobenzamide (50 mg, 1 eq) followed by BPPO (2 mol %), CuI (2 mol %) and $K_3PO_4$ (2 eq). The flash was degassed and refilled with argon and dry DMF (1 ml) was added. The mixture was degassed and refilled with argon and heated up to 110° C. overnight (Scheme 8). The mixture was filtrated over celite, dissolved in MeOH and purified by RP-flash column chromatography. Mobile phase: $H_2O/CH_3CN$ (20-100%). Product was crystalized from THF. Yield: 4 mg (6%). $^1H$ NMR (500 MHz, DMSO-$d_6$) δ 8.36 (d, J=6.9 Hz, 1H), 8.05 (d, J=2.5 Hz, 1H), 7.96 (s, 1H), 7.85-7.80 (m, 2H), 7.71 (s, 1H), 7.67-7.62 (m, 4H), 7.50 (dd, J=9.4, 2.6 Hz, 1H), 7.48-7.43 (m, 2H), 7.33 (ddd, J=8.9, 6.8, 1.2 Hz, 1H), 6.94 (td, J=6.8, 1.2 Hz, 1H), 6.69 (d, J=9.4 Hz, 1H). $^{13}C$ NMR (126 MHz, DMSO) δ 167.32, 160.73, 144.41, 143.38, 141.21, 140.86, 139.01, 137.62, 133.12, 132.42, 130.28, 129.69, 129.48, 129.23, 128.81, 127.32, 125.87, 125.10, 121.99, 116.95, 116.82, 112.87, 107.21. HRMS: calcd for [M+H], 474.06503; found, 474.06512.

Scheme 9.

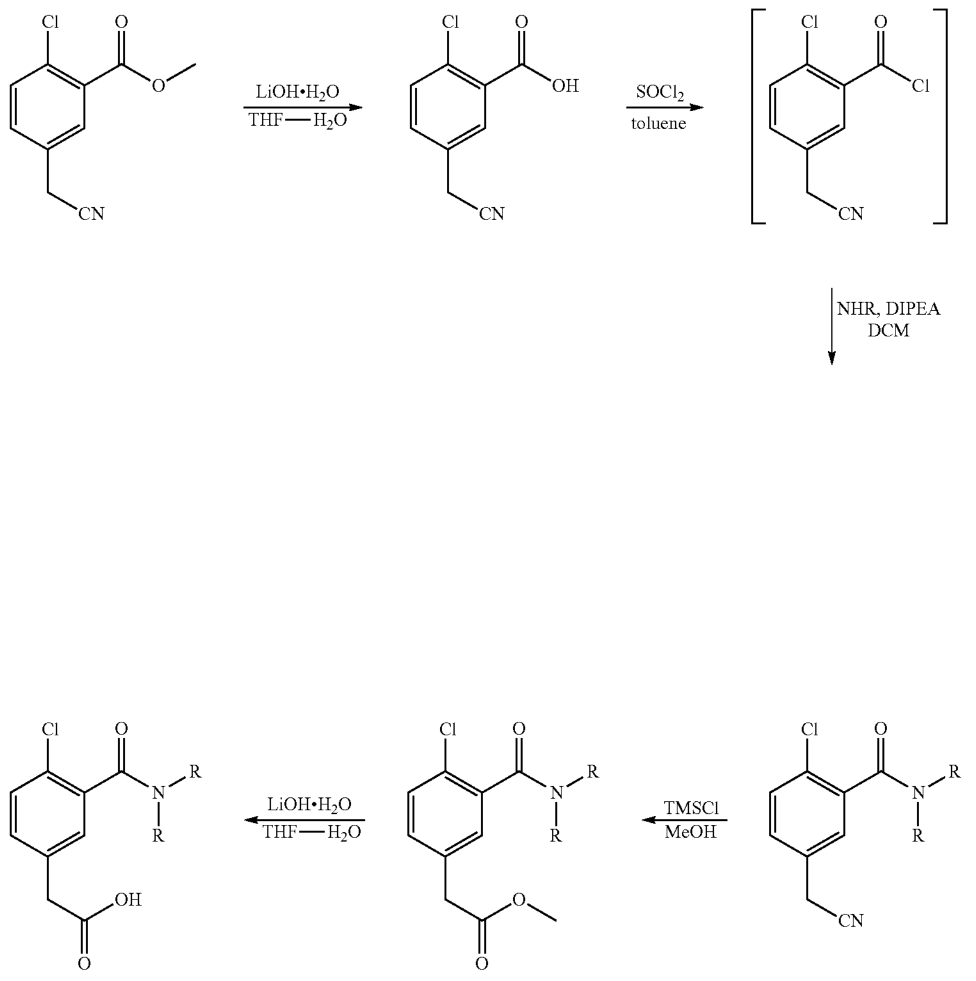

Example 129

Methyl 2-chloro-5-(cyanomethyl)benzoate (Intermediate Compound)

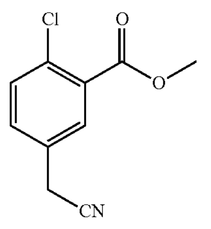

Methyl-(bromomethyl)-2-chlorobenzoate (1 g, 3.54 mmol) was dissolved in dry $CH_3CN$ and the mixture was degassed and refilled with argon. $K_2CO_3$ (540 mg, 1.1 eq) was added in one portion followed by TMSCN (0.66 mL, 1.5 eq). The reaction mixture was stirred at 60° C. for 7 hours (Scheme 9). After cooling to r.t. the mixture was quenched with 1 M NaOH, extracted with EtOAc and dried over sodium sulfate. Residue was purified by flash column chromatography, mobile phase petrolether/EtOAc (15-60%). Yield 415 mg (56%) as oil. $^1$H NMR (401 MHz, DMSO-$d_6$) δ 7.83-7.81 (m, 1H), 7.63 (d, J=8.4 Hz, 1H), 7.57 (ddt, J=8.3, 2.3, 0.7 Hz, 1H), 4.14 (t, J=0.7 Hz, 2H), 3.88 (s, 3H). $^{13}$C NMR (101 MHz, DMSO) δ 165.50, 133.30, 131.85, 131.61, 131.45, 131.08, 130.72, 119.14, 53.16, 22.12. HRMS: calcd for [M+H], 210.03163; found, 210.03151.

Example 130

2-Chloro-5-(cyanomethyl)benzoic acid (Intermediate Compound)

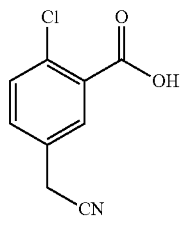 [SMILES: N#CCc1ccc(Cl)c(C(=O)O)c1]

Title compound was prepared according to the General procedure VII (Scheme 9). Mobile phase $H_2O/CH_3CN$ 10-70%. $^1$H NMR (401 MHz, DMSO-$d_6$) δ 13.16 (s, 3H), 7.78 (d, J=2.3 Hz, 1H), 7.58 (d, J=8.2 Hz, 1H), 7.51 (dd, J=8.3, 2.3 Hz, 1H), 4.11 (s, 2H). HRMS: calcd for [M−H], 194.00143; found, 194.00129.

Example 131

2-Chloro-5-(cyanomethyl)-N,N-dimethylbenzamide (Intermediate Compound)

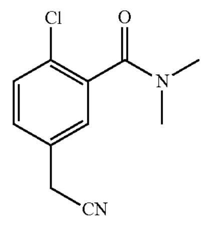

Title compound was prepared according to the General procedure VII (Scheme 9). Mobile phase $H_2O/CH_3CN$ (10-70%). Yield: 125 mg (86%). $^1$H NMR (401 MHz, DMSO-$d_6$) δ 7.56 (d, J=8.3 Hz, 1H), 7.48-7.39 (m, 1H), 7.33 (d, J=2.2 Hz, 1H), 4.08 (s, 2H), 3.01 (s, 3H), 2.77 (s, 3H). $^{13}$C NMR (101 MHz, DMSO) δ 166.66, 136.91, 131.34, 130.23, 130.10, 128.50, 127.71, 118.97, 37.67, 34.21, 21.93. HRMS: calcd for [M+H], 223.06327; found, 223.06327.

Example 132

2-Chloro-5-(cyanomethyl)-N-methylbenzamide (Intermediate Compound)

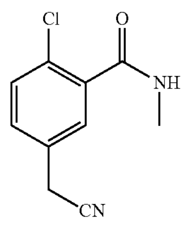

Title compound was prepared according to the General Procedure VIII (Scheme 9). Mobile phase $H_2O/CH_3CN$ (10-70%). Yield: 235 mg (91%). $^1$H NMR (401 MHz, DMSO-$d_6$) δ 8.41 (q, J=4.7 Hz, 1H), 7.53 (dd, J=8.0, 0.7 Hz, 1H), 7.47-7.33 (m, 2H), 4.07 (t, J=0.7 Hz, 2H), 2.75 (d, J=4.6 Hz, 3H). $^{13}$C NMR (101 MHz, DMSO) δ 166.70, 137.91, 130.98, 130.81, 130.62, 129.59, 129.01, 119.26, 26.85, 22.11. HRMS: calcd for [M+H], 209.04762; found, 209.04754.

Example 133

2-Chloro-5-(cyanomethyl)benzamide (Intermediate Compound)

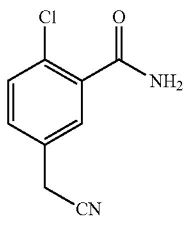 [SMILES: N#CCc1ccc(Cl)c(C(N)=O)c1]

Title compound was prepared according to the General Procedure VIII (Scheme 9). Mobile phase $H_2O/CH_3CN$ (10-70%). Yield: 235 mg (91%). $^1H$ NMR (401 MHz, DMSO-$d_6$) δ 7.93 (s, 1H), 7.66 (s, 1H), 7.52 (d, J=8.1 Hz, 1H), 7.47-7.36 (m, 2H), 4.08 (s, 2H). $^{13}C$ NMR (101 MHz, DMSO) δ 167.87, 137.76, 130.62, 130.39, 130.34, 129.07, 128.51, 119.00, 21.84. HRMS: calcd for [M+Na], 217.01391; found, 217.01405.

General Procedure X. Esterification of Cyano Group

Cyanomethyl benzamide derivative was dissolved in small amount of dry MeOH and TMSCl (2 eq) was added. A reaction mixture was stirred at 50° C. for 4 h and then ar r.t. overnight. The reaction mixture was diluted with water and extracted with EtOAc. Combined organic phases were dried over sodium sulfate and purified by reverse-phase column chromatography (Scheme 9).

Example 134

Methyl 2-(4-chloro-3-(dimethylcarbamoyl)phenyl)acetate (Intermediate Compound)

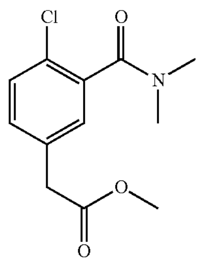 [SMILES: COC(=O)Cc1ccc(Cl)c(C(=O)N(C)C)c1]

Title compound was prepared according to the General Procedure X (Scheme 9). Mobile phase $H_2O/CH_3CN$ (10-70%). Yield: 110 mg (97%). $^1H$ NMR (401 MHz, DMSO-$d_6$) δ 7.47 (d, J=8.3 Hz, 1H), 7.33 (dd, J=8.3, 2.2 Hz, 1H), 7.25 (d, J=2.1 Hz, 1H), 3.74 (s, 2H), 3.62 (s, 2H), 3.00 (s, 2H), 2.76 (s, 2H). $^{13}C$ NMR (101 MHz, DMSO) δ 171.65, 167.31, 136.55, 134.58, 131.89, 129.66, 129.31, 127.98, 52.30, 39.39, 37.96, 34.45. HRMS: calcd for [M+H], 256.07350; found, 256.07370.

Example 135

Methyl 2-(4-chloro-3-(methylcarbamoyl)phenyl)acetate (Intermediate Compound)

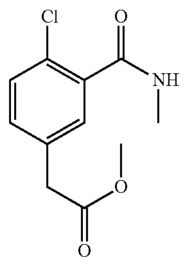 [SMILES: CNC(=O)c1cc(CC(=O)OC)ccc1Cl]

Title compound was prepared according to the General procedure X (Scheme 9). Mobile phase $H_2O/CH_3CN$ (10-70%). Yield: 118 mg (61%). $^1H$ NMR (401 MHz, DMSO-$d_6$) δ 8.35 (d, J=5.0 Hz, 1H), 7.46-7.43 (m, 1H), 7.35-7.31 (m, 2H), 3.74 (s, 2H), 3.63 (s, 3H), 2.75 (d, J=4.6 Hz, 3H). $^{13}C$ NMR (101 MHz, DMSO) δ 171.64, 167.02, 137.40, 134.00, 132.17, 130.25, 129.91, 128.77, 52.29, 26.42. HRMS: calcd for [M+H], 242.05785; found, 242.05789.

Example 136

Methyl 2-(3-carbamoyl-4-chlorophenyl)acetate (Intermediate Compound)

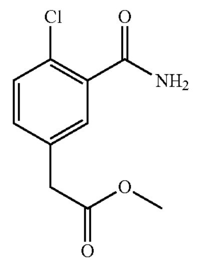

Title compound was prepared according to the General Procedure X (Scheme 9). Mobile phase $H_2O/CH_3CN$ (10-70%). Yield: 51 mg (53%). $^1H$ NMR (401 MHz, DMSO-$d_6$) δ 7.88 (d, J=6.2 Hz, 2H), 7.44 (d, J=8.1 Hz, 1H), 7.36 (d, J=2.1 Hz, 1H), 7.31 (d, J=2.0 Hz, 1H), 3.74 (s, 2H), 3.63 (s, 3H). $^{13}C$ NMR (101 MHz, DMSO) δ 171.66, 168.61, 137.48, 135.75, 132.06, 130.04, 129.79, 128.56, 52.29, 39.46. HRMS: calcd for [M+H], 228.04220; found, 228.04221.

Example 137

2-(4-Chloro-3-(dimethylcarbamoyl)phenyl)acetic acid (Intermediate Compound)

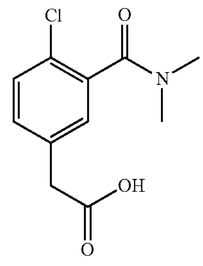 [SMILES: CN(C)C(=O)c1cc(CC(=O)O)ccc1Cl]

Title compound was prepared according to the General Procedure VII (Scheme 9). Mobile phase $H_2O/CH_3CN$ (10-70%). Yield: 228 mg (97%). $^1H$ NMR (401 MHz, DMSO-$d_6$) δ 12.47 (s, 1H), 7.45 (d, J=8.3 Hz, 1H), 7.32 (dd, J=8.3, 2.2 Hz, 1H), 7.23 (d, J=2.2 Hz, 1H), 3.62 (s, 2H), 3.00 (s, 3H), 2.76 (s, 3H). $^{13}C$ NMR (101 MHz, DMSO) δ 172.36, 167.09, 136.17, 134.98, 131.63, 129.24, 129.01, 127.44, 37.67, 34.16 dmso overlap HRMS: calcd for [M+H], 242.05785; found, 242.05764.

Example 138

2-(4-Chloro-3-(methylcarbamoyl)phenyl)acetic acid (Intermediate Compound)

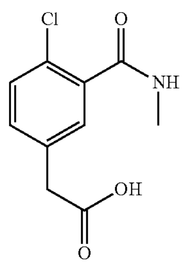

Title compound was prepared according to the General Procedure VII (Scheme 9). Mobile phase $H_2O/CH_3CN$ (10-70%). Yield: 180 mg (97%). $^1H$ NMR (401 MHz, DMSO-$d_6$) δ 12.45 (s, 1H), 8.34 (q, J=4.6 Hz, 1H), 7.45-7.40 (m, 1H), 7.35-7.30 (m, 2H), 3.62 (s, 2H), 2.75 (d, J=4.6 Hz, 3H). $^{13}C$ NMR (101 MHz, DMSO) δ 172.67, 167.13, 137.28, 134.66, 132.19, 130.24, 129.79, 128.54, 39.99, 26.42. HRMS: calcd for [M+Na], 250.02414; found, 250.02402.

Example 139

2-(3-Carbamoyl-4-chlorophenyl)acetic acid (Intermediate Compound)

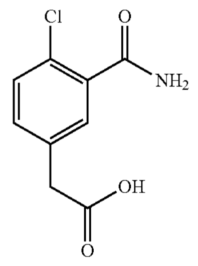 [SMILES: NC(=O)c1cc(CC(=O)O)ccc1Cl]

Title compound was prepared according to the General Procedure VII (Scheme 9). Mobile phase $H_2O/CH_3CN$ (10-70%). Yield: 34 mg (90%). $^1H$ NMR (401 MHz, DMSO-$d_6$) δ 12.51 (bs, 1H), 7.87 (s, 1H), 7.58 (s, 1H), 7.41 (d, J=8.1 Hz, 1H), 7.32 (dt, J=8.1, 4.0 Hz, 2H), 3.61 (s, 2H). $^{13}C$ NMR (101 MHz, DMSO) δ 172.45, 168.32, 137.11, 134.39, 131.82, 129.76, 129.53, 128.01, 39.81. HRMS: calcd for [M+Na], 236.00849; found, 236.00852.

Scheme 10.

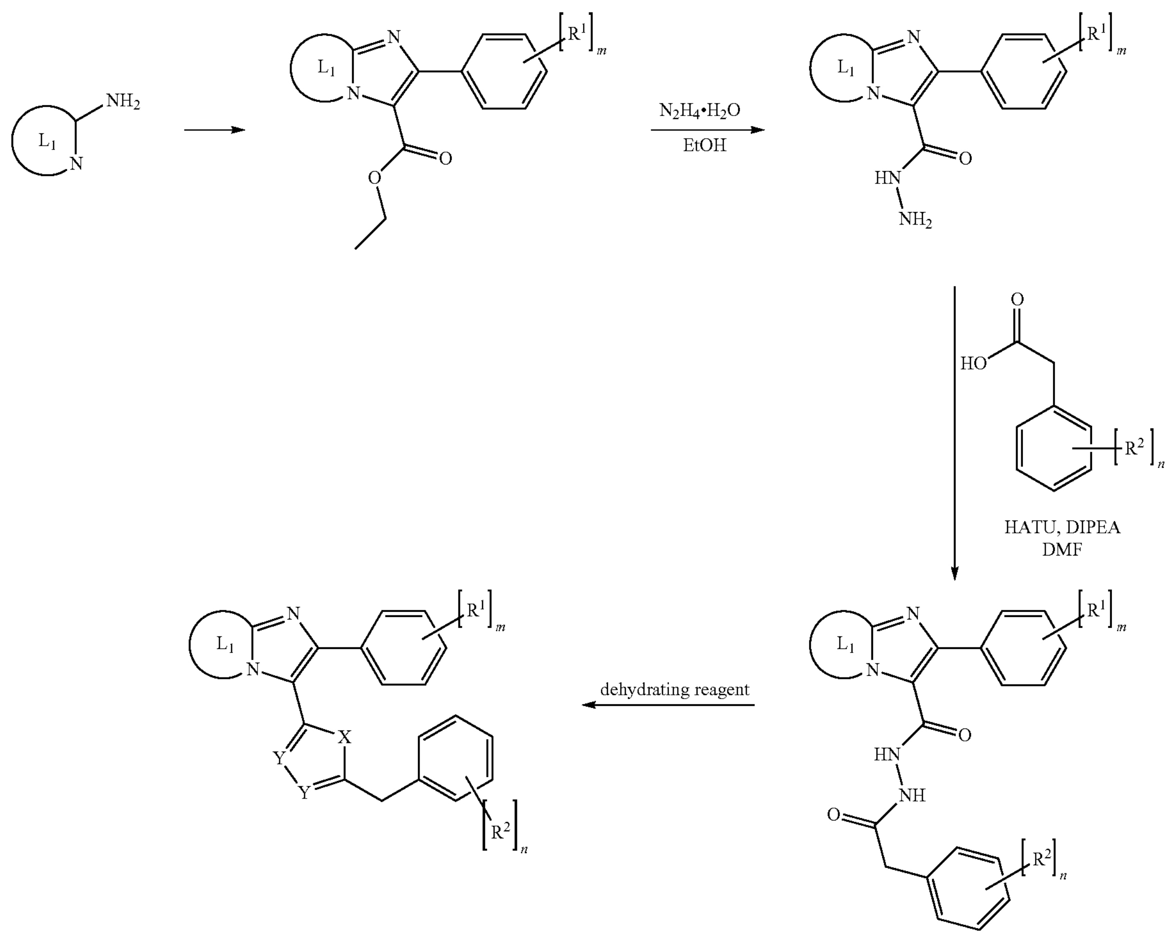

General Procedure XI.

2-Aminothiazole/2-Aminopyridine (3 eq) was dissolved in $CH_3CN$ and ethyl 3-(4-chlorophenyl)-3-oxopropanoate (1 eq) was added as a solution in $CH_3CN$ followed by an addition of $CBr_4$ (2 eq). A reaction mixture was stirred at 80° C. overnight. After the completion of the reaction, the mixture was evaporated to a minimal volume, diluted with water and extracted with EtOAc. Combined organic phases were dried over sodium sulfate and purified by flash column chromatography (Scheme 10).

Example 140

Ethyl 6-(4-chlorophenyl)imidazo[2,1-b]thiazole-5-carboxylate (Intermediate Compound)

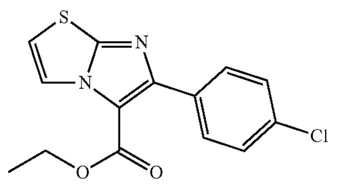 [SMILES: CCOC(=O)c1c(-c2ccc(Cl)cc2)nc2sccn12]

Title compound was prepared according to the General Procedure XI (Scheme 10). Mobile phase petrolether/EtOAc (25-50%). Yield: 365 mg (82%). $^1$H NMR (401 MHz, DMSO-$d_6$) δ 8.22 (d, J=4.5 Hz, 1H), 7.89-7.85 (m, 2H), 7.54 (d, J=4.5 Hz, 2H), 7.52-7.48 (m, 2H), 4.30 (q, J=7.1 Hz, 2H), 1.27 (t, J=7.1 Hz, 3H). $^{13}$C NMR (101 MHz, DMSO) δ 159.18, 152.65, 151.43, 133.50, 132.49, 131.49, 127.90, 121.94, 116.12, 114.53, 60.83, 14.12. HRMS: calcd for [M+H], 307.03025; found, 307.03034.

General Procedure XII. Hydrazide Preparation

Ester derivative was dissolved in absolute EtOH and $N_2H_4 \cdot H_2O$ (10 eq) was added. The reaction mixture was refluxed overnight. The reaction mixture was cooled to r.t. and the formed precipitate was filtered, washed with EtOH and dried (Scheme 10).

Example 141

2-(4-Chlorophenyl)imidazo[1,2-a]pyridine-3-carbohydrazide (Intermediate Compound)

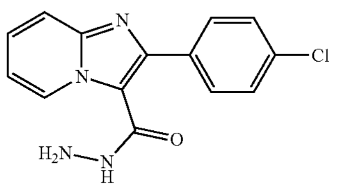 [SMILES: NNC(=O)c1c(-c2ccc(Cl)cc2)nc2ccccn12]

Title compound was prepared according to the General Procedure XII (Scheme 10). Yield: 412 mg (87%). $^1$H NMR (401 MHz, DMSO-$d_6$) δ 9.70 (s, 1H), 8.57 (d, J=7.0 Hz, 1H), 7.92-7.77 (m, 2H), 7.66 (d, J=9.1 Hz, 1H), 7.56-7.43 (m, 2H), 7.40 (t, J=8.0 Hz, 1H), 7.04 (t, J=6.9 Hz, 1H), 4.67 (s, 2H). $^{13}$C NMR (101 MHz, DMSO) δ 160.38, 144.68, 143.00, 132.96, 132.64, 129.97, 128.57, 126.85, 126.37, 117.04, 115.62, 113.53. HRMS: calcd for [M+H], 287.06942; found, 287.06950.

Example 142

6-(4-Chlorophenyl)imidazo[2,1-b]thiazole-5-carbohydrazide (Intermediate Compound)

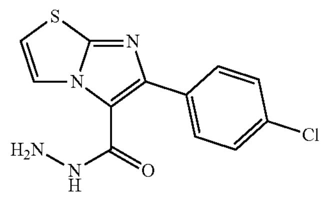 [SMILES: NNC(=O)c1c(-c2ccc(Cl)cc2)nc2sccn12]

Title compound was prepared according to the General Procedure XII (Scheme 10). Yield: 440 mg (64%). $^1$H NMR (401 MHz, DMSO-$d_6$) δ 9.44 (s, 1H), 7.93 (d, J=4.5 Hz, 1H), 7.84-7.78 (m, 2H), 7.50-7.44 (m, 2H), 7.41 (d, J=4.5 Hz, 1H), 4.56 (s, 2H). $^{13}$C NMR (101 MHz, DMSO) δ 160.40, 150.25, 145.32, 133.13, 132.89, 130.02, 128.77, 120.65, 117.89, 115.20. HRMS: calcd for [M+H], 293.02584; found, 293.02590.

General Procedure XIII. HATU Acylation

Hydrazide derivative was dissolved with dry DMF and phenylacetic acid derivative (1 eq) was added. The reaction mixture was degassed and refilled with argon. HATU (1.2 eq) was added followed by an addition of DIPEA (1.2 eq) (Scheme 10). The reaction mixture was stirred at r.t. and monitored by UPLC. After the completion of the reaction, the solution was evaporated to a minimal volume and purified by reverse-phase flash column chromatography.

Example 143

2-(4-Chlorophenyl)-N'-(2-(3,4-dichlorophenyl)acetyl)imidazo[1,2-a]pyridine-3-carbohydrazide (Intermediate Compound)

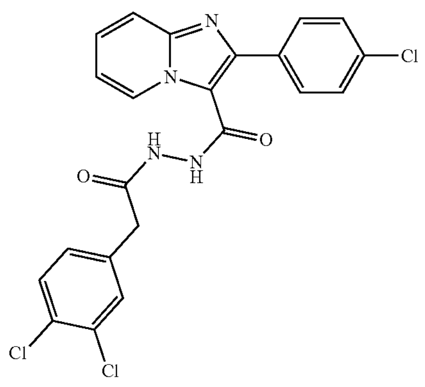 [SMILES: O=C(Cc1ccc(Cl)c(Cl)c1)NNC(=O)c1c(-c2ccc(Cl)cc2)nc2ccccn12]

Title compound was prepared according to the General Procedure XIII (Scheme 10). Mobile phase petrolether/EtOAc (40-80%). Yield: 298 mg (90%). $^1$H NMR (401 MHz, DMSO-$d_6$) δ 10.49 (s, 1H), 10.43 (s, 1H), 8.80 (dt, J=7.0, 1.2 Hz, 1H), 8.06-7.98 (m, 2H), 7.95 (s, 1H), 7.71 (dt, J=9.0, 1.2 Hz, 1H), 7.65-7.60 (m, 2H), 7.49 (dd, J=9.0, 2.3 Hz, 2H), 7.44 (ddd, J=9.0, 6.8, 1.3 Hz, 1H), 7.34 (dd, J=8.3, 2.1 Hz, 1H), 7.10 (td, J=6.9, 1.2 Hz, 1H), 3.63 (s, 2H). $^{13}$C NMR (101 MHz, DMSO) δ 169.21, 160.31, 145.02, 144.01, 136.78, 133.29, 132.28, 131.35, 130.97, 130.62, 130.18, 129.86, 129.58, 128.59, 127.33, 126.68, 117.16, 114.63, 113.89, 35.98. HRMS: calcd for [M+H], 473.03334; found, 473.03327.

Example 144

6-(4-Chlorophenyl)-N'-(2-(3,4-dichlorophenyl)acetyl)imidazo[2,1-b]thiazole-5-carbohydrazide (Intermediate Compound)

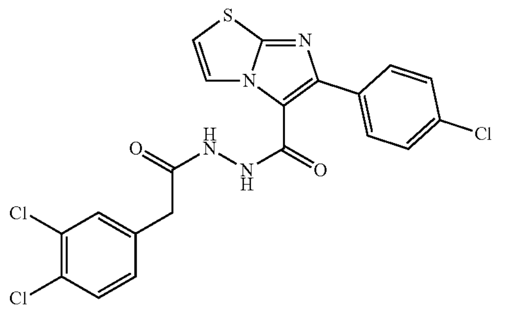 [SMILES: O=C(Cc1ccc(Cl)c(Cl)c1)NNC(=O)c1c(-c2ccc(Cl)cc2)nc2sccn12]

Title compound was prepared according to the General Procedure XIII (Scheme 10). Mobile phase petrolether/EtOAc (40-80%). Yield: 253 mg (78%). $^1$H NMR (401 MHz, DMSO-$d_6$) δ 10.41 (s, 1H), 10.25 (s, 1H), 8.05 (d, J=4.5 Hz, 1H), 7.97-7.92 (m, 2H), 7.62 (dd, J=5.1, 3.1 Hz, 2H), 7.48-7.44 (m, 3H), 7.34 (dd, J=8.3, 2.0 Hz, 1H), 3.61 (s, 2H). $^{13}$C NMR (101 MHz, DMSO) δ 169.40, 159.92, 150.93, 146.58, 137.08, 133.22, 132.72, 131.59, 131.23, 130.88, 130.17, 130.10, 129.84, 128.80, 120.86, 116.88, 115.67, 46.20. HRMS: calcd for [M+H], 476.97520; found, 476.97455

Example 145

2-Chloro-5-(2-(2-(2-(4-chlorophenyl)imidazo[1,2-a]pyridine-3-carbonyl)hydrazineyl)-2-oxoethyl)-N,N-dimethylbenzamide (Intermediate Compound)

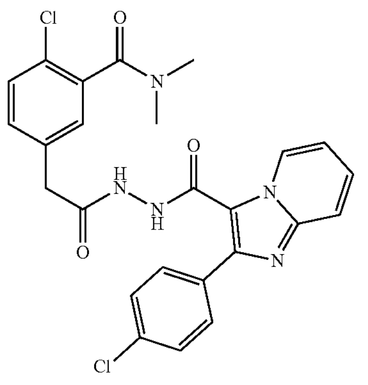 [SMILES: CN(C)C(=O)c1cc(CC(=O)NNC(=O)c2c(-c3ccc(Cl)cc3)nc3ccccn23)ccc1Cl]

Title compound was prepared according to the General Procedure XIII (Scheme 10). Mobile phase $H_2O/CH_3CN$ (10-70%). Yield: 290 mg (83%). $^1$H NMR (401 MHz, DMSO-$d_6$) δ 10.54-10.48 (m, 1H), 10.46-10.41 (m, 1H), 8.81 (dt, J=6.9, 1.3 Hz, 1H), 8.04-7.96 (m, 2H), 7.72-7.66 (m, 1H), 7.52-7.46 (m, 4H), 7.42 (td, J=9.2, 8.3, 1.8 Hz, 2H), 7.32 (d, J=2.1 Hz, 1H), 7.11 (td, J=6.9, 1.2 Hz, 1H), 3.64 (s, 2H), 3.01 (s, 3H), 2.79 (s, 3H). $^{13}$C NMR (101 MHz, DMSO) δ 169.40, 167.10, 160.27, 144.95, 143.91, 136.29, 135.35, 133.31, 132.19, 131.26, 130.18, 129.41, 128.64, 128.57, 127.55, 127.37, 126.70, 117.09, 114.66, 113.92, 48.79, 37.71, 34.20. HRMS: calcd for [M+H], 510.10942; found, 510.10991.

Example 146

2-Chloro-5-(2-(2-(2-(4-chlorophenyl)imidazo[1,2-a]pyridine-3-carbonyl)hydrazineyl)-2-oxoethyl)-N-methylbenzamide (Intermediate Compound)

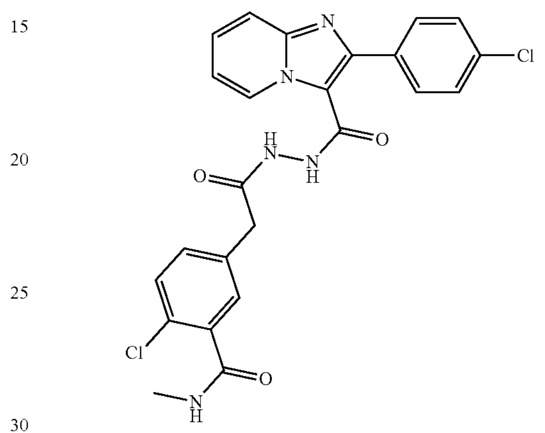

Title compound was prepared according to the General Procedure XIII (Scheme 10). Mobile phase $H_2O/CH_3CN$ (20-80%). Yield: 312 mg (86%). $^1$H NMR (401 MHz, DMSO-$d_6$) δ 10.50 (s, 1H), 10.46 (s, 0H), 8.85-8.78 (m, 1H), 8.36 (q, J=4.6 Hz, 1H), 8.04-7.97 (m, 2H), 7.75-7.67 (m, 1H), 7.52-7.36 (m, 7H), 7.10 (td, J=6.9, 1.2 Hz, 1H), 3.62 (s, 2H), 2.75 (d, J=4.6 Hz, 3H). $^{13}$C NMR (101 MHz, DMSO) δ 169.39, 166.80, 160.29, 144.98, 143.94, 137.09, 134.74, 133.27, 132.26, 131.57, 130.14, 129.68, 129.64, 128.58, 128.30, 127.29, 126.68, 117.14, 114.67, 113.86, 26.16. HRMS: calcd for [M+Na], 496.09377; found, 496.09422.

Example 147

2-Chloro-5-(2-(2-(2-(4-chlorophenyl)imidazo[1,2-a]pyridine-3-carbonyl)hydrazineyl)-2-oxoethyl)benzamide (Intermediate Compound)

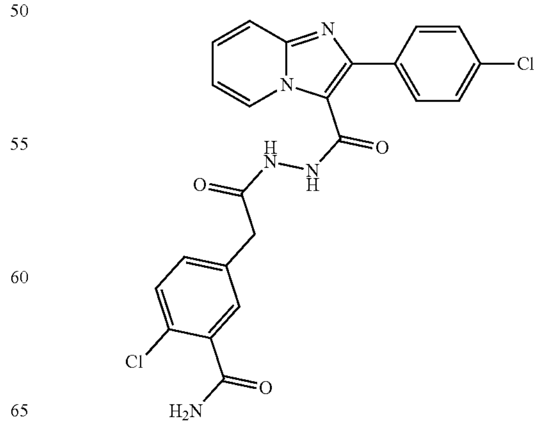

Title compound was prepared according to the General Procedure XIII (Scheme 10). Mobile phase $H_2O$/MeOH (30-100%). Yield: 288 mg (98%). $^1$H NMR (401 MHz, DMSO-$d_6$) δ 10.50 (s, 1H), 10.44 (s, 1H), 8.82 (d, J=6.9 Hz, 1H), 8.02 (d, 2H), 7.89 (s, 1H), 7.71 (d, J=9.0 Hz, 1H), 7.62 (s, 1H), 7.54-7.37 (m, 6H), 7.11 (t, J=6.9 Hz, 1H), 3.63 (s, 2H). $^{13}$C NMR (101 MHz, DMSO) δ 169.46, 168.30, 160.33, 145.02, 143.98, 137.20, 134.70, 133.31, 132.28, 131.49, 130.18, 129.69, 129.51, 128.62, 128.11, 127.34, 126.72, 117.16, 114.70, 113.90, 52.04. HRMS: calcd for [M+Na], 504.06007; found, 504.06048.

General Procedure XIV. Cyclization to 1,3,4-thiadiazole

A round bottom flask was charged with a hydrazide derivative, degassed and refilled with argon. Dry toluene was added and the mixture was degassed once more and refilled with argon. Lawesson's reagent (3 eq) or $P_2S_5$ (2 eq) was added and the mixture was stirred at 100° C. overnight (Scheme 10). After cooling to r.t. the mixture was diluted with water and extracted with EtOAc. An organic phase was dried over sodium sulfate and evaporated. A residue was purified by flash column chromatography.

Example 148

2-(2-(4-Chlorophenyl)imidazo[1,2-a]pyridin-3-yl)-5-(3,4-dichlorobenzyl)-1,3,4-thiadiazole

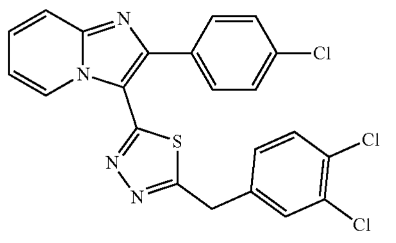 [SMILES: Clc1ccc(-c2nc3ccccn3c2-c2nnc(Cc3ccc(Cl)c(Cl)c3)s2)cc1]

Title compound was prepared according to the General Procedure XIV (Scheme 10) using Lawesson's reagent. Mobile phase $H_2O$/MeOH (30-100%). Yield: 44 mg (21%). $^1$H NMR (500 MHz, DMSO-$d_6$) δ 9.35 (dt, J=7.0, 1.2 Hz, 1H), 7.85 (dt, J=9.0, 1.2 Hz, 1H), 7.78-7.73 (m, 2H), 7.65-7.57 (m, 3H), 7.42-7.38 (m, 2H), 7.31 (ddd, J=8.2, 4.5, 1.7 Hz, 2H), 4.35 (s, 2H). $^{13}$C NMR (126 MHz, DMSO) δ 163.75, 158.07, 147.63, 146.86, 135.84, 134.23, 132.26, 131.72, 131.62, 131.43, 131.16, 130.56, 130.10, 128.84, 128.55, 128.08, 117.70, 115.31, 106.65, 29.99. HRMS: calcd for [M+Na], 477.00472; found, 477.00467.

Example 149

2-Chloro-5-((5-(2-(4-chlorophenyl)imidazo[1,2-a]pyridin-3-yl)-1,3,4-thiadiazol-2-yl)methyl)-N,N-dimethylbenzamide

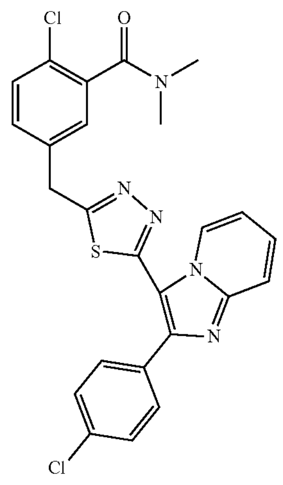 [SMILES: CN(C)C(=O)c1cc(Cc2nnc(-c3c(-c4ccc(Cl)cc4)nc4ccccn34)s2)ccc1Cl]

Title compound was prepared according to the General Procedure XIV (Scheme 10) using P255 reagent. Mobile phase $H_2O$/MeOH (30-100%). Yield: 75 mg (36%). $^1$H NMR (401 MHz, DMSO-$d_6$) δ 9.49 (dt, J=7.0, 1.2 Hz, 1H), 7.81 (dt, J=9.1, 1.2 Hz, 1H), 7.67-7.62 (m, 2H), 7.57 (td, J=8.4, 6.7 Hz, 3H), 7.44 (dd, J=8.5, 5.0 Hz, 1H), 7.34-7.22 (m, 3H), 4.49 (s, 2H), 3.50 (s, 3H), 3.01 (s, 3H). $^{13}$C NMR (101 MHz, DMSO) δ 166.88, 158.33, 148.17, 145.97, 137.17, 136.65, 134.40, 132.20, 131.49, 131.13, 131.05, 129.82, 129.04, 128.38, 128.32, 128.25, 127.94, 127.59, 117.29, 114.84, 112.08, 37.63, 34.17, 33.67. HRMS: calcd for [M+H], 508.07601; found, 508.07605.

Example 150

2-Chloro-5-((5-(2-(4-chlorophenyl)imidazo[1,2-a]pyridin-3-yl)-1,3,4-oxadiazol-2-yl)methyl)-N-methylbenzothioamide

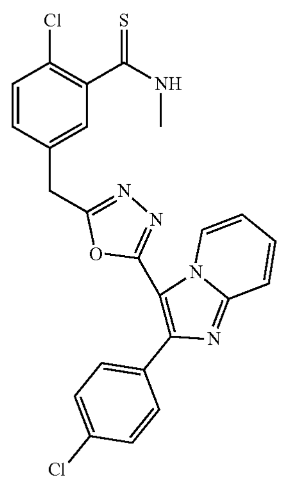 [SMILES: CNC(=S)c1cc(Cc2nnc(-c3c(-c4ccc(Cl)cc4)nc4ccccn34)o2)ccc1Cl]

Title compound was prepared according to the General Procedure XIV (Scheme 10) using $P_2S_5$ reagent. Mobile phase $H_2O$/MeOH (30-100%). Yield: 35 mg (29%). $^1$H NMR (401 MHz, DMSO-$d_6$) δ 10.50 (p, J=5.0 Hz, 1H), 9.60-9.37 (m, 1H), 7.80 (dt, J=9.0, 1.2 Hz, 1H), 7.68-7.63 (m, 1H), 7.57 (dq, J=9.5, 3.4, 2.3 Hz, 1H), 7.45-7.39 (m, 1H), 7.33 (d, J=7.4 Hz, 1H), 7.24 (td, J=6.9, 1.3 Hz, 1H), 4.50 (s, 1H), 3.09 (d, J=4.7 Hz, 2H). $^{13}$C NMR (101 MHz, DMSO) δ 195.66, 166.53, 158.33, 148.12, 145.98, 142.68, 136.41, 134.43, 132.18, 131.47, 130.43, 129.81, 129.25, 129.10, 128.25, 127.56, 127.05, 117.29, 114.84, 112.05, 33.47, 32.60. HRMS: calcd for [M+H], 494.06036; found, 494.06045.

General Procedure XV. 1,3,4-Oxadiazole Formation

Hydrazide intermediate was dissolved in dry DCM and tosyl chloride (1.5 eq) was added followed by TEA (3 eq) at 0° C. The reaction mixture was stirred at r.t. overnight (Scheme 10). The mixture was diluted with water, extracted with EtOAc and the organic phase was washed with saturated $NaHCO_3$ solution. The organic phase was dried over sodium sulfate. Product was isolated by RP-flash column chromatography, mobile phase ($H_2O/CH_3CN$ 10-80%).

Example 151

2-(2-(4-Chlorophenyl)imidazo[1,2-a]pyridin-3-yl)-5-(3,4-dichlorobenzyl)-1,3,4-oxadiazole

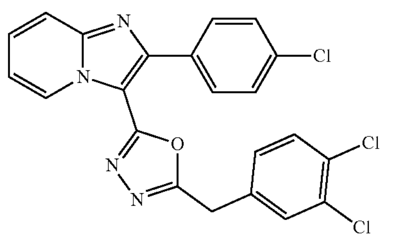 [SMILES: Clc1ccc(-c2nc3ccccn3c2-c2nnc(Cc3ccc(Cl)c(Cl)c3)o2)cc1]

Title compound was obtained from 2-(4-chlorophenyl)-N'-(2-(3,4-dichloro-phenyl)acetyl)imidazo[1,2-a]pyridine-3-carbohydrazide according to the General Procedure XV (Scheme 10). Mobile phase hexane/EtOAc (30-60%). Yield 16 mg (6%). $^1$H NMR (500 MHz, DMSO-$d_6$) δ 9.30 (dt, J=7.0, 1.2 Hz, 1H), 7.82 (dt, J=9.0, 1.2 Hz, 1H), 7.79-7.75 (m, 2H), 7.61-7.57 (m, 3H), 7.43-7.39 (m, 2H), 7.31-7.25 (m, 2H), 4.35 (s, 2H). $^{13}$C NMR (126 MHz, DMSO) δ 163.81, 158.08, 147.83, 146.98, 135.75, 134.31, 132.41, 131.77, 131.62, 131.32, 131.12, 130.70, 129.92, 128.65, 128.52, 127.96, 117.70, 115.12, 106.70, 30.17. HRMS: calcd for [M+H], 455.02277; found, 455.02282.

Example 152

2-Chloro-5-((5-(2-(4-chlorophenyl)imidazo[1,2-a]pyridin-3-yl)-1,3,4-oxadiazol-2-yl)methyl)-N-methylbenzamide

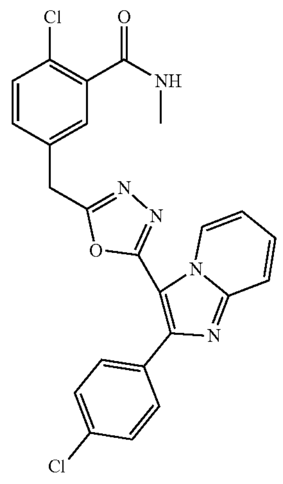 [SMILES: CNC(=O)c1cc(Cc2nnc(-c3c(-c4ccc(Cl)cc4)nc4ccccn34)o2)ccc1Cl]

Title compound was prepared according to the General Procedure XV (Scheme 10). Mobile phase: hexane/EtOAc (30-100%). Yield 16 mg (6%). $^1$H NMR (401 MHz, DMSO-$d_6$) δ 9.34 (dt, J=6.9, 1.2 Hz, 1H), 8.35 (q, J=4.5 Hz, 1H), 7.85 (dt, J=9.0, 1.2 Hz, 1H), 7.81-7.76 (m, 2H), 7.61 (ddd, J=9.0, 6.9, 1.3 Hz, 1H), 7.49-7.43 (m, 3H), 7.40-7.33 (m, 2H), 7.30 (td, J=6.9, 1.3 Hz, 1H), 4.34 (s, 2H), 2.75 (d, J=4.6 Hz, 3H). $^{13}$C NMR (101 MHz, DMSO) δ 166.56, 163.71, 157.77, 147.36, 146.56, 137.36, 133.96, 133.63, 132.00, 131.53, 131.16, 129.96, 129.50, 129.01, 128.53, 128.37, 127.79, 117.40, 115.00, 106.35, 29.84, 26.14. HRMS: calcd for [M+Na], 500.06515; found, 500.06550.

Scheme 11.

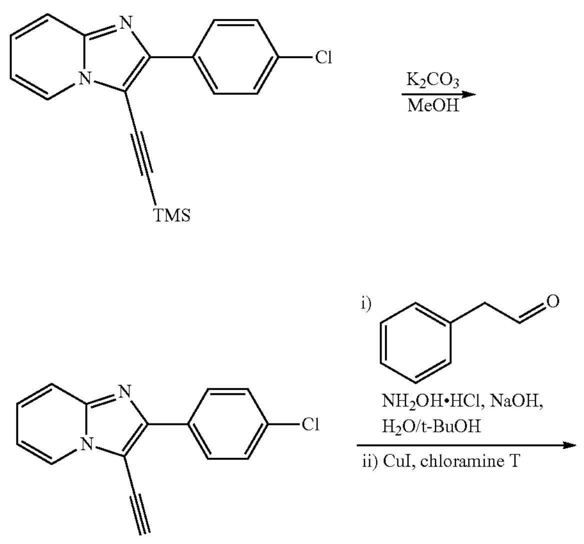

-continued

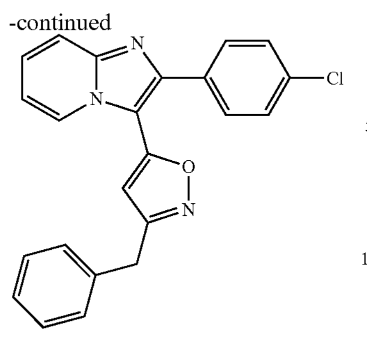

Example 153

2-(4-Chlorophenyl)-3-ethynylimidazo[1,2-a]pyridine (Intermediate Compound)

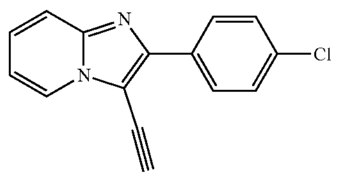 [SMILES: C#Cc1c(-c2ccc(Cl)cc2)nc2ccccn12]

2-(4-Chlorophenyl)-3-((trimethylsilyl)ethynyl)imidazo[1,2-a]pyridine (513 mg, 1.58 mmol) was dissolved in MeOH and $K_2CO_3$ (435 mg, 2 eq) was added in one portion (Scheme 11). Reaction was stirred at r.t. and monitored by TLC. After the completion of the reaction, the mixture was diluted with DCM and washed with water. Combined organic phases were dried over sodium sulfate, evaporated and the residue was purified by flash column chromatography. Mobile phase petrolether/EtOAc (30-50%). Yield 362 mg (90%). $^1H$ NMR (401 MHz, DMSO-$d_6$) δ 8.46 (dt, J=6.8, 1.2 Hz, 1H), 8.28-8.20 (m, 2H), 7.71 (dt, J=9.0, 1.1 Hz, 1H), 7.60-7.52 (m, 2H), 7.45 (ddd, J=9.0, 6.8, 1.3 Hz, 1H), 7.12 (td, J=6.8, 1.2 Hz, 1H), 5.44 (s, 1H). $^{13}C$ NMR (101 MHz, DMSO) δ 145.95, 144.71, 133.40, 131.99, 128.97, 128.32, 128.28, 127.70, 125.77, 117.27, 114.16, 103.47, 94.39, 72.47. HRMS: calcd for [M+Na], 253.05270; found, 253.05273.

Example 154

3-Benzyl-5-(2-(4-chlorophenyl)imidazo[1,2-a]pyridin-3-yl)isoxazole

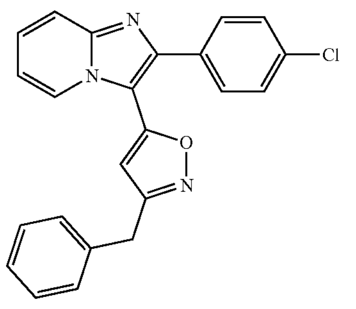 [SMILES: Clc1ccc(-c2nc3ccccn3c2-c2cc(Cc3ccccc3)no2)cc1]

Phenylacetaldehyde (0.045 mL, 1 eq) was dissolved in $H_2O$/t-BuOH mixture (4 mL) and $NH_2OH \cdot HCl$ (30 mg, 1 eq) followed by NaOH (20 mg, 1 eq) was added. The reaction mixture was stirred at r.t for 3 h and then 2-(4-chlorophenyl)-3-ethynylimidazo[1,2-a]pyridine (100 mg, 0.39 mmol), chloramine T (120 mg, 1 eq) and CuI (8 mg, 10 mol %) were added and the reaction mixture was stirred overnight (Scheme 10). The reaction mixture was diluted with water and extracted with EtOAc. Combined organic phases were dried over sodium sulfate and evaporated. The residue was purified by RP-flash column chromatography. Mobile phase $H_2O/CH_3CN$ (10-100%). Yield 99 mg (66%). $^1H$ NMR (401 MHz, DMSO-$d_6$) δ 8.48 (dt, J=6.9, 1.1 Hz, 1H), 7.76 (dt, J=9.1, 1.2 Hz, 1H), 7.68-7.63 (m, 2H), 7.51-7.46 (m, 3H), 7.35 (m, 4H), 7.26 (ddt, J=6.9, 4.6, 3.1 Hz, 1H), 7.12 (td, J=6.9, 1.2 Hz, 1H), 6.82 (s, 1H), 4.11 (s, 2H). $^{13}C$ NMR (101 MHz, DMSO) δ 163.90, 160.02, 146.13, 145.18, 137.73, 133.78, 132.59, 130.33, 129.23, 129.09, 129.04, 127.82, 127.16, 126.15, 117.66, 114.67, 105.32, 31.94. Anal. ($C_{23}H_{16}ClN_3O.0.75H_2O$) C, H, N. HRMS: calcd for [M+H], 386.10547; found, 386.10564. EA: C, 69.17; H, 4.42; N, 10.52. Found: C, 68.94; H, 4.11; N, 10.41.

Scheme 12.

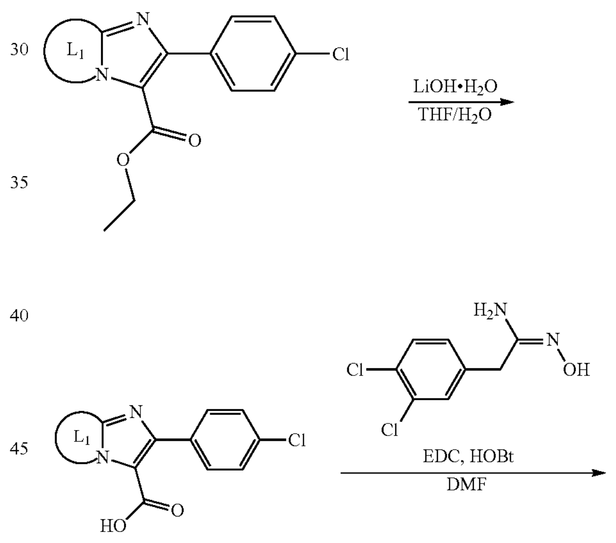

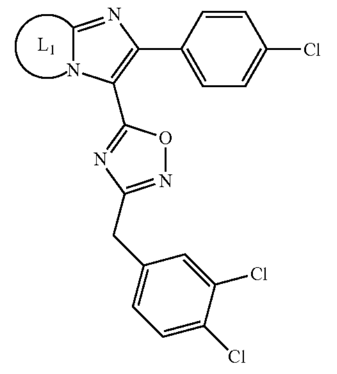

Example 155

2-(4-Chlorophenyl)imidazo[1,2-a]pyridine-3-carboxylic acid (Intermediate Compound)

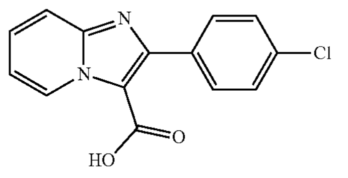 [SMILES: O=C(O)c1c(-c2ccc(Cl)cc2)nc2ccccn12]

Title compound was prepared according to the General Procedure VII (Scheme 12) with a minor modification. Product was filtered as a precipitate after acidification. Yield: 548 mg (quant.). $^{1}H$ NMR (401 MHz, DMSO-$d_6$) δ 9.40-9.32 (m, 1H), 7.83-7.75 (m, 3H), 7.59-7.52 (m, 1H), 7.50 (dd, J=9.0, 2.5 Hz, 2H), 7.21 (td, J=6.9, 1.3 Hz, 1H). $^{13}C$ NMR (101 MHz, DMSO) δ 162.11, 151.23, 146.75, 133.77, 133.70, 132.35, 129.28, 128.92, 128.80, 128.04, 127.77, 117.53, 115.02, 112.51. HRMS: calcd for [M+H], 273.04253; found, 273.04262.

General Procedure XVI. 1,2,4-Oxadiazole Formation

Carboxylic acid derivative was dissolved in dry DMF, degassed and refilled with argon. EDC (1 eq) and HOBt (1 eq) were added in one portion and the mixture was stirred at r.t. for 30 min. Then a solution of (E)-2-(3,4-dichlorophenyl)-N'-hydroxyacetimidamide in dry DMF was added and the reaction mixture was stirred at 80° C. overnight (Scheme 10). After cooling to r.t., the mixture was diluted with EtOAc, washed with $NaHCO_3$ solution, water and the organic phase was dried over sodium sulfate. Product was isolated by flash column chromatography, mobile phase petrolether/EtOAc (20-60%).

Example 156

5-(2-(4-Chlorophenyl)imidazo[1,2-a]pyridin-3-yl)-3-(3,4-dichlorobenzyl)-1,2,4-oxadiazole

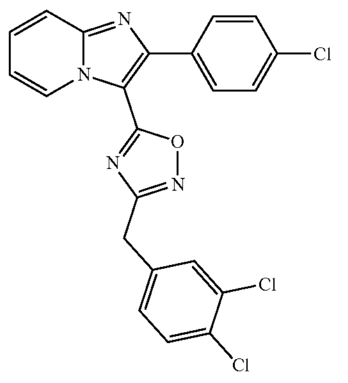 [SMILES: Clc1ccc(-c2nc3ccccn3c2-c2nc(Cc3ccc(Cl)c(Cl)c3)no2)cc1]

Title compound was prepared according to the General Procedure XVI (Scheme 12). Mobile phase petrolether/EtOAc (50-70%). Yield: 250 mg (52%). $^{1}H$ NMR (401 MHz, DMSO-$d_6$) δ 9.41 (dt, J=6.9, 1.2 Hz, 1H), 7.90 (dt, J=9.0, 1.2 Hz, 1H), 7.88-7.84 (m, 2H), 7.71 (d, J=2.0 Hz, 1H), 7.67 (ddd, J=9.0, 6.9, 1.3 Hz, 1H), 7.63 (d, J=8.3 Hz, 1H), 7.60-7.54 (m, 2H), 7.42 (dd, J=8.3, 2.1 Hz, 1H), 7.36 (td, J=7.0, 1.3 Hz, 1H), 4.27 (s, 2H). $^{13}C$ NMR (101 MHz, DMSO) δ 168.27, 167.90, 150.18, 147.19, 137.02, 134.29, 132.16, 131.54, 131.33, 131.19, 130.82, 129.90, 129.77, 129.38, 128.39, 128.01, 117.58, 115.47, 30.46. HRMS: calcd for [M+H], 455.02277; found, 455.02288.

Example 157

5-(6-(4-Chlorophenyl)imidazo[2,1-b]thiazol-5-yl)-3-(3,4-dichlorobenzyl)-1,2,4-oxadiazole

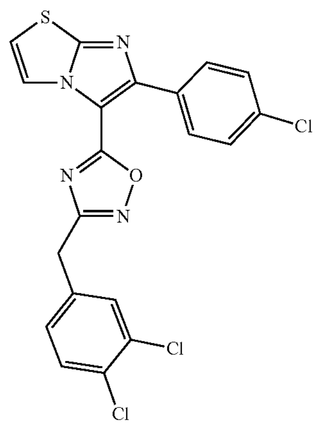 [SMILES: Clc1ccc(-c2nc3sccn3c2-c2nc(Cc3ccc(Cl)c(Cl)c3)no2)cc1]

Title compound was prepared according to the General Procedure XVI (Scheme 12). Mobile phase petrolether/EtOAc (50-70%). Yield: 250 mg (52%). $^{1}H$ NMR (500 MHz, DMSO-$d_6$) δ 8.33 (d, J=4.4 Hz, 1H), 7.94-7.91 (m, 2H), 7.71 (d, J=2.1 Hz, 1H), 7.63 (d, J=4.0 Hz, 1H), 7.62 (s, 1H), 7.57-7.53 (m, 2H), 7.42-7.39 (m, 1H), 4.23 (s, 2H). $^{13}C$ NMR (126 MHz, DMSO) δ 168.78, 167.94, 153.92, 150.51, 137.29, 134.31, 132.08, 131.65, 131.45, 131.25, 131.09, 130.18, 130.10, 128.70, 121.58, 117.20, 109.75, 30.64. HRMS: calcd for [M+H], 460.97919; found, 460.97921.

Scheme 13.

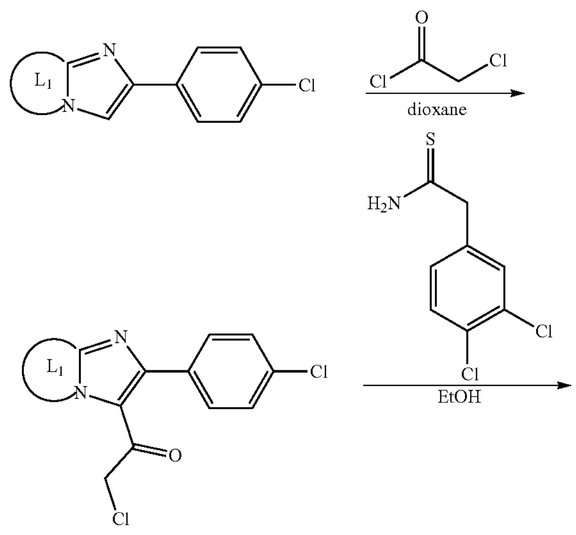

-continued

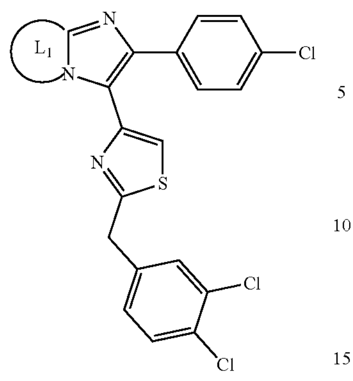

General Procedure XVII. Chloromethylacylation of Heteroaryle 6-(4-Chlorophenyl)imidazo[2,1-b]thiazole or 2-(4-chlorophenyl)imidazo[1,2-a]pyridine (1 mmol) was dissolved in dry dioxane (4 ml) and chloroacetyl chloride (3 eq) was added in one portion. The reaction mixture was stirred at 70° C. under the argon atmosphere for 30 min and then at 100° C. overnight (Scheme 13). After cooling to r.t. a precipitate was formed. Suspension was diluted with saturated $NaHCO_3$ solution and extracted with EtOAc. Organic phase was dried over sodium sulfate and purified by flash column chromatography, mobile phase petrolether/EtOAc (30-60%).

Example 158

2-Chloro-1-(6-(4-chlorophenyl)imidazo[2,1-b]thiazol-5-yl)ethan-1-one (Intermediate Compound)

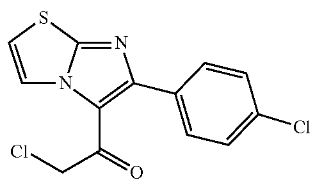 [SMILES: O=C(CCl)c1c(-c2ccc(Cl)cc2)nc2sccn12]

Title compound was prepared according to the described procedure XVII (Scheme 13). Yield: 273 mg (91%). $^1H$ NMR (401 MHz, DMSO-$d_6$) δ 8.46 (d, J=4.4 Hz, 1H), 7.73-7.68 (m, 2H), 7.64 (d, J=4.4 Hz, 1H), 7.62-7.57 (m, 2H), 4.41 (s, 2H). $^{13}C$ NMR (101 MHz, DMSO) δ 180.76, 154.65, 153.23, 134.82, 133.38, 132.00, 129.02, 122.62, 122.19, 117.57, 47.18. HRMS: calcd for [M+H], 310.98072; found, 310.98089.

Example 159

2-Chloro-1-(2-(4-chlorophenyl)imidazo[1,2-a]pyridin-3-yl)ethan-1-one (Intermediate Compound)

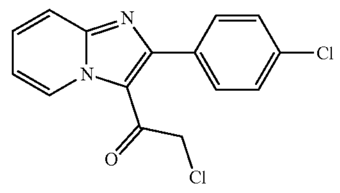 [SMILES: O=C(CCl)c1c(-c2ccc(Cl)cc2)nc2ccccn12]

Title compound was prepared according to the described procedure XVII (Scheme 13). Yield: 492 mg (76%). $^1H$ NMR (401 MHz, DMSO-$d_6$) δ 9.63 (d, J=6.9 Hz, 1H), 7.94 (d, J=8.9 Hz, 1H), 7.85 (t, J=7.9 Hz, 1H), 7.73 (d, J=8.2 Hz, 2H), 7.65 (d, J=8.2 Hz, 2H), 7.45 (t, J=6.9 Hz, 1H), 4.36 (s, 2H). $^{13}C$ NMR (101 MHz, DMSO) δ 182.37, 151.37, 145.94, 135.44, 132.49, 132.19, 132.15, 129.23, 129.22, 119.42, 117.34, 116.76, 47.93. HRMS: calcd for [M+H], 305.02429; found, 305.02434.

General Procedure XVIII. Preparation of 1,3-thiazole.

Chloromethyl intermediates were dissolved in EtOH and 2-(3,4-dichlorophenyl)ethanethioamide (1.5 eq) was added. A reaction mixture was stirred at reflux overnight (Scheme 13). After cooling to r.t. the mixture was purified by RP-flash column chromatography.

Example 160

4-(2-(4-Chlorophenyl)imidazo[1,2-a]pyridin-3-yl)-2-(3,4-dichlorobenzyl)thiazole

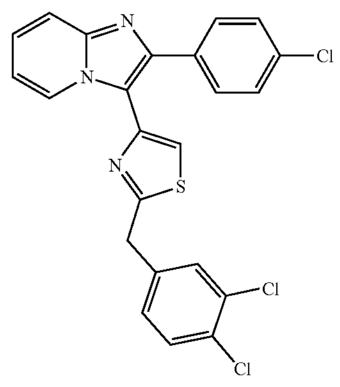 [SMILES: Clc1ccc(-c2nc3ccccn3c2-c2csc(Cc3ccc(Cl)c(Cl)c3)n2)cc1]

Title compound was prepared according to the described procedure XVIII (Scheme 13). Mobile phase $H_2O/CH_3CN$ (20-80%). Yield: 112 mg (62%). $^1H$ NMR (401 MHz, DMSO-$d_6$) δ 8.42 (d, J=6.9 Hz, 1H), 7.83 (s, 1H), 7.74 (d, J=2.1 Hz, 1H), 7.67 (q, J=8.1 Hz, 4H), 7.45-7.35 (m, 4H), 6.99 (t, J=6.9 Hz, 1H), 4.51 (s, 2H). $^{13}C$ NMR (101 MHz, DMSO) δ 169.57, 144.48, 143.11, 142.15, 139.27, 133.16, 132.66, 131.29, 131.25, 130.96, 129.86, 129.73, 129.68, 128.56, 126.10, 125.41, 121.39, 117.09, 115.60, 113.16, 37.34. HRMS: calcd for [M+H], 470.00468; found, 470.00488.

Example 161

6-(4-Chlorophenyl)-5-(2-(3,4-dichlorobenzyl)thiazol-4-yl)imidazo[2,1-b]thiazole

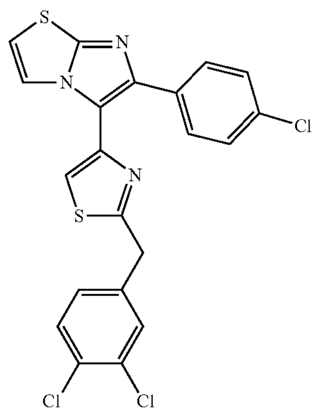 [SMILES: Clc1ccc(-c2nc3sccn3c2-c2csc(Cc3ccc(Cl)c(Cl)c3)n2)cc1]

Title compound was prepared according to the described procedure XVIII (Scheme 13). Mobile phase $H_2O/CH_3CN$ (20-80%). Yield: 213 mg (61%). $^1H$ NMR (401 MHz, DMSO-$d_6$) δ 8.01 (d, J=4.5 Hz, 1H), 7.71 (d, J=2.0 Hz, 1H), 7.68-7.61 (m, 4H), 7.42-7.36 (m, 4H), 4.46 (s, 2H). $^{13}C$ NMR (101 MHz, DMSO) δ 169.35, 149.37, 143.99, 143.09, 139.54, 133.79, 132.56, 131.60, 131.53, 131.24, 130.15, 130.04, 129.84, 128.83, 120.43, 118.35, 117.72, 114.49, 37.55. HRMS: calcd for [M+H], 475.96110; found, 475.96130.

General Procedure XIX. Preparation of Oximes

Aromatic aldehyde was dissolved in DCM and $NH_2OH \cdot HCl$ (1.2 eq) was added followed by an addition of TEA (1.2 eq). The reaction mixture was stirred at r.t., washed with water and the organic phase was dried over sodium sulfate and evaporated. The residue was purified by flash column chromatography.

Example 162

(E)-2-Chloro-5-((4-(2-(4-chlorophenyl)imidazo[1,2-a]pyridin-3-yl)-1H-1,2,3-triazol-1-yl)methyl)benzaldehyde oxime

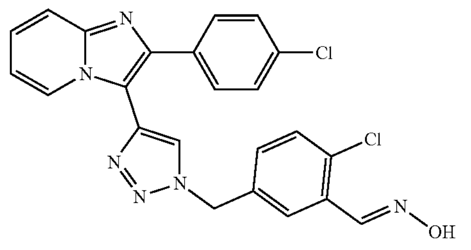 [SMILES: O/N=C/c1cc(Cn2cc(-c3c(-c4ccc(Cl)cc4)nc4ccccn34)nn2)ccc1Cl]

Title compound was prepared according to the described procedure XIX. Mobile phase petrolether/EtOAc (50-100%). Yield: 75 mg (90%). $^1H$ NMR (401 MHz, DMSO-$d_6$) δ 11.75 (s, 1H), 8.51 (s, 1H), 8.46 (dt, J=7.0, 1.2 Hz, 1H), 8.36 (s, 1H), 7.78 (d, J=2.2 Hz, 1H), 7.71-7.66 (m, 4H), 7.56 (d, J=8.3 Hz, 1H), 7.43-7.35 (m, 4H), 7.00 (td, J=6.8, 1.3 Hz, 1H), 5.77 (s, 2H). $^{13}C$ NMR (101 MHz, DMSO) δ 145.22, 144.72, 142.75, 136.69, 136.00, 133.29, 133.13, 132.37, 131.02, 130.78, 130.63, 129.89, 128.97, 126.54, 126.35, 126.16, 125.63, 117.41, 113.67, 111.85, 52.64. HRMS: calcd for [M+H], 463.08354; found, 463.08301.

Scheme 14.

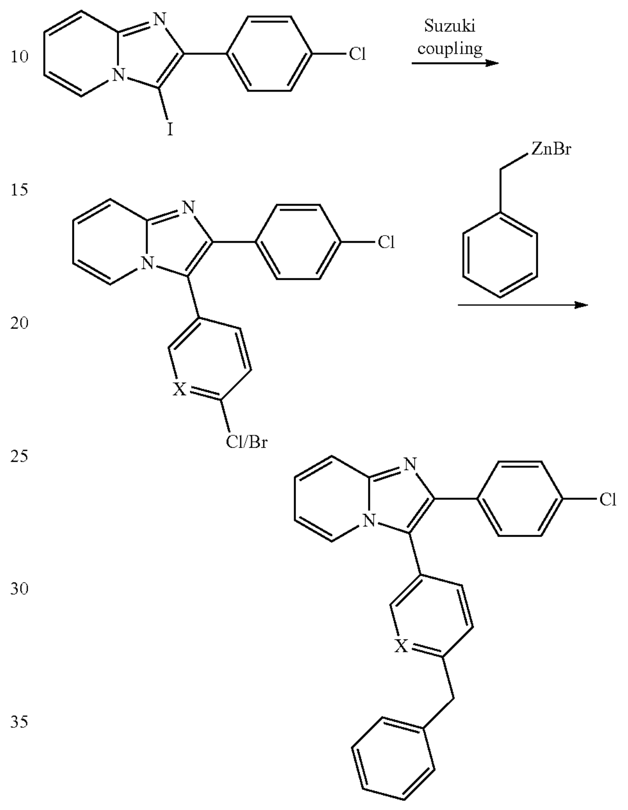

Example 163

3-(4-Bromophenyl)-2-(4-chlorophenyl)imidazo[1,2-a]pyridine (Intermediate Compound)

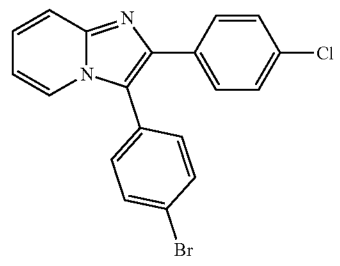 [SMILES: Clc1ccc(-c2nc3ccccn3c2-c2ccc(Br)cc2)cc1]

2-(4-Chlorophenyl)-3-iodoimidazo[1,2-a]pyridine

Example 23 (300 mg, 0.846 mmol) was combined with (4-bromophenyl)boronic acid (1 eq) and diluted with dioxane/$H_2O$ mixture (4:1; 8 ml). $Na_2CO_3$ (3 eq) was added and the mixture was degassed and refilled with argon. $Pd(dppf)Cl_2 \cdot DCM$ (5 mol %) was added and the mixture wad degassed again and refilled with argon. The mixture was stirred at 95° C. overnight (Scheme 14). After the completion of the reaction, the mixture was diluted with water and extracted with EtOAc. The organic phases were dried over sodium sulfate and evaporated. The residue was purified by flash column chromatography. Mobile phase: cyclohexane/EtOAc (20-60%). Yield: 193 mg (59%). $^{13}C$ NMR (101 MHz, DMSO) δ 144.73, 140.86, 133.34, 133.20, 133.17, 132.72, 129.61, 129.22, 128.92, 128.75, 126.10, 124.32, 123.04, 117.42, 113.42.

Example 164

2-(4-Chlorophenyl)-3-(6-chloropyridin-3-yl)imidazo[1,2-a]pyridine (Intermediate Compound)

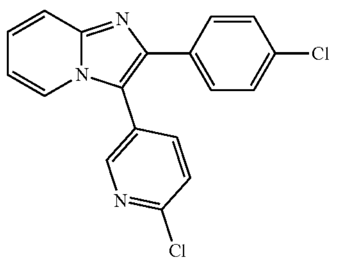 [SMILES: Clc1ccc(-c2nc3ccccn3c2-c2ccc(Cl)nc2)cc1]

2-(4-Chlorophenyl)-3-iodoimidazo[1,2-a]pyridine Example 23 (300 mg, 0.846 mmol) was combined with (6-chloropyridin-3-yl)boronic acid (1.3 eq) and diluted with dioxane/$H_2O$ mixture (4:1; 8 ml). $Na_2CO_3$ (3 eq) was added and the mixture was degassed and refilled with argon. Pd(dppf)$Cl_2$·DCM (5 mol %) was added and the mixture wad degassed again and refilled with argon. The mixture was stirred at 95° C. overnight (Scheme 14). After the completion of the reaction, the mixture was diluted with water and extracted with EtOAc. The organic phases were dried over sodium sulfate and evaporated. The residue was purified by flash column chromatography. Mobile phase: cyclohexane/EtOAc (15-60%). Yield: 183 mg (63%). $^1H$ NMR (401 MHz, DMSO-$d_6$) δ 8.53 (dd, J=2.5, 0.8 Hz, 1H), 8.17 (dt, J=6.9, 1.2 Hz, 1H), 8.06 (dd, J=8.2, 2.5 Hz, 1H), 7.74 (dd, J=8.2, 0.8 Hz, 1H), 7.68 (dt, J=9.1, 1.2 Hz, 1H), 7.58-7.52 (m, 2H), 7.42-7.33 (m, 3H), 6.93 (td, J=6.8, 1.2 Hz, 1H). $^{13}C$ NMR (101 MHz, DMSO) δ 151.85, 151.07, 145.19, 142.40, 142.01, 133.04, 132.95, 129.75, 129.07, 126.53, 125.76, 125.37, 124.70, 117.40, 116.95, 113.59.

Example 165

3-(4-Benzylphenyl)-2-(4-chlorophenyl)imidazo[1,2-a]pyridine

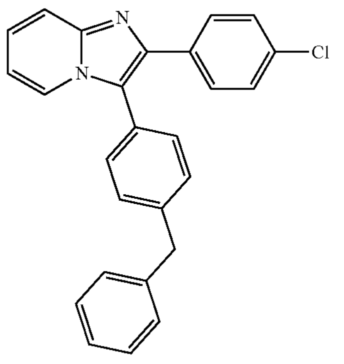 [SMILES: Clc1ccc(-c2nc3ccccn3c2-c2ccc(Cc3ccccc3)cc2)cc1]

3-(4-Bromophenyl)-2-(4-chlorophenyl)imidazo[1,2-a]pyridine Example 163 was dissolved in anhydrous THF (6 ml) under the argon atmosphere. $Pd_2dba_3$ (5 mol %) was added followed by the addition of XantPhos (15 mol %). To the mixture, benzylzinc bromide solution 0.5 M in THF (2 eq) was added and the mixture was stirred at 60° C. overnight (Scheme 14). The mixture was evaporated to a minimal volume, adsorbed onto silica, and purified by flash column chromatography followed by reverse-phase flash column chromatography. Mobile phase: cyclohexane/EtOAc (30-100%) and $H_2O$/ACN (30-100%). Yield: 143 mg (72%). $^1H$ NMR (401 MHz, DMSO-$d_6$) δ 7.95 (d, J=6.8 Hz, 1H), 7.63 (d, J=9.0 Hz, 1H), 7.61-7.55 (m, 2H), 7.42 (d, J=8.0 Hz, 2H), 7.37 (d, J=8.2 Hz, 2H), 7.35-7.25 (m, 6H), 7.24-7.17 (m, 1H), 6.83 (td, J=6.8, 1.2 Hz, 1H), 4.04 (s, 2H). $^{13}C$ NMR (101 MHz, DMSO) δ 144.17, 142.47, 140.85, 140.15, 133.33, 132.22, 130.77, 130.13, 129.17, 129.03, 128.71, 128.50, 126.78, 126.30, 125.51, 123.96, 120.97, 117.06, 112.93, 66.52.

Example 166

3-(6-Benzylpyridin-3-yl)-2-(4-chlorophenyl)imidazo[1,2-a]pyridine

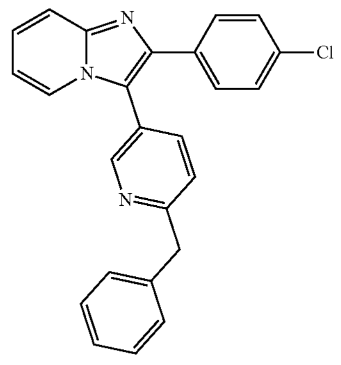 [SMILES: Clc1ccc(-c2nc3ccccn3c2-c2ccc(Cc3ccccc3)nc2)cc1]

2-(4-chlorophenyl)-3-(6-chloropyridin-3-yl)imidazo[1,2-a]pyridine Example 164 was dissolved in anhydrous THF (6 ml) under the argon atmosphere. $Pd_2dba_3$ (5 mol %) was added followed by the addition of XantPhos (15 mol %). To the mixture, benzylzinc bromide solution 0.5 M in THF (2 eq) was added and the mixture was stirred at 60° C. overnight (Scheme 14). The mixture was evaporated to a minimal volume, adsorbed onto silica, and purified by flash column chromatography followed by reverse-phase flash column chromatography. Mobile phase: cyclohexane/EtOAc (30-100%) and $H_2O$/ACN (30-100%). Yield: 158 mg (75%). $^1H$ NMR (401 MHz, DMSO-$d_6$) δ 8.57 (dd, J=2.3, 0.9 Hz, 1H), 8.06 (dt, J=6.9, 1.2 Hz, 1H), 7.89 (dd, J=8.0, 2.3 Hz, 1H), 7.67 (dt, J=9.1, 1.1 Hz, 1H), 7.57-7.52 (m, 2H), 7.48 (dd, J=8.1, 0.9 Hz, 1H), 7.39-7.30 (m, 7H), 7.23 (ddt, J=8.6, 6.2, 1.8 Hz, 1H), 6.88 (td, J=6.8, 1.2 Hz, 1H), 4.21 (s, 2H). $^{13}C$ NMR (101 MHz, DMSO) δ 161.60, 151.00, 144.97, 141.61, 139.81, 139.36, 133.35, 132.78, 129.65, 129.58, 128.97, 126.78, 126.27, 124.52, 124.11, 123.37, 118.26, 117.41, 113.49, 66.82.

Scheme 15.

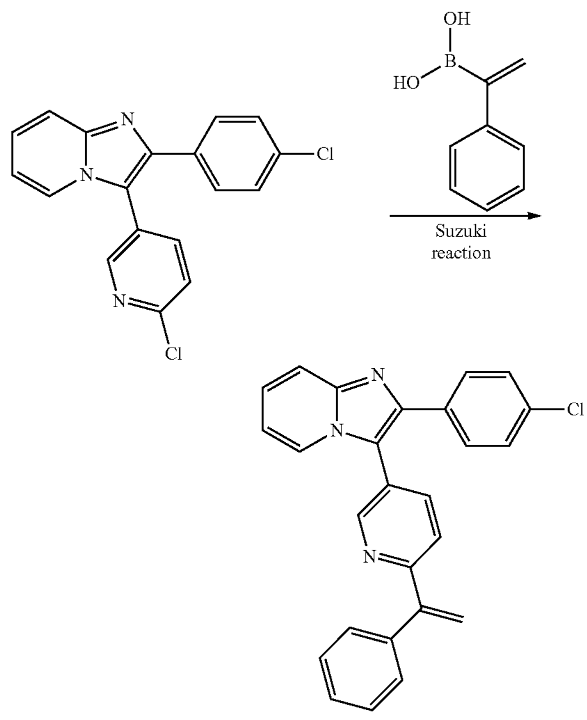

Example 167

2-(4-Chlorophenyl)-3-(6-(1-phenylvinyl)pyridin-3-yl)imidazo[1,2-a]pyridine

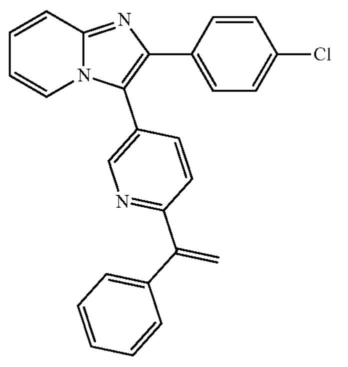 [SMILES: C=C(c1ccccc1)c1ccc(-c2c(-c3ccc(Cl)cc3)nc3ccccn23)cn1]

2-(4-chlorophenyl)-3-(6-chloropyridin-3-yl)imidazo[1,2-a]pyridine Example 164 was combined with (1-phenylvinyl) boronic acid (1.3 eq) and diluted with dioxane/$H_2O$ mixture (4:1; 8 ml). $Na_2CO_3$ (3 eq) was added and the mixture was degassed and refilled with argon. Pd(dppf)$Cl_2$·DCM (5 mol %) was added and the mixture wad degassed again and refilled with argon. The mixture was stirred at 95° C. overnight (Scheme 15). After the completion of the reaction, the mixture was diluted with water and extracted with EtOAc. The organic phases were dried over sodium sulfate and evaporated. The residue was purified by flash column chromatography. Mobile phase: cyclohexane/EtOAc (15-60%). Yield: 189 mg (66%). $^{1}H$ NMR (401 MHz, DMSO-$d_6$) δ 8.66 (dd, J=2.3, 0.9 Hz, 1H), 8.18 (dt, J=6.9, 1.2 Hz, 1H), 7.97 (dd, J=8.1, 2.3 Hz, 1H), 7.69 (dt, J=9.1, 1.2 Hz, 1H), 7.63-7.57 (m, 2H), 7.53 (dd, J=8.1, 0.9 Hz, 1H), 6.93 (td, J=6.8, 1.2 Hz, 1H), 6.16 (d, J=1.5 Hz, 1H), 5.67 (d, J=1.5 Hz, 1H), 4.37 (t, J=5.0 Hz, 2H), 3.45 (qd, J=7.0, 4.9 Hz, 2H), 1.06 (t, J=7.0 Hz, 4H). $^{13}C$ NMR (101 MHz, DMSO) δ 157.45, 150.73, 148.28, 144.82, 141.51, 139.92, 139.01, 133.00, 132.56, 129.42, 128.74, 128.52, 128.49, 128.05, 126.10, 124.37, 124.33, 122.95, 118.88, 117.83, 117.15, 113.26, 113.26, 56.22, 18.73.

Scheme 16.

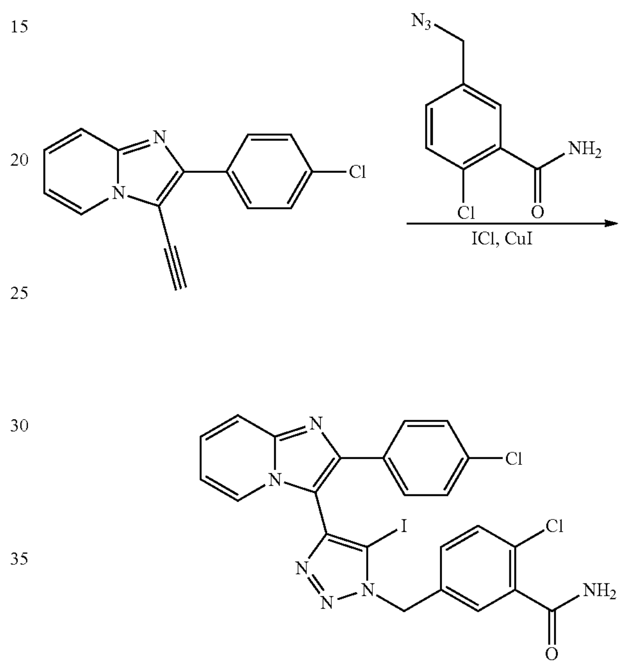

Example 168

2-Chloro-5-((4-(2-(4-chlorophenyl)imidazo[1,2-a]pyridin-3-yl)-5-iodo-1H-1,2,3-triazol-1-yl)methyl)benzamide 2-(4-chlorophenyl)-3-ethynylimidazo[1,2-a]pyridine (74 mg, 0.35 mmol) was combined with 5-(azidomethyl)-2-chlorobenzamide (1 eq) and acetonitrile (3 ml) was added. The mixture was degassed and refilled with argon. CuI (1 eq) was added followed by an addition of ICl (1 eq, 1M in DCM). The mixture was stirred at 65° C. (Scheme 16). After the completion of the reaction, the mixture was diluted with EtOAc, washed with water and combined organic phases were dried over sodium sulfate, evaporated and purified by flash column chromatography. Mobile phase cyclohexane/EtOAc (50-100%). Yield 90 mg (44%). $^{1}H$ NMR (401 MHz, DMSO-$d_6$) δ 8.08 (dt, J=6.9, 1.2 Hz, 1H), 7.97 (d, J=5.3 Hz, 3H), 7.77-7.70 (m, 2H), 7.63-7.56 (m, 3H), 7.48-7.39 (m, 3H), 7.34-7.27 (m, 2H), 7.00 (td, J=6.8, 1.2 Hz, 1H), 5.84 (s, 2H). $^{13}C$ NMR (101 MHz, DMSO) δ 168.22, 145.48, 143.27, 142.28, 137.97, 134.83, 133.25, 133.15, 130.62, 129.79, 129.76, 129.16, 127.83, 126.92, 125.49, 117.52, 114.34, 113.67, 110.99, 90.16, 53.32.

Example 169

3-(1-(3-Carbamoyl-4-chlorobenzyl)-1H-1,2,3-triazol-4-yl)-2-(4-chlorophenyl)imidazo[1,2-a]pyridin-1-ium chloride

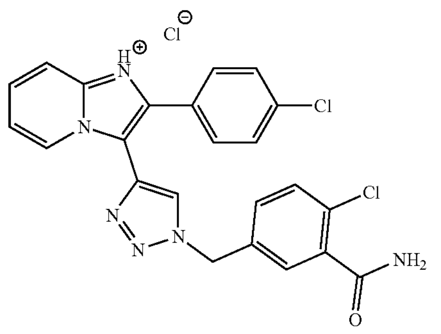

2-Chloro-5-((4-(2-(4-chlorophenyl)imidazo[1,2-a]pyridin-3-yl)-1H-1,2,3-triazol-1-yl)methyl)benzamide Example 110 was dissolved in THF, cooled in an ice bath and HCl 1M in ether wa added while stirred vigorously. The formed salt was stirred at r.t. for 20 minutes, diluted with dry diethylether, filtered and washed with more diethylether. EA: C, 54.96%; H, 3.51%; N, 16.54%; Cl, 21.48%.

Scheme 17.

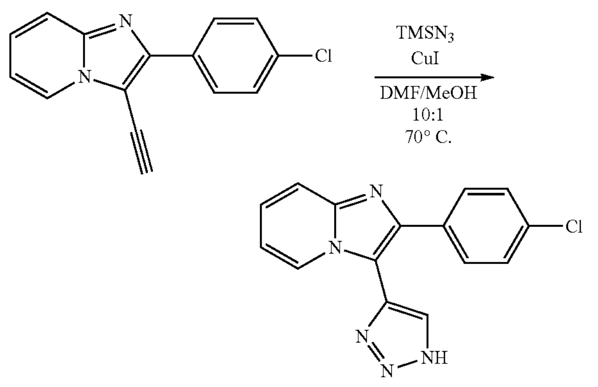

Example 170

2-(4-Chlorophenyl)-3-(1H-1,2,3-triazol-4-yl)imidazo[1,2-a]pyridine (Intermediate Compound)

2-(4-Chlorophenyl)-3-ethynylimidazo[1,2-a]pyridine Example 153 (100 mg, 0.396 mmol) was dissolved in DMF/MeOH (10:1) mixture, degassed and purged with argon. To this solution CuI (10 mol %) and $TMSN_3$ (1 eq) were added and the mixture was stirred at 70° C. overnight. After the completion of the reaction, the mixture was diluted with EtOAc, washed with water and combined organic phases were dried over sodium sulfate and evaporated. Residue was purified by flash column chromatography, mobile phase cyclohexan/EtOAc (10-70%). Yield: 98 mg (84%). $^1H$ NMR (401 MHz, DMSO-$d_6$) δ 8.42 (dt, J=7.0, 1.2 Hz, 1H), 8.13 (s, 1H), 7.76-7.66 (m, 3H), 7.47-7.41 (m, 2H), 7.37 (ddd, J=9.0, 6.7, 1.2 Hz, 1H), 6.99 (td, J=6.8, 1.2 Hz, 1H). $^{13}C$ NMR (101 MHz, DMSO) δ 145.21, 142.71, 135.51, 133.42, 133.08, 130.22, 129.90, 129.90, 128.95, 126.44, 125.60, 117.35, 113.58, 112.24. HRMS: calcd for [M+H], 296.06975; found, 296.06964.

Scheme 18.

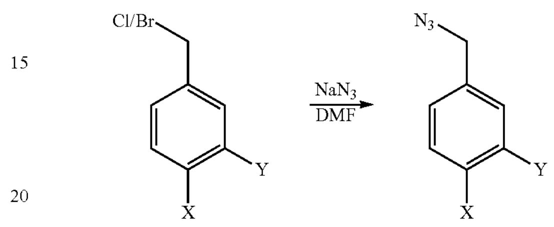

General Procedure XX. Preparation of Azides.

To a solution of appropriate benzyl halide (1 eq) in DMF was added $NaN_3$ (2 eq) and the mixture was stirred at 50° C. till the completion of the reaction (Scheme 18). The mixture was quenched with water and extracted with EtOAc three times. The organic phase was dried over sodium sulfate and evaporated. The residue was purified by flash column chromatography or reverse-phase flash column chromatography if needed.

Example 171

1-((4-(Azidomethyl)phenyl)sulfonyl)pyrrolidine (Intermediate Compound)

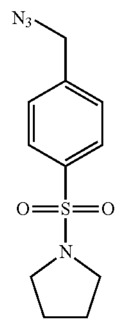

Title compound was prepared according to the General procedure XX (Scheme 18). Mobile phase petrolether/EtOAc (10-60%). Yield 134 mg (79%). $^1H$ NMR (401 MHz, DMSO-$d_6$) δ 7.86-7.82 (m, 2H), 7.69-7.52 (m, 2H), 4.63 (s, 2H), 3.16-3.07 (m, 4H), 1.66-1.53 (m, 4H). $^{13}C$ NMR (101 MHz, DMSO) δ 141.12, 135.90, 129.11, 127.88, 52.94, 47.99, 24.88. HRMS: calcd for [M+H], 267.09102; found, 267.09079.

Example 172

5-(1-Bromoethyl)-2-chlorobenzamide (Intermediate Compound)

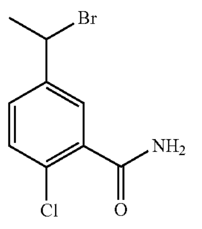

A solution of 2-chloro-5-ethylbenzamide in $CCl_4$ was degassed prior to an addition of NBS (1.5 eq) followed by the addition of catalytic amount of benzoylperoxide. The mixture was stirred at 70° C. overnight. After the completion, the mixture was evaporated, diluted with EtOAc and washed with water and $Na_2S_2O_3$ solution. The organic phase was dried over sodium sulfate, evaporated and purified by flash column chromatography. Mobile phase petrolether/EtOAc (10-50%. Yield: 189 mg (79%). $^1$H NMR (401 MHz, DMSO-$d_6$) δ 7.95 (s, 1H), 7.66 (s, 1H), 7.62-7.53 (m, 2H), 7.51-7.45 (m, 1H), 5.52 (q, J=6.9 Hz, 1H), 1.97 (d, J=6.9 Hz, 3H). $^{13}$C NMR (101 MHz, DMSO) δ 168.01, 142.38, 137.49, 130.14, 129.50, 129.30, 127.24, 127.24, 49.24, 26.46. HRMS: calcd for [M+H], 261.96288; found, 261.96296.

Example 173

5-(1-Azidoethyl)-2-chlorobenzamide (Intermediate Compound)

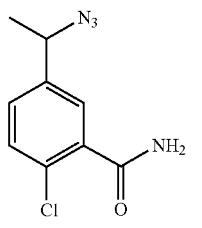

Title compound was prepared according to the described procedure XX (Scheme 18). Yield: 89 mg (89%). $^1$H NMR (401 MHz, DMSO-$d_6$) δ 7.94 (s, 1H), 7.67-7.61 (m, 1H), 7.53-7.47 (m, 1H), 7.45 (d, J=7.8 Hz, 2H), 4.91 (t, J=6.8 Hz, 1H), 1.47 (d, J=6.8 Hz, 3H). $^{13}$C NMR (101 MHz, DMSO) δ 168.36, 140.39, 137.79, 130.39, 130.36, 129.58, 128.94, 127.24, 59.59, 21.45. HRMS: calcd for [M+H], 225.0543; found, 225.0547.

Example 174

4-(Azidomethyl)-1-chloro-2-nitrobenzene (Intermediate Compound)

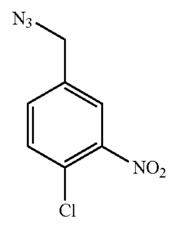 [SMILES: [N-]=[N+]=NCc1ccc(Cl)c([N+](=O)[O-])c1]

(4-Chloro-3-nitrophenyl)methanol (1 g, 5.33 mmol) was dissolved in chloroform (20 ml) and $SOCl_2$ (5 ml, in excess) was added and the reaction mixture was stirred at r.t. overnight. After the completion of the reaction, the mixture was evaporated to dryness, dissolved in DMF (8 ml) and $NaN_3$ (2 eq) was added. The reaction mixture was stirred at 55° C. overnight. The reaction mixture was diluted with water and extracted with EtOAc (3×50 ml). Combined organic phases were dried over sodium sulfate and evaporated. The residue was purified by flash column chromatography. Mobile phase cyclohexan/EtOAc (10-50%). $^1$H NMR (401 MHz, DMSO-$d_6$) δ 8.11 (d, J=2.1 Hz, 1H), 7.81 (d, J=8.3 Hz, 1H), 7.71 (dd, J=8.3, 2.1 Hz, 1H), 4.62 (s, 2H). $^{13}$C NMR (101 MHz, DMSO) δ 137.32, 133.75, 132.11, 125.29, 124.59, 51.93. Yield 655 mg (58%). HRMS: calcd for [M+H], 212.0101; found, 212.0102.

Example 175

5-(Azidomethyl)-2-chlorobenzamide (Intermediate Compound)

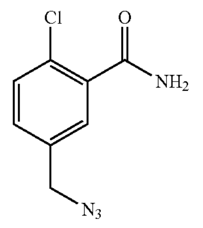 [SMILES: [N-]=[N+]=NCc1ccc(Cl)c(C(N)=O)c1]

Title compound was prepared according to the described procedure XX (Scheme 18) and used as crude for the next reaction step.

Example 176

3-(1-(3,4-Dichlorobenzyl)-1H-1,2,3-triazol-4-yl)-2-(3,4-dichlorophenyl)imidazo[1,2-a]pyridine

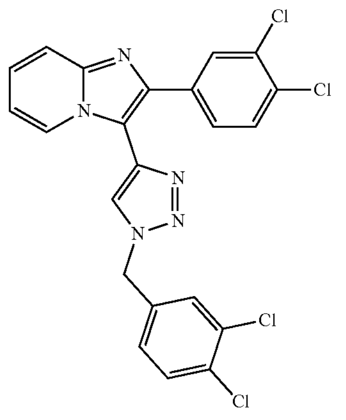 [SMILES: Clc1ccc(Cn2cc(-c3c(-c4ccc(Cl)c(Cl)c4)nc4ccccn34)nn2)cc1Cl]

Title compound was prepared according to the General procedure IV (Scheme 1). Mobile phase petrolether/EtOAc (30-60%). Yield 56 mg (90%). $^{1}$H NMR (401 MHz, DMSO-$d_6$) δ 8.62 (s, 1H), 8.46 (dt, J=7.0, 1.2 Hz, 1H), 7.85 (d, J=1.9 Hz, 1H), 7.74-7.69 (m, 3H), 7.69-7.66 (m, 1H), 7.65 (d, J=2.0 Hz, 1H), 7.62 (d, J=8.4 Hz, 1H), 7.41 (ddd, J=9.1, 6.7, 1.3 Hz, 1H), 7.37 (dd, J=8.3, 2.1 Hz, 1H), 7.02 (td, J=6.8, 1.2 Hz, 1H), 5.76 (s, 2H). $^{13}$C NMR (101 MHz, DMSO) δ 144.96, 141.00, 136.95, 136.02, 134.78, 131.55, 131.40, 131.26, 130.91, 130.65, 130.39, 129.30, 128.58, 127.85, 126.58, 126.09, 125.46, 117.20, 113.57, 112.06, 51.97. HRMS: calcd for [M+H], 487.99978; found, 487.99980.

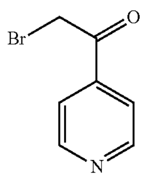

Example 177

2-Bromo-1-(pyridin-4-yl)ethan-1-one (Intermediate Compound)

1-(Pyridin-4-yl)ethan-1-one was dissolved in HBr in acetic acid (3 eq) and $Br_2$ (1.1 eq) was added dropwise while stirred. After completion of the reaction (monitored by TLC or UPLC), $Et_2O$ was added and precipitated product was filtered. Solid compound was dissolved in DCM and washed with aq. solution of $NaHCO_3$ and brine. Organic phase was dried over sodium sulphate and evaporated. The residue was pure enough for the further steps. Yield: 7.71 g (93%). $^{1}$H NMR (401 MHz, DMSO) δ 8.46 (d, J=6.7 Hz, 2H), 8.35 (d, J=6.7 Hz, 2H), 4.88 (s, 2H). $^{13}$C NMR (101 MHz, DMSO) δ 194.59, 144.34, 142.40, 126.73, 31.27. LC-MS: calcd for [M+H], 199.971, found, 199.591.

Example 178

2-(4-Chlorophenyl)imidazo[1,2-a]pyridine-3-carbonitrile (Intermediate Compound)

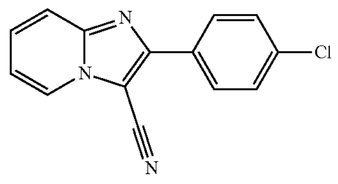 [SMILES: N#Cc1c(-c2ccc(Cl)cc2)nc2ccccn12]

2-(4-Chlorophenyl)-3-iodoimidazo[1,2-a]pyridine, $Pd_2(dba)_3$ (0.1 eq), dppf (0.1 eq), $Zn(CN)_2$ (1.5 eq) and Zn (0.1 eq) were placed in dried round bottom flask, dissolved in DMF and degassed at 0° C. and flushed with argon. DIPEA (1.5 eq) was added and the reaction was stirred at 80° C. under argon atmosphere overnight. After the completion of the reaction, the mixture was diluted with EtOAc and washed with water. The water phase was extracted twice more with EtOAc, combined organic phases were dried over sodium sulphate and evaporated. The residue was purified by flash column chromatography. Mobile phase cy/EtOAc (10-50%). Yield 389 mg (49%). $^{1}$H NMR (401 MHz, $CDCl_3$) δ 8.34 (dt, J=6.8, 1.2 Hz, 1H), 8.16-8.08 (m, 2H), 7.74 (dt, J=9.1, 1.1 Hz, 1H), 7.51-7.42 (m, 3H), 7.09 (td, J=6.8, 1.2 Hz, 1H). $^{13}$C NMR (101 MHz, $CDCl_3$) δ 152.17, 146.89, 136.30, 129.77, 129.37, 129.10, 128.64, 125.75, 118.29, 115.06, 112.67, 93.96. LC-MS: calcd for [M+H], 254.048, found, 254.070.

Example 179

2-(Pyridin-4-yl)-3-((trimethylsilyl)ethynyl)imidazo[1,2-a]pyridine (Intermediate Compound)

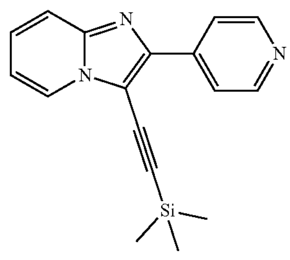 [SMILES: C[Si](C)(C)C#Cc1c(-c2ccncc2)nc2ccccn12]

Title compound was prepared according to the General Procedure III (Scheme 1). Mobile phase cy/EtOAc (20-60%). Yield 431 mg (50%). $^{1}$H NMR (401 MHz, $CDCl_3$) δ 8.75-8.68 (m, 2H), 8.48 (dt, J=7.0, 1.1 Hz, 1H), 7.99-7.93 (m, 2H), 7.51 (dt, J=9.0, 1.1 Hz, 1H), 7.21 (ddd, J=9.0, 6.8, 1.1 Hz, 1H), 6.86 (td, J=6.8, 1.2 Hz, 1H), 0.18 (s, 9H). $^{13}$C NMR (101 MHz, $CDCl_3$) δ 149.82, 145.13, 143.93, 138.76, 126.27, 126.19, 116.63, 114.24, 110.68, 107.03, 87.53, 3.56. LC-MS: calcd for [M+H], 292.126, found, 292.098.

Example 180

2-Chloro-5-((4-(2-(pyridine-4-yl)imidazo[1,2-a]pyridine-3-yl)-1H-1,2,3-triazol-1-yl)methyl)benzamide

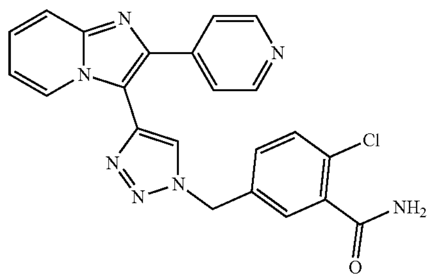 [SMILES: NC(=O)c1cc(Cn2cc(-c3c(-c4ccncc4)nc4ccccn34)nn2)ccc1Cl]

Title compound was prepared according to the General procedure IV (Scheme 1). Mobile phase: water/MeCN with 0.1% formic acid (0-70%). Yield: 99.1 mg (63%). $^{1}$H NMR (401 MHz, MeOD) δ 8.34 (dt, J=7.0, 1.1 Hz, 1H), 8.31 (s, 1H), 7.55 (dt, J=9.1, 1.1 Hz, 3H), 7.48 (d, J=2.0 Hz, 1H), 7.45-7.38 (m, 2H), 7.35 (ddd, J=9.1, 6.8, 1.2 Hz, 1H), 6.91 (td, J=6.9, 1.2 Hz, 1H), 5.70 (s, 2H), 4.84 (s, 4H). $^{13}$C NMR (101 MHz, MeOD) δ 171.39, 150.19, 147.04, 143.52, 141.71, 137.91, 137.29, 135.88, 131.99, 131.80, 131.74, 129.62, 128.58, 127.00, 126.47, 117.75, 115.04, 114.52, 54.02, 49.85. LC-MS: calcd for [M+H], 430.130, found, 430.118.

Example 181

Lemieux-Johnson Oxidation (5-(2-(4-Chlorophenyl)imidazo[1,2-a]pyridin-3-yl)pyridin-2-yl)(phenyl)methanone

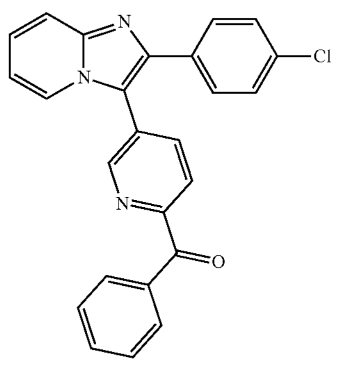

2-(4-Chlorophenyl)-3-(6-(1-phenylvinyl)pyridin-3-yl)imidazo[1,2-a]pyridine was dissolved in DCM/water mixture (1:1) and $NaIO_4$ (2 eq), solution of $OsO_4$ in $CCl_4$ (0.25 eq) and 2,6-lutidine (4 eq) were added. The reaction was stirred at r.t. and monitored by TLC. After the completion of the reaction the mixture was diluted with DCM and washed with saturated $NaHSO_3$ solution. The water phase was extracted twice more with DCM, combined organic phases were dried over sodium sulphate and evaporated. The residue was purified by flash column chromatography. Mobile phase cy/EtOAc (10-50%). Yield 42 mg (84%). $^{1}$H NMR (401 MHz, $CDCl_3$) δ 8.80 (dd, J=2.2, 0.9 Hz, 1H), 8.24 (dd, J=8.1, 0.9 Hz, 1H), 8.20-8.13 (m, 2H), 8.10 (dt, J=6.9, 1.2 Hz, 1H), 8.01 (dd, J=8.1, 2.2 Hz, 1H), 7.80 (dt, J=9.2, 1.1 Hz, 1H), 7.68-7.60 (m, 1H), 7.58-7.48 (m, 4H), 7.38-7.34 (m, 1H), 7.33-7.29 (m, 2H), 6.90 (td, J=6.8, 1.2 Hz, 1H). $^{13}$C NMR (101 MHz, $CDCl_3$) δ 192.96, 154.74, 149.78, 145.71, 143.27, 138.74, 136.32, 136.09, 134.58, 133.34, 131.49, 131.15, 129.81, 129.13, 128.40, 126.59, 125.39, 122.93, 118.02, 117.13, 113.85. LC-MS: calcd for [M+H], 410.105, found, 410.197.

Example 182

Dihydroxylation 1-(5-(2-(4-Chlorophenyl)imidazo[1,2-a]pyridin-3-yl)pyridin-2-yl)-1-phenylethane-1,2-diol

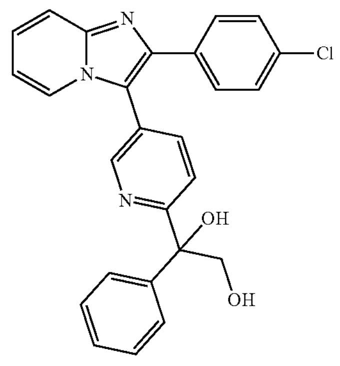 [SMILES: OCC(O)(c1ccccc1)c1ccc(-c2c(-c3ccc(Cl)cc3)nc3ccccn23)cn1]

2-(4-Chlorophenyl)-3-(6-(1-phenylvinyl)pyridin-3-yl)imidazo[1,2-a]pyridine Example 167 and NBS (1.1 eq) were dissolved in water/1,4-dioxane mixture (1:3). The reaction was stirred at r.t. for 3 h, monitored by TLC. After the completion of the reaction the mixture was diluted with EtOAc and washed with water. The water phase was extracted twice more with EtOAc, combined organic phases were dried over sodium sulphate and evaporated. The residue was dissolved in iPrOH and its pH was adjusted to ~10 by aqueous solution of NaOH. Mixture was stirred for 1 h, monitored by TLC. After the completion of the reaction the mixture was diluted with EtOAc and washed with water. The water phase was extracted twice more with EtOAc, combined organic phases were dried over sodium sulphate and evaporated. The residue was dissolved in water/MeCN mixture (1:1) with 10% of formic acid. The reaction was stirred for 3 h, monitored by TLC. After the completion of the reaction the mixture was diluted with EtOAc and washed with water. The water phase was extracted twice more with EtOAc, combined organic phases were dried over sodium sulphate and evaporated. The residue was purified by flash reverse phase chromatography. Eluent water/MeCN with 0.1% formic acid (0-60%). Yield 36 mg (61%). $^{1}$H NMR (401 MHz, $CDCl_3$) δ 8.59 (dd, J=2.2, 0.9 Hz, 1H), 7.95 (dt, J=6.9, 1.2 Hz, 1H), 7.77 (dd, J=8.2, 2.2 Hz, 1H), 7.71 (dt, J=9.1, 1.2 Hz, 1H), 7.63 (dd, J=8.2, 0.9 Hz, 1H), 7.59-7.48 (m, 5H), 7.43-7.35 (m, 2H), 7.35-7.30 (m, 1H), 7.30-7.24 (m, 4H), 6.81 (td, J=6.8, 1.2 Hz, 1H), 4.54 (d, J=11.5 Hz, 1H), 4.06 (d, J=11.5 Hz, 1H). $^{13}$C NMR (101 MHz, $CDCl_3$) δ 163.49, 149.10, 145.50, 142.71, 139.23, 136.25, 134.03, 132.02, 129.53, 128.86, 128.56, 127.77, 125.96, 125.87, 124.69, 123.01, 122.86, 117.86, 117.27, 113.23, 78.67, 69.30. LC-MS: calcd for [M+H], 442.132, found, 442.149.

Example 183

Wittig Reaction

8-Benzylidene-1,4-dioxaspiro[4.5]decane (Intermediate Compound)

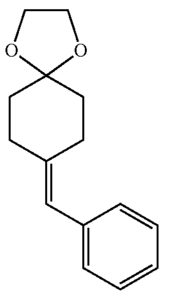 [SMILES: C(=C1CCC2(CC1)OCCO2)c1ccccc1]

To the dispersion of NaH (1.2 eq, 60% in min. oil) in DMSO in round bottom flask a solution of benzyltriphenylphosphonium bromide in DMSO (1.2 eq) was added dropwise. The reaction was stirred at r.t. for 30 min. The mixture was heated to 50° C. and stirred for 30 min. 1,4-Dioxaspiro[4.5]decan-8-one was added to the mixture dropwise. Mixture was stirred at 50° C. overnight. After the completion of the reaction the mixture was diluted with EtOAc and washed with water. The water phase was extracted twice more with EtOAc, combined organic phases were dried over sodium sulphate and evaporated. The residue was purified by flash column chromatography. Mobile phase cy/EtOAc (0-10%). Yield 584 mg (26%). $^{1}$H NMR (401 MHz, $CDCl_3$) δ 7.37-7.28 (m, 2H), 7.25-7.17 (m, 3H), 6.32 (s, 1H), 3.99 (s, 4H), 2.54 (ddd, J=7.8, 5.2, 1.3 Hz, 2H), 2.45 (ddd, J=7.8, 5.2, 1.3 Hz, 2H), 1.81 (ddt, J=7.3, 5.2, 0.9 Hz, 2H), 1.74-1.66 (m, 2H). $^{13}$C NMR (101 MHz, $CDCl_3$) δ 140.36, 138.07, 128.91, 128.11, 126.11, 123.45, 64.39, 36.13, 35.41, 34.17. LC-MS: calcd for [M+H], 231.138, found, 231.092.

Example 184

Hydrogenation

8-Benzyl-1,4-dioxaspiro[4.5]decane (Intermediate Compound)

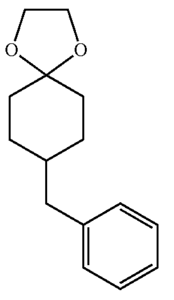 [SMILES: c1ccc(CC2CCC3(CC2)OCCO3)cc1]

8-Benzylidene-1,4-dioxaspiro[4.5]decane was dissolved in EtOAc in round bottom flask. The reaction mixture was degassed at 0° C., refilled with argon and Pd/C (7.5 mol %) was added in one portion. The flask was evacuated and refilled with hydrogen. The mixture was stirred at r.t. After the completion of the reaction (monitored by TLC), the mixture was diluted with EtOAc and filtered over celite. Filtrate was washed with water, water phase was extracted twice more with EtOAc, combined organic phases were dried over sodium sulphate and evaporated. A residue was purified by flash column chromatography. Mobile phase cy/EtOAc (0-10%). Yield 542 mg (92%). $^{1}$H NMR (401 MHz, $CDCl_3$) δ 7.33-7.23 (m, 2H), 7.19-7.10 (m, 3H), 3.94 (s, 4H), 2.53 (d, J=7.2 Hz, 2H), 1.79-1.64 (m, 4H), 1.52-1.41 (m, 1H), 1.37-1.22 (m, 4H). $^{13}$C NMR (101 MHz, $CDCl_3$) δ 141.29, 129.23, 128.30, 125.88, 109.25, 64.33, 43.07, 38.57, 34.60, 30.16. LC-MS: calcd for [M+H], 233.154, found, 233.205.

Example 185

Ketone Deprotection

4-Benzylcyclohexan-1-one (Intermediate Compound)

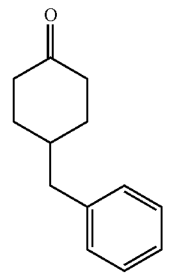 [SMILES: O=C1CCC(Cc2ccccc2)CC1]

8-Benzyl-1,4-dioxaspiro[4.5]decane was dissolved in acetone/conc. HCl mixture (2:1). The reaction was stirred at r.t. for 1 h, monitored by TLC. After the completion of the reaction the mixture was diluted with EtOAc and washed with water. The water phase was extracted twice more with EtOAc, combined organic phases were dried over sodium sulphate and evaporated. The residue was purified by flash column chromatography. Mobile phase cy/EtOAc (0-10%). Yield 356 mg (81%). $^{1}$H NMR (401 MHz, $CDCl_3$) δ 7.36-7.27 (m, 2H), 7.25-7.14 (m, 3H), 2.61 (d, J=6.8 Hz, 2H), 2.44-2.22 (m, 4H), 2.10-1.94 (m, 4H), 1.53-1.37 (m, 1H). $^{13}$C NMR (101 MHz, $CDCl_3$) δ 212.12, 140.44, 129.10, 128.43, 126.19, 42.26, 40.84, 38.20, 32.52. LC-MS: calcd for [M+H], 189.127, found, 189.196.

Example 186

Addition Reaction

4-Benzyl-1-(2-(4-chlorophenyl)imidazo[1,2-a]pyridin-3-yl)cyclohexan-1-ol

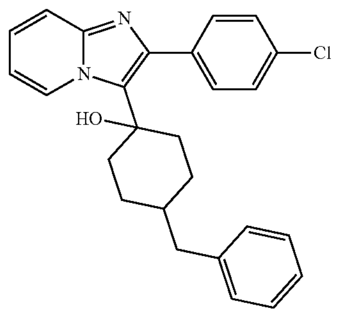 [SMILES: OC1(c2c(-c3ccc(Cl)cc3)nc3ccccn23)CCC(Cc2ccccc2)CC1]

2-(4-Chlorophenyl)-3-iodoimidazo[1,2-a]pyridine Example 23 was added to round bottom flask and flushed with argon. Compound was dissolved in freshly distilled THF and cooled to −78° C. under argon atmosphere. 1.6M solution of BuLi in hexane (1.1 eq) was added dropwise. The reaction was stirred for 20 min. Solution of 4-benzylcyclohexan-1-one in fresh THF (1 eq) was added. The mixture was stirred at r.t. under argon overnight. After the completion of the reaction the mixture was diluted with EtOAc and washed with water. The water phase was extracted twice more with EtOAc, combined organic phases were dried over sodium sulphate and evaporated. The residue was purified by flash column chromatography. Mobile phase cy/EtOAc (10-60%). Yield 132 mg (30%). $^1$H NMR (401 MHz, $CDCl_3$) δ 8.93 (tt, J=7.1, 1.2 Hz, 1H), 7.88-7.77 (m, 2H), 7.51-7.46 (m, 3H), 7.29-7.04 (m, 6H), 6.84-6.73 (m, 1H), 4.11 (q, J=7.1 Hz, 1H), 2.50 (d, J=5.5 Hz, 2H), 2.44-2.16 (m, 1H), 2.11-1.91 (m, 4H), 1.46 (dd, J=18.3, 6.5 Hz, 4H). $^{13}$C NMR (101 MHz, $CDCl_3$) δ 140.81, 140.44, 139.38, 133.88, 132.03, 131.57 (d, J=6.7 Hz), 129.10, 129.01, 127.42, 126.20, 125.33, 117.44, 112.91, 108.38, 71.03, 43.75, 42.25, 40.84, 32.52. LC-MS: calcd for [M+H], 417.173, found, 417.234.

Example 187

Hydroxyl Elimination 3-(4-Benzylcyclohex-1-en-1-yl)-2-(4-chlorophenyl)imidazo[1,2-a]pyridine

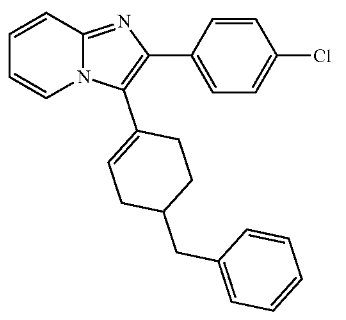 [SMILES: Clc1ccc(-c2nc3ccccn3c2C2=CCC(Cc3ccccc3)CC2)cc1]

4-Benzyl-1-(2-(4-chlorophenyl)imidazo[1,2-a]pyridin-3-yl)cyclohexan-1-ol was dissolved in dry pyridine. Mixture was cooled to 0° C. and trifluoroacetic anhydride (6 eq) was added dropwise. After the completion of the reaction (2 h) pyridine was removed by co-distillation with toluene. The residue was purified by flash column chromatography. Mobile phase cy/EtOAc (10-60%). Yield 94 mg (99%). $^1$H NMR (400 MHz, $CDCl_3$) δ 8.03 (dt, J=6.9, 1.2 Hz, 1H), 7.90-7.82 (m, 2H), 7.71 (dt, J=9.0, 1.1 Hz, 1H), 7.45-7.38 (m, 2H), 7.38-7.31 (m, 2H), 7.32-7.18 (m, 5H), 6.83 (td, J=6.8, 1.2 Hz, 1H), 6.15-6.07 (m, 1H), 2.73 (d, J=6.5 Hz, 2H), 2.45-2.35 (m, 1H), 2.28-2.16 (m, 2H), 2.14-2.03 (m, 2H), 1.59-1.43 (m, 1H). $^{13}$C NMR (101 MHz, $CDCl_3$) δ 144.09, 140.49, 139.06, 133.89, 133.72, 132.48, 129.27, 128.92, 128.81, 128.48, 127.37, 126.20, 125.32, 123.69, 122.79, 117.21, 42.93, 35.28, 32.43, 28.93, 28.26. LC-MS: calcd for [M+H], 399.162, found, 399.231.

Biological Methods

Method for Assessing Biological Activities:

Cellular Models

Human hepatocellular carcinoma HepG2 and African green monkey kidney COS-1 cell lines were purchased from the European Collection of Cell Cultures (ECACC, Salisbury, UK). Long term primary human hepatocytes in monolayers have been purchased from Biopredic International (Cat. No. HEP22000, batch HEP2201023, France).

HepaRG and CAR Knockout HepaRG™ human hepatoma cell line have been from Sigma-Aldrich (Cat. No. MTOX1012).

TR-FRET CAR Coactivator Binding Assay

The LanthaScreen® TR-FRET CAR Coactivator Binding Assay Kit (ThermoFisher Scientific, Cat. No PV4836) with goat terbium (Tb) bound anti-GST antibody was used with slight modifications of the manufacturer's protocol as we described before (Carazo and Pavek, 2015). The assay uses two fluorophores: a terbium-labeled anti-GST antibody interacting with glutathione-S-transferase tagged human CAR ligand-binding domain (LBD) and a fluorescein-labeled PGC1α coactivator peptide. The interaction of a ligand stimulates interactions of the components, resulting in a FRET emission shift from 495 nm to 520 nm. TR-FRET fluorescence was measured with a Synergy Biotek plate reader (Bio-tek, Winooski, VT) using an excitation wavelength of 340 nm with a filter detecting the fluorescent emission signals of terbium at 495 nm and fluorescein at 520 nm and 520 nm/495 nm TR-FRET ratio was calculated. Values above 1 represent the agonistic activity on CAR with subsequent CAR-PGC1α interaction. Half maximal effective concentration ($EC_{50}$) to activate CAR in the assay has been calculated from at least 7 points (range 10 pM/L to 30 μM/L) using GraphPad Prism software.

CAR LBD Assembly Assay

The CAR LBD assembly assay was performed with the below-mentioned described constructs in HepG2 cells (Carazo and Pavek, 2015). The LBD assembly assay is based on a two hybrid luciferase gene reporter assay in which two hybrid expression constructs encoding C (151-349 aa) and N (103-150 aa) terminal parts of human CAR LBD (pCAR-C/VP16 and pCAR-N/GAL4) are co-transfected together with the pGL5-luc luciferase reporter plasmid (Catalog number C9360, Promega, Madison, USA) containing UAS binding sites. A ligand promotes connection of the two parts of CAR LBD resulting in luciferase transactivation. Luminescence activity in the cell lysate was measured using a commercially available luciferase detection system (Catalog Number E1960, Dual Luciferase Reporter Assay Kit, Promega, Madison, WI, USA). The data are presented as means and S.D. and expressed as the fold-change of firefly luciferase activity normalized to *Renilla* luciferase activity in each sample and relative to the vehicle (DMSO 0.1%)-treated controls, which were set at 1. Half maximal effective concentration ($EC_{50}$) to activate CAR in the assay has been calculated from at least 5 point (concentration range from 0.01 to 30 μM) using GraphPad Prism software.

Reporter Gene Assay to Determine Interactions with CAR Variant 3 and Pregnane X Receptor In HepG2 cells, luciferase gene reporter assay has been performed with transiently transfected DNA luciferase constructs responsive for CAR variant 3 (1.6 kb reporter construct of CYP2B6 promoter) or PXR (CYP3A4 gene promoter construct with XREM and proximal promoter regions). At the same time, expression constructs for CAR variant 3 and human PXR have been cotransfected. HepG2 cells were then treated with compounds of the invention for 24 h. Dose-response curves with concentrations from 0.01 up to 30 μM of tested compounds have been analyzed using a plate reader luminometr to determine $EC_{50}$ concentration (in μM/L) for CAR3 variant activation, to determine relative activation of CAR3 variant with selected compounds in comparison with the activity of CITCO at 1 μM concentration or for the relative value of PXR activation (% of rifampicin-mediated PXR activation at 10 μM concentration) (Table 1).

Cytotoxicity

Cell viability in HepG2 and COS-1 cells after a 48 h treatment with test compounds at a concentration from 1 up to 30 μM was determined using the modified formazan-based MTT assay. $IC_{50}$ indicates the concentration of 50% decrease in viability determined by the CellTiter 96®$AQ_{ueous}$One Solution Cell Proliferation Assay (Cat. No. G3582, Promega, Madison, WI, USA). Briefly, the cells were treated with the test compounds or vehicle alone (DMSO) for 48 h. At the end of the treatment, 20 μl of MTS reagent was added directly to each culture wells and further cultivated for 1.5 h. Finally, the absorbance of converted formazan was recorded at 490 nm by plate reader (BioTec Synergy 2. Winooski. VT. USA). Vehicle (DMSO) and TritonX100 (0.9%; v/v) controls of cell viability were set to be 100% and 0%, respectively. In cytotoxic control, TritonX-100 (0.9% v/v) was added to cells 45 minutes before the addition of MTS reagent.

Cytochrome P450 Interaction Assays

Genetically modified microsomes with human CYP3A4, CYP2C9, CYP2D6 and CYP1A2 enzymes (CYP450-Glo™ CYP3A4 Assay with Luciferin-IPA (Cat. No. V8802), CYP450-Glo™ CYP1A2 with Luciferin-1A2 (Cat. No. V8772), CYP450-Glo™ CYP2C9 Assay with Luciferin-H (Cat. No. V8792, Promega, Madison, CA) and P450-Glo™ CYP2D6 Assay Cat. No. V8891, Promega) were used according to manufacturer's procedures. Selected compounds of the invention shown in FIG. 8 have been tested in the concentration range from 0.01 up to 30 μM. Each point was tested in triplicates and experiments have been repeated three times.

In addition, the potential for CYP450 inhibition of 7 major cytochromes P450, 3A4, 1A2, 2C9, 2C19, 2C8, 2D6, and 2B6 by compounds of EXAMPLES 93 and 110 was assessed using LC-MS/MS based assay, in which biotransformations of the CYP450 specific substrates (CYP1A2-Phenacetin/Acetaminophen; CYP3A4-Testosterone/6(3-Hydroxy Testosterone; CYP2C9-Diclofenac/4'-Hydroxydiclofenac; CYP2C19-S-Mephenytoin/4-Hydroxy Mephenytoin; 2D6-Dextromethorphan/Dextrorphan; CYP2B6-Efavirenz/8-Hydroxyefavirenz; CYP2C8-Amodiaquine/Desethylamodiaquine) were used as markers in liver microsomes to quantify the enzymatic activity. The enzymatic reactions were performed under linear conditions with substrate concentration below Km values and conversion of substrate below 20%. Gradient HPLC system VP (Shimadzu) equipped with MS/MS detector API 3000 with TurbolonSpray Electrospray module (PE Sciex, Canada) with Nitrogen generator N2-04-L1466, nitrogen purity 99%+(Whatman). XTreme 200 Pooled Human Liver Microsomes (mixed gender, 200 donors, XenoTech, H2630) were used. Prototype CYP inhibitors were used such as ketoconazole, quinidine, furafylline, sulphaphenazole, tranylcypromine, ticlopidine, and montelukast.

Genotoxicity Testing—Bacterial Reverse Mutation Test (Ames Test)

Evaluation of mutagenicity in Ames fluctuation assay has been performed with compounds in EXAMPLE 109 and 110 on *Salmonella typhimurium* TA100 and TA98 strains at a concentration of 30 μM using a commercial Muta-Chromoplate Kit (EBPI, Canada). Compound of EXAMPLE 93 was assayed for the mutagenicity by the Bacterial Reverse Mutation Test performed according to the OECD Test Guideline No. 471 in agreement with the ICH guideline S2 (R1) on genotoxicity testing and in accordance with GLP principles [OECD Principles on Good Laboratory Practice (as revised in 1997), C (97) 186 (Final)]. *Salmonella typhimurium* strains TA 98, TA 100, TA 1535, TA 1537 and one indicator *Escherichia coli* WP2 uvrA strain were used (strain of density $10^8$-$10^9$ CFU/mL). The test items were dissolved in dimethyl sulfoxide (DMSO) in maximum recommended concentration 5000 m per plate (0.1 mL).

Animal Experiments

Humanized PXR-CAR-CYP3A4/3A7 mice (model No. 11585, Taconic, USA), which express human CAR, but not murine Car or Pxr on C57BL/6 background have been purchased from Taconic (Rensselaer, NY, USA). In the single dose study, compounds of the invention were applied by per os probe (gavage) (10 mg/kg b.w.) in a form of microsuspension formulation of hydrochloride salt in 5% glycerol solution (compound of EXAMPLE 169) or dissolved in olive oil with 5% PEG300 (compound of EXAMPLE 93). Four males were used in each group. Livers were sampled 24 hours after application into liquid nitrogen for qRT-PCR analysis.

In long-term study, humanized PXR-CAR-CYP3A4/3A7 mice have been fed with 60% high-fat died for 8 weeks and invented compound of EXAMPLE 93 has been administed (10 mg/kg of b.w) by gavage for 4 weeks in comparison with vehicle-treated control animals. Livers were sampled 24 hours after the last application into liquid nitrogen. In case of i.p. Glucose Tolerance test (IPGTT), each mouse on chronic high fat diet received i.p. application of 20% glucose solution at the dose of 1 g glucose per kg b.w. Blood glucose concentration was analyzed with a glucometer from blood sampled from the tail. In case of i.p. Isulin Tolerance test (IPITT), mice received insulin administered via i.p. application in the dose of 0.75 mU/g b.w.

Pharmacokinetic studies have been performed in C57BL/6 mice. The pharmacokinetic characteristics of the compounds of EXAMPLES 93 and 169 in plasma, bile and in the liver have been studied following peroral, intraperitoneal and intravenous administrations of 10 mg/kg of b.w. Levels of the parent compounds in EXAMPLE 169 and 93 and potential metabolites (structures in EXAMPLE 111, 112 and 169 (product of Scheme 17)) were determined by LC-MS/MS in the blood plasma, bile and the liver tissue over time in the following intervals: 0, 10, 120, 240, 480, 720 and 140 minutes.

The concentration of compound in EXAMPLE 110 (a base of compound in EXAMPLE 110) and 93 and their potential metabolites was determined using high performance liquid chromatography/tandem mass spectrometry (HPLC-MS/MS). Shimadzu HPLC system comprised 2 isocratic pumps LC-10ADvp, an autosampler SIL-20AC, a sub-controller FCV-14AH and a degasser DGU-14A. Mass spectrometric analysis was performed using an API 3000 (triple-quadrupole) instrument from AB Sciex (Canada) with an electro-spray (ESI) interface. The data acquisition and system control were performed using Analyst 1.5.2 software from AB Sciex. The pharmacokinetic data analysis was performed using noncompartmental, bolus injection or extravascular input analysis models in WinNonlin 5.2 software (PharSight).

Human plasma protein binding for compounds of EXAMPLE 110 and 93 has been analyzed using micro-equilibrium dialysis and HPLC-MS/MS. The human plasma has been spiked with the test compounds at concentration of 1 μM and dialyzed against buffer until equilibrium was achieved. 96-well dialysis membrane strips (HTDialysis LLC, USA; Cat #1101) and HTD96b dialyzer (HTDialysis LLC, USA; #1006) were used.

Metabolic Stability in Human Liver S9 Fraction for compounds of EXAMPLE 93 and in liver microsomes for compound in EXAMPLE 110 was performed with S9 fraction from human liver (XenoTech, H0630.59) or in pooled microsomes from human male and female adult liver (XenoTech H0630/lotN1210097). Glucose-6-phosphate dehydrogenase from baker's yeast, type XV was purchased from Sigma-Aldrich, now Merck (Cat. No. G6378). Control incubations were performed replacing the cofactors system with PBS. Test compound (2 μM, final solvent concentration 1.6%) was incubated with S9 at 37° C. Five time points over 40 minutes had been analyzed. Supernatants were analyzed using the HPLC system coupled with HPLC-MS/MS analysis as described above.

RT-qPCR Experiments

Expressions of CAR target genes mRNAs in HepaRG/CAR Knockout HepaRG cells, in primary human hepatocytes in monolayers or in livers of humanized mice have been performed using TaqMan probes-based RT-qPCR after isolation of total RNA by Trizol® (Catalog number: 15596026, ThermoFischer Scientific) reagent and reverse transcription synthesis of cDNA in Quant Studio cycler. Real-time qPCR TaqMan probes have been purchased prom ThermoFisher scientific (Cat. No. 4351372 and 433118). Delta-delta method and GAPDH/Gapdh or B2M/B2m housekeeping genes were used for relative quantification. Data are expressed as fold up-/down-regulation compare to vehicle-treated samples/mice.

Most of these novel compounds do not significantly affect viability of HepG2 and COS-1 cell lines after 48 h-treatment as determined with CellTiter 96® AQ$_{ueous}$ One Solution Cell Proliferation Assay (MTS)(Catalog number selected: G3582, Promega, Madison, USA). Mainly, compounds of EXAMPLES 93, 97, 89, 109, 110, 112, and 149 have no significant effect on HepG2 or COS-1 viability after 48-h treatment at 30 μM/L concentration indicating their $IC_{50}$ substantially higher than 30 μM/L. Similarly, no effect on viability/cytotoxicity was observed after 48 h treatment with selected compounds of the invention in differentiated HepaRG cells or in primary human hepatocytes (including compounds in EXAMPLES 93, 109, 110, 111 and 112).

No significant genotoxicity of the compound in EXAMPLE 110 was found in *Salmonella typhimurium* reverse mutation Ames Test with ST TA 98 and ST TA 100 strains (Muta-Chromoplate Kit, EBPI, Canada) at the 10 μM concentration either with or without metabolic activation with S9 fraction. Compounds of EXAMPLE 93 was non-mutagenic for all the used indicator strains in Bacterial Reverse Mutation Test in all experiments.

Repeated Dose 7-day Oral Toxicity Study in Rats was carried out according to ICH Guidelines M3 (R2) on non-clinical safety studies for the conduct of human clinical trials and marketing authorization for pharmaceuticals, EMA/CPMP/ICH/286/1995, 2009. The studies were conducted on female rats.

Human Ether-a-go-go-Related Gene (hERG) binding for compound of EXAMPLE 110 has been done using the Predictor™ hERG Fluorescence Polarization Assay kit (Invitrogen; Cat #PV5365). For compound of EXAMPLE 93, The FluxOR™ II Green Potassium Ion Channel Assay with HEK293-hERG cells (stably expressing human potassium channel hERG) seeded on Poly-D-Lysine-coated 384-well microplates (Corning, Cat. #356663) was used according to the manufacturer's instructions. hERG stimulation buffer containing thallium and potassium was added and the intracellular fluorescence was measured. The tested compound of EXAMPLE 110 was assessed at the range of concentration from 1 μM/L to 20 μM/L, for compound of EXAMPLE 93, the concentration range of 0.045-100 μM/L (8 points, 3-fold serial dilutions) was used.

Results

Compounds of EXAMPLE 110 and 93 at the concentration of 10 μM/L significantly stimulates CAR+A-EGFP fusion protein translocation into nucleus in COS-1 cells after 48 h. Compounds in EXAMPLE 110, and 93 at 10 μM/L do not activate human androgen, farnesoid X, glucocorticoid, estradion α and β, PPARα, γ or δ, vitamin D, live X receptors α and β, thyroid hormone receptors as determined using luciferase reporter assays with a GAL4 constructs with LBD of tested nuclear receptors.

For example, the compound of EXAMPLE 110 and 93 do not interfere with hERG activity at 20 μM/L.

Compounds of EXAMPLES 93 and 110 are stable in human plasma over 120 minutes.

Plasma protein binding in human plasma for compounds of EXAMPLE 110 and 93 have been found to be 98% and 99%, respectively, at 1 μM/L.

Assessment of metabolic stability in human liver microsomes or in S9 fraction with the compound of EXAMPLE 110 indicates moderate stability ($T_{1/2}$=38 and 42 minutes, respectively). Compound of EXAMPLE 93 is very stable in human S9 fraction with estimated $T_{1/2}$ being higher than 170 min.

Figure 8:
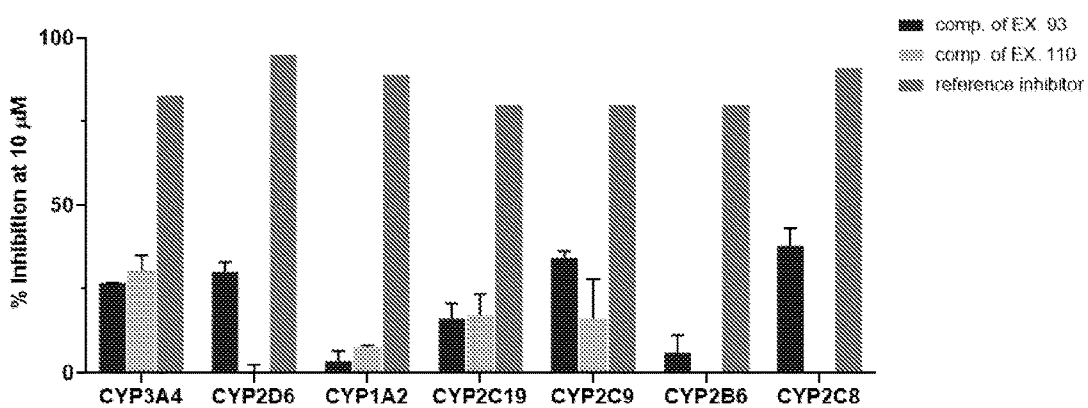
FIG. 8 shows the effect of compound of EXAMPLE 93 and 110 on the panel of major cytochrome P450 enzymes. Both compounds are weak inhibitors of these enzymes with $IC_{50}$ being higher than 10 μM.

Inhibition of the panel of CYPs enzymes in liver microsomes by compound of EXAMPLES 93 and 110 is shown at FIG. 8 indicating that both compounds have $IC_{50}$ higher tan 10 μM/L and are not potent inhibitors of CYPs. Consistently, the half maximal inhibitory concentration ($IC_{50}$) of human CYP3A4, CYP2D6, CYP1A2 and CYP2C19 for compounds of EXAMPLE 110 and 93 are higher than 10 μM/L in commercial assays. The compound of EXAMPLE 111 has $IC_{50}$ for CYP3A4, CYP2D6 and CYP1A2 higher than 20 μM/L.

In pilot Maximum Tolerated Dose (MTD) study in female Wistar rats with oral administration of the compound of EXAMPLE 110 as hydrochloric salt (compound in EXAMPLE 169) in three doses groups (30 mg/kg, 10 mg/kg, 1 mg/kg of b.w.) and in one control group, no significant clinical signs of toxicity (changes in behavior, body weight decrease, systematic changes in hematology and in biochemistry parameters, gross pathology and histopathology systematic group findings) were observed after the seven days of oral administration. No significant clinical signs of toxicity were observed in the Repeated Dose 7-day Oral Toxicity Study in Rats after oral administration of compound of EXAMPLE 93 at the doses of 1 and 10 mg/kg.

In Maximal Tolerated Dose (MTD) study in normal C57BL/6 female mice, with oral administration of the compound of EXAMPLE 169 (a hydrochloric salt of compound in EXAMPLE 110) in two doses groups (10 mg/kg, 1 mg/kg of b.w.) and in one control group (3-4 animal per group), no significant clinical signs of toxicity or changes in hematology and in biochemistry parameters, gross pathology and histopathology systematic group findings) were observed after the seven days of oral administration.

In Repeated Dose 28 days oral toxicity study according to the guidelines OECD Test Guideline No. 407 (Repeated Dose 28-day Oral Toxicity Study in Rodents), ICH Topic M 3 (R2) (Non-Clinical Safety Studies for the Conduct of Human Clinical Trials and Marketing Authorization for Pharmaceuticals) and Guideline on repeated dose toxicity (EMA), no significant clinical signs of toxicity (changes in behavior, body weight decrease, systematic changes in hematology and in biochemistry parameters, gross pathology and histopathology systematic group findings) after oral administration of the compound of EXAMPLE 110 as hydrochloric salt (compound in EXAMPLE 169) in three dose groups (30 mg/kg, 10 mg/kg, 1 mg/kg of b.w.) and in one control group (vehicle only) were observed. In the study, 4 males of Wistar rats were used per each group.

The compound of EXAMPLE 169 has no statistically significant influence on relative liver weight (normalized to body weight) in rats in the repeated Dose 28-days oral toxicity study, when relative liver weight was 3% in control group, 3.2% in group administered with 1 mg/kg, 3.4% in group administered with 10 mg/kg and 3.7% in group administered with 30 mg/kg of the compound of EXAMPLE 169, respectively.

Evaluation of mutagenicity in modified Ames fluctuation assay performed with compounds of EXAMPLE 109 and 110, on *Salmonella typhimurium* TA100 and TA98 strains at a concentration of 10 μM/L, but no significant genotoxicity was observed up to the concentration of 10 μM. Compounds of Example 93 was non-mutagenic for all the used indicator strains in all experiments with and without metabolic activation and there was no significant increases in the number of revertants when compared to that in solvent controls (Rt/Rc<2) either with or without metabolic activation with S9 fraction.

Figure 3:
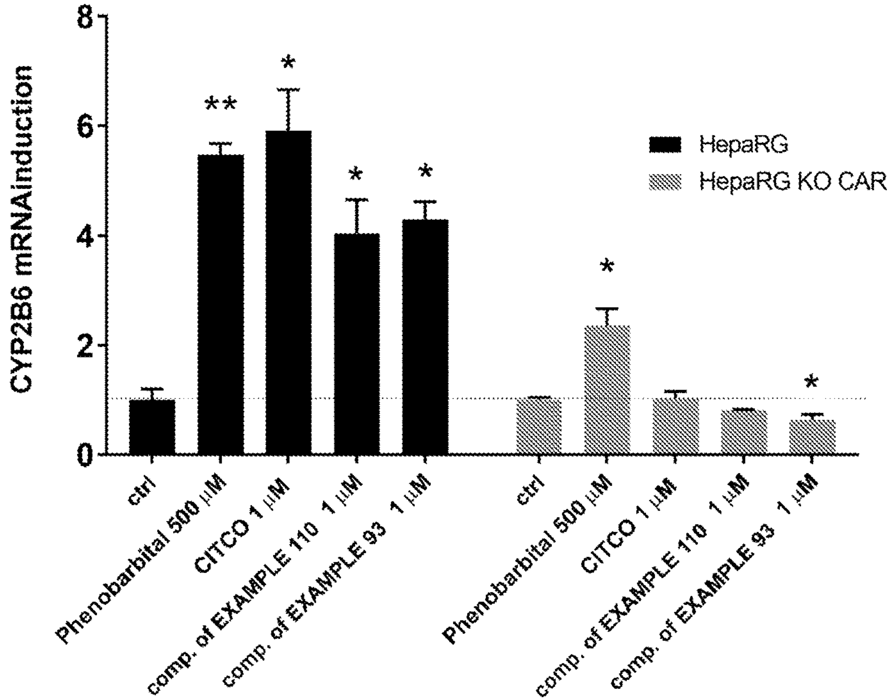
FIG. 3 demonstrates that the compounds of EXAMPLES 110 and 93 show up-regulation of the major human CAR target gene CYP2B6 in HepaRG, but not in CAR-deficient HepaRG KO CAR cells as determined by RT-qPCR. Fold induction of the target gene mRNA versus vehicle-treated control samples are presented after 24 hours treatment. At the same time, activities of prototype CAR (CITCO) and common PXR/CAR activator (phenobarbital) are shown. *,** denotes statistical significance $p<0.05$ or $p<0.01$, respectively, compared to controls.

In another embodiment, this invention shows that the compounds of EXAMPLE 110 and 93 upregulates CYP2B6 mRNA in differentiate HepaRG cells, but not in HepaRG KO CAR cells lacking functional CAR expression after 24 h of treatment (FIG. 3.).

Figure 4:
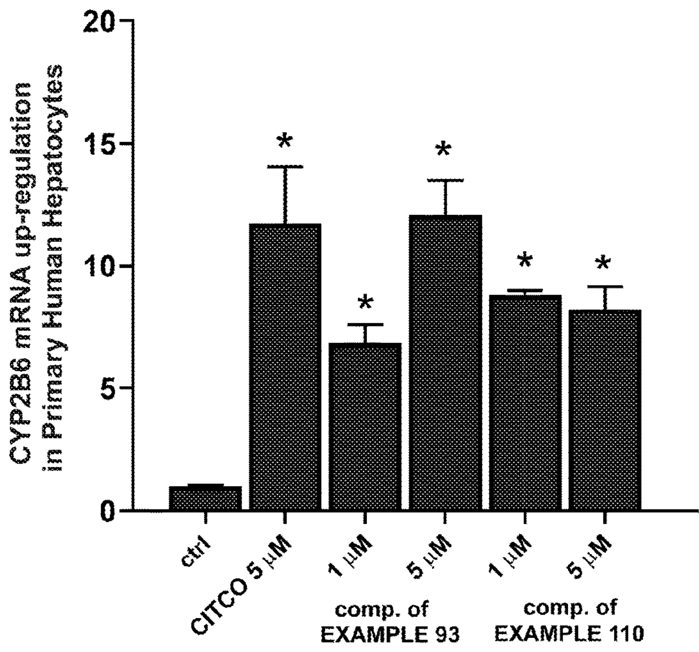
FIG. 4 demonstrates that the compounds of EXAMPLES 110 and 93 up-regulates CYP2B6 mRNA in primary human hepatocytes after 48 hours of treatment with 1 and 5 μM/L. CITCO is a prototype CAR ligand.

The compounds in EXAMPLEs 110 and 93 activate human CAR in plated primary human hepatocytes to upregulate the major CAR target gene CYP2B6 mRNA expression (FIG. 4).

Figure 5:
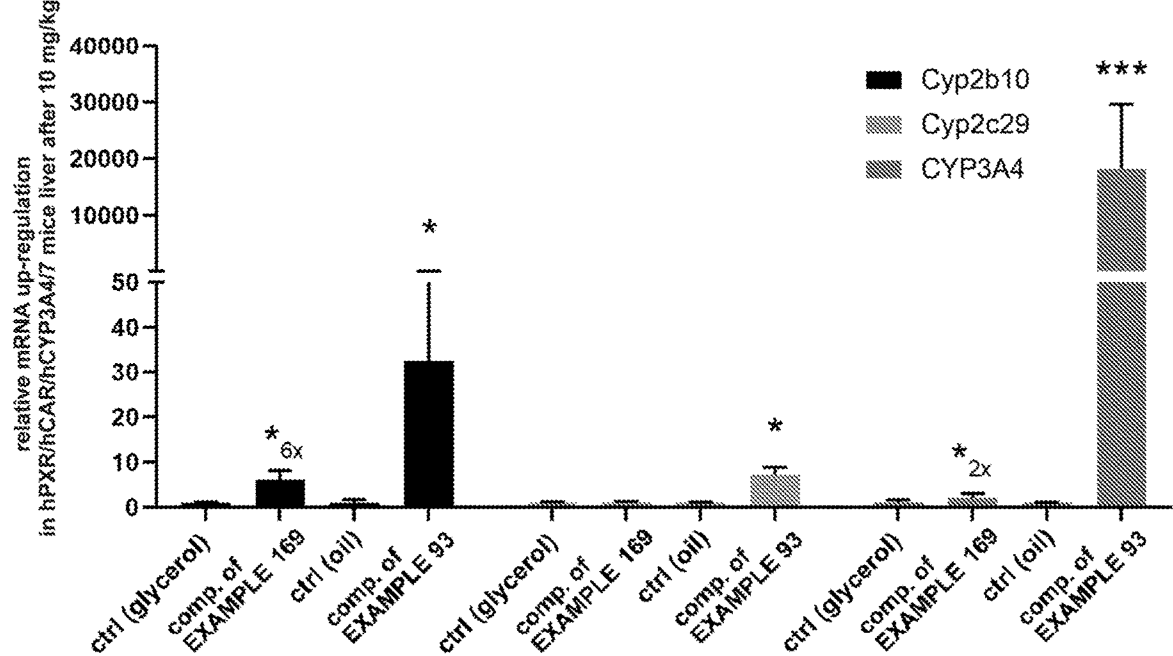
FIG. 5 shows that the compounds of EXAMPLES 169 (a hydrochloric salt of compound in EXAMPLE 110) and 93 up-regulate Cyp2b10, Cyp2c29 and CYP3A4 mRNA, in the liver of humanized huPXR/huCAR/huCYP3A4/huCYP3A7 mice after peroral (gavage) administration of 10 mg/kg of the invented compounds. Data show fold mRNA upregulation of CAR target genes in the liver of humanized mouse model analyzed after 24 hours after application using RT-qPCR with specific TaqMan probes. * and *** denotes statistical significance at the level of $p<0.05$ or $p<0.001$ compared to vehicle controls (either 5% glycerol solution or olive oil).

In addition, selected compounds of the invention with the lowest activity towards PXR (Compounds of EXAMPLE 169 and 93) activate CAR to up-regulate Cyp2b10, Cyp2c29 and CYP3A4 mRNAs in the liver of humanized PXR-CAR-CYP3A4/3A7 Mouse model (model No. 11585, Taconic, USA) after single p.o. administration of 10 mg/kg of compounds in EXAMPLE 169 and 93, respectively (FIG. 5).

Figure 6:
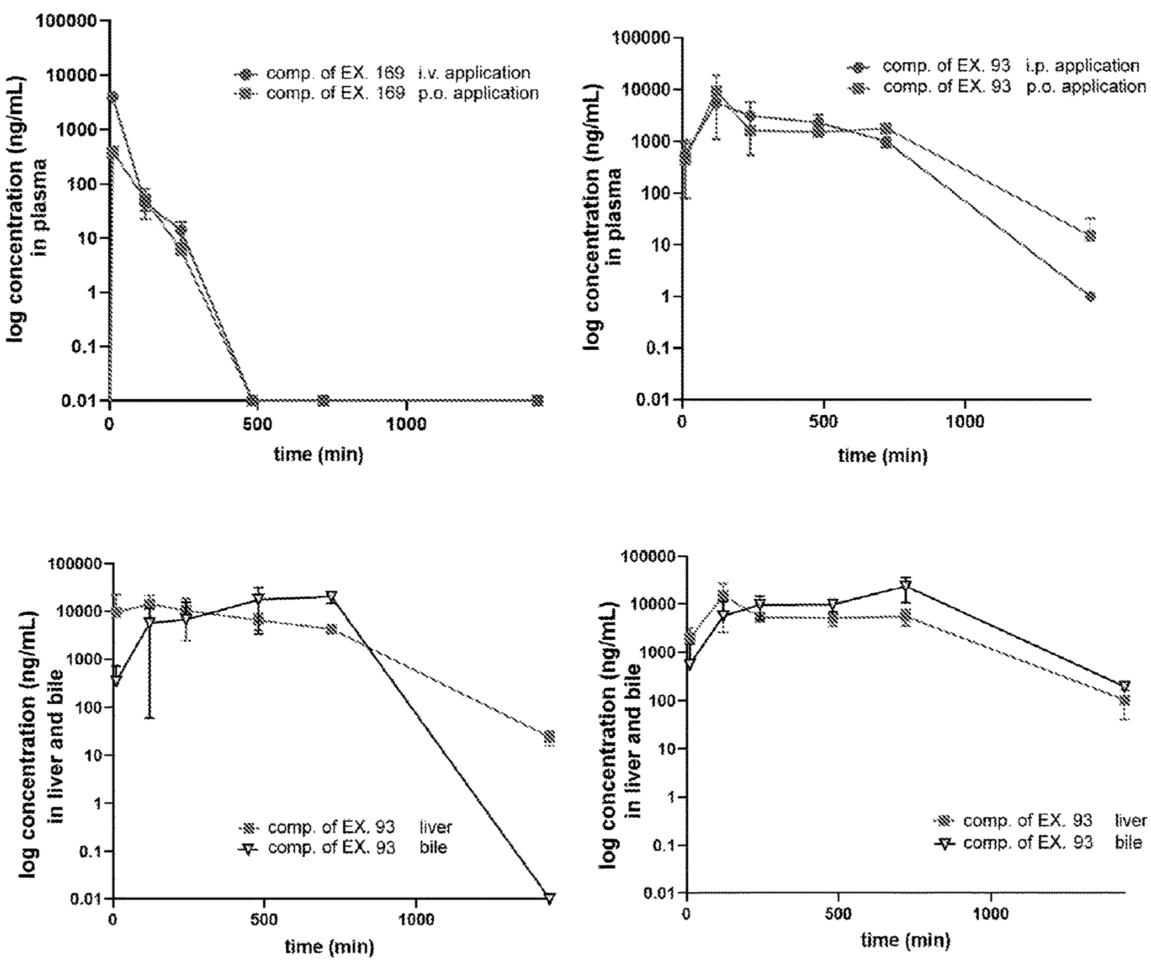
FIG. 6 show pharmakokinetics (PK) in humanized huPXR/huCAR/huCYP3A4/huCYP3A7 male mice after peroral, i.p. or i.v. application of compounds of EXAMPLES 169 and 93. Plasma as well as liver and bile concentrations have been analyzed over 1440 minutes (24 h) in at least three animals per time point.

Compound in EXAMPLE 93 has favourable pharmacokinetics and biological half-life $T_{1/2}$. Moreover, compound of EXAMPLE 93 has excellent delivery into the liver and bile (FIG. 6). $T_{1/2}$ of the compound of EXAMPLE 93 in C57BL/6N mice in pharmacokinetic studies following intraperitoneal or peroral administration (10 mg/kg) was found to be 217 and 170 minutes, respectively. Bioavailability (F) of the compound of EXAMPLE 93 has bee evaluated to be 98.6% base on AUCp.o./AUCi.p. ratio (FIG. 6).

In pilot pharmacokinetic study with compound in EXAMPLE 169 (10 mg/kg) in C57BL/6 male mice, the following PK parameters have been found after peroral application: $T_{1/2}$=38 minutes, F (bioavailability)=16% and Vd=2700 mL/kg. For i.v. application of the compound of EXAMPLE 169, $T_{1/2}$ were found to be 29 minutes. Traces of metbolites with structures in EXAMPLES 111, 112 and 169 have been found in mouse blood in early intervals (10 minutes).

Compound in EXAMPLE 169 does not stimulate liver hypertrophy in humanized PXR-CAR-CYP3A4/3A7 Mouse model (model No. 11585, Taconic, USA) feeded with 60% high-fat died for 8 weeks and administered with 2.5 mg/kg of b.w of compound of EXAMPLE 169 by gavage for 5 weeks in comparison with vehicle treated control animals. At least four animals were involved in each group.

Figure 7:
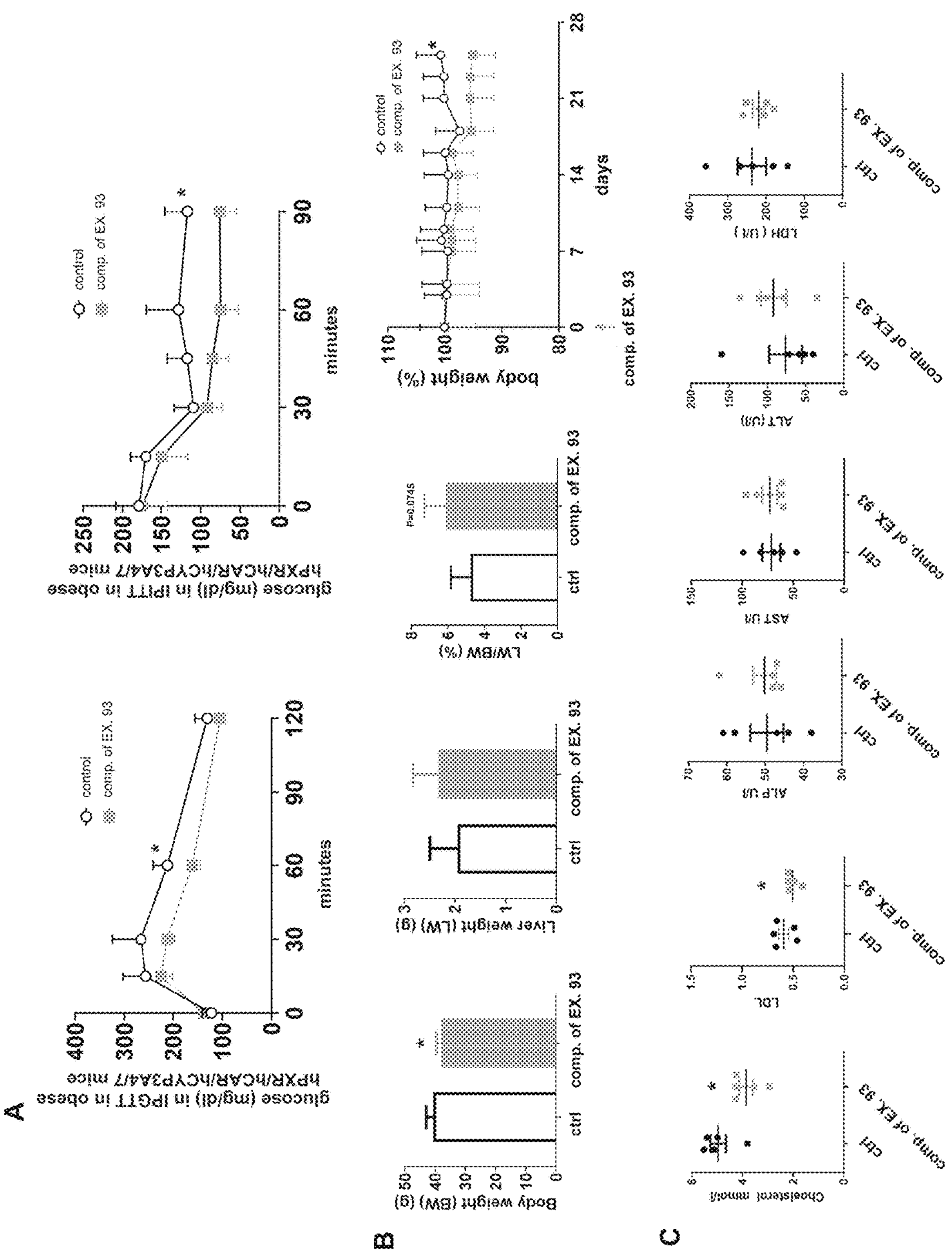
FIG. 7 shows that the compound of EXAMPLE 93 alleviates insuline resistance and stimulates the effect of insuline in i.p. glucose tolerance test (IPGTT) and i.p. in insulin tolerance test (ITT), but does not stimulate significantly liver hypertrophy (indicated as live-to-body weight ratio, LW/BW) in humanized PXR-CAR-CYP3A4/3A7 mice (n=5) feeded with 60% high-fat died for 8 weeks and administed with 10 mg/kg of b.w of invented compound of EXAMPLE 93 by gavage for 4 weeks (3 times per week) in comparison with vehicle treated control animals.

Compound in EXAMPLE 93 has stimulatory effect on insulin sensitivity in IPGTT and IPITT in humanized PXR-CAR-CYP3A4/3A7 Mouse model (model No. 11585, Taconic, USA) feeded with 60% high-fat died for 8 weeks and administered with 10 mg/kg of b.w of compound of EXAMPLE 93 by gavage for 4 weeks in comparison with vehicle treated control animals. At least four animals were involved in each group (FIG. 7A).

Compound in EXAMPLE 93 does not stimulate liver hypertrophy in humanized PXR-CAR-CYP3A4/3A7 Mouse model (model No. 11585, Taconic, USA) feeded with 60% high-fat died for 8 weeks and administered with 10 mg/kg of b.w of compound of EXAMPLE 93 by gavage for last 4 weeks in comparison with vehicle treated control animals. At least four animals were involved in each group (FIG. 7B). Compound of EXAMPLE 93 decrease body weight of animals in the experiments after 4 weeks of application (FIG. 7B). Compound of EXAMPLE 93 did not significantly up-regulate Mki67 mRNA in the experiments, but significantly decrease the RNA levels of Scd1 and Fasn in mouse liver.

Compound in EXAMPLE 93 has an effect on plasma cholesterol and LDL concentrations in humanized PXR-CAR-CYP3A4/3A7 Mouse model (model No. 11585, Taconic, USA) feeded with 60% high-fat died for 8 weeks and administered with 10 mg/kg of b.w of compound of EXAMPLE 93 by gavage for 4 weeks in comparison with vehicle treated control animals. At least four animals were involved in each group (FIG. 7C).

Figure 2:
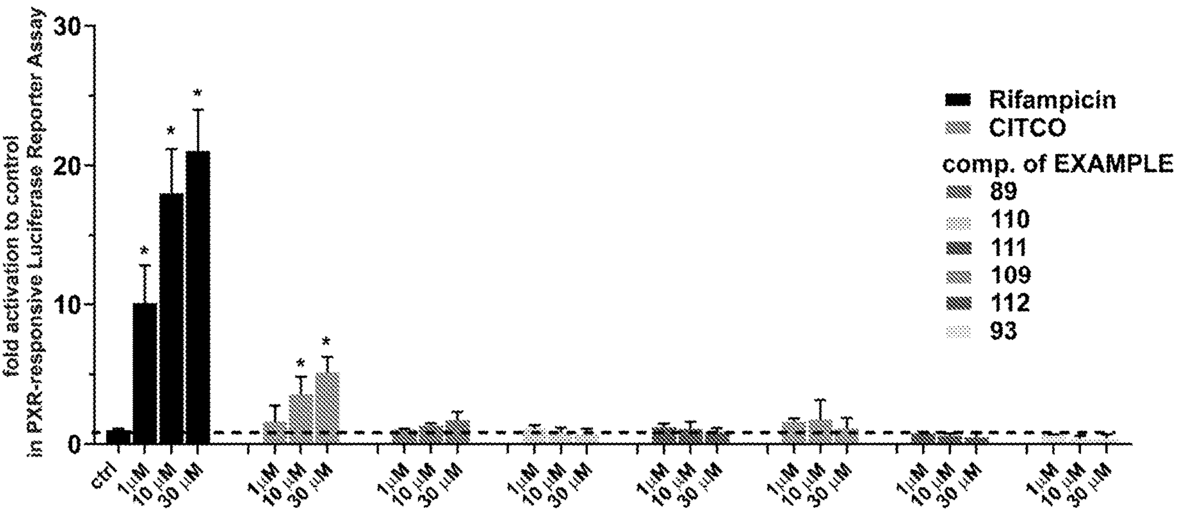
FIG. 2 evidences no activation of PXR by selected compounds of the invention in human PXR-responsive luciferase reporter gene assay in HepG2 cells. The embodiment indicates fold activation of PXR-responsive luciferase construct in response to compounds of the invention treatment for 24 hours. Rifampicin has been used as the prototype PXR ligand. * denotes statistical significance at the level of $p<0.05$ compared to controls.

The results show (see Table 1) that selected compounds of the invention activate human CAR or its variant CAR3 in CAR TR-FRET Coactivator assay (FIG. 1.) or in luciferase reporter assays, but have marginal or no effects on PXR activation up to 30 μM concentration or may slightly decrease activity of PXR-responsive luciferase construct (FIG. 2.).

FIG. 8 show potential of compounds of EXAMPLES 93 and 110 to interfere with the panel of major human cytochrome P450 enzymes.

TABLE 1

Selected compounds of the invention activate human CAR, but have minimum or no activity to activate PXR. Activation of recombinant human CAR receptor was performed using TR-FRET LanthaScreen CAR Coactivation. Gene reporter assays with human wild-type CAR and its transcription variant 3 or with human PXR have been performed with CAR/PXR responsive luciferase constructs.

| EXAMPLE | CAR TR-FRET $EC_{50}$ (µM) | CAR assembly assay $EC_{50}$ (µM) | CAR3 % of CITCO (1 µM) activity at 1 µM | PXR % of RIF activity (10 µM) at 10 µM |
|---|---|---|---|---|
| 63 | <0.01 | 1.5 | 167 | 38 |
| 160 | <0.02 | 3.6 | 138 | 36 |
| 148 | <0.02 | 8.8 | 93 | 20 |
| 82 | <0.01 | N.D. | 184 | 47 |
| 89 | 0.00036 | 1.48 | 137 | 4 |
| 110 | 0.611 | 1.29 | 68 | No activation |
| 111 | 1.06 | 1.09 | 91 | 4 |
| 109 | 0.317 | 2.06 | 44 | 9 |
| 113 | <0.01 | <0.01 | 333 | 30 |
| 112 | 1.69 | 1.53 | 63 | No activation |
| 114 | 0.01 | 0.8 | 224 | 26 |
| 149 | <0.02 | 0.3 | 168 | 16 |
| 150 | 0.16 | 1 | 176 | 45 |
| 152 | 0.40 | 1 | 91 | 23 |
| 117 | <0.01 | <0.1 | 345 | 37 |
| 92 | 0.11 | 4.1 | 21 | 4 |
| 93 | 0.071 | 0.38 | 83 | No activation |
| 115 | <0.01 | <0.1 | 69 | 43 |
| 162 | <0.01 | 0.16 | 82 | 29 |
| 102 | <0.01 | <0.1 | 59 | 35 |
| 105 | <0.01 | <0.1 | 70 | 43 |
| CITCO | 0.013 | 0.646 | | |
| CITCO 10 µM | | | 396 | 27 |
| CITCO 1 µM | | | 100% | 8 |
| Rifampicin 10 µM | | | | 100% |

N.D.—not determined $EC_{50}$ is the concentration required to achieve half-maximum TF-FRET CAR LBD coactivation or CAR-activated luciferase construct activation (in µM/L)

INDUSTRIAL APPLICABILITY

The compounds of the present invention are industrially manufacturable and usable for the treatment of many diseases which are mediated by the action, or by loss of action, of Constitutive androstane receptor (CAR) receptor or its endogenous ligands, such as lipid metabolic disorders, liver diseases or related pathologies, or condition or disease connected with malignancy.

REFERENCES CITED

Baskin-Bey E S, Anan A, Isomoto H, Bronk S F and Gores G J. *World J Gastroenterol* 13:5635-5641 (2007).

Carazo A and Pavek P. *Sensors* 15:9265-9276 (2015).

Dibba P, Li A A, Perumpail B J, John N, Sallam S, Shah N D, Kwong W, Cholankeril G, Kim D and Ahmed A. *Diseases* 6 (2018).

Dong B, Saha P K, Huang W, Chen W, Abu-Elheiga L A, Wakil S J, Stevens R D, Ilkayeva O, Newgard C B, Chan L and Moore D D. *Proc Natl Acad Sci USA* 106:18831-18836 (2009).

Fuchs C D, Traussnigg S A and Trauner M. *Semin Liver Dis* 36:69-86 (2016).

Gao J and Xie W. *Trends in pharmacological sciences* 33:552-558 (2012).

Gao J, Yan J, Xu M, Ren S and Xie W. *Mol Endocrinol* 29:1558-1570 (2015).

Hakkola J, Bernasconi C, Coecke S, Richert L, Andersson T B and Pelkonen O. *Basic Clin Pharmacol Toxicol* (2018).

Chai S C, Cherian M T, Wang Y M and Chen T. *Biochim Biophys Acta* (2016a).

Chai S C, Cherian M T, Wang Y M and Chen T. *Biochim Biophys Acta* 1859:1141-1154 (2016b).

Cheng S, Zou M, Liu Q, Kuang J, Shen J, Pu S, Chen L, Li H, Wu T, Li R, Li Y, Jiang W, Zhang Z and He J. *Am J Pathol* 187:808-818 (2017).

Lake B G. *Toxicol Res* (*Camb*) 7:697-717 (2018).

Mackowiak B, Hodge J, Stern S and Wang H. *Drug metabolism and disposition: the biological fate of chemicals* (2018).

Maglich J M, Parks D J, Moore L B, Collins J L, Goodwin B, Billin A N, Stoltz C A, Kliewer S A, Lambert M H, Willson T M and Moore J T. *The Journal of biological chemistry* 278:17277-17283 (2003).

Pu S, Wu X, Yang X, Zhang Y, Dai Y, Zhang Y, Wu X, Liu Y, Cui X, Jin H, Cao J, Li R, Cai J, Cao Q, Hu L and Gao Y. *Current drug metabolism* 20:15-22 (2019).

Rezen T, Tamasi V, Lovgren-Sandblom A, Bjorkhem I, Meyer U A and Rozman D. *BMC Genomics* 10:384 (2009).

Sberna A L, Assem M, Gautier T, Grober J, Guiu B, Jeannin A, Pais de Barros J P, Athias A, Lagrost L and Masson D. *J Hepatol* 55:154-161 (2011a).

Sberna A L, Assem M, Xiao R, Ayers S, Gautier T, Guiu B, Deckert V, Chevriaux A, Grober J, Le Guern N, Pais de Barros J P, Moore D D, Lagrost L and Masson D. *Arterioscler Thromb Vasc Biol* 31:2232-2239 (2011b).

Tschuor C, Kachaylo E, Limani P, Raptis D A, Linecker M, Tian Y, Herrmann U, Grabliauskaite K, Weber A, Columbano A, Graf R, Humar B and Clavien P A. *J Hepatol* 65:66-74 (2016).

Wagner M, Halilbasic E, Marschall H U, Zollner G, Fickert P, Langner C, Zatloukal K, Denk H and Trauner M. *Hepatology* 42:420-430 (2005).

Wang D, Li L, Yang H, Ferguson S S, Baer M R, Gartenhaus R B and Wang H. *Blood* 121:329-338 (2013).

Xu P, Zhai Y and Wang J. *Int J Mol Sci* 19 (2018).

The invention claimed is:

1. A compound of general formula I, selected from the group consisting of:

2-(4-Chlorophenyl)-3-(1-(3,4-dichlorobenzyl)-1H-1,2,3-triazol-4-yl)imidazo[1,2-a]pyridine, 6-(4-Chlorophenyl)-5-(1-(3,4-dichlorobenzyl)-1H-1,2,3-triazol-4-yl)imidazo[2,1-b]thiazole, 5-(1-(3,4-Dimethoxybenzyl)-1H-1,2,3-triazol-4-yl)-6-phenylimidazo[2,1-b]thiazole, 6-(4-Chlorophenyl)-5-(1-(4-methoxybenzyl)-1H-1,2,3-triazol-4-yl)imidazo[2,1-b]thiazole, 2-(4-Chlorophenyl)-3-(1-(3,4-dimethoxybenzyl)-1H-1,2,3-triazol-4-yl)imidazo[1,2-a]pyridine, 2-(4-Chlorophenyl)-3-(1-(4-methoxybenzyl)-1H-1,2,3-triazol-4-yl)imidazo[1,2-a]pyridine, 3-(1-Benzyl-1H-1,2,3-triazol-4-yl)-2-(4-chlorophenyl)imidazo[1,2-a]pyridine, 2-(4-Chlorophenyl)-3-(1-(pyridin-2-ylmethyl)-1H-1,2,3-triazol-4-yl)imidazo[1,2-a]pyridine, 5-(1-Benzyl-1H-1,2,3-triazol-4-yl)-6-(4-chlorophenyl)imidazo[2,1-b]thiazole, 6-(4-Chlorophenyl)-5-(1-(pyridin-2-ylmethyl)-1H-1,2,3-triazol-4-yl)imidazo[2,1-b]thiazole, 3-(1-(4-Chlorobenzyl)-1H-1,2,3-triazol-4-yl)-2-(4-chlorophenyl)imidazo[1,2-a]pyridine, 5-(1-(4-Chlorobenzyl)-1H-1,2,3-triazol-4-yl)-6-(4-chlorophenyl)imidazo[2,1-b]thiazole, 3-Benzyl-5-(2-(4-chlorophenyl)imidazo[1,2-a]pyridin-3-yl)isoxazole, 4-((4-(2-(4-Chlorophenyl)imidazo[1,2-a]pyridin-3-yl)-1H-1,2,3-triazol-1-yl)methyl)benzonitrile, 2-(4-Chlorophenyl)-3-(1-(3,4-dichlorobenzyl)-1H-1,2,3-triazol-4-yl)imidazo[1,2-b]pyridazine, 3-(1-(3,4-Dichlorobenzyl)-1H-1,2,3-triazol-4-yl)-2-(3,4-dichlorophenyl)imidazo[1,2-a]pyridine, 5-(1-(3,4-Dichlorobenzyl)-1H-1,2,3-triazol-4-yl)-6-(3,4-dichlorophenyl)imidazo[2,1-b]thiazole, 3-(1-Benzyl-1H-1,2,3-triazol-4-yl)-6-chloro-2-(4-chlorophenyl)imidazo[1,2-b]pyridazine, 5-(2-(4-Chlorophenyl)imidazo[1,2-a]pyridin-3-yl)-3-(3,4-dichlorobenzyl)-1,2,4-oxadiazole, 2-(2-(4-Chlorophenyl)imidazo[1,2-a]pyridin-3-yl)-5-(3,4-dichlorobenzyl)-1,3,4-oxadiazole, 5-(6-(4-Chlorophenyl)imidazo[2,1-b]thiazol-5-yl)-3-(3,4-dichlorobenzyl)-1,2,4-oxadiazole, 2-(4-Chlorophenyl)-3-(5-(3,4-dichlorobenzyl)-1H-1,2,4-triazol-3-yl)imidazo[1,2-a]pyridine, 6-(4-Chlorophenyl)-5-(2-(3,4-dichlorobenzyl)thiazol-4-yl)imidazo[2,1-b]thiazole, 4-(2-(4-Chlorophenyl)imidazo[1,2-a]pyridin-3-yl)-2-(3,4-dichlorobenzyl)thiazole, 2-(2-(4-Chlorophenyl)imidazo[1,2-a]pyridin-3-yl)-5-(3,4-dichlorobenzyl)-1,3,4-thiadiazole, 3-(1-(3,4-Dichlorobenzyl)-1H-1,2,3-triazol-4-yl)-2-(p-tolyl)imidazo[1,2-a]pyridine, 3-(1-(3,4-Dichlorobenzyl)-1H-1,2,3-triazol-4-yl)-2-(2,4-dichlorophenyl)imidazo[1,2-a]pyridine, 4-(3-(1-(3,4-Dichlorobenzyl)-1H-1,2,3-triazol-4-yl)imidazo[1,2-a]pyridin-2-yl)benzonitrile, 3-(1-(3,4-Dichlorobenzyl)-1H-1,2,3-triazol-4-yl)-2-(4-methoxyphenyl)imidazo[1,2-a]pyridine, 3-(1-(3,4-Dichlorobenzyl)-1H-1,2,3-triazol-4-yl)-2-(4-(trifluoromethyl)phenyl)imidazo[1,2-a]pyridine, 3-(1-(3,4-Dichlorobenzyl)-1H-1,2,3-triazol-4-yl)-2-(4-fluorophenyl)imidazo[1,2-a]pyridine, 3-(1-(3,4-Dichlorobenzyl)-1H-1,2,3-triazol-4-yl)-2-(4-ethylphenyl)imidazo[1,2-a]pyridine, Methyl2-chloro-5-((4-(2-(4-chlorophenyl)imidazo[1,2-a]pyridin-3-yl)-1H-1,2,3-triazol-1-yl)methyl)benzoate, (2-Chloro-5-((4-(2-(4-chlorophenyl)imidazo[1,2-a]pyridin-3-yl)-1H-1,2,3-triazol-1-yl)methyl) phenyl)methanol, 2-(4-Chlorophenyl)-3-(1-(3,4-dichlorobenzyl)-1H-pyrazol-4-yl)imidazo[1,2-a]pyridine, 2-(4-Chlorophenyl)-3-(1-(3,4-dichlorobenzyl)-1H-pyrrol-2-yl)imidazo[1,2-a]pyridine, 2-(4-Chlorophenyl)-3-(1-(3,4-dichlorophenethyl)-1H-1,2,3-triazol-4-yl)imidazo[1,2-a]pyridine, 2-Chloro-5-((4-(2-(4-chlorophenyl)imidazo[1,2-a]pyridin-3-yl)-1H-1,2,3-triazol-1-yl)methyl) benzamide, 2-Chloro-5-((4-(2-(4-chlorophenyl)imidazo[1,2-a]pyridin-3-yl)-1H-1,2,3-triazol-1-yl)methyl)-N,N-dimethylbenzamide, 2-Chloro-5-((4-(2-(4-chlorophenyl)imidazo[1,2-a]pyridin-3-yl)-1H-1,2,3-triazol-1-yl)methyl)-N-methoxy-N-methylbenzamide, 1-(2-Chloro-5-((4-(2-(4-chlorophenyl)imidazo[1,2-a]pyridin-3-yl)-1H-1,2,3-triazol-1-yl)methyl)phenyl)ethan-1-one, 2-Chloro-5-((4-(2-(4-chlorophenyl)imidazo[1,2-a]pyridin-3-yl)-1H-1,2,3-triazol-1-yl)methyl)-N-methylbenzamide, 1-(2-Chloro-5-((4-(2-(4-chlorophenyl)imidazo[1,2-a]pyridin-3-yl)-1H-1,2,3-triazol-1-yl)methyl)phenyl)propan-1-one, 2-Chloro-5-((5-(2-(4-chlorophenyl)imidazo[1,2-a]pyridin-3-yl)-1,3,4-thiadiazol-2-yl)methyl)-N,N-dimethylbenzamide, 2-Chloro-5-((5-(2-(4-chlorophenyl)imidazo[1,2-a]pyridin-3-yl)-1,3,4-thiadiazol-2-yl)methyl)-N,N-dimethylbenzothioamide, 2-Chloro-5-((5-(2-(4-chlorophenyl)imidazo[1,2-a]pyridin-3-yl)-1,3,4-oxadiazol-2-yl)methyl)-N-methylbenzothioamide, 2-Chloro-5-((5-(2-(4-chlorophenyl)imidazo[1,2-a]pyridin-3-yl)-1,3,4-oxadiazol-2-yl)methyl)-N-methylbenzamide, 2-(4-Chlorophenyl)-3-(1-(4-(methylsulfonyl)benzyl)-1H-1,2,3-triazol-4-yl)imidazo[1,2-a]pyridine, 2-(4-Chlorophenyl)-3-(1-(1-phenylethyl)-1H-1,2,3-triazol-4-yl)imidazo[1,2-a]pyridine, 2-(4-Chlorophenyl)-3-(1-(4-nitrobenzyl)-1H-1,2,3-triazol-4-yl)imidazo[1,2-a]pyridine, 4-((4-(2-(4-Chlorophenyl)imidazo[1,2-a]pyridin-3-yl)-1H-1,2,3-triazol-1-yl)methyl)aniline, 2-Chloro-5-(1-(4-(2-(4-chlorophenyl)imidazo[1,2-a]pyridin-3-yl)-1H-1,2,3-triazol-1-yl)ethyl)benzamide, 2-(4-Chlorophenyl)-3-(1-(4-(methylthio)benzyl)-1H-1,2,3-triazol-4-yl)imidazo[1,2-a]pyridine, 2-Chloro-5-((4-(2-(4-chlorophenyl)-8-fluoroimidazo[1,2-a]pyridin-3-yl)-1H-1,2,3-triazol-1-yl)methyl) benzamide, 2-Chloro-5-((4-(2-(4-chlorophenyl)-7-fluoroimidazo[1,2-a]pyridin-3-yl)-1H-1,2,3-triazol-1-yl)methyl) benzamide, 2-Chloro-5-((4-(2-(4-chlorophenyl)-6-fluoroimidazo[1,2-a]pyridin-3-yl)-1H-1,2,3-triazol-1-yl)methyl)benzamide, 2-Chloro-5-((4-(2-(4-chlorophenyl)-6,8-difluoroimidazo[1,2-a]pyridin-3-yl)-1H-1,2,3-triazol-1-yl)methyl)benzamide, 2-Chloro-5-((4-(2-(4-chlorophenyl)imidazo[1,2-a]pyridin-3-yl)-1H-1,2,3-triazol-1-yl)methyl) benzaldehyde, (E)-2-chloro-5-((4-(2-(4-chlorophenyl)imidazo[1,2-a]pyridin-3-yl)-1H-1,2,3-triazol-1-yl)methyl) benzaldehyde oxime, N-(4-((4-(2-(4-chlorophenyl)imidazo[1,2-a]pyridin-3-yl)-1H-1,2,3-triazol-1-yl)methyl)phenyl)acetamide, 3-(1-(4-Chloro-3-nitrobenzyl)-1H-1,2,3-triazol-4-yl)-2-(4-chlorophenyl)imidazo[1,2-a]pyridine, 2-Chloro-5-((4-(2-(4-chlorophenyl)imidazo[1,2-a]pyridin-3-yl)-1H-1,2,3-triazol-1-yl)methyl) aniline, 3-(4-Benzylphenyl)-2-(4-chlorophenyl)imidazo[1,2-a]pyridine, 3-(6-Benzylpyridin-3-yl)-2-(4-chlorophenyl)imidazo[1,2-a]pyridine, 2-(4-Chlorophenyl)-3-(6-(1-phenylvinyl)pyridin-3-yl)imidazo[1,2-a]pyridine, 2-Chloro-5-((4-(2-(4-chlorophenyl)imidazo[1,2-a]pyridin-3-yl)-5-iodo-1H-1,2,3-triazol-1-yl)methyl)benzamide, 2-(4-Chlorophenyl)-3-(1H-1,2,3-triazol-4-yl)imidazo[1,2-a]pyridine, 3-(4-Benzylcyclohex-1-en-1-yl)-2-(4-chlorophenyl)imidazo[1,2-a]pyridine, 4-Benzyl-1-(2-(4-chlorophenyl)imidazo[1,2-a]pyridin-3-yl)cyclohexan-1-ol, 1-(5-(2-(4-Chlorophenyl)imidazo[1,2-a]pyridin-3-yl)pyridin-2-yl)-1-phenylethane-1,2-diol, (5-(2-(4-Chlorophenyl)imidazo[1,2-a]pyridin-3-yl)pyridin-2-yl)(phenyl)methanone, and 2-Chloro-5-((4-(2-(pyridine-4-yl)imidazo[1,2-a]pyridine-3-yl)-1H-1,2,3-triazol-1-yl)methyl)benzamide.

2. A pharmaceutical composition characterized in that it comprises as an active ingredient the compound according to claim 1 or its pharmaceutically acceptable salt or solvate, and one or more pharmaceutically acceptable carriers, polymers and/or excipients.

3. The pharmaceutical composition according to claim 2, characterized in that it comprises one or more additional therapeutic agents.

* * * * *